US011407766B2

(12) United States Patent
Parham et al.

(10) Patent No.: US 11,407,766 B2
(45) Date of Patent: Aug. 9, 2022

(54) MATERIALS FOR ORGANIC ELECTROLUMINESCENT DEVICES

(71) Applicant: Merck Patent GmbH, Darmstadt (DE)

(72) Inventors: Amir Parham, Frankfurt am Main (DE); Jonas Kroeber, Frankfurt am Main (DE); Dominik Joosten, Frankfurt am Main (DE); Aurélie Ludemann, Frankfurt am Main (DE); Tobias Grossmann, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 441 days.

(21) Appl. No.: 16/481,596

(22) PCT Filed: Jan. 29, 2018

(86) PCT No.: PCT/EP2018/052057
§ 371 (c)(1),
(2) Date: Jul. 29, 2019

(87) PCT Pub. No.: WO2018/138306
PCT Pub. Date: Aug. 2, 2018

(65) Prior Publication Data
US 2020/0002358 A1 Jan. 2, 2020

(30) Foreign Application Priority Data

Jan. 30, 2017 (EP) .................... 17153706

(51) Int. Cl.
| C07D 513/04 | (2006.01) |
| C07D 498/04 | (2006.01) |
| C07D 417/04 | (2006.01) |
| C07D 417/10 | (2006.01) |
| C07D 417/14 | (2006.01) |
| C07D 401/04 | (2006.01) |
| C07D 401/14 | (2006.01) |
| C07D 219/02 | (2006.01) |
| C07D 279/22 | (2006.01) |
| C07D 403/04 | (2006.01) |
| H01L 51/00 | (2006.01) |
| H01L 51/50 | (2006.01) |

(52) U.S. Cl.
CPC ......... *C07D 513/04* (2013.01); *C07D 219/02* (2013.01); *C07D 279/22* (2013.01); *C07D 401/04* (2013.01); *C07D 401/14* (2013.01); *C07D 403/04* (2013.01); *C07D 417/04* (2013.01); *C07D 417/10* (2013.01); *C07D 417/14* (2013.01); *C07D 498/04* (2013.01); *H01L 51/0067* (2013.01); *H01L 51/0069* (2013.01); *H01L 51/0072* (2013.01); *H01L 51/0073* (2013.01); *H01L 51/5016* (2013.01); *H01L 51/5056* (2013.01); *H01L 51/5072* (2013.01)

(58) Field of Classification Search
CPC .. C07D 513/04; C07D 219/02; C07D 279/22; C07D 401/04; C07D 401/14; C07D 403/04; C07D 417/04; C07D 417/10; C07D 417/14; C07D 498/04; H01L 51/0067; H01L 51/0069; H01L 51/0072; H01L 51/0073; H01L 51/5016; H01L 51/5056; H01L 51/5072
See application file for complete search history.

(56) References Cited

U.S. PATENT DOCUMENTS

| 10,297,758 | B2 | 5/2019 | Lee et al. |
| 2010/0032658 | A1 | 2/2010 | Lee et al. |
| 2017/0077416 | A1 | 3/2017 | Kim et al. |
| 2018/0069182 | A1* | 3/2018 | Hatakeyama ............. C07F 9/90 |

FOREIGN PATENT DOCUMENTS

| CN | 103664894 A | 3/2014 |
| CN | 103614133 B | 11/2014 |
| CN | 103614134 B | 11/2014 |
| CN | 103589420 B | 4/2015 |
| CN | 103589421 B | 5/2015 |
| CN | 103183638 B | 9/2015 |
| KR | 20120081539 A | 7/2012 |
| KR | 20140096002 A | 8/2014 |
| KR | 20150086071 A | 7/2015 |
| WO | WO-2010104047 A1 | 9/2010 |
| WO | WO-2016003202 A2 | 1/2016 |
| WO | WO-2016006791 A1 | 1/2016 |

OTHER PUBLICATIONS

Gao et al., Angew. Chem. Int. Ed. 2010, 49, 6764-6767.*
Ito et al., Angew. Chem. Int. Ed. 2015, 54, 7256-7260.*
Tran et al., J. Phys. Chem. A 2004, 108, 9155-9160.*
Eshimbetov et al., Spectrochimica Acta Part A 67 (2007), 1139-1143.*
Casanovas et al., JACS 1996, 118, 8071-8076.*
Zagranyarski et al., Org. Chem. Front., 2016, 3, 1520-1523.*
International Search Report for PCT/EP2018/052057 dated Mar. 21, 2018.
Written Opinion of the International Searching Authority for PCT/EP2018/052057 dated Mar. 21, 2018.
Zagranyarski, Y., et al., Supplementary Information Facile Synthesis of Annulated Heterocyclic Benzo[kl]acridine Derivatives via One-pot N—H/C—H Coupling—Electronic Supplementary Material (ESI) for Organic Chemistry Frontiers, Journal of Partner Organisations 2016, 2016, XP055458771, pp. S1-S16.

* cited by examiner

*Primary Examiner* — Vu A Nguyen
(74) *Attorney, Agent, or Firm* — Faegre Drinker Biddle & Reath LLP

(57) ABSTRACT

The present invention relates to compounds, which are suitable for use in electronic devices, and to electronic devices, in particular organic electroluminescent devices, containing said compounds.

16 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2018/052057, filed Jan. 29, 2018, which claims benefit of European Application No. 17153706.1, filed Jan. 30, 2017, both of which are incorporated herein by reference in their entirety.

The present invention relates to materials for use in electronic devices, especially in organic electroluminescent devices, and to electronic devices, especially organic electroluminescent devices comprising these materials.

Emitting materials used in organic electroluminescent devices (OLEDs) are frequently organometallic complexes which exhibit phosphorescence rather than fluorescence. For quantum-mechanical reasons, up to four times the energy efficiency and power efficiency is possible using organometallic compounds as phosphorescent emitters. In general terms, there is still a need for improvement in OLEDs, especially also in OLEDs which exhibit triplet emission (phosphorescence), for example with regard to efficiency, operating voltage and lifetime. The properties of phosphorescent OLEDs are not just determined by the triplet emitters used. More particularly, the other materials used, such as matrix materials, are also of particular significance here. Improvements to these materials and the charge transport properties thereof can thus also lead to distinct improvements in the OLED properties.

It is an object of the present invention to provide compounds suitable for use in an OLED, especially as matrix material for phosphorescent emitters. A further problem addressed by the present invention is that of providing further organic semiconductors for organic electroluminescent devices, in order thus to enable the person skilled in the art to have a greater possible choice of materials for the production of OLEDs.

It has been found that, surprisingly, particular compounds described in detail below solve this problem and are of good suitability for use in OLEDs and lead to improvements in the organic electroluminescent device, especially in relation to lifetime, efficiency and operating voltage. The present invention therefore provides these compounds and electronic devices, especially organic electroluminescent devices, comprising such compounds.

WO 2010/104047 discloses N-arylazabenzoanthracene derivatives that have a single bond between the nitrogen-bonded aryl group and the azabenzoanthracene base skeleton. There is no disclosure of compounds according to the present invention.

The present invention provides a compound of formula (1)

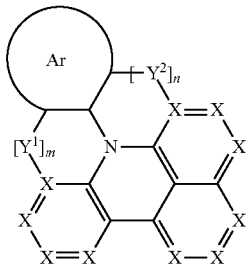

Formula (1)

where the symbols and indices used are as follows:
X is the same or different at each instance and is CR or N, where X=C when a $Y^1$ or $Y^2$ group is bonded to this X;
Ar together with the carbon atoms explicitly shown is an aryl or heteroaryl group which has 5 to 14 aromatic ring atoms and may be substituted by one or more R radicals;
$Y^1$ is $C(R')_2$, NR', O, S, C=O, $Si(R')_2$, BR', PR', P(=O)R, SO or $SO_2$;
$Y^2$ is a single bond, $C(R')_2$, C(=C(R'')_2), NR', O, S, C=O, $Si(R')_2$, BR', PR', P(=O)R', SO or $SO_2$;
R is the same or different at each instance and is H, D, F, Cl, Br, I, $N(R^1)_2$, $N(Ar')_2$, CN, $NO_2$, $OR^1$, $SR^1$, $COOR^1$, $C(=O)N(R^1)_2$, $Si(R^1)_3$, $B(OR^1)_2$, $C(=O)R^1$, P(=O)$(R^1)_2$, $S(=O)_2R^1$, $OSO_2R^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals and where one or more nonadjacent $CH_2$ groups may be replaced by $Si(R^1)_2$, C=O, $NR^1$, O, S or $CONR^1$, or an aromatic or heteroaromatic ring system which has 5 to 60 aromatic ring atoms, preferably 5 to 40 aromatic ring atoms, and may be substituted in each case by one or more $R^1$ radicals; at the same time, two R radicals together may also form an aliphatic or heteroaliphatic ring system;
R' is the same or different at each instance and is a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals and where one or more nonadjacent $CH_2$ groups may be replaced by $Si(R^1)_2$, C=O, $NR^1$, O, S or $CONR^1$, or an aromatic or heteroaromatic ring system which has 5 to 60 aromatic ring atoms, preferably 5 to 40 aromatic ring atoms and may be substituted in each case by one or more $R^1$ radicals; at the same time, two R' radicals together may also form an aromatic, heteroaromatic, aliphatic or heteroaliphatic ring system;
R'' is the same or different at each instance and is R, or one R'' is R and the other R'' is $CR^1=CR^1$ or $CR^1=N$ and, together with Ar, forms an aromatic or heteroaromatic ring system;
Ar' is the same or different at each instance and is an aromatic or heteroaromatic ring system which has 5 to 40 aromatic ring atoms and may be substituted by one or more $R^1$ radicals;
$R^1$ is the same or different at each instance and is H, D, F, Cl, Br, I, $N(R^2)_2$, CN, $NO_2$, $OR^2$, $SR^2$, $Si(R^2)_3$, $B(OR^2)_2$, $C(=O)R^2$, P(=O)$(R^2)_2$, $S(=O)R^2$, $S(=O)_2R^2$, $OSO_2R^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^2$ radicals, where one or more nonadjacent $CH_2$ groups may be replaced by $Si(R^2)_2$, C=O, $NR^2$, O, S or $CONR^2$, or an aromatic or heteroaromatic ring system which has 5 to 40 aromatic ring atoms and may be substituted in each case by one or more $R^2$ radicals; at the same time, two or more $R^1$ radicals together may form a ring system;
$R^2$ is the same or different at each instance and is H, D, F or an aliphatic, aromatic or heteroaromatic organic radical, especially a hydrocarbyl radical, having 1 to 20 carbon atoms, in which one or more hydrogen atoms may also be replaced by F;
m, n is independently 0 or 1, with the proviso that m n=1 or 2; m=0 means that the $Y^1$ is absent and an R radical is bonded to the carbon atom in Ar to which $Y^1$ would be bonded; in addition, n=0 means that the $Y^2$ group is absent and an R radical is bonded to the carbon atom in Ar to which $Y^2$ would be bonded;

where the following compounds are excluded from the invention:

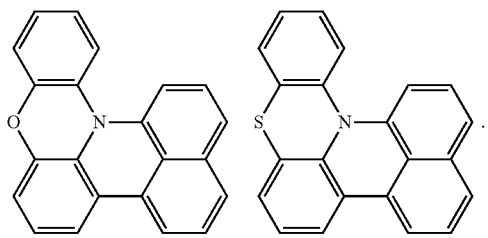

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatic systems joined to one another by a single bond, for example biphenyl, by contrast, are not referred to as an aryl or heteroaryl group but as an aromatic ring system.

An aromatic ring system in the context of this invention contains 6 to 60 carbon atoms in the ring system. A heteroaromatic ring system in the context of this invention contains 2 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit, for example a carbon, nitrogen or oxygen atom. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group. Preferably, the aromatic ring system is selected from fluorene, 9,9'-spirobifluorene, 9,9-diarylamine or groups in which two or more aryl and/or heteroaryl groups are joined to one another by single bonds.

In the context of the present invention, an aliphatic hydrocarbyl radical or an alkyl group or an alkenyl or alkynyl group which may contain 1 to 40 carbon atoms and in which individual hydrogen atoms or $CH_2$ groups may also be substituted by the abovementioned groups is preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cycloheptenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more nonadjacent $CH_2$ groups may be replaced by the abovementioned groups; in addition, it is also possible for one or more hydrogen atoms to be replaced by D, F, Cl, Br, I, CN or $NO_2$, preferably F, Cl or CN, further preferably F or CN, especially preferably CN.

An aromatic or heteroaromatic ring system which has 5-60 aromatic ring atoms and may also be substituted in each case by the abovementioned radicals and which may be joined to the aromatic or heteroaromatic system via any desired positions is especially understood to mean groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or groups derived from combinations of these systems.

When two R or R' or $R^1$ radicals together form a ring system, it may be mono- or polycyclic. In this case, the radicals which together form a ring system are preferably adjacent, meaning that these radicals are bonded to the same carbon atom or to carbon atoms directly bonded to one another. When R" is $CR^1$=$CR^1$ or $CR^1$=N and forms an aromatic or heteroaromatic ring system with Ar, the cycle thus formed results in an aryl or heteroaryl group fused onto Ar, as set out in more detail further down.

The wording that two or more radicals together may form a ring, in the context of the present description, shall be understood to mean, inter alia, that the two radicals are joined to one another by a chemical bond with formal elimination of two hydrogen atoms. This is illustrated by the following scheme:

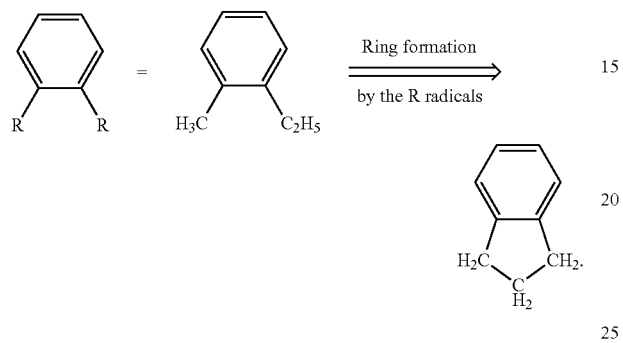

In addition, however, the abovementioned wording shall also be understood to mean that, if one of the two radicals is hydrogen, the second radical binds to the position to which the hydrogen atom was bonded, forming a ring. This shall be illustrated by the following scheme:

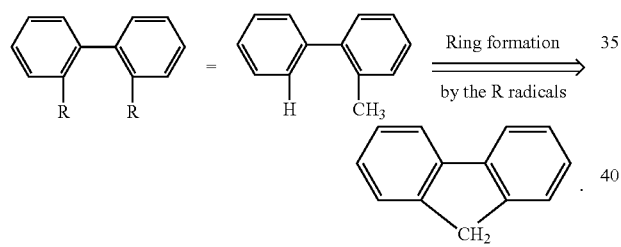

In a preferred embodiment of the invention, m+n=1.

In a preferred embodiment of the invention, m=1 and n=0, and $Y^1$ is NR', O or S, and more preferably NR' where R' represents an aromatic or heteroaromatic ring system which has 5 to 40 aromatic ring atoms and may be substituted by one or more $R^1$ radicals, O or S.

In a further preferred embodiment of the invention, n=1 and m=0, and $Y^2$ is a single bond, NR', O, S or C(=C(R")$_2$) where one R" group is R and the other R" group is $CR^1=CR^1$ and forms a fused aryl group with Ar, and is more preferably a single bond, NR' where R' represents an aromatic or heteroaromatic ring system which has 5 to 40 aromatic ring atoms and may be substituted by one or more $R^1$ radicals, O or S.

More preferably, n=1 and m=0.

Preferably, when m=1, the compound is thus of one of the following formulae (2a), (2b) and (2c) and, when n=1, it is of one of the following formulae (2d), (2e), (2f), (2g) and (2h):

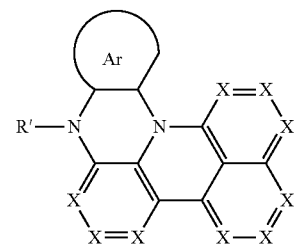

Formula (2a)

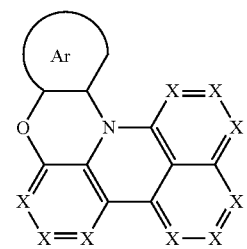

Formula (2b)

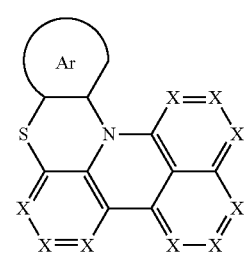

Formula (2c)

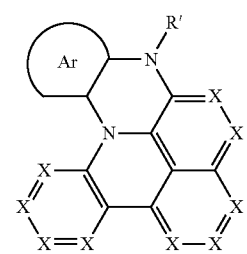

Formula (2d)

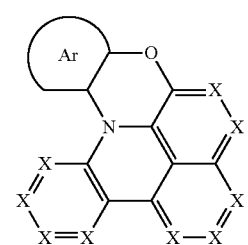

Formula (2e)

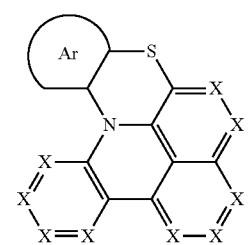

Formula (2f)

Formula (2g)

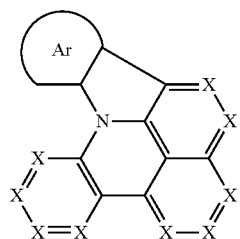

Formula (2h)

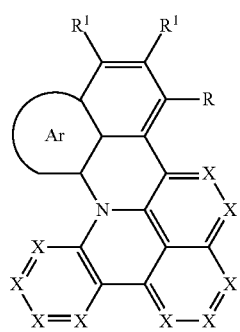

where the symbols used have the definitions given above. In this case, R' in the formulae (2a) and (2d) is preferably represents an aromatic or heteroaromatic ring system which has 5 to 40 aromatic ring atoms and may also be substituted by one or more $R^1$ radicals.

In a further preferred embodiment, Ar in formula (1) and (2a) to (2h) is a group of one of the following formulae (Ar-a), (Ar-b) and (Ar-c):

(Ar-a)

(Ar-b)

(Ar-c)

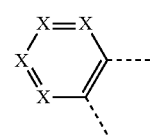

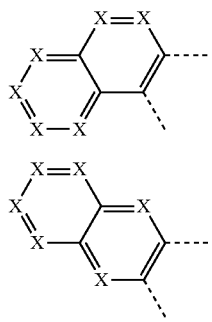

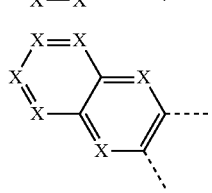

where one of the dotted bonds represents the bond to the nitrogen atom, the other of the dotted bonds represents the bond to $Y^1$ or $Y^2$ and X has the definitions given above. At the same time, preferably not more than two symbols X per Ar group are N, and the remaining symbols X are the same or different at each instance and are CR. Preferably, not more than one symbol X is N, and the remaining symbols X are the same or different at each instance and are CR, and, most preferably, all symbols X are the same or different at each instance and are CR.

Preferably, Ar is a group of the formula (Ar-a), especially a group of the formula (Ar-a) in which all symbols X are CR. Preferably, the compounds of the formula (1) are therefore selected from the compounds of the following formula (3):

Formula (3)

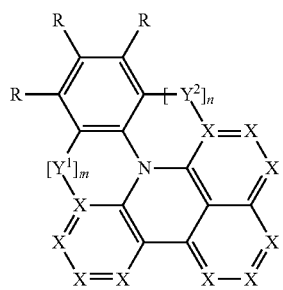

where the symbols and indices used have the definitions given above. In this case, one R radical is still bonded to the carbon atom on the phenyl ring that constitutes the Ar group when no $Y^1$ or $Y^2$ group is bonded in this position.

Correspondingly, the compounds of the formulae (2a) to (2h) are preferably selected from the structures of the following formulae (4a) to (4h):

Formula (4a)

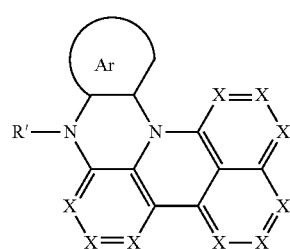

Formula (4b)

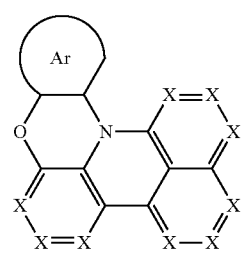

Formula (4c)

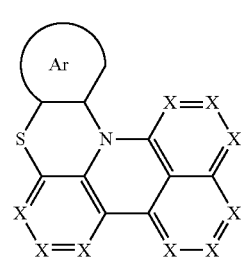

-continued

Formula (4d)
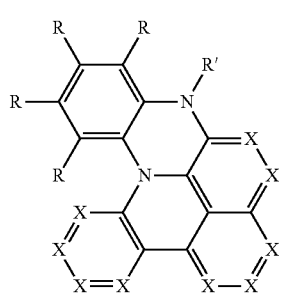

Formula (4e)
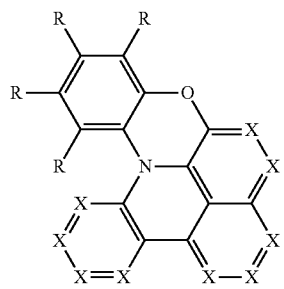

Formula (4f)
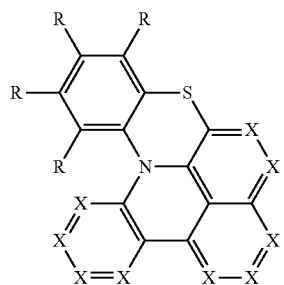

Formula (4g)
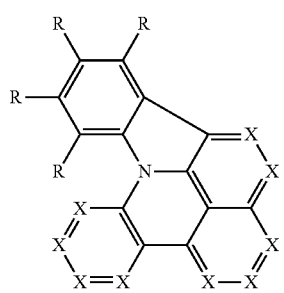

Formula (4h)
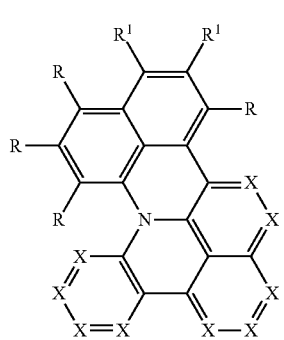

where the symbols used have the definitions given above. In this case, R' in the formulae (4a) and (4d) is preferably represents an aromatic or heteroaromatic ring system which has 5 to 40 aromatic ring atoms and may also be substituted by one or more $R^1$ radicals.

In a further preferred embodiment, compounds of the formula (1) or of the abovementioned preferred embodiments contain a maximum of two nitrogen atoms per ring in the base skeleton, meaning that a maximum of two symbols X per ring are N. Preferably, the compounds contain a maximum of one nitrogen atom per ring in the base skeleton, meaning that a maximum of one symbol X per ring is N. More preferably, zero, one or two symbols X in the base skeleton, and especially zero or one symbol X in the base skeleton, is/are N. Most preferably, all symbols X in the base skeleton are CR. The term "base skeleton" refers in formula (1) to the part of the structure that contains the symbols X, without the Ar group. This is analogously applicable to the preferred structures detailed above.

Preferred compounds of the formula (1), when m=1, are the compounds of the following formulae (5a) to (5k) and, when n=1, the compounds of the following formulae (5l) to (5u):

Formula (5a)
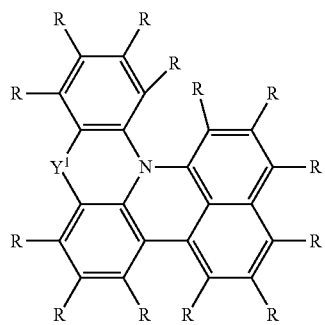

Formula (5b)
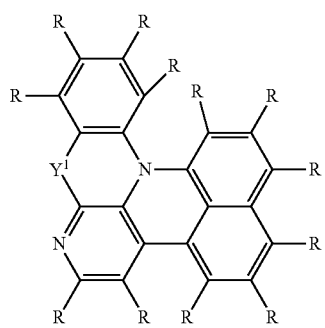

Formula (5c)
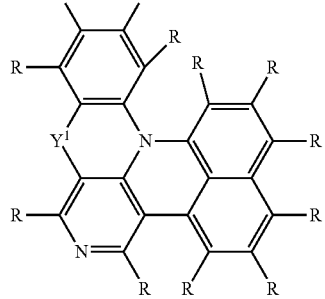

-continued
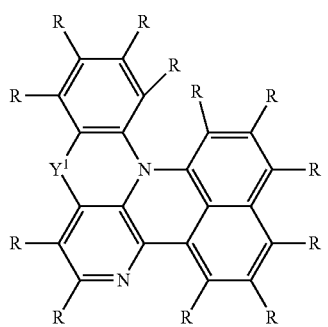
Formula (5d)
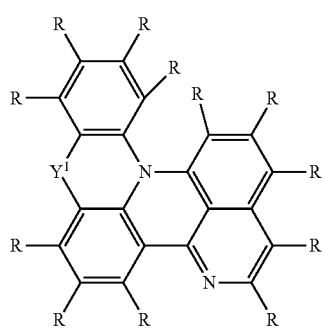
Formula (5e)
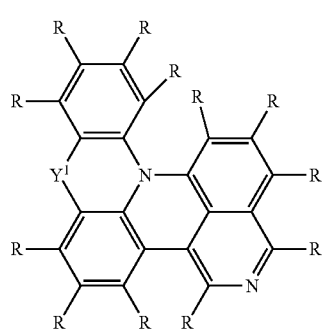
Formula (5f)
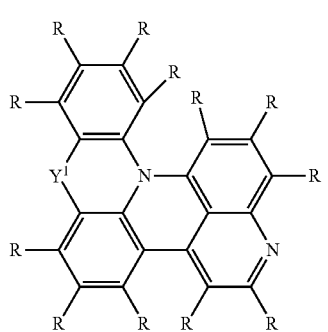
Formula (5g)
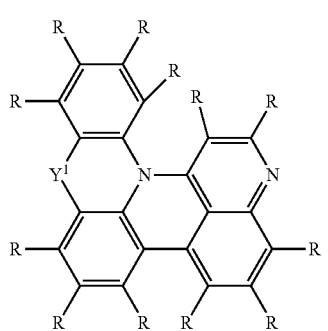
Formula (5h)
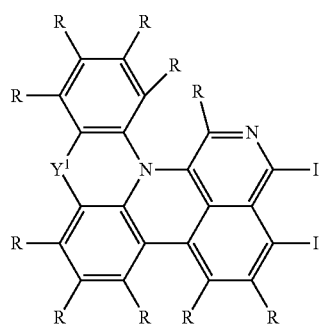
Formula (5i)
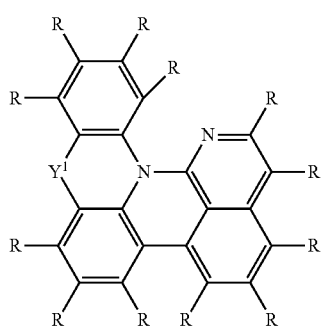
Formula (5j)
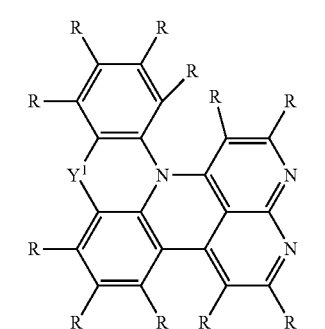
Formula (5k)
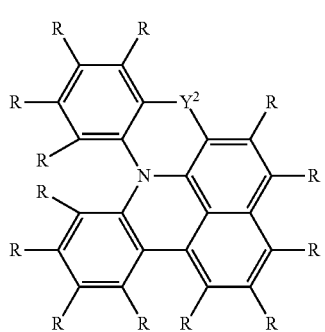
Formula (5l)
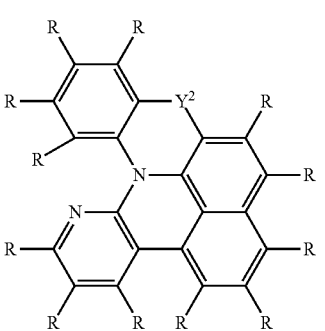
Formula (5m)

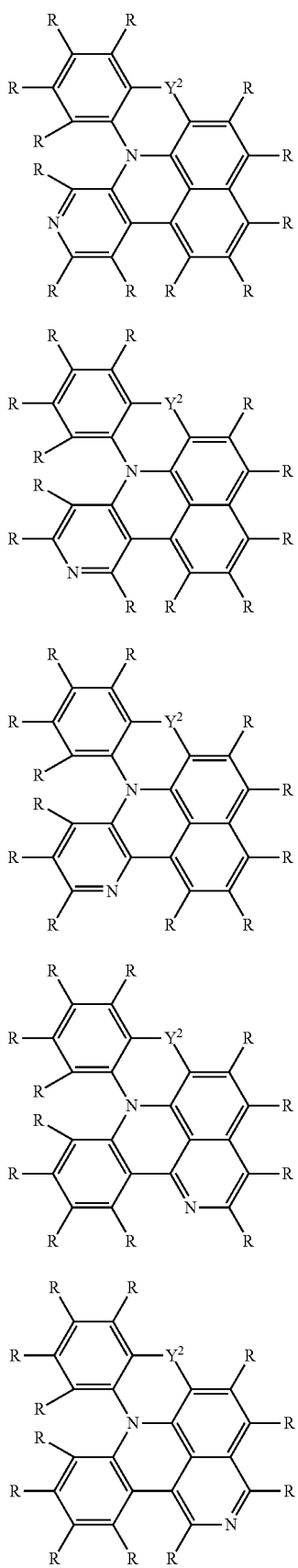

Formula (5n)

Formula (5o)

Formula (5p)

Formula (5q)

Formula (5r)

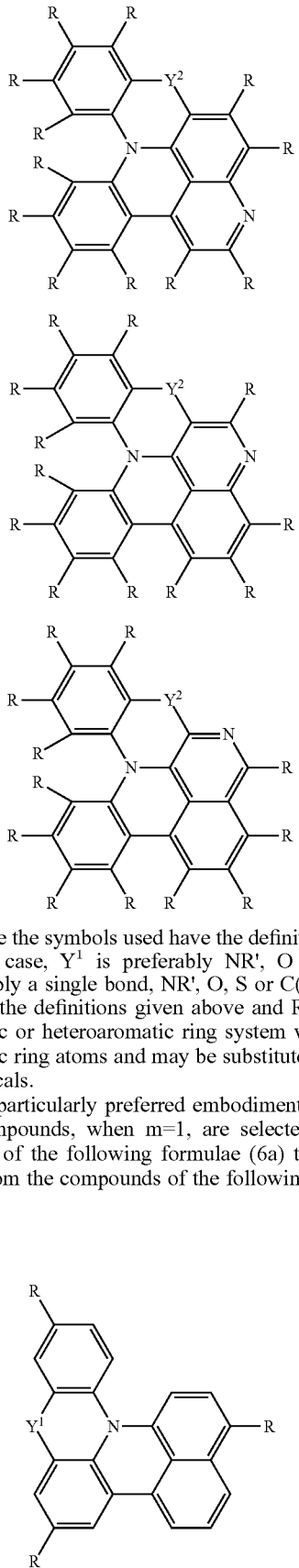

Formula (5s)

Formula (5t)

Formula (5u)

where the symbols used have the definitions given above. In this case, $Y^1$ is preferably NR', O or S, and $Y^2$ is preferably a single bond, NR', O, S or C(=C(R'')$_2$), where R'' has the definitions given above and R' is preferably an aromatic or heteroaromatic ring system which has 5 to 40 aromatic ring atoms and may be substituted by one or more $R^1$ radicals.

In a particularly preferred embodiment of the invention, the compounds, when m=1, are selected from the compounds of the following formulae (6a) to (6k) and, when n=1, from the compounds of the following formulae (6l) to (6u):

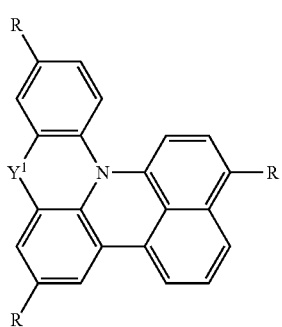

Formula (6a)

Formula (6b)
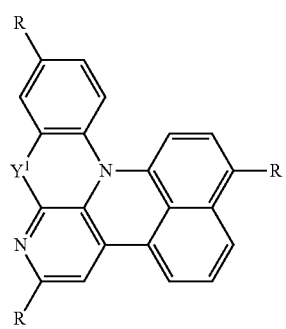
Formula (6c)
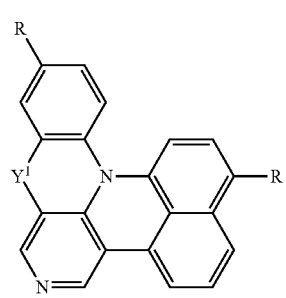
Formula (6d)
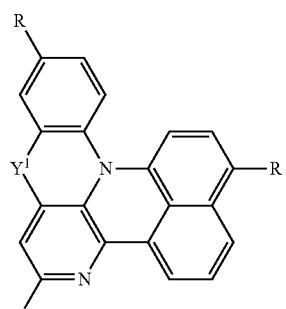
Formula (6e)
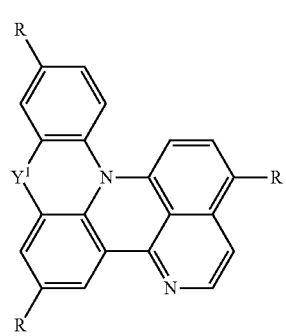
Formula (6f)
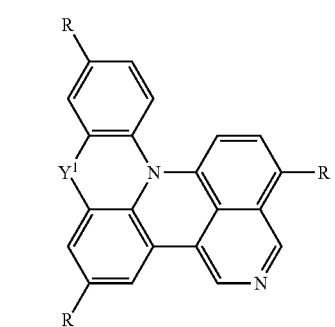
Formula (6g)
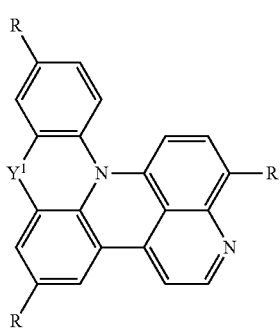
Formula (6h)
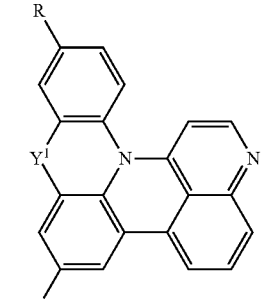
Formula (6i)
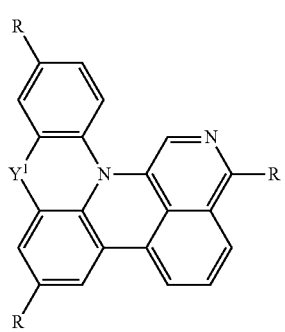
Formula (6j)
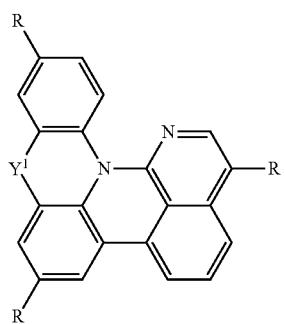
Formula (6k)
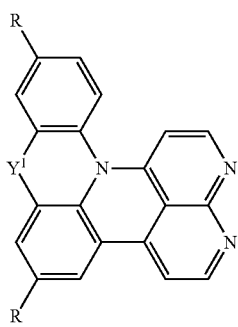

Formula (6l)
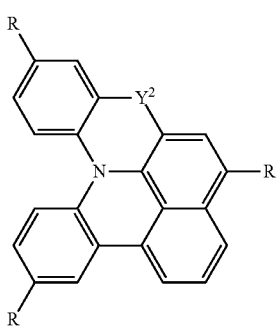
Formula (6m)
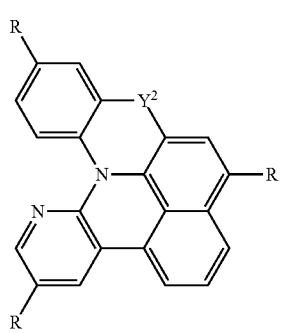
Formula (6n)
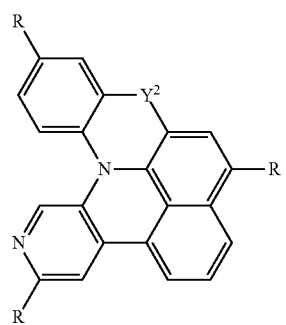
Formula (6o)
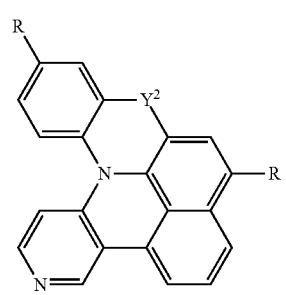
Formula (6p)
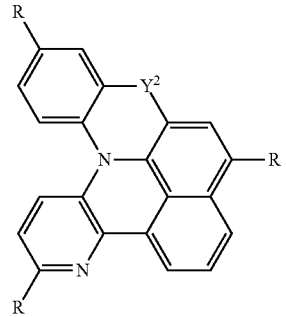
Formula (6q)
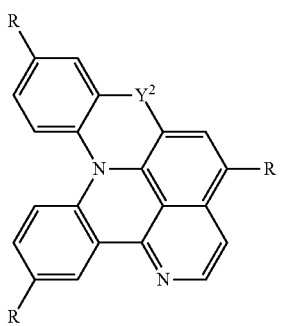
Formula (6r)
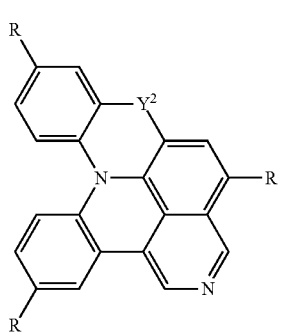
Formula (6s)
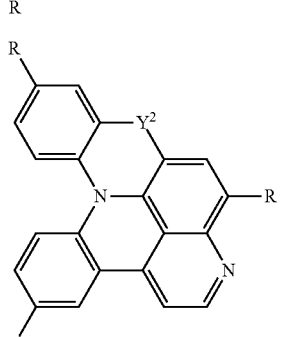
Formula (6t)
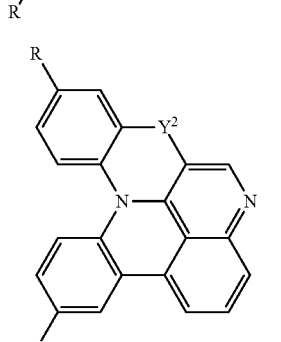
Formula (6u)
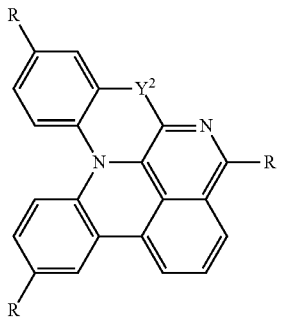
where the symbols used have the definitions given above.
In this case, $Y^1$ is preferably NR', O or S, and $Y^2$ is preferably a single bond, NR', O, S or C(=C(R")$_2$), where R" has the definitions given above and R' is preferably an aromatic or heteroaromatic ring system which has 5 to 40 aromatic ring atoms and may be substituted by one or more R$^1$ radicals.

When m=1, particular preference is given to the compound of the formula (5a) or (5k) or (6a) or (6k), and, when n=1, to the compound of the formula (5l) or (6l).

Very particular preference is given to the compounds of the following formulae (7a) to (7h):

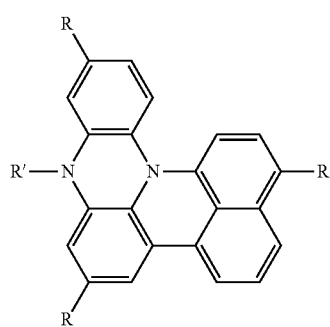
Formula (7a)

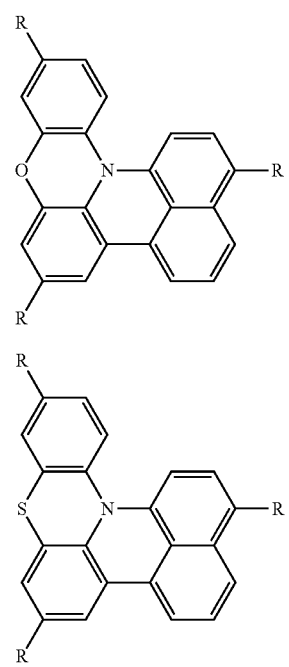
Formula (7b)

Formula (7c)

Formula (7d)

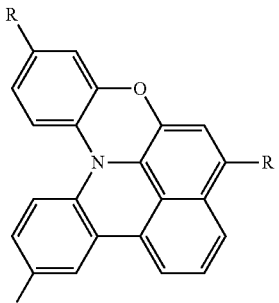
Formula (7e)

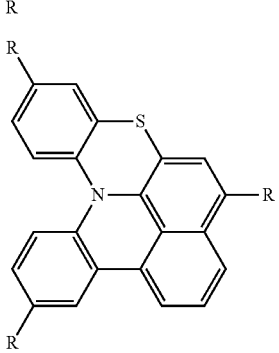
Formula (7f)

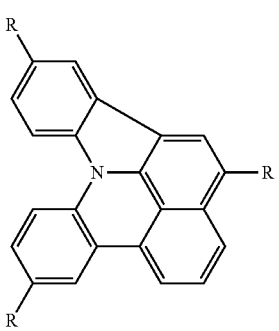
Formula (7g)

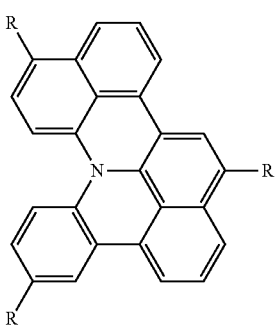
Formula (7h)

where the symbols used have the definitions given above.

There follows a description of preferred substituents R and R' in the compounds of the invention.

In a preferred embodiment of the invention, at least one substituent R, more preferably exactly one substituent R, is different than H, and the other substituents R are H. In a further preferred embodiment of the invention, two substituents R are different than H, and the other substituents R are H. In a further preferred embodiment of the invention, three substituents R are different than H. At the same time, preferably, at least one of the substituents R is selected from an aromatic or heteroaromatic ring system. In a further embodiment of the invention, all substituents R are H, and the Y$^1$ or Y$^2$ group is NR' where R' is an aromatic or heteroaromatic ring system having 5 to 60 and preferably having 5 to 40 aromatic ring atoms, which may be substituted by one or more $R^1$ radicals.

In a preferred embodiment of the invention, R is the same or different at each instance and is selected from the group consisting of H, D, F, N(Ar')$_2$, CN, OR$^1$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may each be substituted by one or more $R^1$ radicals, and where one or more nonadjacent CH$_2$ groups may be replaced by O, or an aromatic or heteroaromatic ring system which has 6 to 30 aromatic ring atoms and may be substituted in each case by one or more $R^1$ radicals; at the same time, two R radicals together may also form an aliphatic ring system. More preferably, R is the same or different at each instance and is selected from the group consisting of H, N(Ar')$_2$, a straight-chain alkyl group having 1 to 6 carbon atoms, especially having 1, 2, 3 or 4 carbon atoms, or a branched or cyclic alkyl group having 3 to 6 carbon atoms, where the alkyl group in each case may be substituted by one or more $R^1$ radicals, but is preferably unsubstituted, or an aromatic or heteroaromatic ring system which has 6 to 24 aromatic ring atoms and may be substituted in each case by one or more preferably nonaromatic $R^1$ radicals. Most preferably, R is the same or different at each instance and is selected from the group consisting of H, N(Ar')$_2$ or an aromatic or heteroaromatic ring system which has 6 to 24 aromatic ring atoms and may be substituted in each case by one or more preferably nonaromatic $R^1$ radicals.

When $Y^1$ or $Y^2$ is NR', BR', PR' or P(=O)R', R" is preferably an aromatic or heteroaromatic ring system which has 6 to 40, preferably 6 to 30, aromatic ring atoms and may be substituted by one or more $R^1$ radicals, and is more preferably an aromatic or heteroaromatic ring system which has 6 to 24 aromatic ring atoms and may be substituted by one or more preferably nonaromatic $R^1$ radicals.

When $Y^1$ or $Y^2$ is C(R')$_2$ or Si(R')$_2$, R' is preferably the same or different at each instance and is selected from the group consisting of a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may in each case be substituted by one or more $R^1$ radicals, and where one or more nonadjacent CH$_2$ groups may be replaced by O, or an aromatic or heteroaromatic ring system which has 6 to 30 aromatic ring atoms and may be substituted in each case by one or more $R^1$ radicals; at the same time, two R' radicals together may also form an aliphatic, aromatic or heteroaromatic ring system. More preferably, these substituents R' are the same or different at each instance and are selected from the group consisting of a straight-chain alkyl group having 1 to 6 carbon atoms, especially having 1, 2, 3 or 4 carbon atoms, or a branched or cyclic alkyl group having 3 to 6 carbon atoms, where the alkyl group in each case may be substituted by one or more $R^1$ radicals, but is preferably unsubstituted, or an aromatic or heteroaromatic ring system which has 6 to 24 aromatic ring atoms, preferably 6 to 12 aromatic ring atoms, and may be substituted in each case by one or more preferably nonaromatic $R^1$ radicals. At the same time, two R' radicals together may also form an aliphatic or aromatic ring system. Most preferably, R' is the same or different at each instance and is methyl or phenyl, where two phenyl groups together may also form an aromatic ring system.

In a further embodiment of the invention, when $Y^2$=C (=C(R")$_2$), one of the two R" groups is H and the other of the two R" groups is CR$^1$=CR$^1$ and forms a ring system with Ar, where $R^1$ is preferably H.

In a further preferred embodiment of the invention, $R^1$ is the same or different at each instance and is selected from the group consisting of H, D, F, CN, OR$^2$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may in each case be substituted by one or more $R^2$ radicals, and where one or more nonadjacent CH$_2$ groups may be replaced by O, or an aromatic or heteroaromatic ring system which has 6 to 30 aromatic ring atoms and may be substituted in each case by one or more $R^2$ radicals; at the same time, two or more $R^1$ radicals together may form an aliphatic ring system. In a particularly preferred embodiment of the invention, $R^1$ is the same or different at each instance and is selected from the group consisting of H, a straight-chain alkyl group having 1 to 6 carbon atoms, especially having 1, 2, 3 or 4 carbon atoms, or a branched or cyclic alkyl group having 3 to 6 carbon atoms, where the alkyl group may be substituted by one or more $R^2$ radicals, but is preferably unsubstituted, or an aromatic or heteroaromatic ring system which has 6 to 24 aromatic ring atoms and may be substituted in each case by one or more $R^2$ radicals, but is preferably unsubstituted.

In a further preferred embodiment of the invention, $R^2$ is the same or different at each instance and is H, an alkyl group having 1 to 4 carbon atoms or an aryl group having 6 to 10 carbon atoms, which may be substituted by an alkyl group having 1 to 4 carbon atoms, but is preferably unsubstituted.

In a further preferred embodiment of the invention, the compound of the invention contains at least one substituent R selected from an aromatic or heteroaromatic ring system or N(Ar')$_2$, and/or it contains at least one $Y^1$ or $Y^2$ group which is NR' where R' is selected from an aromatic or heteroaromatic ring system. In this case, when X=CR, the substituent R may be bonded to the base skeleton of the compound or to the Ar group.

There follows a description of preferred aromatic and heteroaromatic ring systems which may be present as substituent R or R' or as Ar' group within the N(Ar')$_2$ substituent in the compound of the invention.

Suitable aromatic or heteroaromatic ring systems R, R' or Ar" are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene, especially 1- or 2-bonded naphthalene, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, isoquinoline, quinazoline, quinoxaline, phenanthrene, triphenylene or a combination of two or three of these groups, each of which may be substituted by one or more $R^1$ radicals.

The R, R' and Ar' groups here are preferably selected from the groups of the following formulae Ar-1 to Ar-75:

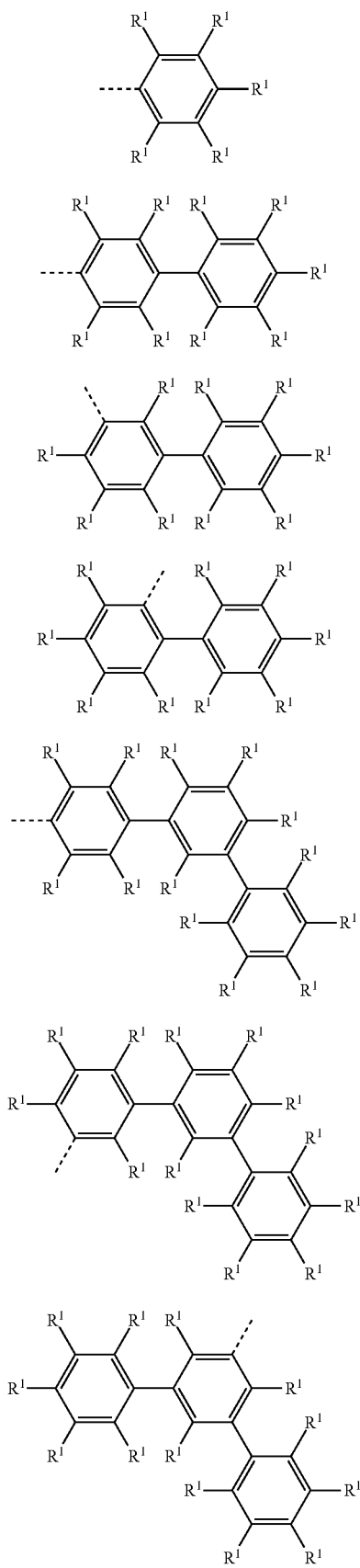
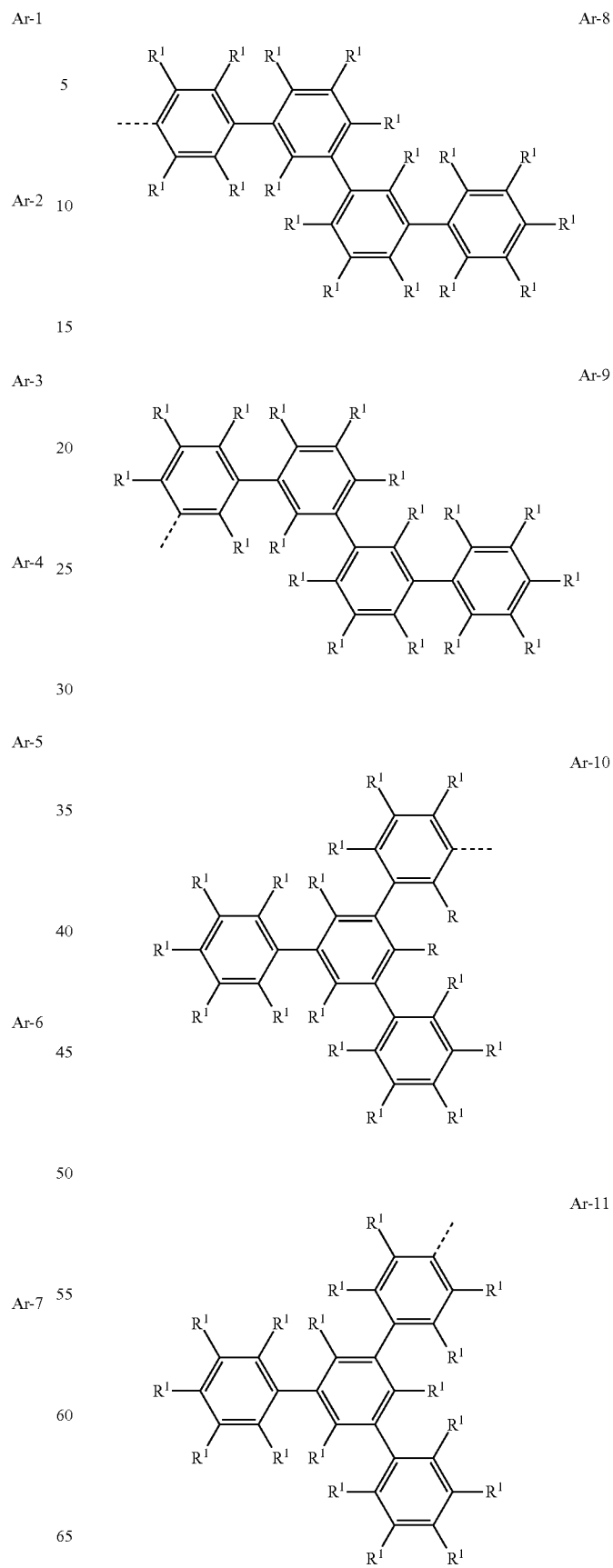

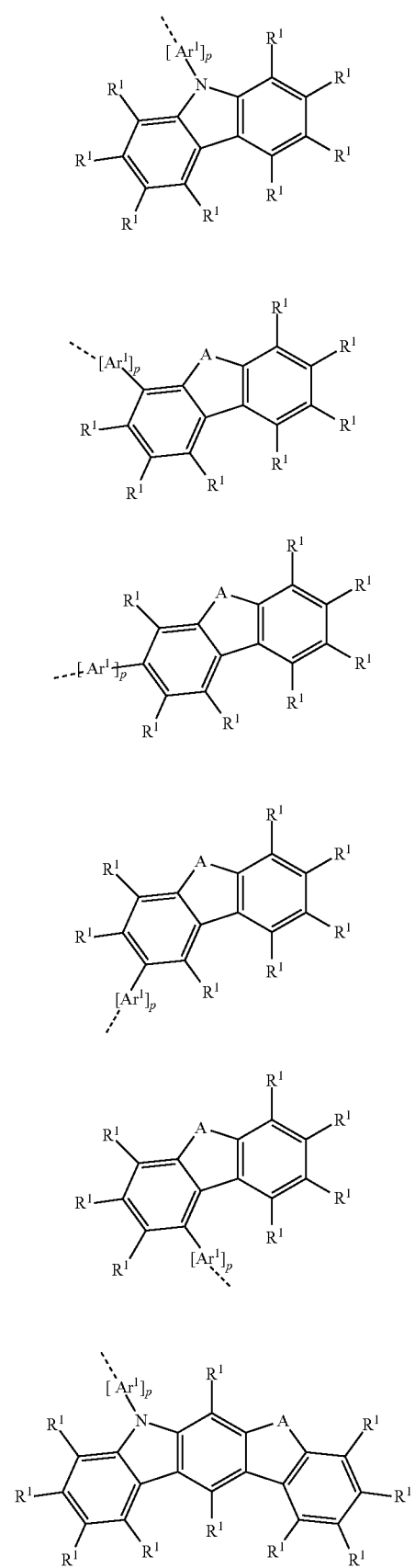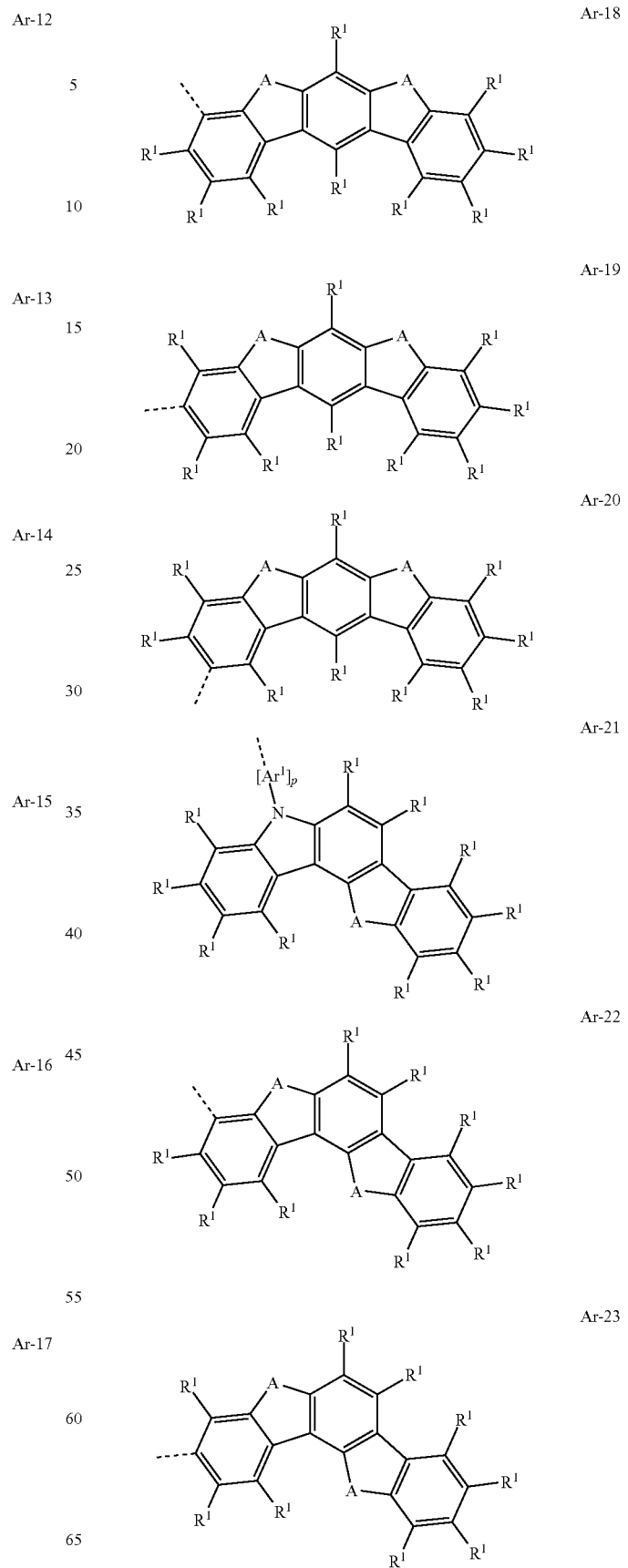

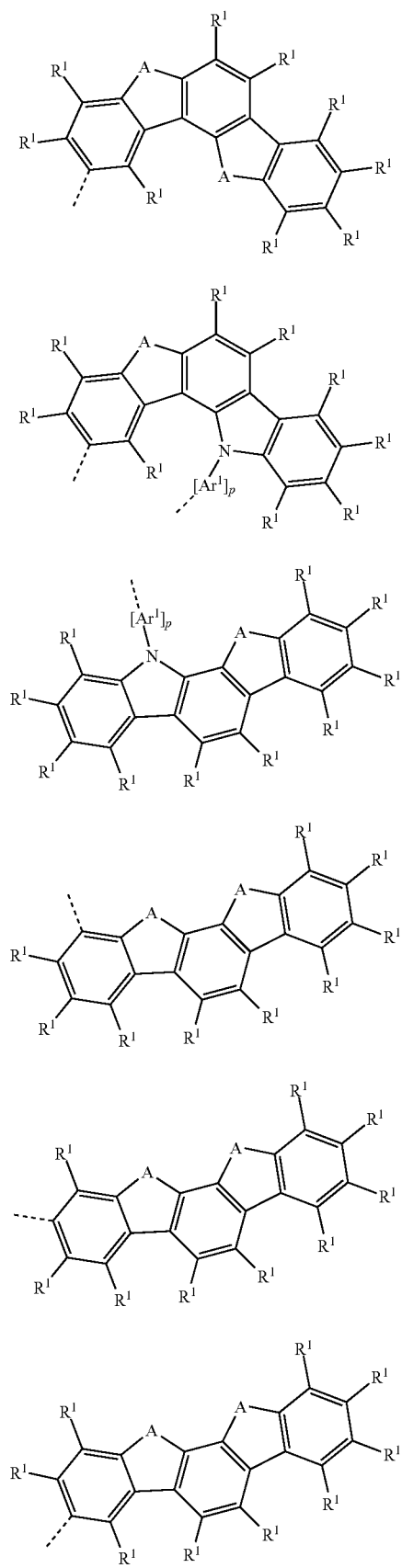
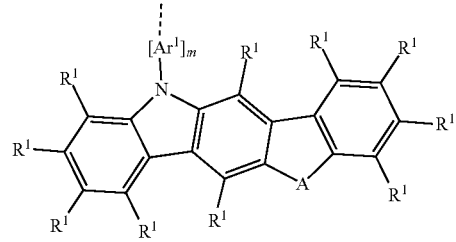
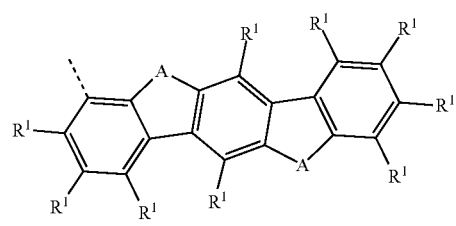
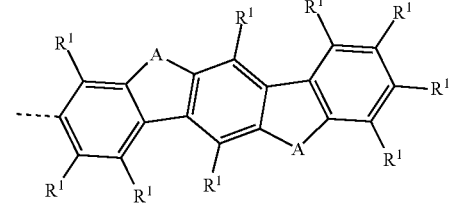
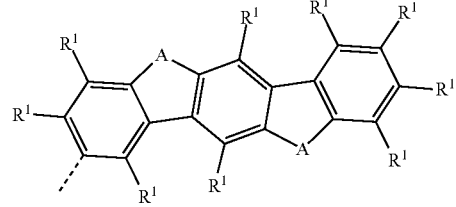
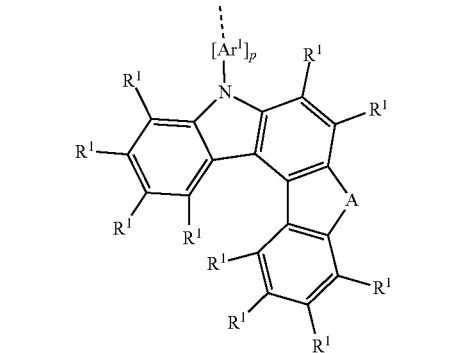
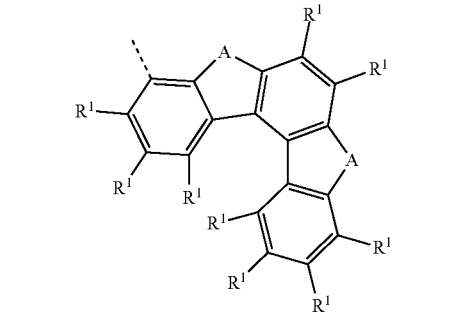

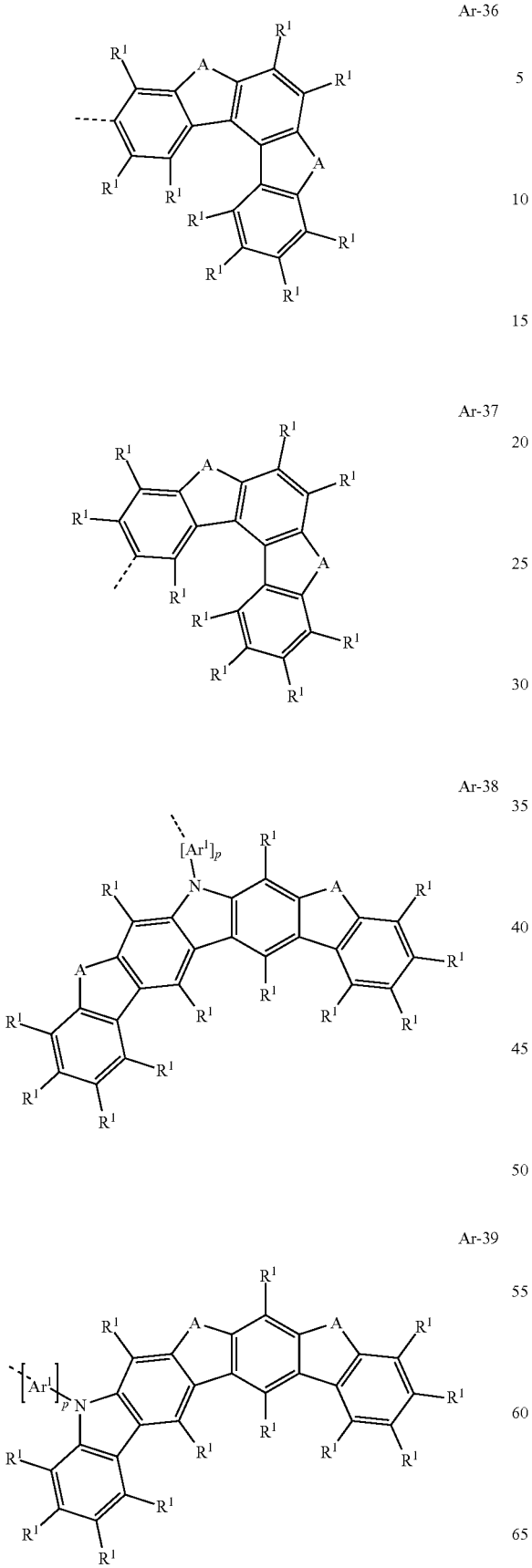
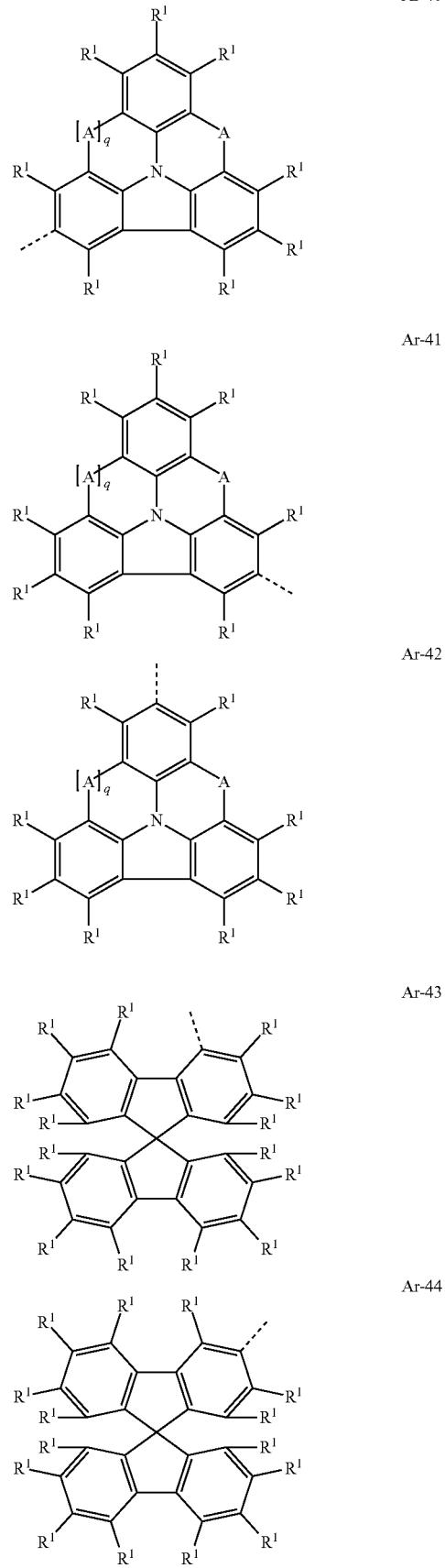

Ar-45
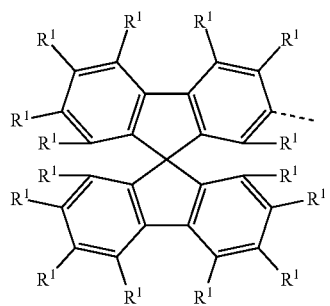
Ar-46
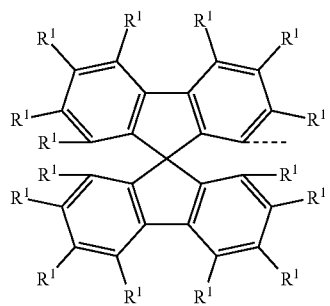
Ar-47
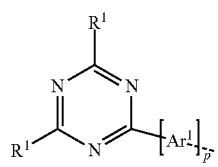
Ar-48
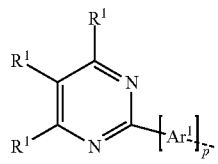
Ar-49
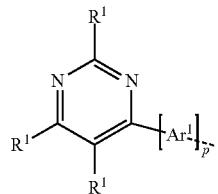
Ar-50
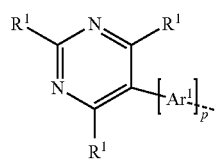
Ar-51
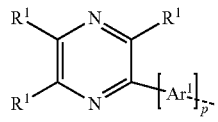
Ar-52
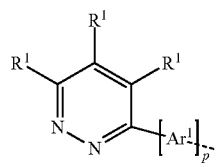
Ar-53
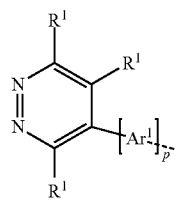
Ar-54
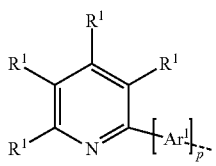
Ar-55
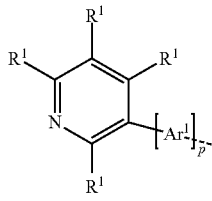
Ar-56
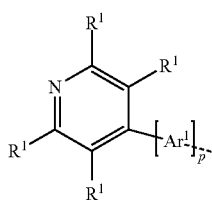
Ar-57
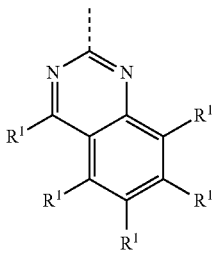
Ar-58
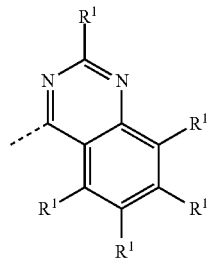
Ar-59
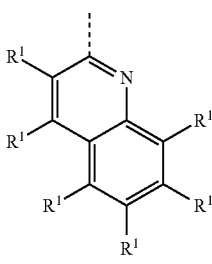

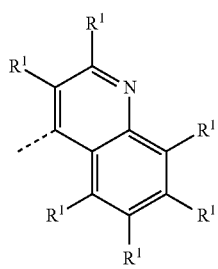
Ar-60
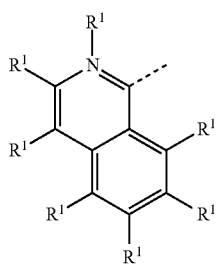
Ar-61
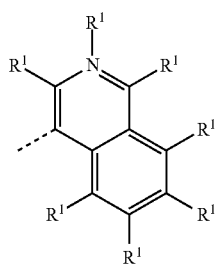
Ar-62
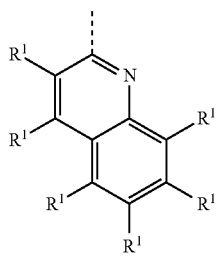
Ar-63
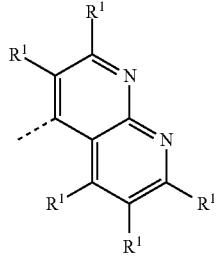
Ar-64
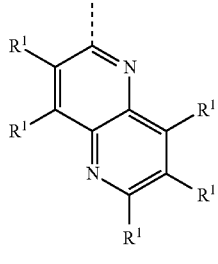
Ar-65
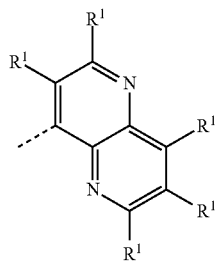
Ar-66
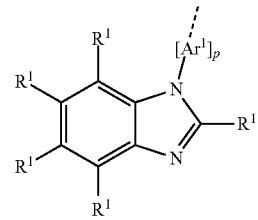
Ar-67
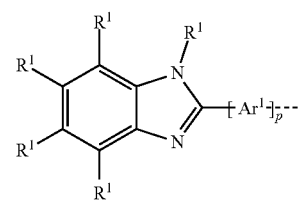
Ar-68
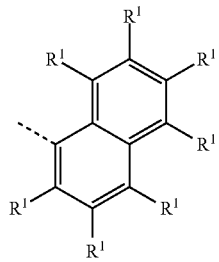
Ar-69
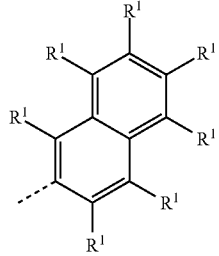
Ar-70
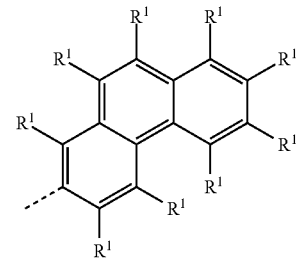
Ar-71

-continued

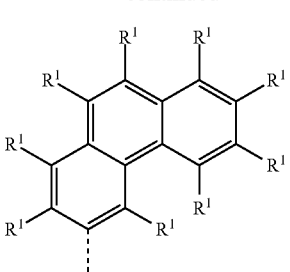

Ar-72

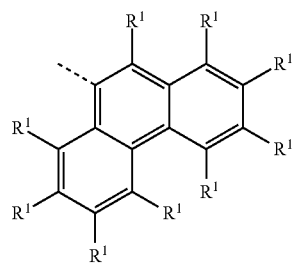

Ar-73

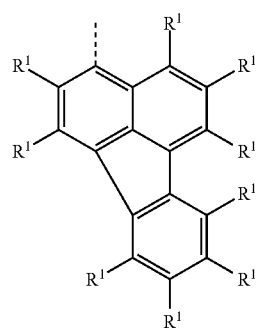

Ar-74

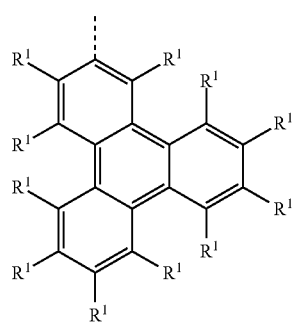

Ar-75 where $R^1$ has the definitions given above, the dotted bond represents the bond to the nitrogen atom in $Y^1$ or $Y^2$ or to a carbon atom of the base skeleton in formula (1) or to Ar or to the nitrogen atom in the $N(Ar')_2$ group and, in addition:

$Ar^1$ is the same or different at each instance and is a bivalent aromatic or heteroaromatic ring system which has 6 to 18 aromatic ring atoms and may be substituted in each case by one or more $R^1$ radicals;

A is the same or different at each instance and is $C(R^1)_2$, $NR^1$, O or S;

p is 0 or 1, where p=0 means that the $Ar^1$ group is absent and that the corresponding aromatic or heteroaromatic group is bonded directly to the nitrogen atom in $Y^1$ or $Y^2$ or to a carbon atom of the base skeleton in formula (1) or in the preferred embodiments, or to the nitrogen atom in the $N(Ar')^2$ group; with the proviso that p=1 for the structures (Ar-12), (Ar-17), (Ar-21), (Ar-25), (Ar-26), (Ar-30), (Ar-34), (Ar-38) and (Ar-39) when these groups are embodiments of R' or Ar';

q is 0 or 1, where q=0 means that no A group is bonded at this position and $R^1$ radicals are bonded to the corresponding carbon atoms instead.

When the abovementioned groups for R, R' or Ar' have two or more A groups, possible options for these include all combinations from the definition of A. Preferred embodiments in that case are those in which one A group is $NR^1$ and the other A group is $C(R^1)_2$ or in which both A groups are $NR^1$ or in which both A groups are O. In a particularly preferred embodiment of the invention, in R or Ar groups having two or more A groups, at least one A group is $C(R^1)_2$ or is $NR^1$.

When A is $NR^1$, the substituent $R^1$ bonded to the nitrogen atom is preferably an aromatic or heteroaromatic ring system which has 5 to 24 aromatic ring atoms and may also be substituted by one or more $R^2$ radicals. In a particularly preferred embodiment, this $R^1$ substituent is the same or different at each instance and is an aromatic or heteroaromatic ring system which has 6 to 24 aromatic ring atoms, especially 6 to 18 aromatic ring atoms, which does not have any fused aryl groups and which does not have any fused heteroaryl groups in which two or more aromatic or heteroaromatic 6-membered ring groups are fused directly to one another, and which may also be substituted in each case by one or more $R^2$ radicals. Preference is given to phenyl, biphenyl, terphenyl and quaterphenyl having bonding patterns as listed above for Ar-1 to Ar-11, where these structures, rather than by $R^1$, may be substituted by one or more $R^2$ radicals, but are preferably unsubstituted. Preference is further given to triazine, pyrimidine and quinazoline as listed above for Ar-47 to Ar-50, Ar-57 and Ar-58, where these structures, rather than by $R^1$, may be substituted by one or more $R^2$ radicals.

When A is $C(R^1)_2$, the substituents $R^1$ bonded to this carbon atom are preferably the same or different at each instance and are a linear alkyl group having 1 to 10 carbon atoms or a branched or cyclic alkyl group having 3 to 10 carbon atoms or an aromatic or heteroaromatic ring system having 5 to 24 aromatic ring atoms, which may also be substituted by one or more $R^2$ radicals. Most preferably, $R^1$ is a methyl group or a phenyl group. In this case, the $R^1$ radicals together may also form a ring system, which leads to a Spiro system.

Further suitable R, R' or Ar groups are groups of the formula $-Ar^4-N(Ar^2)(Ar^3)$ where $Ar^2$, $Ar^3$ and $Ar^4$ are the same or different at each instance and are an aromatic or heteroaromatic ring system which has 5 to 24 aromatic ring atoms and may be substituted in each case by one or more $R^1$ radicals. The total number of aromatic ring atoms in $Ar^2$, $Ar^3$ and $Ar^4$ here is not more than 60 and preferably not more than 40.

In this case, $Ar^4$ and $Ar^2$ may also be bonded to one another and/or $Ar^2$ and $Ar^3$ to one another by a group selected from $C(R^1)_2$, $NR^1$, O and S. Preferably, $Ar^4$ and $Ar^2$ are joined to one another and $Ar^2$ and $Ar^3$ to one another in the respective ortho position to the bond to the nitrogen atom. In a further embodiment of the invention, none of the $Ar^2$, $Ar^3$ and $Ar^4$ groups are bonded to one another.

Preferably, $Ar^4$ is an aromatic or heteroaromatic ring system which has 6 to 24 aromatic ring atoms, preferably 6 to 12 aromatic ring atoms, and may be substituted in each case by one or more $R^1$ radicals. More preferably, $Ar^4$ is selected from the group consisting of ortho-, meta- or para-phenylene or ortho-, meta- or para-biphenyl, each of which may be substituted by one or more $R^1$ radicals, but are preferably unsubstituted. Most preferably, $Ar^4$ is an unsubstituted phenylene group.

Preferably, Ar² and Ar³ are the same or different at each instance and are an aromatic or heteroaromatic ring system which has 6 to 24 aromatic ring atoms and may be substituted in each case by one or more R¹ radicals. Particularly preferred Ar² and Ar³ groups are the same or different at each instance and are selected from the group consisting of benzene, ortho-, meta- or para-biphenyl, ortho-, meta- or para-terphenyl or branched terphenyl, ortho-, meta- or para-quaterphenyl or branched quaterphenyl, 1-, 2-, 3- or 4-fluorenyl, 1-, 2-, 3- or 4-spirobifluorenyl, 1- or 2-naphthyl, indole, benzofuran, benzothiophene, 1-, 2-, 3- or 4-carbazole, 1-, 2-, 3- or 4-dibenzofuran, 1-, 2-, 3- or 4-dibenzothiophene, indenocarbazole, indolocarbazole, 2-, 3- or 4-pyridine, 2-, 4- or 5-pyrimidine, pyrazine, pyridazine, triazine, phenanthrene, triphenylene or combinations of two, three or four of these groups, each of which may be substituted by one or more R¹ radicals. More preferably, Ar² and Ar³ are the same or different at each instance and are an aromatic ring system which has 6 to 24 aromatic ring atoms and may be substituted by one or more R¹ radicals, especially selected from the groups consisting of benzene, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene, especially 1-, 2-, 3- or 4-fluorene, or spirobifluorene, especially 1-, 2-, 3- or 4-spirobifluorene.

At the same time, in compounds of the invention that are processed by vacuum evaporation, the alkyl groups preferably have not more than five carbon atoms, more preferably not more than 4 carbon atoms, most preferably not more than 1 carbon atom. For compounds which are processed from solution, suitable compounds are also those substituted by alkyl groups, especially branched alkyl groups, having up to 10 carbon atoms or those substituted by oligoarylene groups, for example ortho-, meta- or para-terphenyl or quaterphenyl or branched terphenyl or quaterphenyl groups.

When the compounds of the formula (1) or the preferred embodiments are used as matrix material for a phosphorescent emitter or in a layer directly adjoining a phosphorescent layer, it is further preferable when the compound does not contain any fused aryl or heteroaryl groups in which more than two six-membered rings are fused directly to one another. It is especially preferable when the R, R', Ar, R¹ and R² radicals do not contain any fused aryl or heteroaryl groups in which two or more six-membered rings are fused directly to one another. An exception to this is formed by phenanthrene and triphenylene which, because of their high triplet energy, may be preferable in spite of the presence of fused aromatic six-membered rings.

The abovementioned preferred embodiments may be combined with one another as desired within the restrictions defined in claim 1. In a particularly preferred embodiment of the invention, the abovementioned preferences occur simultaneously.

Examples of preferred compounds according to the embodiments detailed above are the compounds detailed in the following table:

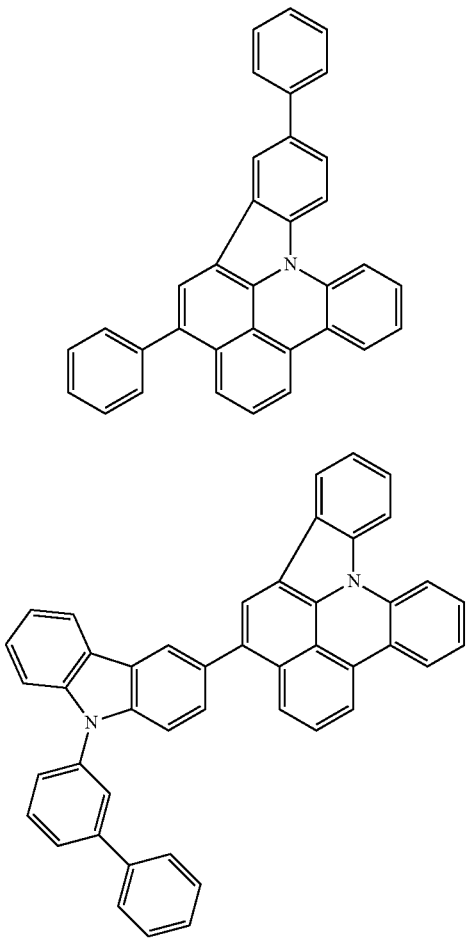

-continued
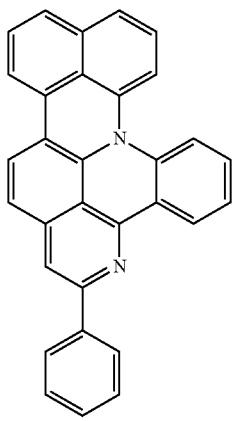 [SMILES: c1ccc(-c2cc3ccc4c5c3c(n2)-c2ccccc2N5c2cccc3cccc-4c23)cc1]
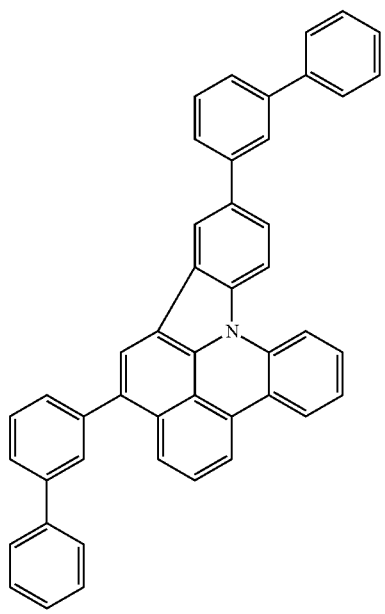 [SMILES: c1ccc(-c2cccc(-c3ccc4c(c3)c3cc(-c5cccc(-c6ccccc6)c5)c5cccc6c7ccccc7n4c3c56)c2)cc1]
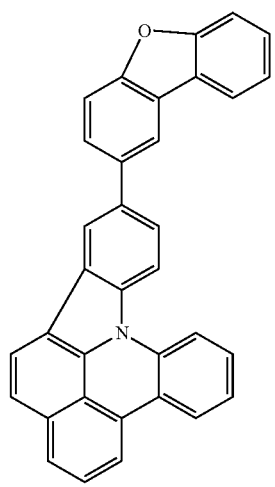 [SMILES: c1ccc2c(c1)oc1ccc(-c3ccc4c(c3)c3ccc5cccc6c7ccccc7n4c3c56)cc12]

-continued
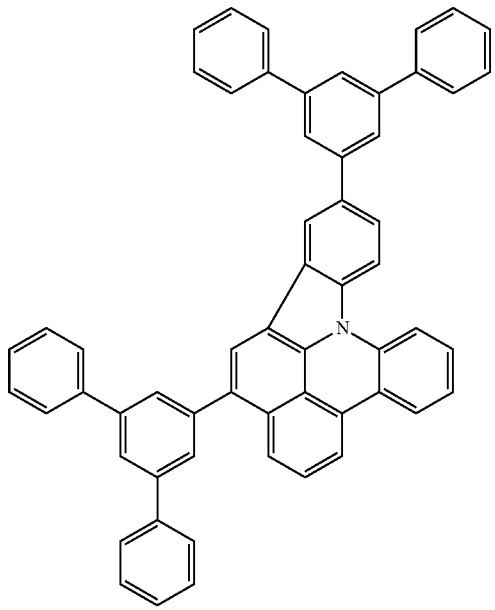 [SMILES: c1ccc(-c2cc(-c3ccccc3)cc(-c3ccc4c(c3)c3cc(-c5cc(-c6ccccc6)cc(-c6ccccc6)c5)c5cccc6c7ccccc7n4c3c56)c2)cc1]
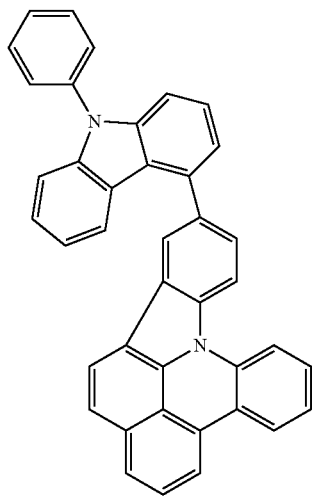 [SMILES: c1ccc(-n2c3ccccc3c3c(-c4ccc5c(c4)c4ccc6cccc7c8ccccc8n5c4c67)cccc32)cc1]
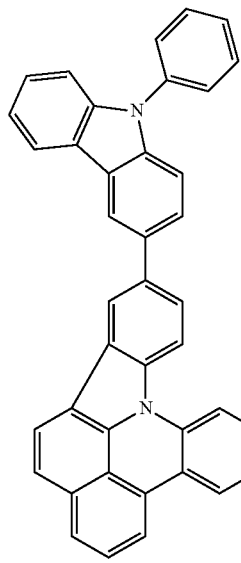

-continued
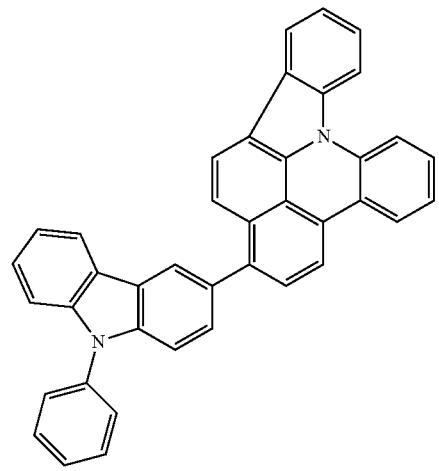 [SMILES: c1ccc(-n2c3ccccc3c3cc(-c4ccc5c6ccccc6n6c7ccccc7c7ccc4c5c76)ccc32)cc1]
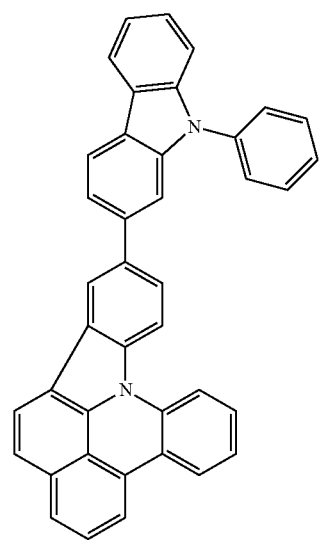 [SMILES: c1ccc(-n2c3ccccc3c3ccc(-c4ccc5c(c4)c4ccc6cccc7c8ccccc8n5c4c67)cc32)cc1]
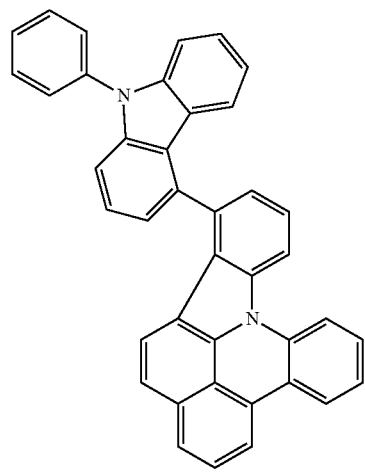 [SMILES: c1ccc(-n2c3ccccc3c3c(-c4cccc5c4c4ccc6cccc7c8ccccc8n5c4c67)cccc32)cc1]

-continued
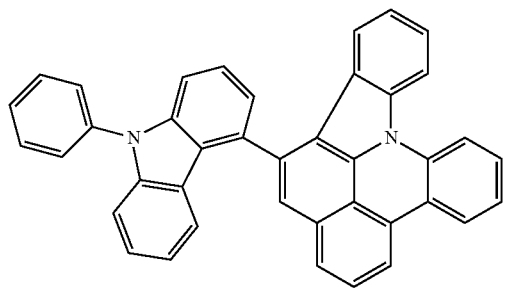 [SMILES: c1ccc(-n2c3ccccc3c3c(-c4cc5cccc6c7ccccc7n7c8ccccc8c4c7c56)cccc32)cc1]
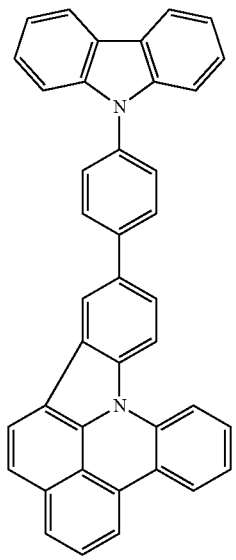 [SMILES: c1cc2ccc3c4cc(-c5ccc(-n6c7ccccc7c7ccccc76)cc5)ccc4n4c5ccccc5c(c1)c2c34]
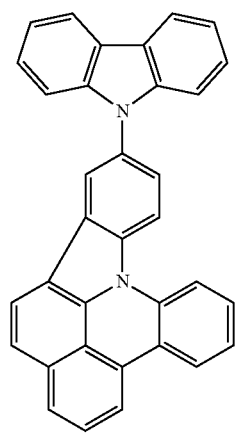 [SMILES: c1cc2ccc3c4cc(-n5c6ccccc6c6ccccc65)ccc4n4c5ccccc5c(c1)c2c34]

-continued
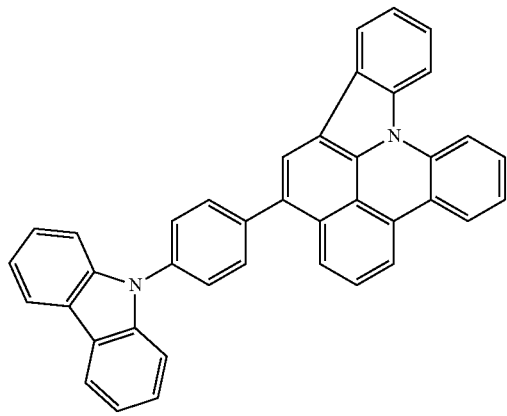 [SMILES: c1cc2c(-c3ccc(-n4c5ccccc5c5ccccc54)cc3)cc3c4ccccc4n4c5ccccc5c(c1)c2c34]
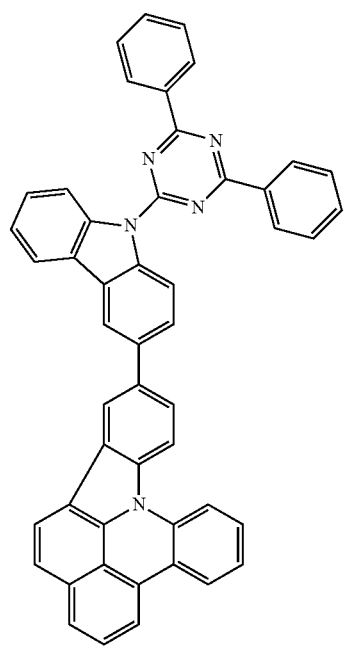 [SMILES: c1ccc(-c2nc(-c3ccccc3)nc(-n3c4ccccc4c4cc(-c5ccc6c(c5)c5ccc7cccc8c9ccccc9n6c5c78)ccc43)n2)cc1]
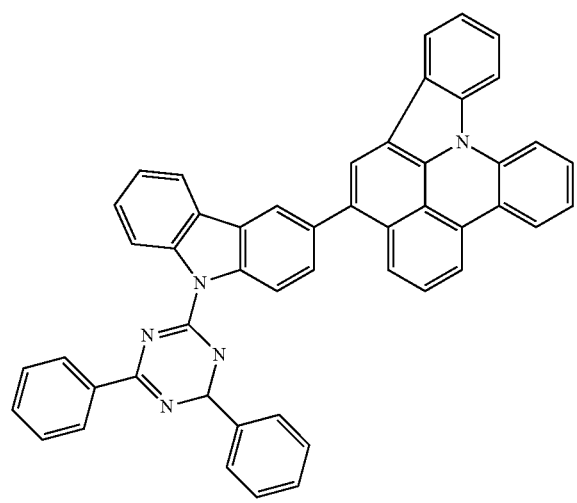 [SMILES: c1ccc(C2=NC(c3ccccc3)NC(n3c4ccccc4c4cc(-c5cc6c7ccccc7n7c8ccccc8c8cccc5c8c67)ccc43)=N2)cc1]

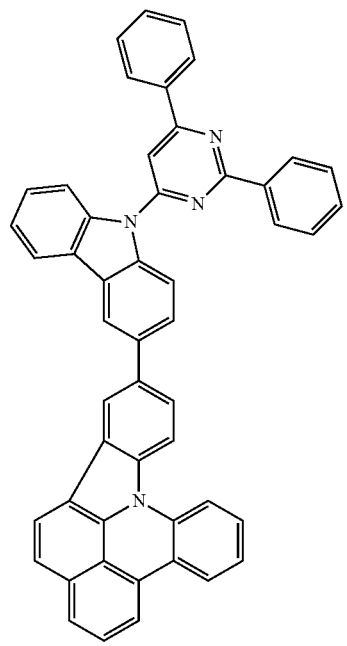 [SMILES: c1ccc(-c2cc(-n3c4ccccc4c4cc(-c5ccc6c(c5)c5ccc7cccc8c9ccccc9n6c5c78)ccc43)nc(-c3ccccc3)n2)cc1]
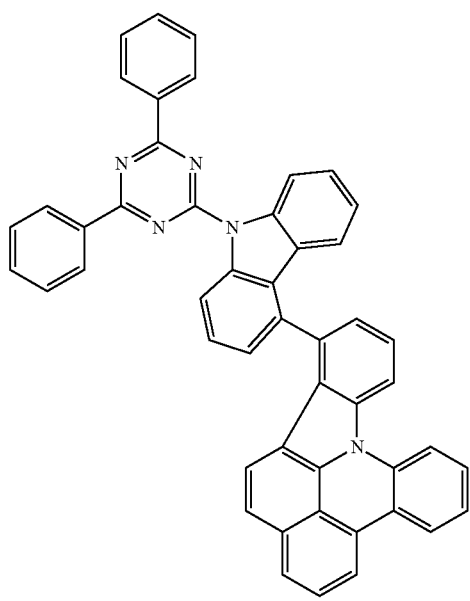 [SMILES: c1ccc(-c2nc(-c3ccccc3)nc(-n3c4ccccc4c4c(-c5cccc6c5c5ccc7cccc8c9ccccc9n6c5c78)cccc43)n2)cc1]

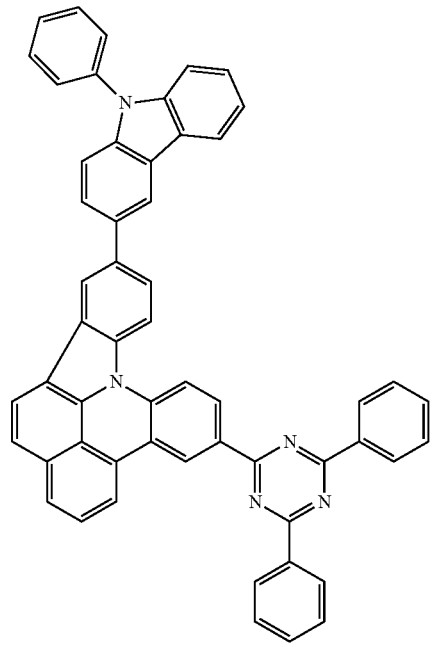 [SMILES: c1ccc(-c2nc(-c3ccccc3)nc(-c3ccc4c(c3)c3cccc5ccc6c7cc(-c8ccc9c(c8)c8ccccc8n9-c8ccccc8)ccc7n4c6c53)n2)cc1]
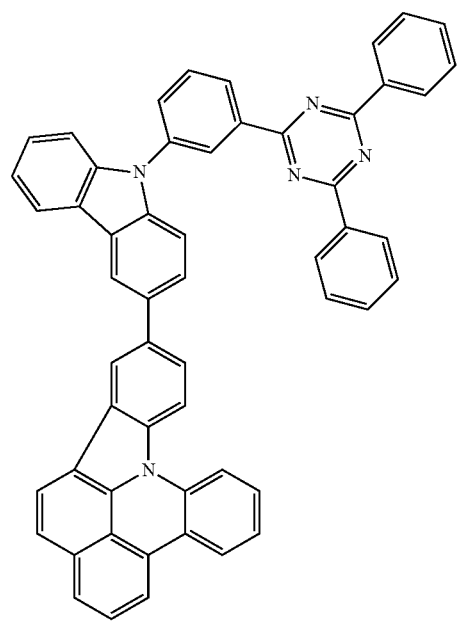 [SMILES: c1ccc(-c2nc(-c3ccccc3)nc(-c3cccc(-n4c5ccccc5c5cc(-c6ccc7c(c6)c6ccc8cccc9c%10ccccc%10n7c6c89)ccc54)c3)n2)cc1]

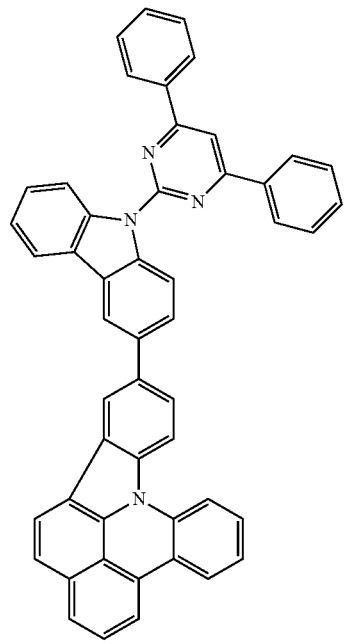 [SMILES: c1ccc(-c2cc(-c3ccccc3)nc(-n3c4ccccc4c4cc(-c5ccc6c(c5)c5ccc7cccc8c9ccccc9n6c5c78)ccc43)n2)cc1]
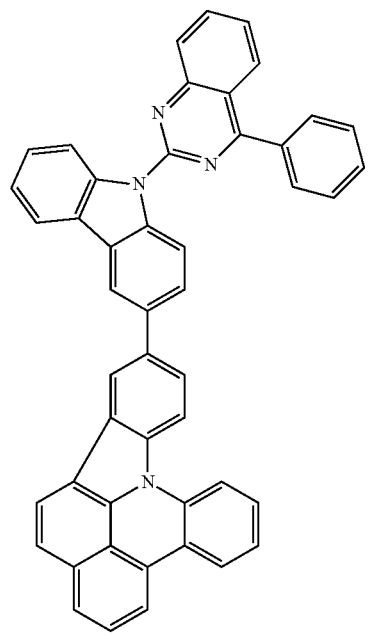 [SMILES: c1ccc(-c2nc(-n3c4ccccc4c4cc(-c5ccc6c(c5)c5ccc7cccc8c9ccccc9n6c5c78)ccc43)nc3ccccc23)cc1]

-continued
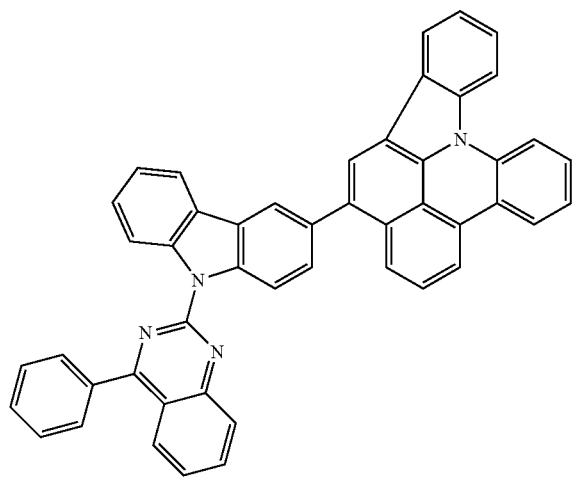 [SMILES: c1ccc(-c2nc(-n3c4ccccc4c4cc(-c5cc6c7ccccc7n7c8ccccc8c8cccc5c8c67)ccc43)nc3ccccc23)cc1]
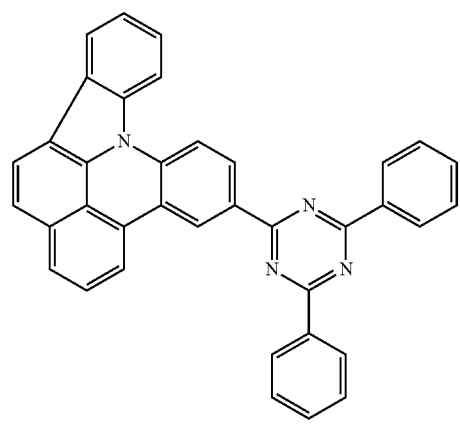 [SMILES: c1ccc(-c2nc(-c3ccccc3)nc(-c3ccc4c(c3)c3cccc5ccc6c7ccccc7n4c6c53)n2)cc1]
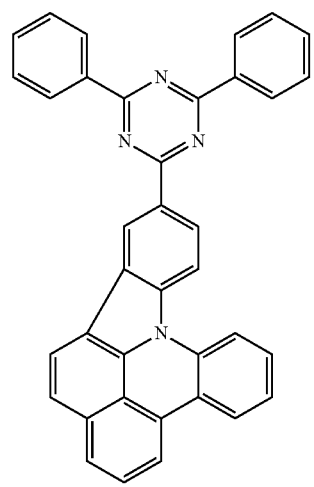 [SMILES: c1ccc(-c2nc(-c3ccccc3)nc(-c3ccc4c(c3)c3ccc5cccc6c7ccccc7n4c3c56)n2)cc1]

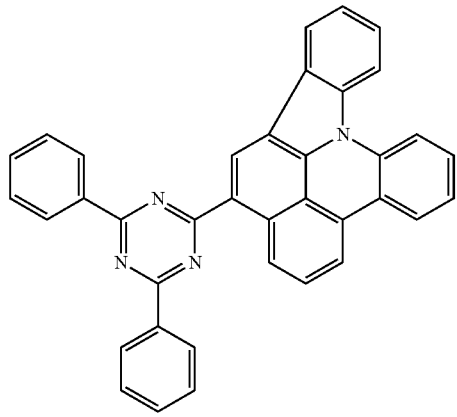 [SMILES: c1ccc(-c2nc(-c3ccccc3)nc(-c3cc4c5ccccc5n5c6ccccc6c6cccc3c6c45)n2)cc1]
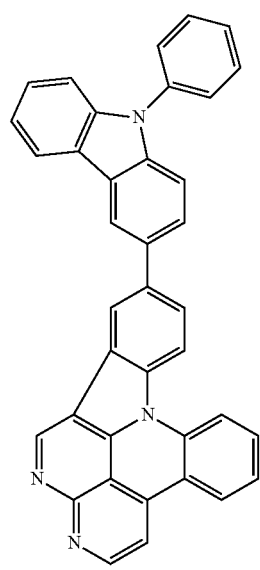 [SMILES: c1ccc(-n2c3ccccc3c3cc(-c4ccc5c(c4)c4cnc6nccc7c8ccccc8n5c4c67)ccc32)cc1]
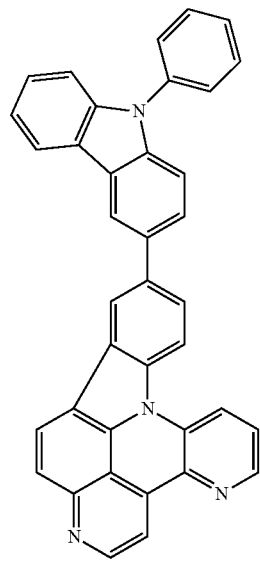 [SMILES: c1ccc(-n2c3ccccc3c3cc(-c4ccc5c(c4)c4ccc6nccc7c8ncccc8n5c4c67)ccc32)cc1]

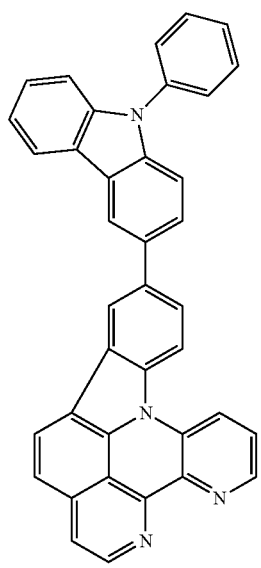 [SMILES: c1ccc(-n2c3ccccc3c3cc(-c4ccc5c(c4)c4ccc6ccnc7c8ncccc8n5c4c67)ccc32)cc1]
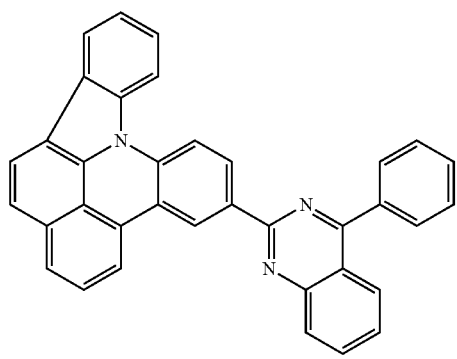 [SMILES: c1ccc(-c2nc(-c3ccc4c(c3)c3cccc5ccc6c7ccccc7n4c6c53)nc3ccccc23)cc1]
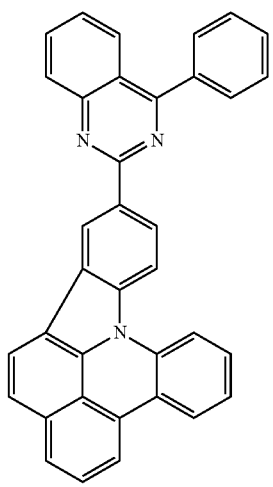 [SMILES: c1ccc(-c2nc(-c3ccc4c(c3)c3ccc5cccc6c7ccccc7n4c3c56)nc3ccccc23)cc1]

-continued
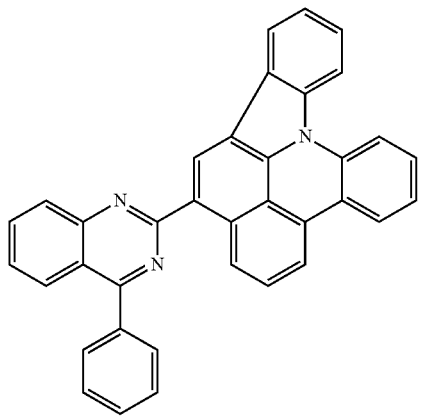 [SMILES: c1ccc(-c2nc(-c3cc4c5ccccc5n5c6ccccc6c6cccc3c6c45)nc3ccccc23)cc1]
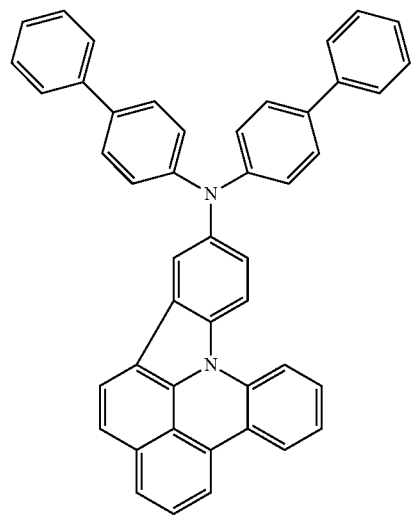 [SMILES: c1ccc(-c2ccc(N(c3ccc(-c4ccccc4)cc3)c3ccc4c(c3)c3ccc5cccc6c7ccccc7n4c3c56)cc2)cc1]
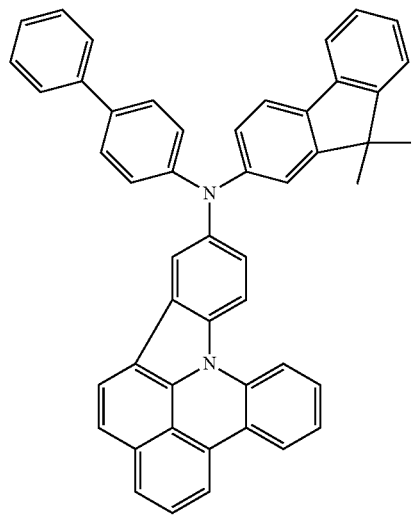 [SMILES: CC1(C)c2ccccc2-c2ccc(N(c3ccc(-c4ccccc4)cc3)c3ccc4c(c3)c3ccc5cccc6c7ccccc7n4c3c56)cc21]

-continued
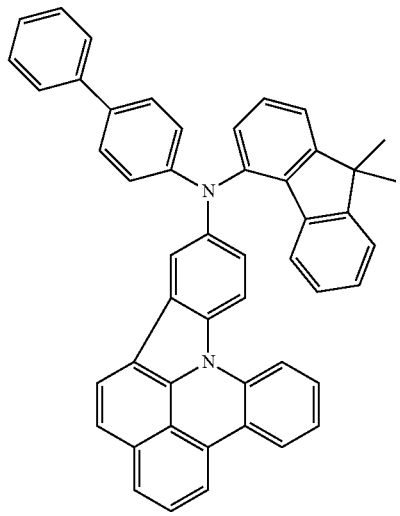 [SMILES: CC1(C)c2ccccc2-c2c(N(c3ccc(-c4ccccc4)cc3)c3ccc4c(c3)c3ccc5cccc6c7ccccc7n4c3c56)cccc21]
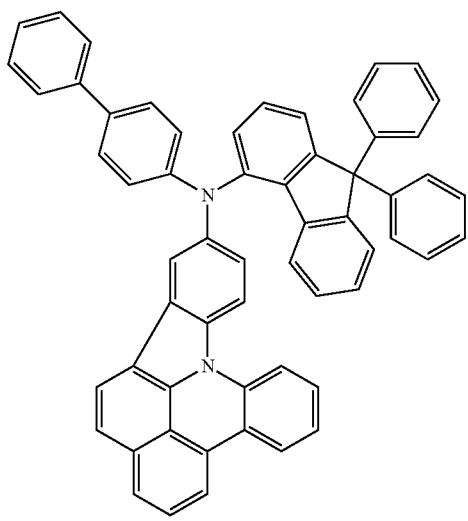 [SMILES: c1ccc(-c2ccc(N(c3ccc4c(c3)c3ccc5cccc6c7ccccc7n4c3c56)c3cccc4c3-c3ccccc3C4(c3ccccc3)c3ccccc3)cc2)cc1]
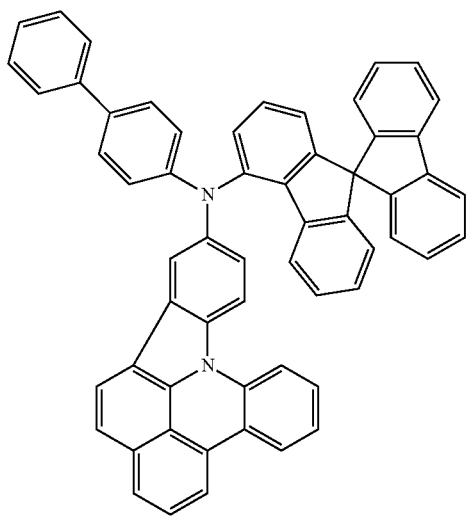 [SMILES: c1ccc(-c2ccc(N(c3ccc4c(c3)c3ccc5cccc6c7ccccc7n4c3c56)c3cccc4c3-c3ccccc3C43c4ccccc4-c4ccccc43)cc2)cc1]

-continued
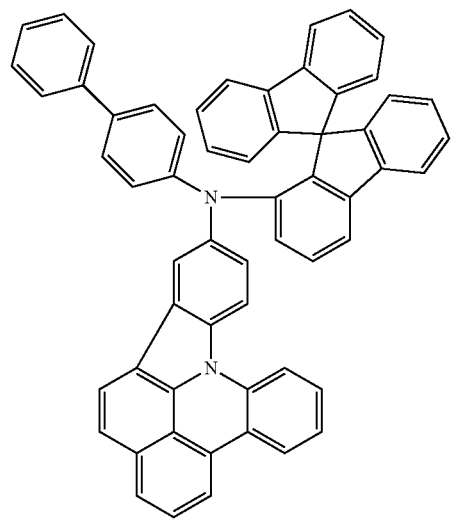 [SMILES: c1ccc(-c2ccc(N(c3ccc4c(c3)c3ccc5cccc6c7ccccc7n4c3c56)c3cccc4c3C3(c5ccccc5-c5ccccc53)c3ccccc3-4)cc2)cc1]
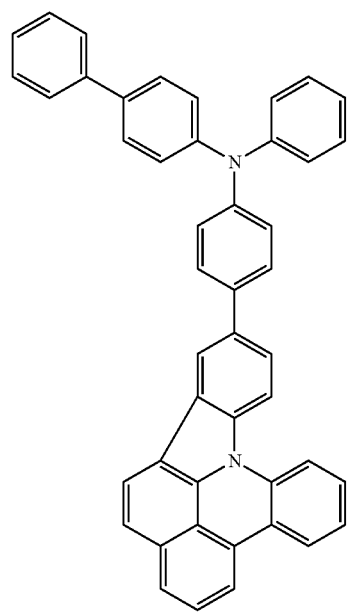 [SMILES: c1ccc(-c2ccc(N(c3ccccc3)c3ccc(-c4ccc5c(c4)c4ccc6cccc7c8ccccc8n5c4c67)cc3)cc2)cc1]

-continued
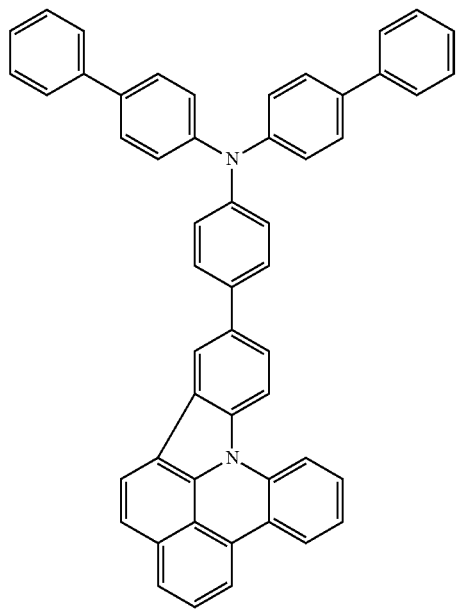 [SMILES: c1ccc(-c2ccc(N(c3ccc(-c4ccccc4)cc3)c3ccc(-c4ccc5c(c4)c4ccc6cccc7c8ccccc8n5c4c67)cc3)cc2)cc1]
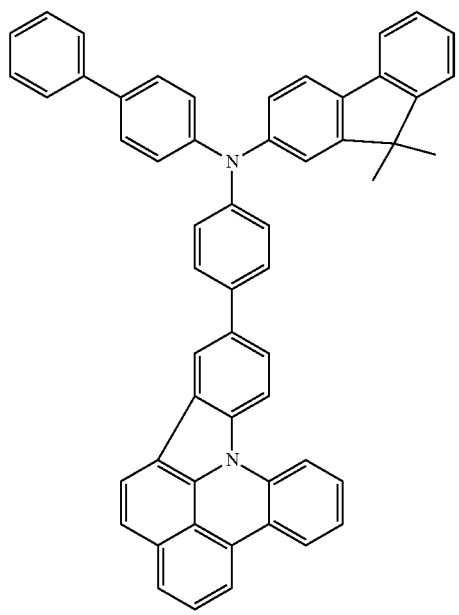 [SMILES: CC1(C)c2ccccc2-c2ccc(N(c3ccc(-c4ccccc4)cc3)c3ccc(-c4ccc5c(c4)c4ccc6cccc7c8ccccc8n5c4c67)cc3)cc21]

-continued
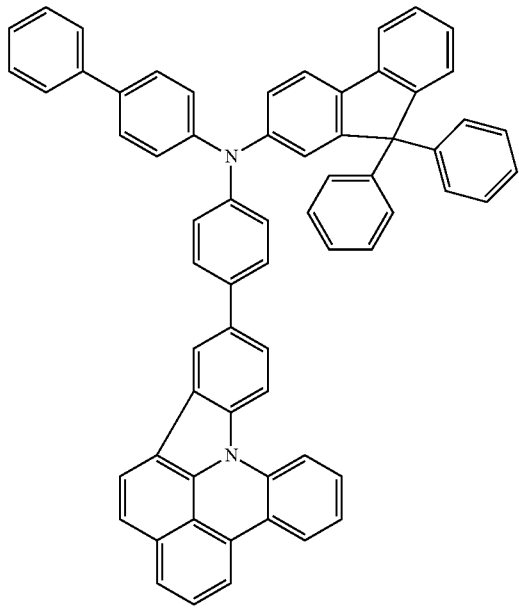 [SMILES: c1ccc(-c2ccc(N(c3ccc(-c4ccc5c(c4)c4ccc6cccc7c8ccccc8n5c4c67)cc3)c3ccc4c(c3)C(c3ccccc3)(c3ccccc3)c3ccccc3-4)cc2)cc1]
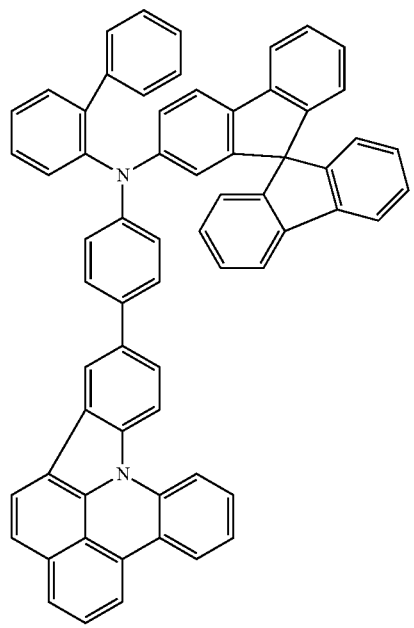 [SMILES: c1ccc(-c2ccccc2N(c2ccc(-c3ccc4c(c3)c3ccc5cccc6c7ccccc7n4c3c56)cc2)c2ccc3c(c2)C2(c4ccccc4-c4ccccc42)c2ccccc2-3)cc1]

-continued
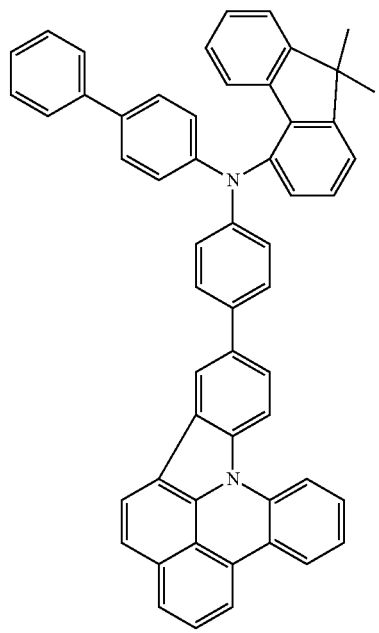 [SMILES: CC1(C)c2ccccc2-c2c(N(c3ccc(-c4ccccc4)cc3)c3ccc(-c4ccc5c(c4)c4ccc6cccc7c8ccccc8n5c4c67)cc3)cccc21]
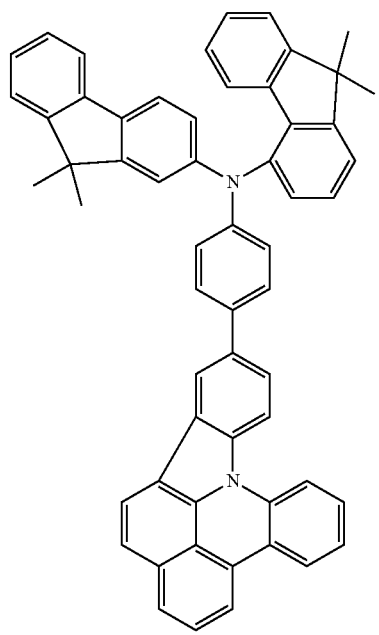 [SMILES: CC1(C)c2ccccc2-c2ccc(N(c3ccc(-c4ccc5c(c4)c4ccc6cccc7c8ccccc8n5c4c67)cc3)c3cccc4c3-c3ccccc3C4(C)C)cc21]

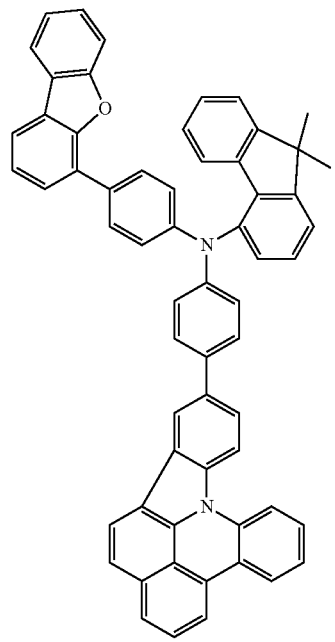 [SMILES: CC1(C)c2ccccc2-c2c(N(c3ccc(-c4ccc5c(c4)c4ccc6cccc7c8ccccc8n5c4c67)cc3)c3ccc(-c4cccc5c4oc4ccccc45)cc3)cccc21]
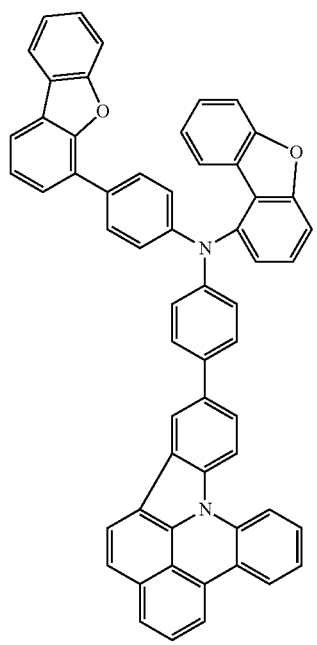 [SMILES: c1ccc2c(c1)oc1c(-c3ccc(N(c4ccc(-c5ccc6c(c5)c5ccc7cccc8c9ccccc9n6c5c78)cc4)c4cccc5oc6ccccc6c45)cc3)cccc12]

-continued
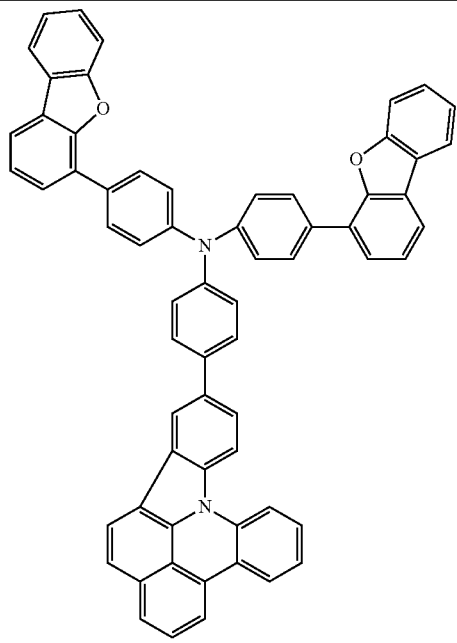
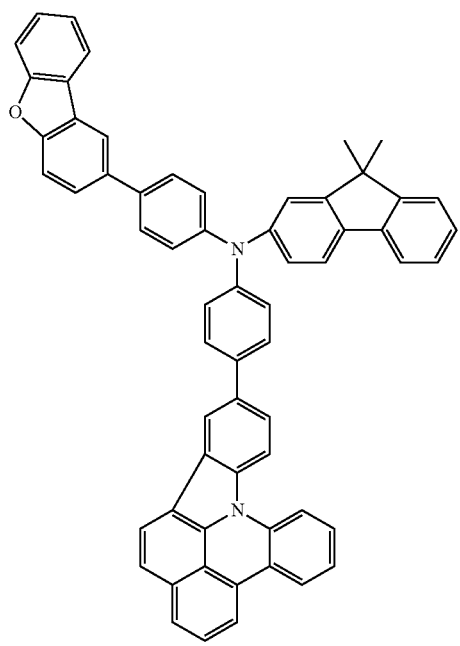 [SMILES: CC1(C)c2ccccc2-c2ccc(N(c3ccc(-c4ccc5oc6ccccc6c5c4)cc3)c3ccc(-c4ccc5c(c4)c4ccc6cccc7c8ccccc8n5c4c67)cc3)cc21]

-continued
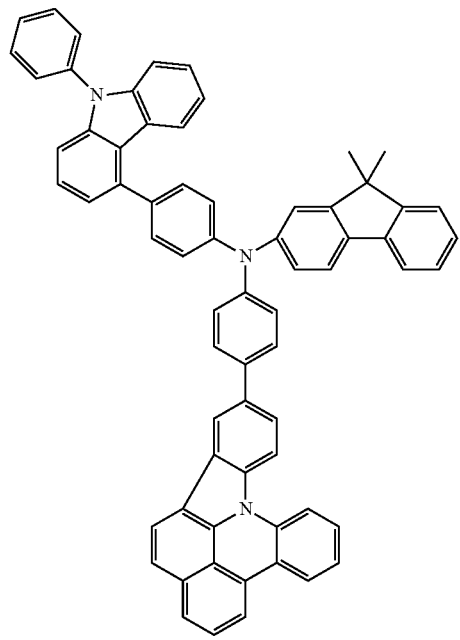 [SMILES: CC1(C)c2ccccc2-c2ccc(N(c3ccc(-c4ccc5c(c4)c4ccc6cccc7c8ccccc8n5c4c67)cc3)c3ccc(-c4cccc5c4c4ccccc4n5-c4ccccc4)cc3)cc21]
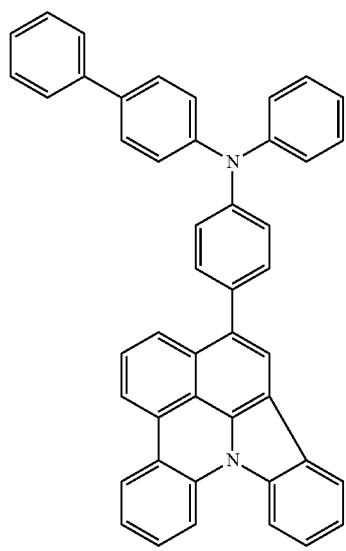 [SMILES: c1ccc(-c2ccc(N(c3ccccc3)c3ccc(-c4cc5c6ccccc6n6c7ccccc7c7cccc4c7c56)cc3)cc2)cc1]

-continued
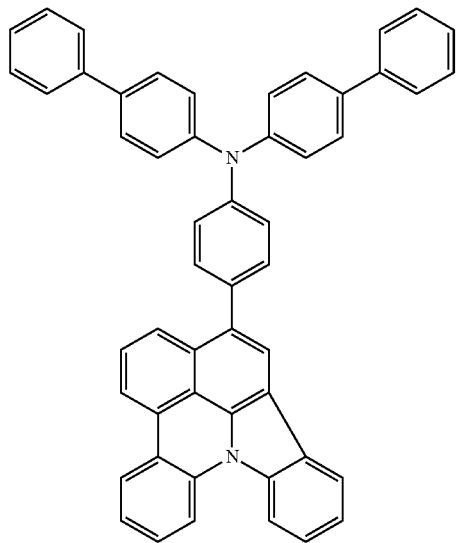 [SMILES: c1ccc(-c2ccc(N(c3ccc(-c4ccccc4)cc3)c3ccc(-c4cc5c6ccccc6n6c7ccccc7c7cccc4c7c56)cc3)cc2)cc1]
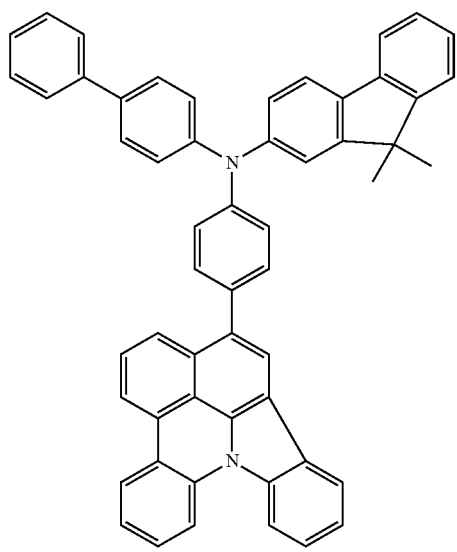 [SMILES: CC1(C)c2ccccc2-c2ccc(N(c3ccc(-c4ccccc4)cc3)c3ccc(-c4cc5c6ccccc6n6c7ccccc7c7cccc4c7c56)cc3)cc21]
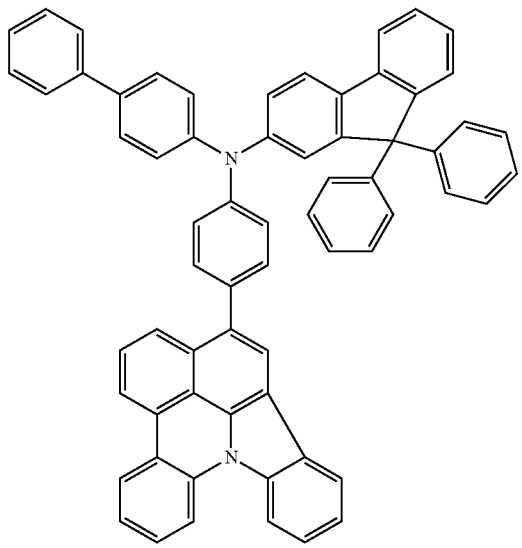 [SMILES: c1ccc(-c2ccc(N(c3ccc(-c4cc5c6ccccc6n6c7ccccc7c7cccc4c7c56)cc3)c3ccc4c(c3)C(c3ccccc3)(c3ccccc3)c3ccccc3-4)cc2)cc1]

-continued
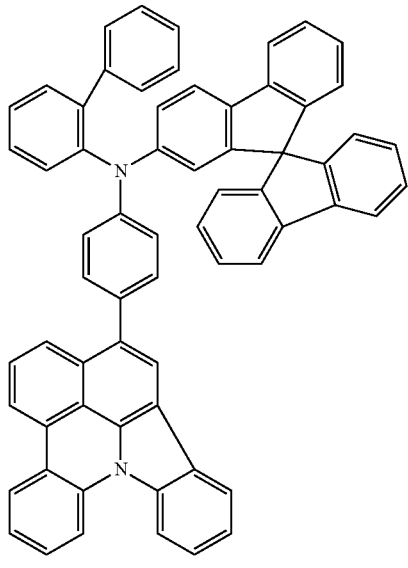 [SMILES: c1ccc(-c2ccccc2N(c2ccc(-c3cc4c5ccccc5n5c6ccccc6c6cccc3c6c45)cc2)c2ccc3c(c2)C2(c4ccccc4-c4ccccc42)c2ccccc2-3)cc1]
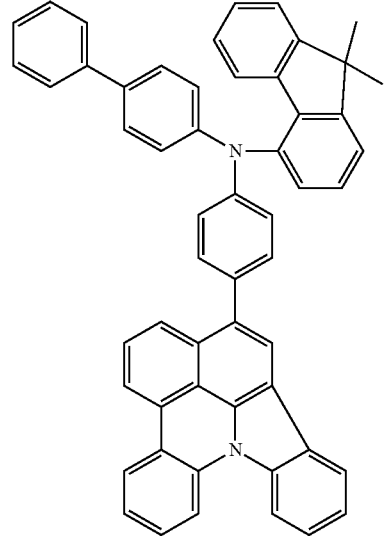 [SMILES: CC1(C)c2ccccc2-c2c(N(c3ccc(-c4ccccc4)cc3)c3ccc(-c4cc5c6ccccc6n6c7ccccc7c7cccc4c7c56)cc3)cccc21]
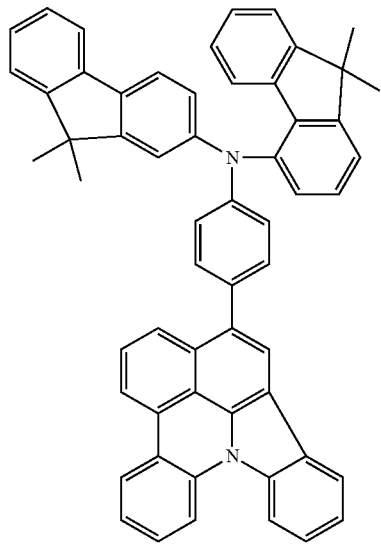 [SMILES: CC1(C)c2ccccc2-c2ccc(N(c3ccc(-c4cc5c6ccccc6n6c7ccccc7c7cccc4c7c56)cc3)c3cccc4c3-c3ccccc3C4(C)C)cc21]

-continued
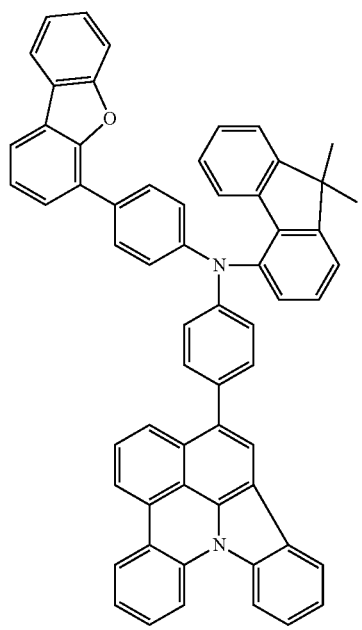 [SMILES: CC1(C)c2ccccc2-c2c(N(c3ccc(-c4cc5c6ccccc6n6c7ccccc7c7cccc4c7c56)cc3)c3ccc(-c4cccc5c4oc4ccccc45)cc3)cccc21]
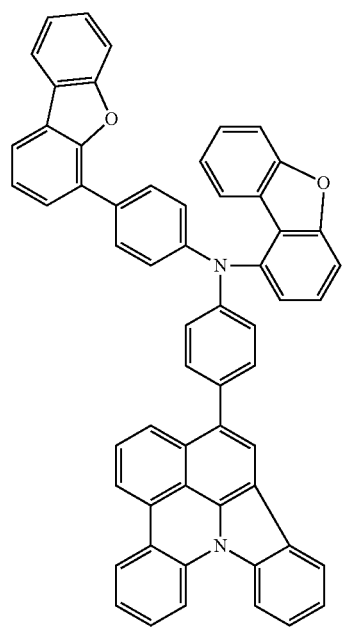 [SMILES: c1ccc2c(c1)oc1c(-c3ccc(N(c4ccc(-c5cc6c7ccccc7n7c8ccccc8c8cccc5c8c67)cc4)c4cccc5oc6ccccc6c45)cc3)cccc12]

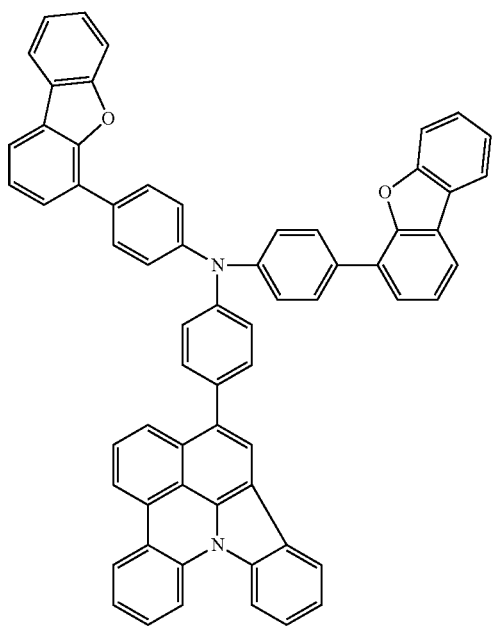 [SMILES: c1ccc2c(c1)oc1c(-c3ccc(N(c4ccc(-c5cc6c7ccccc7n7c8ccccc8c8cccc5c8c67)cc4)c4ccc(-c5cccc6c5oc5ccccc56)cc4)cc3)cccc12]
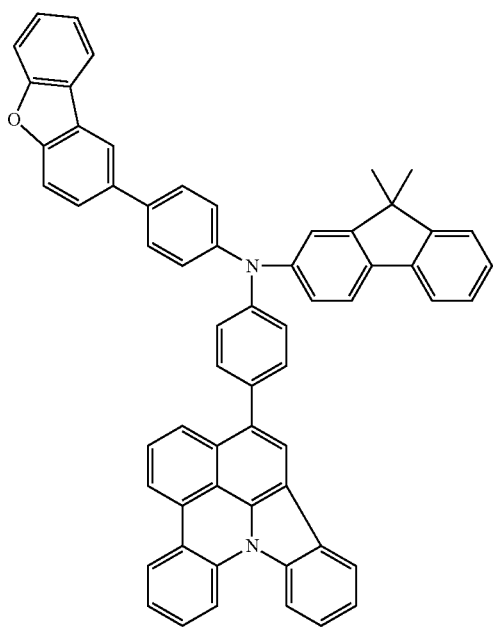 [SMILES: CC1(C)c2ccccc2-c2ccc(N(c3ccc(-c4ccc5oc6ccccc6c5c4)cc3)c3ccc(-c4cc5c6ccccc6n6c7ccccc7c7cccc4c7c56)cc3)cc21]

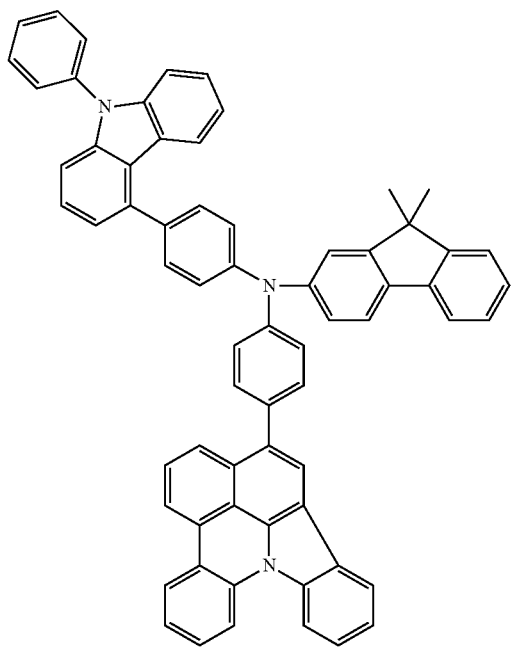 [SMILES: CC1(C)c2ccccc2-c2ccc(N(c3ccc(-c4cc5c6ccccc6n6c7ccccc7c7cccc4c7c56)cc3)c3ccc(-c4cccc5c4c4ccccc4n5-c4ccccc4)cc3)cc21]
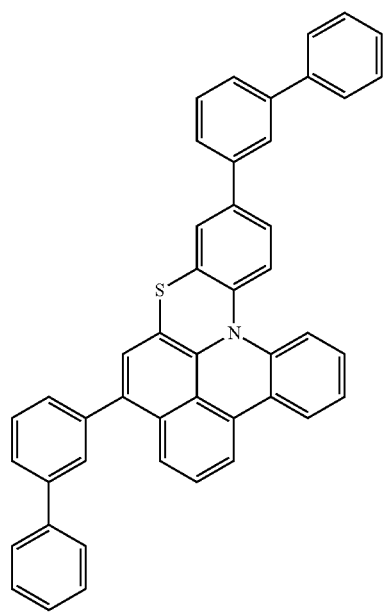 [SMILES: c1ccc(-c2cccc(-c3ccc4c(c3)sc3cc(-c5cccc(-c6ccccc6)c5)c5cccc6c7ccccc7n4-c3c56)c2)cc1]

-continued
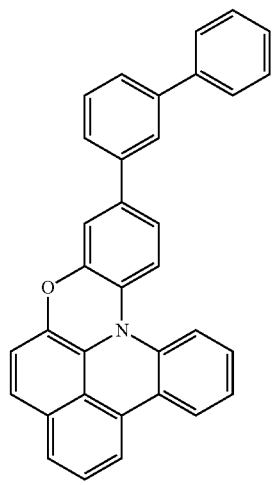 [SMILES: c1ccc(-c2cccc(-c3ccc4c(c3)oc3ccc5cccc6c7ccccc7n4-c3c56)c2)cc1]
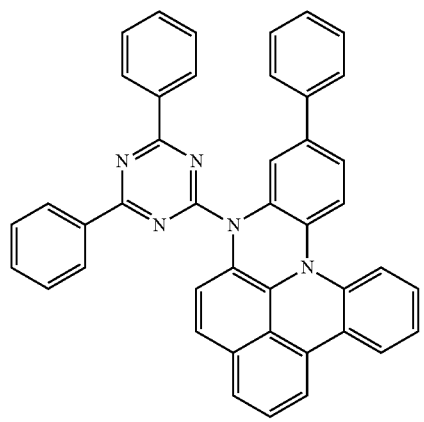 [SMILES: c1ccc(-c2ccc3c(c2)n(-c2nc(-c4ccccc4)nc(-c4ccccc4)n2)c2ccc4cccc5c6ccccc6n3-c2c45)cc1]
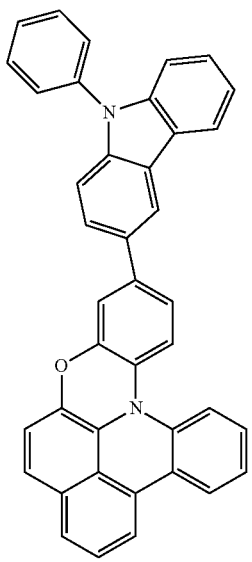 [SMILES: c1ccc(-n2c3ccccc3c3cc(-c4ccc5c(c4)oc4ccc6cccc7c8ccccc8n5-c4c67)ccc32)cc1]

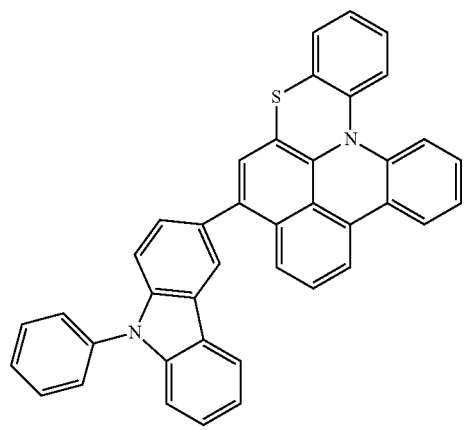 [SMILES: c1ccc(-n2c3ccccc3c3cc(-c4cc5sc6ccccc6n6c7ccccc7c7cccc4c7c5-6)ccc32)cc1]
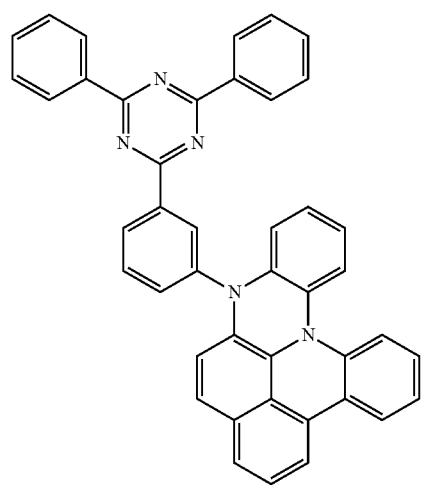 [SMILES: c1ccc(-c2nc(-c3ccccc3)nc(-c3cccc(-n4c5ccc6cccc7c8ccccc8n(c8ccccc84)-c5c67)c3)n2)cc1]
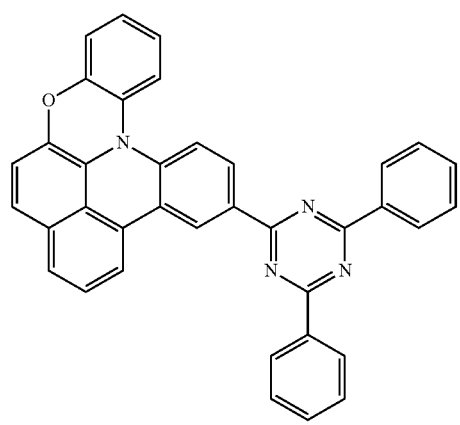 [SMILES: c1ccc(-c2nc(-c3ccccc3)nc(-c3ccc4c(c3)c3cccc5ccc6oc7ccccc7n4-c6c53)n2)cc1]

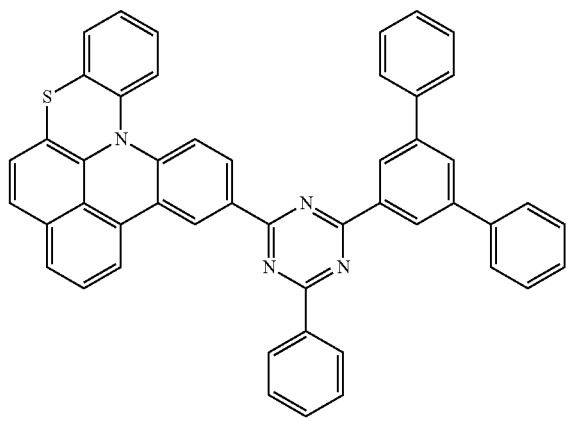 [SMILES: c1ccc(-c2cc(-c3ccccc3)cc(-c3nc(-c4ccccc4)nc(-c4ccc5c(c4)c4cccc6ccc7sc8ccccc8n5-c7c64)n3)c2)cc1]
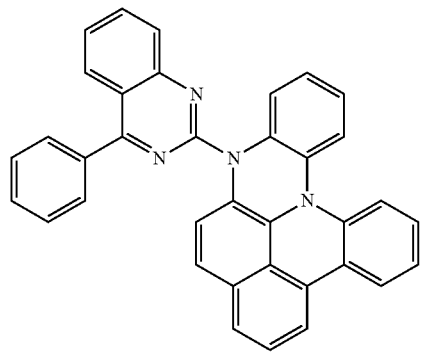 [SMILES: c1ccc(-c2nc(-n3c4ccc5cccc6c7ccccc7n(c7ccccc73)-c4c56)nc3ccccc23)cc1]
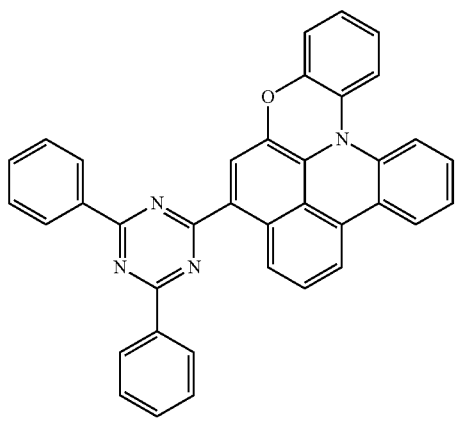 [SMILES: c1ccc(-c2nc(-c3ccccc3)nc(-c3cc4oc5ccccc5n5c6ccccc6c6cccc3c6c4-5)n2)cc1]
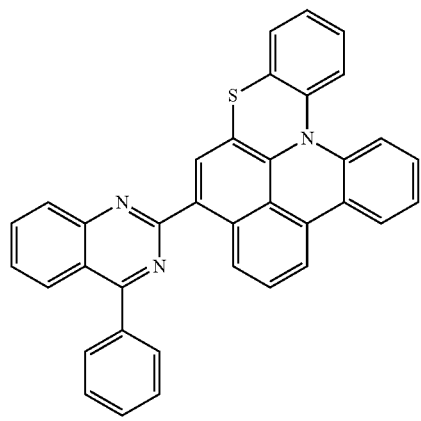 [SMILES: c1ccc(-c2nc(-c3cc4sc5ccccc5n5c6ccccc6c6cccc3c6c4-5)nc3ccccc23)cc1]

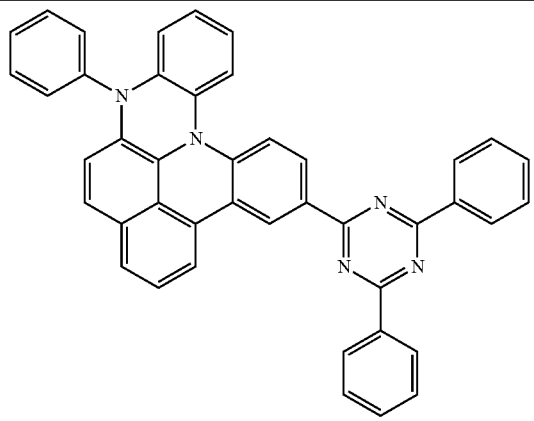
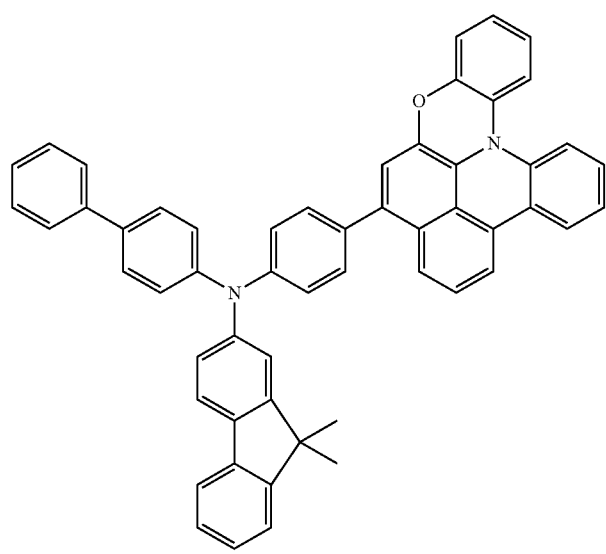 [SMILES: CC1(C)c2ccccc2-c2ccc(N(c3ccc(-c4ccccc4)cc3)c3ccc(-c4cc5oc6ccccc6n6c7ccccc7c7cccc4c7c5-6)cc3)cc21]
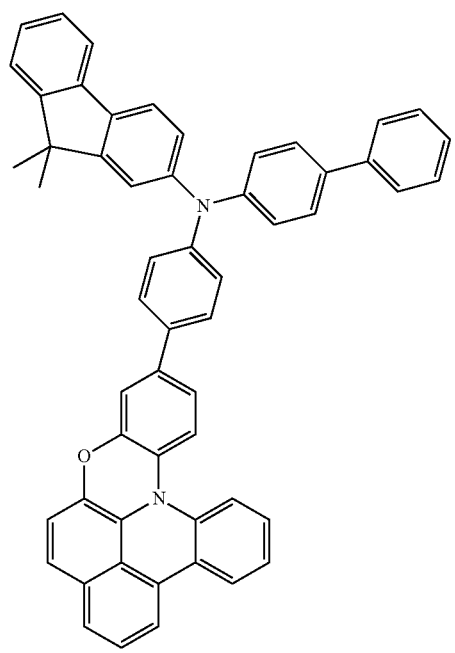 [SMILES: CC1(C)c2ccccc2-c2ccc(N(c3ccc(-c4ccccc4)cc3)c3ccc(-c4ccc5c(c4)oc4ccc6cccc7c8ccccc8n5-c4c67)cc3)cc21]

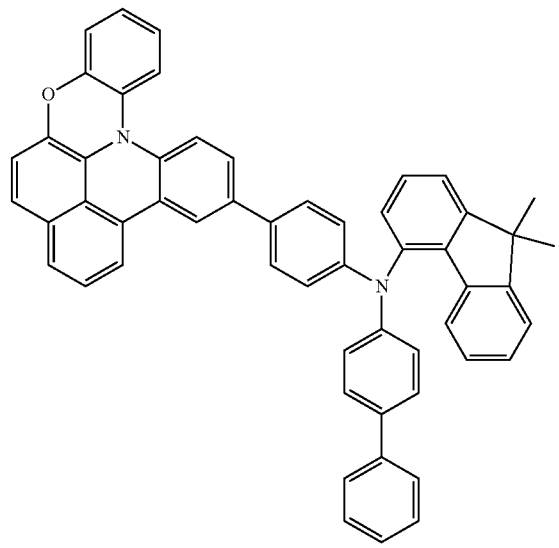 [SMILES: CC1(C)c2ccccc2-c2c(N(c3ccc(-c4ccccc4)cc3)c3ccc(-c4ccc5c(c4)c4cccc6ccc7oc8ccccc8n5-c7c64)cc3)cccc21]
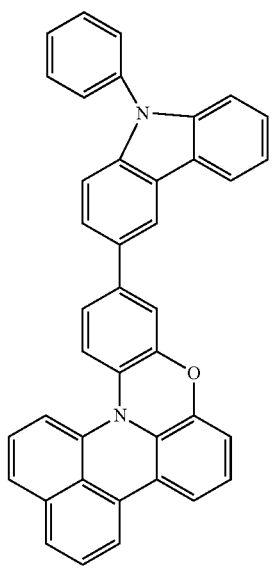 [SMILES: c1ccc(-n2c3ccccc3c3cc(-c4ccc5c(c4)oc4cccc6c4-n5c4cccc5cccc6c54)ccc32)cc1]
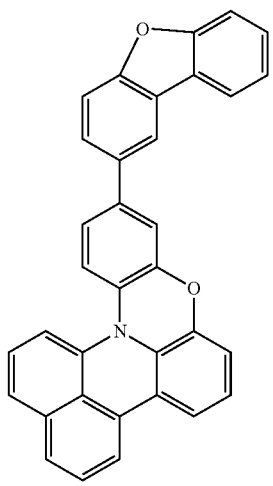 [SMILES: c1ccc2c(c1)oc1ccc(-c3ccc4c(c3)oc3cccc5c3-n4c3cccc4cccc5c43)cc12]

-continued
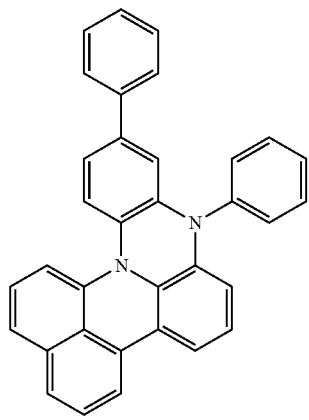 [SMILES: c1ccc(-c2ccc3c(c2)n(-c2ccccc2)c2cccc4c2-n3c2cccc3cccc4c32)cc1]
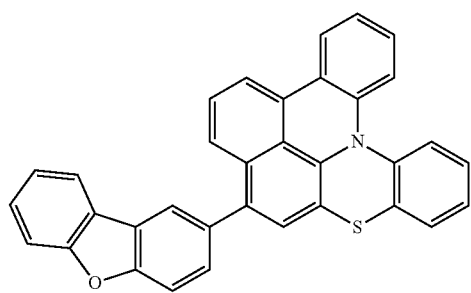 [SMILES: c1ccc2c(c1)oc1ccc(-c3cc4sc5ccccc5n5c6ccccc6c6cccc3c6c4-5)cc12]
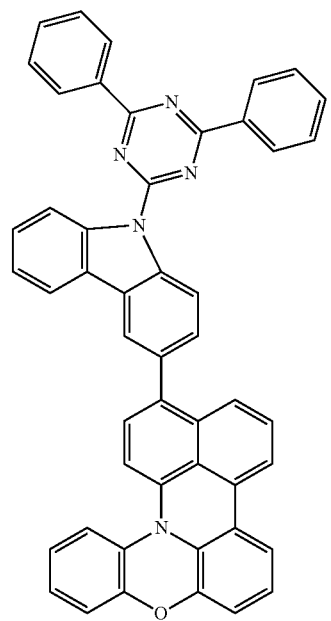 [SMILES: c1ccc(-c2nc(-c3ccccc3)nc(-n3c4ccccc4c4cc(-c5ccc6c7c5cccc7c5cccc7oc8ccccc8n6-c75)ccc43)n2)cc1]

-continued
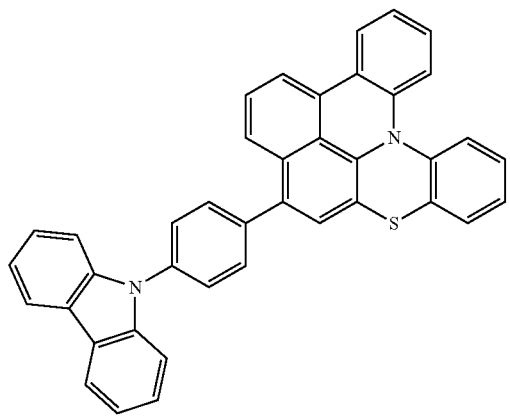 [SMILES: c1ccc2c(c1)sc1cc(-c3ccc(-n4c5ccccc5c5ccccc54)cc3)c3cccc4c5ccccc5n2-c1c34]
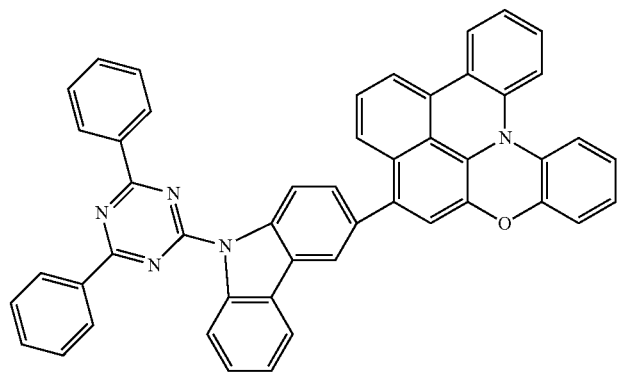 [SMILES: c1ccc(-c2nc(-c3ccccc3)nc(-n3c4ccccc4c4cc(-c5cc6oc7ccccc7n7c8ccccc8c8cccc5c8c6-7)ccc43)n2)cc1]
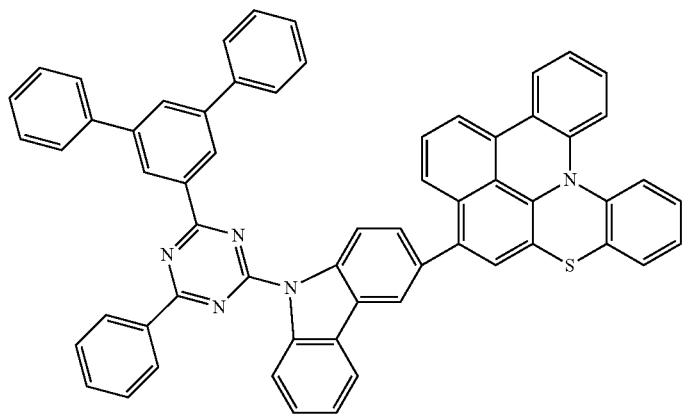 [SMILES: c1ccc(-c2cc(-c3ccccc3)cc(-c3nc(-c4ccccc4)nc(-n4c5ccccc5c5cc(-c6cc7sc8ccccc8n8c9ccccc9c9cccc6c9c7-8)ccc54)n3)c2)cc1]
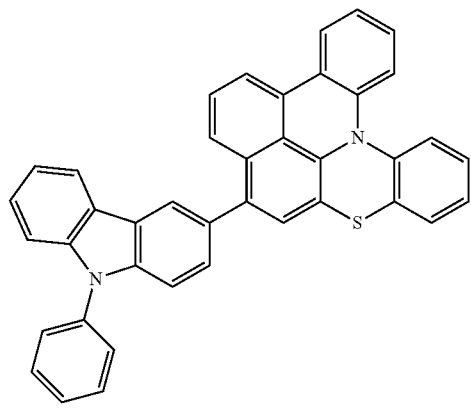 [SMILES: c1ccc(-n2c3ccccc3c3cc(-c4cc5sc6ccccc6n6c7ccccc7c7cccc4c7c5-6)ccc32)cc1]

-continued
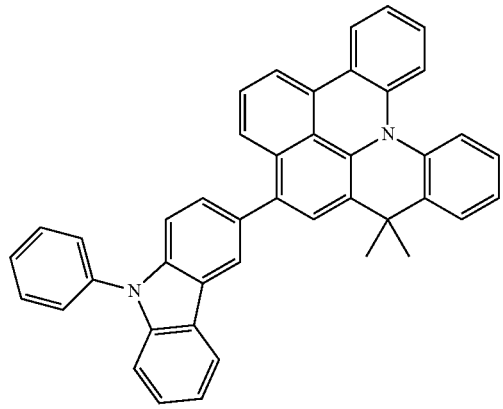 [SMILES: CC1(C)c2ccccc2N2c3ccccc3-c3cccc4c(-c5ccc6c(c5)c5ccccc5n6-c5ccccc5)cc1c2c34]
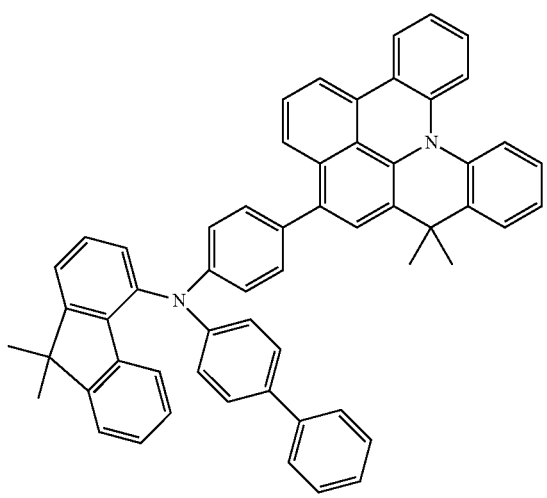 [SMILES: CC1(C)c2ccccc2-c2c(N(c3ccc(-c4ccccc4)cc3)c3ccc(-c4cc5c6c7c(cccc47)-c4ccccc4N6c4ccccc4C5(C)C)cc3)cccc21]
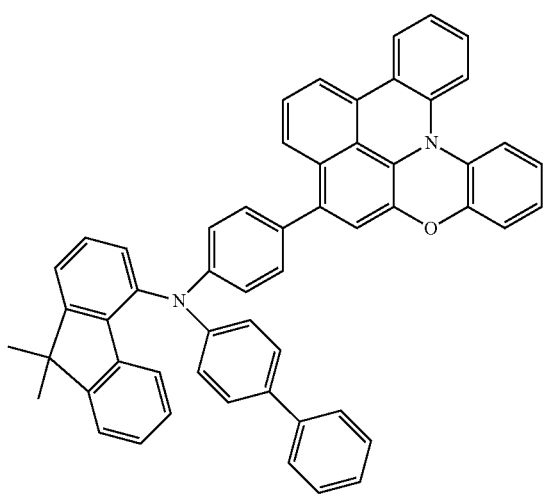 [SMILES: CC1(C)c2ccccc2-c2c(N(c3ccc(-c4ccccc4)cc3)c3ccc(-c4cc5oc6ccccc6n6c7ccccc7c7cccc4c7c5-6)cc3)cccc21]

-continued
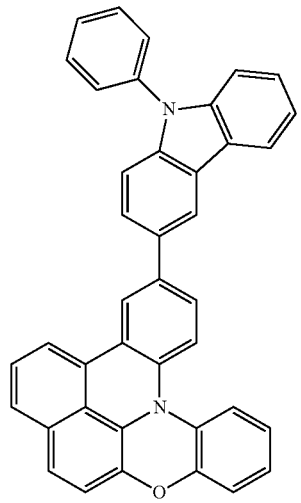 [SMILES: c1ccc(-n2c3ccccc3c3cc(-c4ccc5c(c4)c4cccc6ccc7oc8ccccc8n5-c7c64)ccc32)cc1]
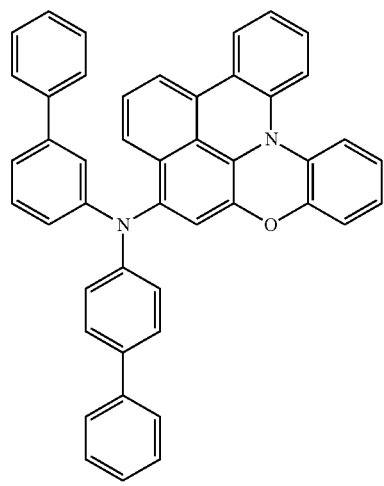 [SMILES: c1ccc(-c2ccc(N(c3cccc(-c4ccccc4)c3)c3cc4oc5ccccc5n5c6ccccc6c6cccc3c6c4-5)cc2)cc1]
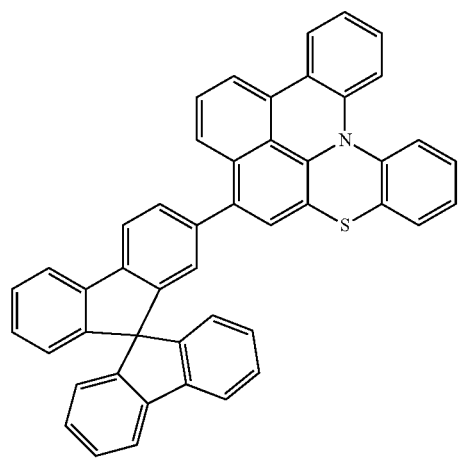 [SMILES: c1ccc2c(c1)-c1ccccc1C21c2ccccc2-c2ccc(-c3cc4sc5ccccc5n5c6ccccc6c6cccc3c6c4-5)cc21]

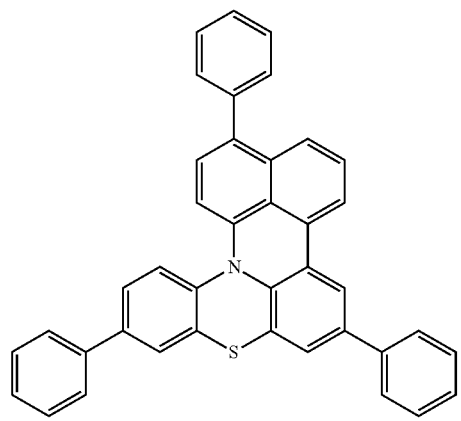
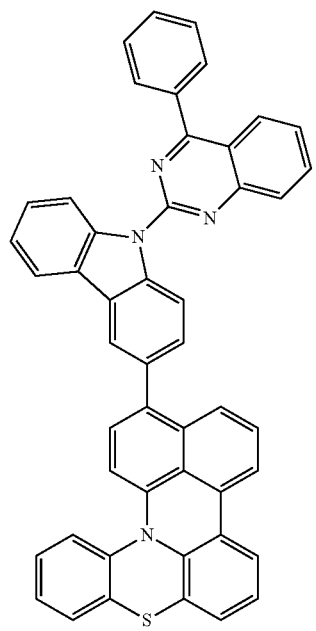 [SMILES: c1ccc(-c2nc(-n3c4ccccc4c4cc(-c5ccc6c7c5cccc7c5cccc7sc8ccccc8n6-c75)ccc43)nc3ccccc23)cc1]
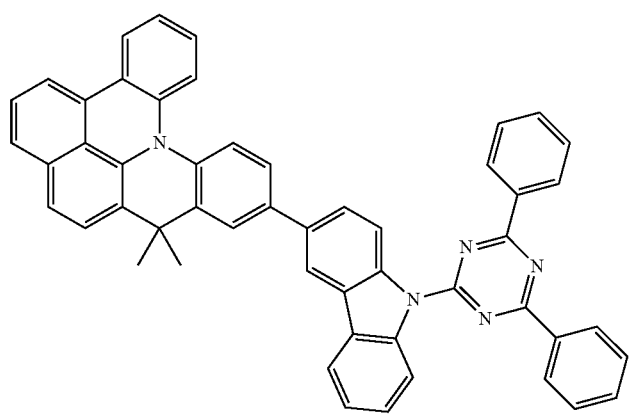 [SMILES: CC1(C)c2cc(-c3ccc4c(c3)c3ccccc3n4-c3nc(-c4ccccc4)nc(-c4ccccc4)n3)ccc2N2c3ccccc3-c3cccc4ccc1c2c34]

-continued
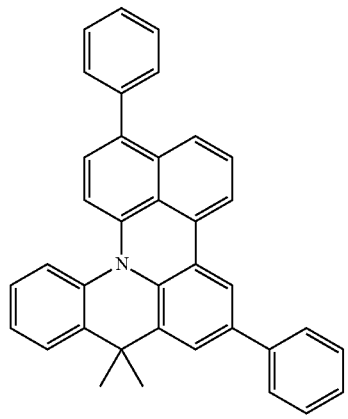 [SMILES: CC1(C)c2ccccc2N2c3c(cc(-c4ccccc4)cc31)-c1cccc3c(-c4ccccc4)ccc2c13]
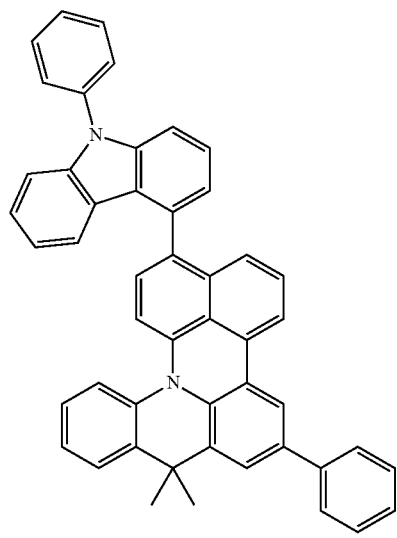 [SMILES: CC1(C)c2ccccc2N2c3c(cc(-c4ccccc4)cc31)-c1cccc3c(-c4cccc5c4c4ccccc4n5-c4ccccc4)ccc2c13]
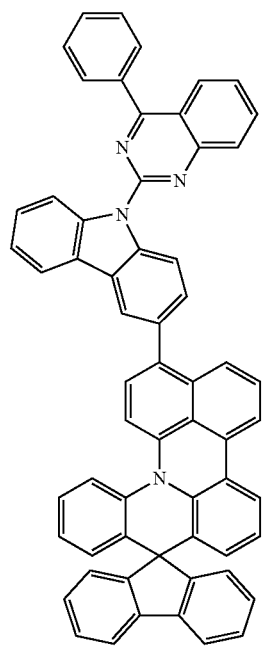 [SMILES: c1ccc(-c2nc(-n3c4ccccc4c4cc(-c5ccc6c7c(cccc57)-c5cccc7c5N6c5ccccc5C75c6ccccc6-c6ccccc65)ccc43)nc3ccccc23)cc1]

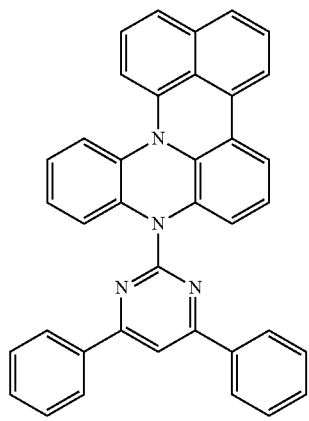 [SMILES: c1ccc(-c2cc(-c3ccccc3)nc(-n3c4cccc5c4-n(c4cccc6cccc5c64)c4ccccc43)n2)cc1]
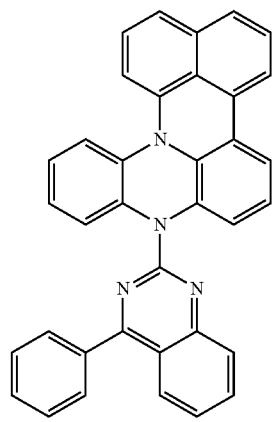 [SMILES: c1ccc(-c2nc(-n3c4cccc5c4-n(c4cccc6cccc5c64)c4ccccc43)nc3ccccc23)cc1]
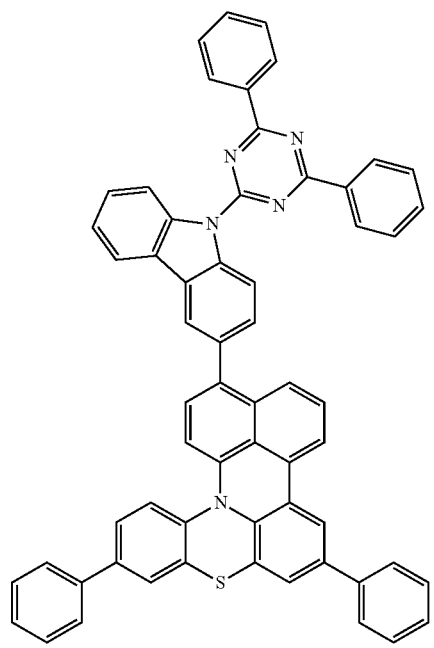 [SMILES: c1ccc(-c2ccc3c(c2)sc2cc(-c4ccccc4)cc4c2-n3c2ccc(-c3ccc5c(c3)c3ccccc3n5-c3nc(-c5ccccc5)nc(-c5ccccc5)n3)c3cccc4c32)cc1]

-continued
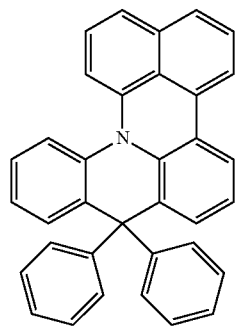 [SMILES: c1ccc(C2(c3ccccc3)c3ccccc3N3c4c(cccc42)-c2cccc4cccc3c24)cc1]
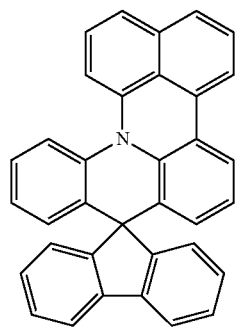 [SMILES: c1ccc2c(c1)-c1ccccc1C21c2ccccc2N2c3c(cccc31)-c1cccc3cccc2c13]
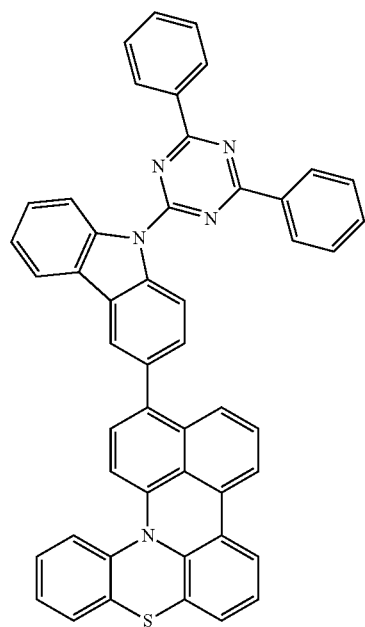 [SMILES: c1ccc(-c2nc(-c3ccccc3)nc(-n3c4ccccc4c4cc(-c5ccc6c7c5cccc7c5cccc7oc8ccccc8n6-c75)ccc43)n2)cc1]

-continued
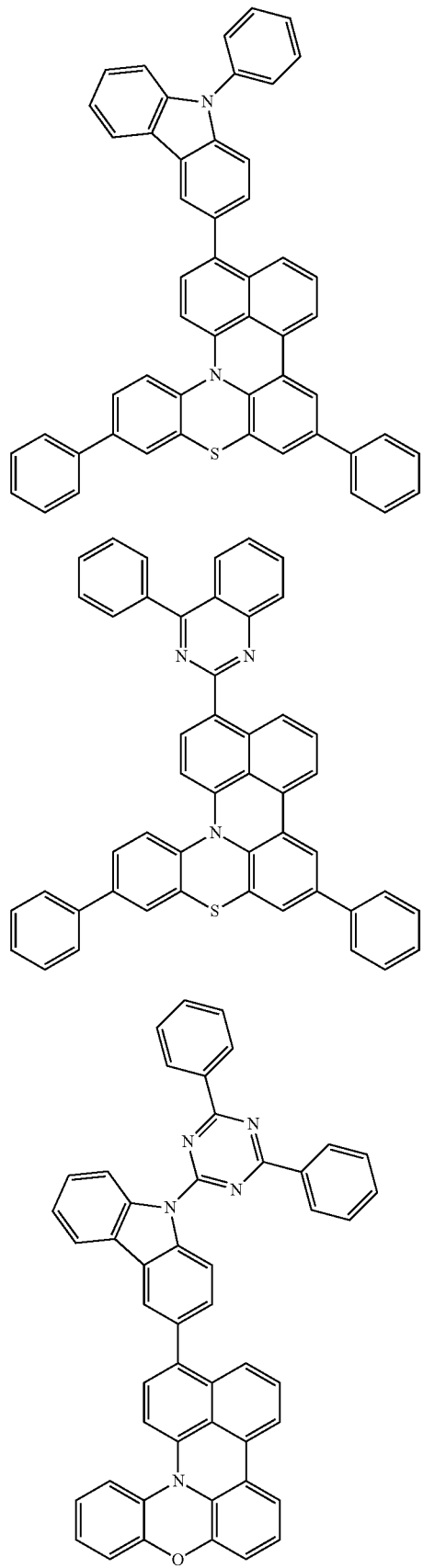

-continued
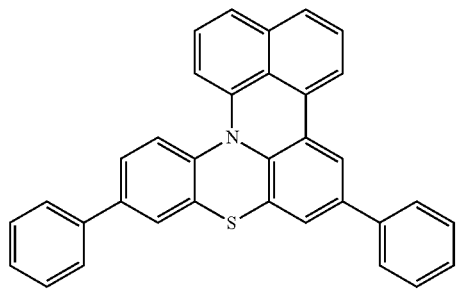 [SMILES: c1ccc(-c2ccc3c(c2)sc2cc(-c4ccccc4)cc4c2-n3c2cccc3cccc4c32)cc1]
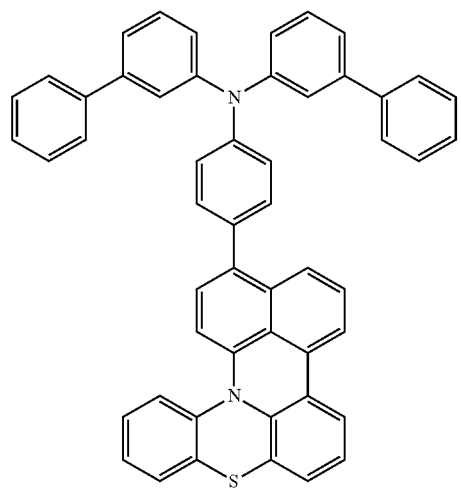 [SMILES: c1ccc(-c2cccc(N(c3ccc(-c4ccc5c6c4cccc6c4cccc6sc7ccccc7n5-c64)cc3)c3cccc(-c4ccccc4)c3)c2)cc1]
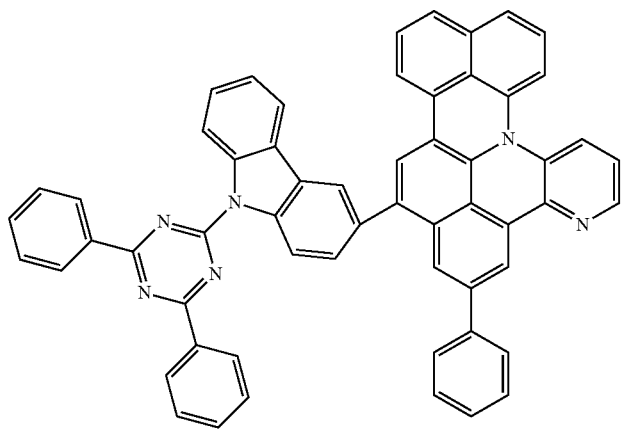 [SMILES: c1ccc(-c2cc3c4c5c(cc(-c6ccc7c(c6)c6ccccc6n7-c6nc(-c7ccccc7)nc(-c7ccccc7)n6)c4c2)-c2cccc4cccc(c24)N5c2cccnc2-3)cc1]
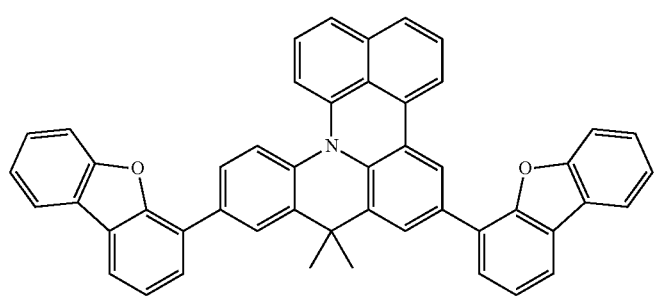 [SMILES: CC1(C)c2cc(-c3cccc4c3oc3ccccc34)ccc2N2c3c(cc(-c4cccc5c4oc4ccccc45)cc31)-c1cccc3cccc2c13]

-continued
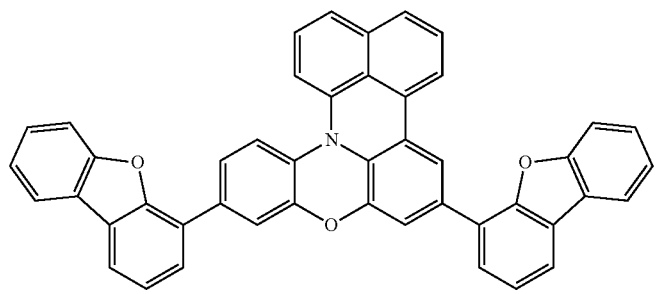 [SMILES: c1ccc2c(c1)oc1c(-c3ccc4c(c3)oc3cc(-c5cccc6c5oc5ccccc56)cc5c3-n4c3cccc4cccc5c43)cccc12]
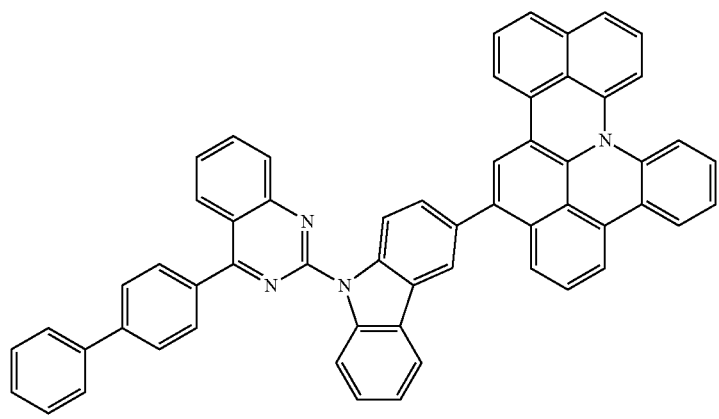 [SMILES: c1ccc(-c2ccc(-c3nc(-n4c5ccccc5c5cc(-c6cc7c8c9c(cccc69)-c6ccccc6N8c6cccc8cccc-7c68)ccc54)nc4ccccc34)cc2)cc1]
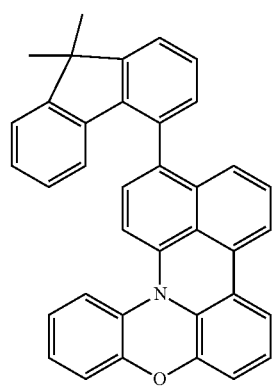 [SMILES: CC1(C)c2ccccc2-c2c(-c3ccc4c5c3cccc5c3cccc5oc6ccccc6n4-c53)cccc21]
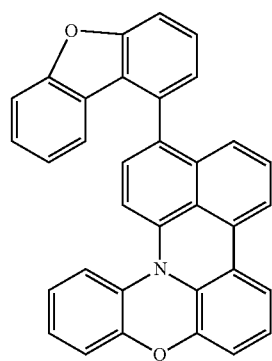 [SMILES: c1ccc2c(c1)oc1cccc(-c3ccc4c5c3cccc5c3cccc5oc6ccccc6n4-c53)c12]

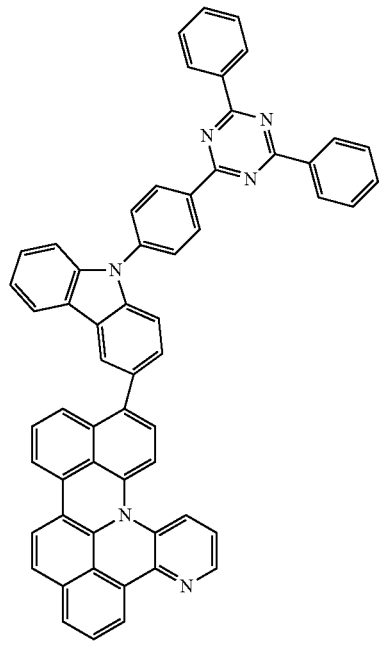 [SMILES: c1ccc(-c2nc(-c3ccccc3)nc(-c3ccc(-n4c5ccccc5c5cc(-c6ccc7c8c(cccc68)-c6ccc8cccc9c8c6N7c6cccnc6-9)ccc54)cc3)n2)cc1]
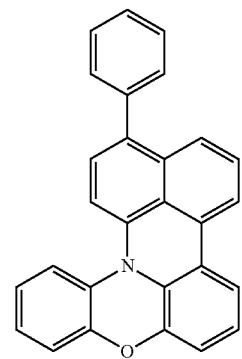 [SMILES: c1ccc(-c2ccc3c4c2cccc4c2cccc4oc5ccccc5n3-c42)cc1]
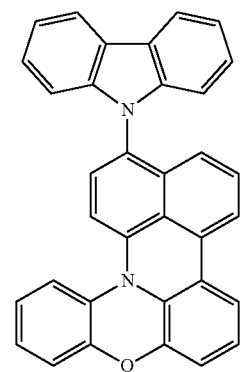 [SMILES: c1ccc2c(c1)oc1cccc3c1-n2c1ccc(-n2c4ccccc4c4ccccc42)c2cccc3c21]

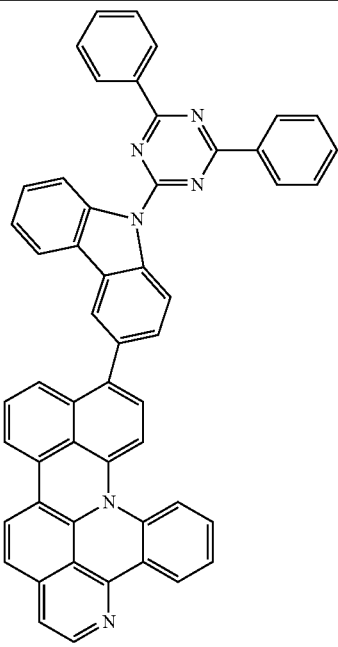
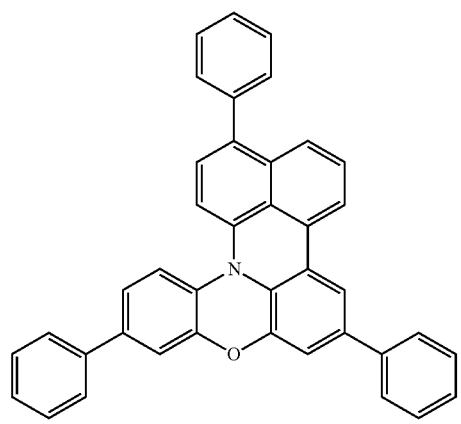 [SMILES: c1ccc(-c2ccc3c(c2)oc2cc(-c4ccccc4)cc4c2-n3c2ccc(-c3ccccc3)c3cccc4c32)cc1]
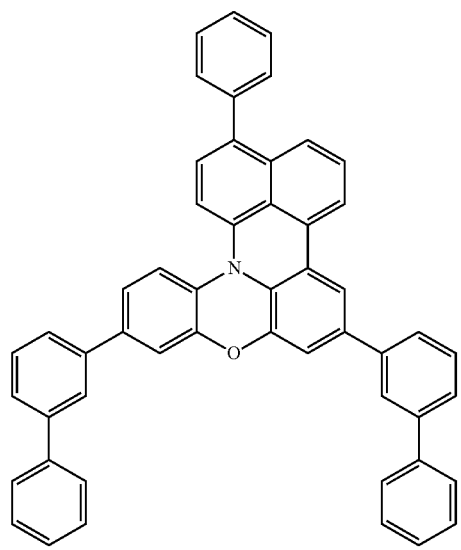 [SMILES: c1ccc(-c2cccc(-c3ccc4c(c3)oc3cc(-c5cccc(-c6ccccc6)c5)cc5c3-n4c3ccc(-c4ccccc4)c4cccc5c43)c2)cc1]

-continued
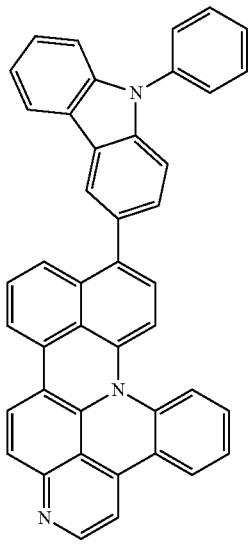 [SMILES: c1ccc(-n2c3ccccc3c3cc(-c4ccc5c6c(cccc46)-c4ccc6nccc7c6c4N5c4ccccc4-7)ccc32)cc1]
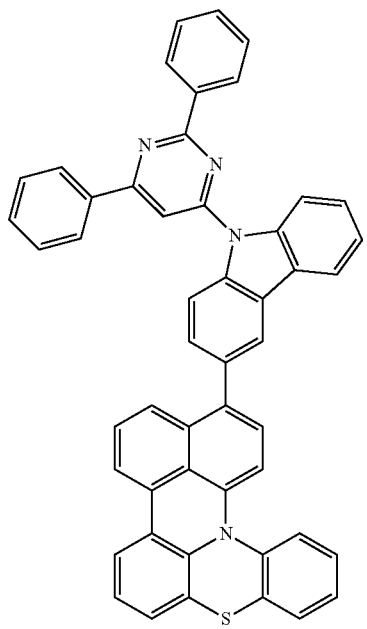 [SMILES: c1ccc(-c2cc(-n3c4ccccc4c4cc(-c5ccc6c7c5cccc7c5cccc7sc8ccccc8n6-c75)ccc43)nc(-c3ccccc3)n2)cc1]
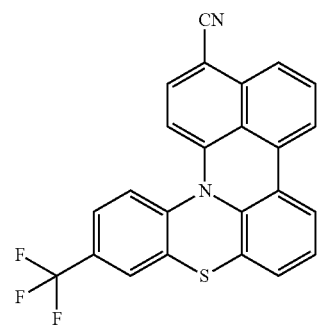 [SMILES: N#Cc1ccc2c3c1cccc3c1cccc3sc4cc(C(F)(F)F)ccc4n2-c31]

-continued
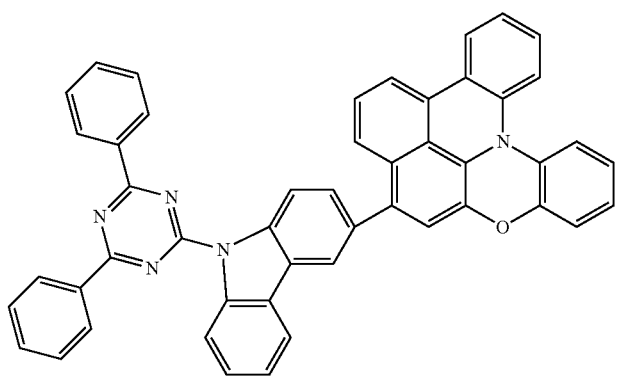 [SMILES: c1ccc(-c2nc(-c3ccccc3)nc(-n3c4ccccc4c4cc(-c5cc6oc7ccccc7n7c8ccccc8c8cccc5c8c6-7)ccc43)n2)cc1]
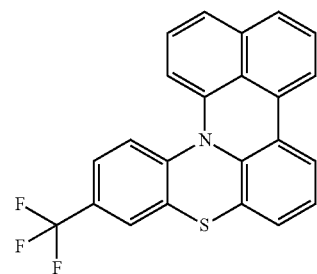 [SMILES: FC(F)(F)c1ccc2c(c1)sc1cccc3c1-n2c1cccc2cccc3c21]
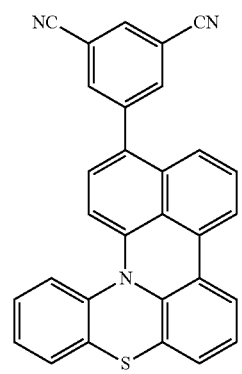 [SMILES: N#Cc1cc(C#N)cc(-c2ccc3c4c2cccc4c2cccc4sc5ccccc5n3-c42)c1]
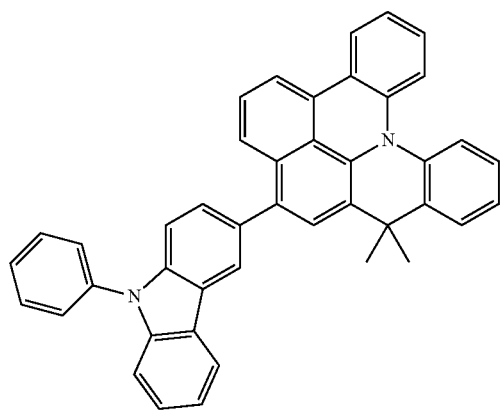 [SMILES: CC1(C)c2ccccc2N2c3ccccc3-c3cccc4c(-c5ccc6c(c5)c5ccccc5n6-c5ccccc5)cc1c2c34]

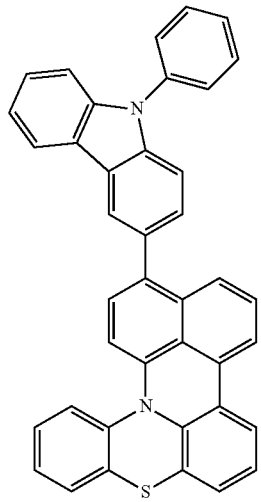 [SMILES: c1ccc(-n2c3ccccc3c3cc(-c4ccc5c6c4cccc6c4cccc6sc7ccccc7n5-c64)ccc32)cc1]
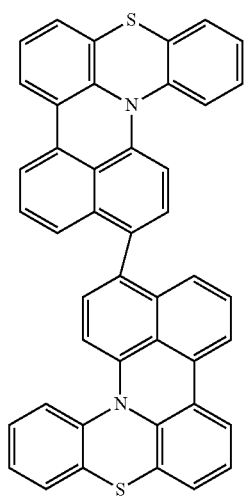 [SMILES: c1ccc2c(c1)sc1cccc3c1-n2c1ccc(-c2ccc4c5c2cccc5c2cccc5sc6ccccc6n4-c52)c2cccc3c21]
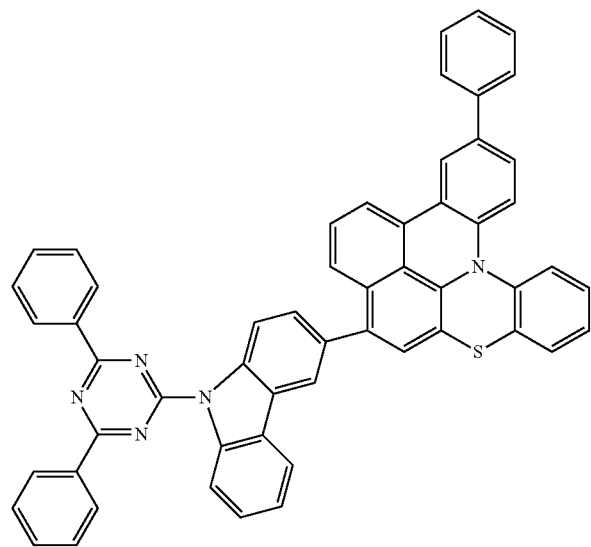 [SMILES: c1ccc(-c2ccc3c(c2)c2cccc4c(-c5ccc6c(c5)c5ccccc5n6-c5nc(-c6ccccc6)nc(-c6ccccc6)n5)cc5sc6ccccc6n3-c5c42)cc1]

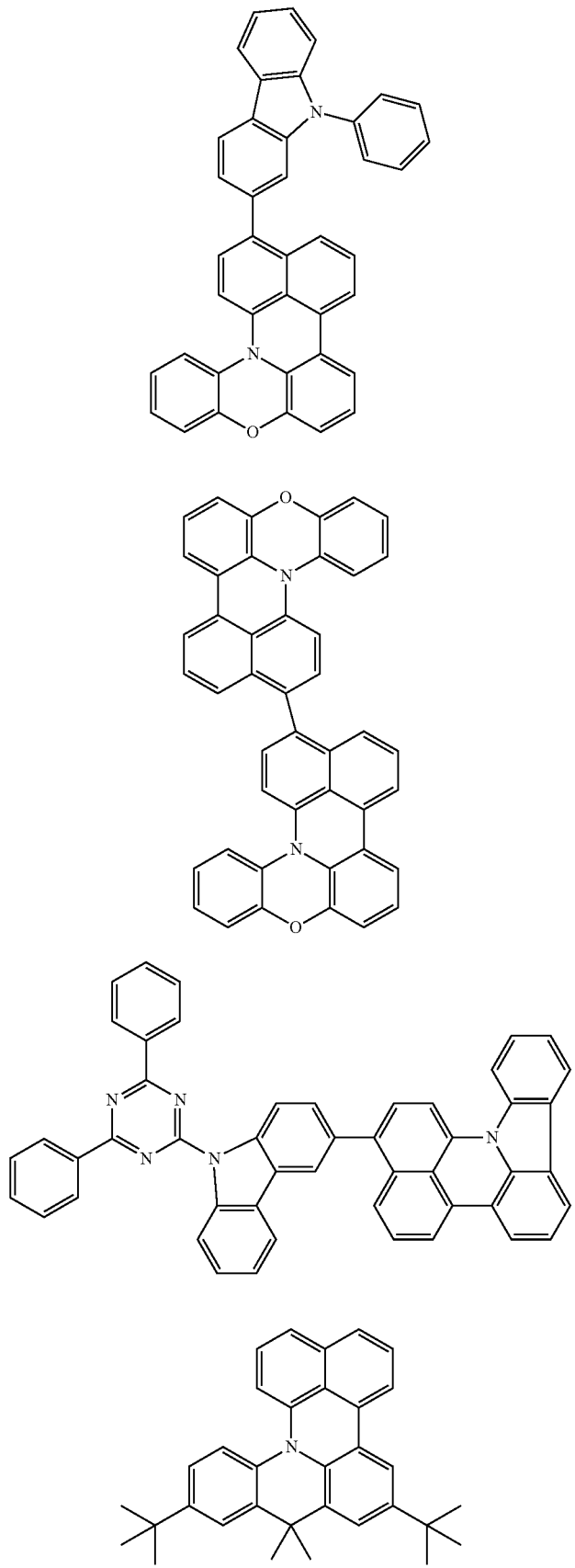

-continued
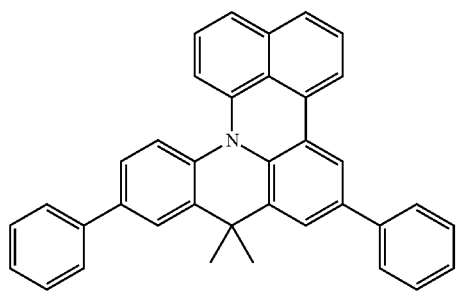 [SMILES: CC1(C)c2cc(-c3ccccc3)ccc2N2c3c(cc(-c4ccccc4)cc31)-c1cccc3cccc2c13]
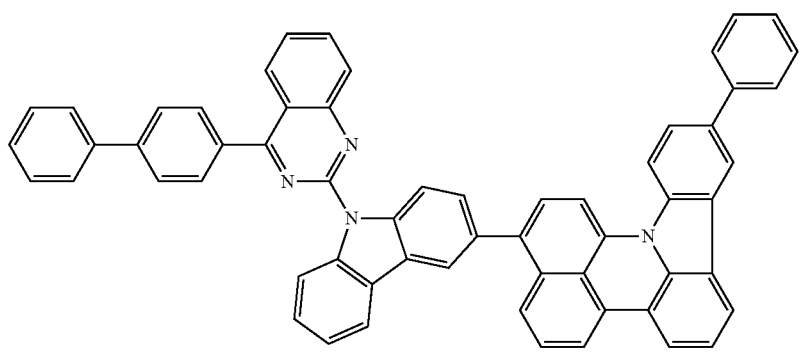 [SMILES: c1ccc(-c2ccc(-c3nc(-n4c5ccccc5c5cc(-c6ccc7c8c6cccc8c6cccc8c9cc(-c%10ccccc%10)ccc9n7c68)ccc54)nc4ccccc34)cc2)cc1]
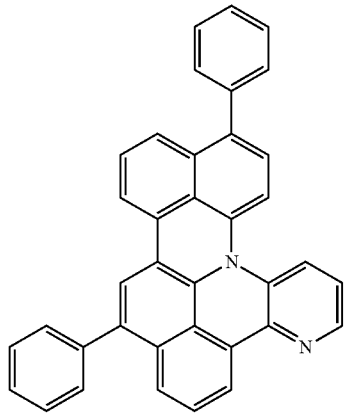 [SMILES: c1ccc(-c2ccc3c4c(cccc24)-c2cc(-c4ccccc4)c4cccc5c4c2N3c2cccnc2-5)cc1]
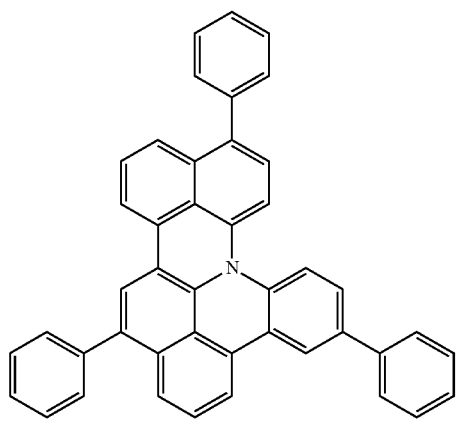 [SMILES: c1ccc(-c2ccc3c(c2)-c2cccc4c(-c5ccccc5)cc5c(c24)N3c2ccc(-c3ccccc3)c3cccc-5c23)cc1]

-continued
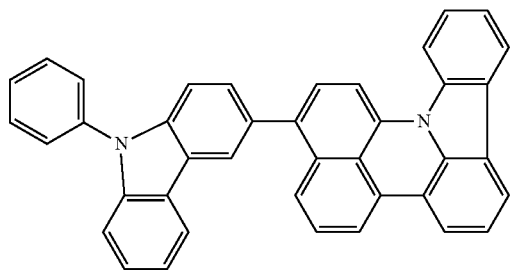 [SMILES: c1ccc(-n2c3ccccc3c3cc(-c4ccc5c6c4cccc6c4cccc6c7ccccc7n5c46)ccc32)cc1]
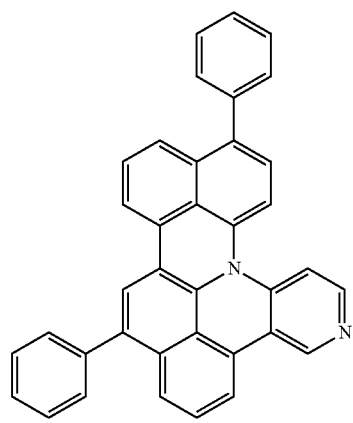 [SMILES: c1ccc(-c2ccc3c4c(cccc24)-c2cc(-c4ccccc4)c4cccc5c4c2N3c2ccncc2-5)cc1]
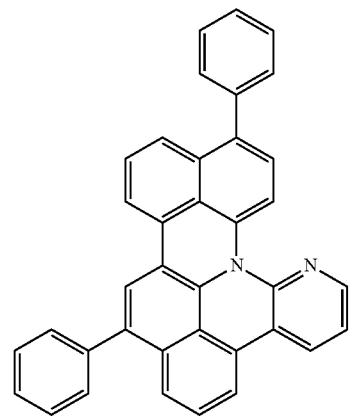 [SMILES: c1ccc(-c2ccc3c4c(cccc24)-c2cc(-c4ccccc4)c4cccc5c4c2N3c2ncccc2-5)cc1]
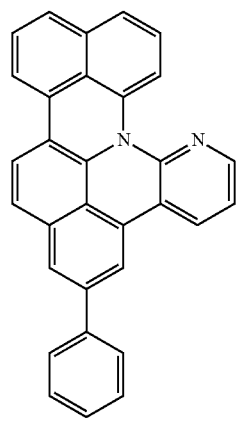 [SMILES: c1ccc(-c2cc3c4c5c(ccc4c2)-c2cccc4cccc(c24)N5c2ncccc2-3)cc1]

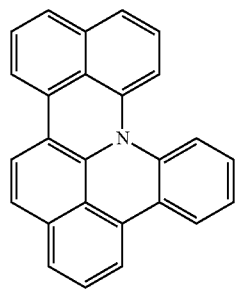 [SMILES: c1ccc2c(c1)-c1cccc3ccc4c(c13)N2c1cccc2cccc-4c12]
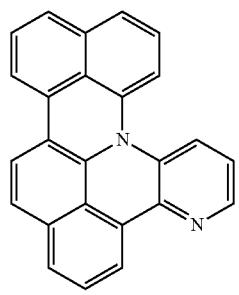 [SMILES: c1cnc2c(c1)N1c3cccc4cccc(c34)-c3ccc4cccc-2c4c31]
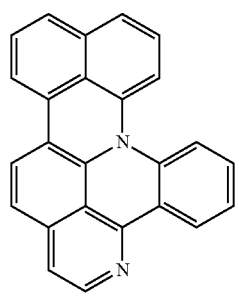 [SMILES: c1ccc2c(c1)-c1nccc3ccc4c(c13)N2c1cccc2cccc-4c12]
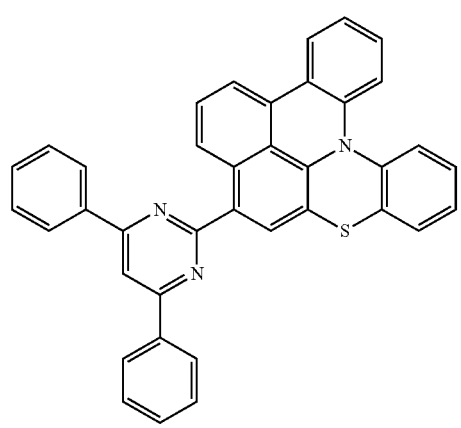 [SMILES: c1ccc(-c2cc(-c3ccccc3)nc(-c3cc4sc5ccccc5n5c6ccccc6c6cccc3c6c4-5)n2)cc1]

-continued
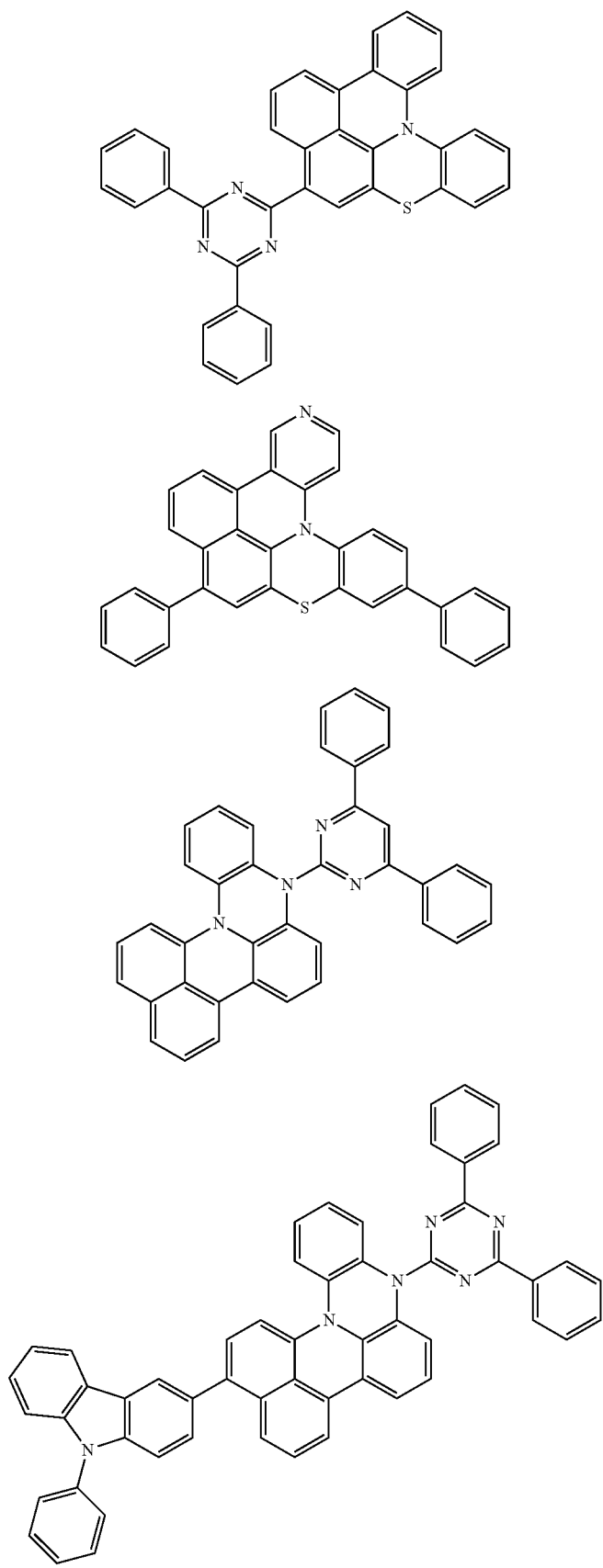

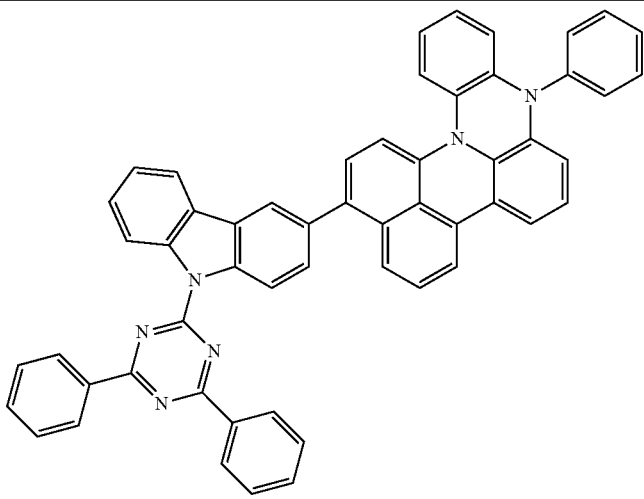

The base structure of the compounds of the invention can be prepared by the routes outlined in the schemes which follow. The individual synthesis steps, for example C—C coupling reactions according to Suzuki, C—N coupling reactions according to Hartwig-Buchwald or cyclization reactions, are known in principle to those skilled in the art. Further information relating to the synthesis of the compounds of the invention can be found in the synthesis examples. Scheme 1 shows the synthesis of compounds with m=1. Scheme 2 shows the synthesis of compounds with n=1 and $Y^2$=single bond. Scheme 3 shows the synthesis of compounds with n=1 and $Y^2$=NR', C(R')$_2$, O or S.

Scheme 1

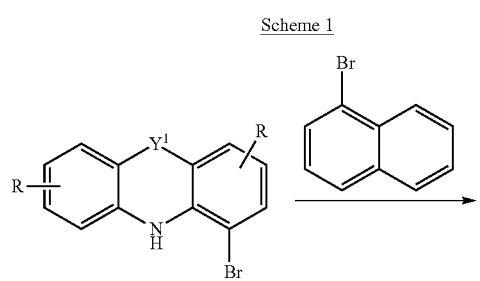

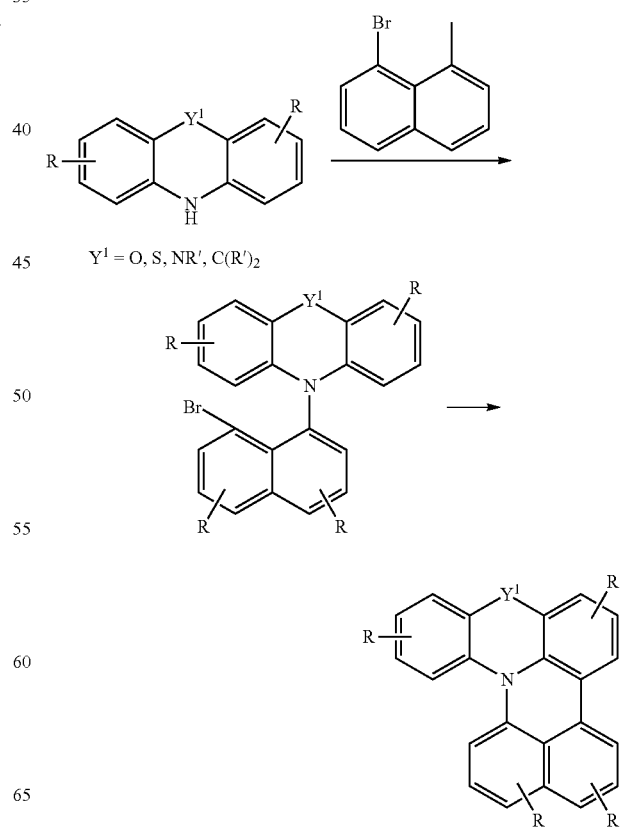

143
-continued
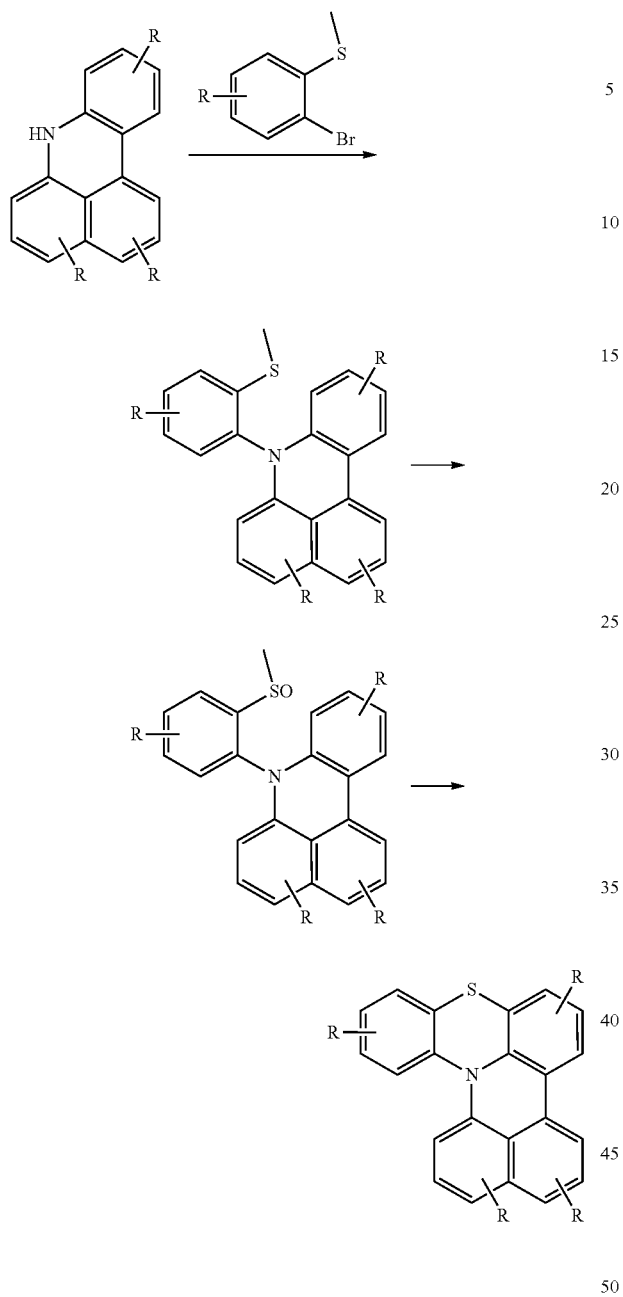
144
-continued
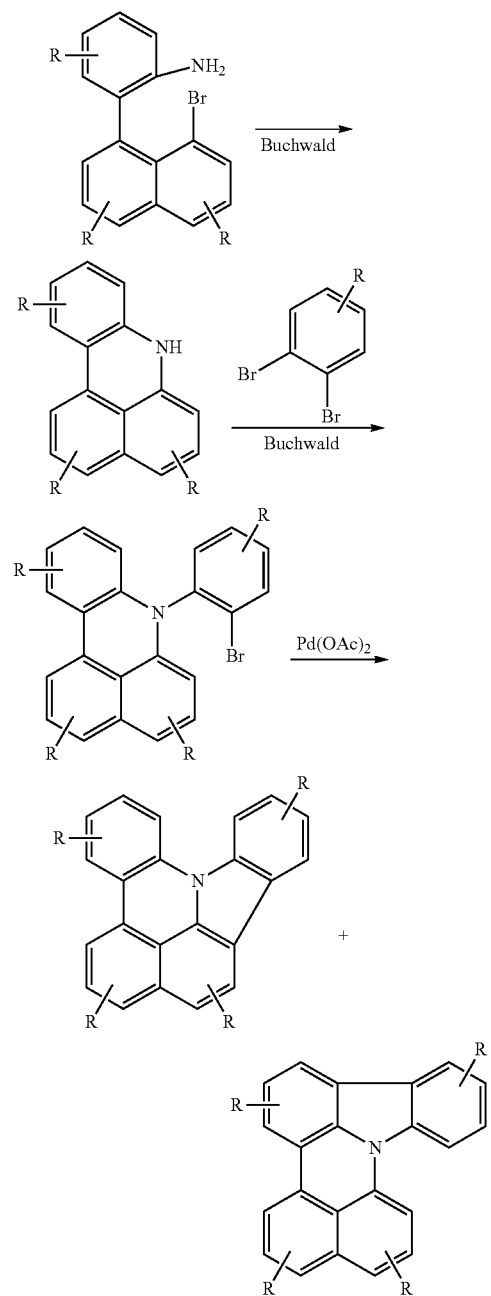
Scheme 2
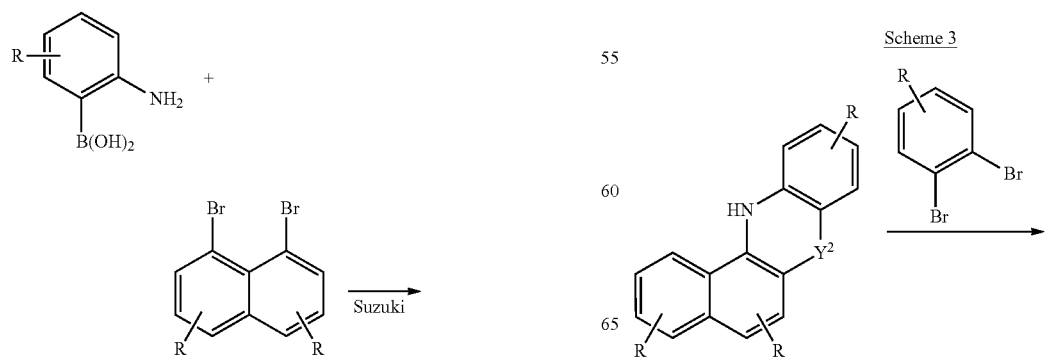
Scheme 3
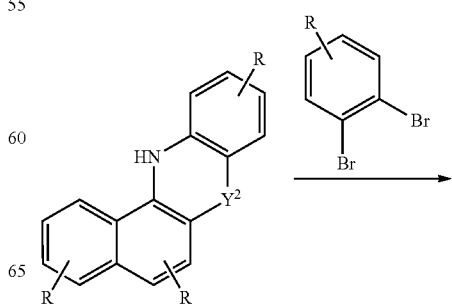

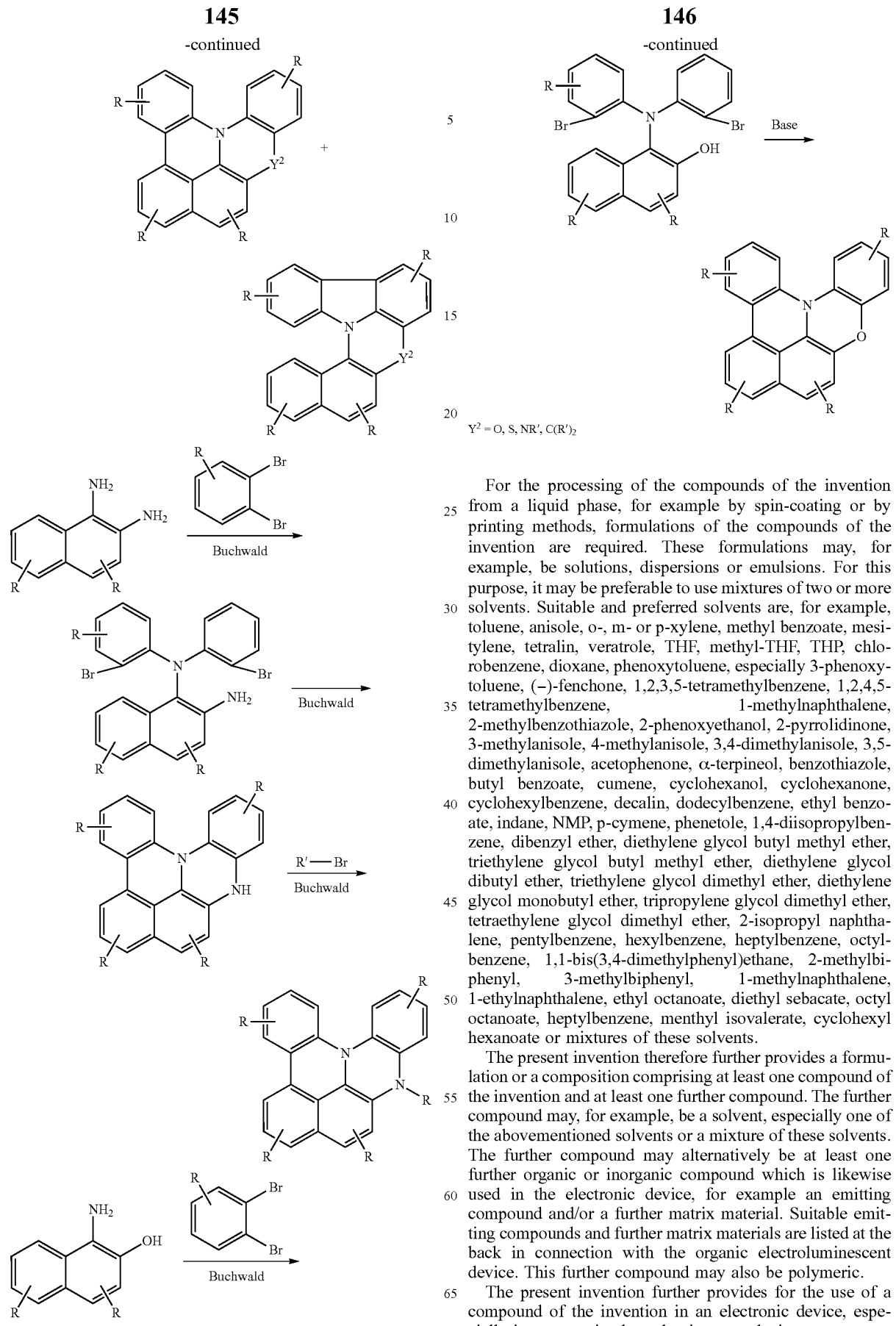

$Y^2$ = O, S, NR′, C(R′)$_2$

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropyl naphthalene, pentylbenzene, hexylbenzene, heptylbenzene, octylbenzene, 1,1-bis(3,4-dimethylphenyl)ethane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation or a composition comprising at least one compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound and/or a further matrix material. Suitable emitting compounds and further matrix materials are listed at the back in connection with the organic electroluminescent device. This further compound may also be polymeric.

The present invention further provides for the use of a compound of the invention in an electronic device, especially in an organic electroluminescent device.

The present invention still further provides an electronic device comprising at least one compound of the invention.

An electronic device in the context of the present invention is a device comprising at least one layer comprising at least one organic compound.

This component may also comprise inorganic materials or else layers formed entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETS), organic solar cells (O-SCs), dye-sensitized organic solar cells (DSSCs), organic optical detectors, organic photoreceptors, organic field-quench devices (O-FQDs), light-emitting electrochemical cells (LECs), organic laser diodes (O-lasers) and organic plasmon emitting devices, but preferably organic electroluminescent devices (OLEDs), more preferably phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission. The organic electroluminescent device of the invention may also be a tandem OLED, especially for white-emitting OLEDs.

The compound of the invention according to the above-detailed embodiments may be used in different layers, according to the exact structure. Preference is given to an organic electroluminescent device comprising a compound of formula (1) or the above-recited preferred embodiments in an emitting layer as matrix material for phosphorescent emitters or for emitters that exhibit TADF (thermally activated delayed fluorescence), especially for phosphorescent emitters. In addition, the compound of the invention can also be used in an electron transport layer and/or in a hole transport layer and/or in an exciton blocker layer and/or in a hole blocker layer. Particular preference is given to using the compound of the invention as matrix material for red-, orange- or yellow-phosphorescing emitters, especially for red-phosphorescing emitters, in an emitting layer or as electron transport material or hole blocker material in an electron transport layer or hole blocker layer.

When the compound of the invention is used as matrix material for a phosphorescent compound in an emitting layer, it is preferably used in combination with one or more phosphorescent materials (triplet emitters). Phosphorescence in the context of this invention is understood to mean luminescence from an excited state having higher spin multiplicity, i.e. a spin state >1, especially from an excited triplet state. In the context of this application, all luminescent complexes with transition metals or lanthanides, especially all iridium, platinum and copper complexes, shall be regarded as phosphorescent compounds.

The mixture of the compound of the invention and the emitting compound contains between 99% and 1% by volume, preferably between 98% and 10% by volume, more preferably between 97% and 60% by volume and especially between 95% and 80% by volume of the compound of the invention, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

A further preferred embodiment of the present invention is the use of the compound of the invention as matrix material for a phosphorescent emitter in combination with a further matrix material. Suitable matrix materials which can be used in combination with the inventive compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, triphenylene derivatives, for example according to WO 2012/048781, or dibenzofuran derivatives, for example according to WO 2015/169412, WO 2016/015810, WO 2016/023608, WO 2017/148564 or WO 2017/148565. It is likewise possible for a further phosphorescent emitter having shorter-wavelength emission than the actual emitter to be present as co-host in the mixture, or a compound not involved in charge transport to a significant extent, if at all, as described, for example, in WO 2010/108579.

Especially suitable in combination with the compound of the invention as co-matrix material are compounds which have a large bandgap and themselves take part at least not to a significant degree, if any at all, in the charge transport of the emitting layer. Such materials are preferably pure hydrocarbons. Examples of such materials can be found, for example, in WO 2009/124627 or in WO 2010/006680.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum.

Examples of the above-described emitters can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439 and the as yet unpublished application EP16179378.1. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Explicit examples of phosphorescent dopants are adduced in the following table:

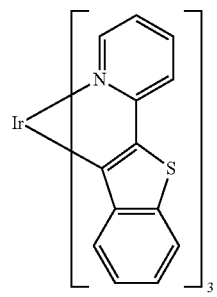

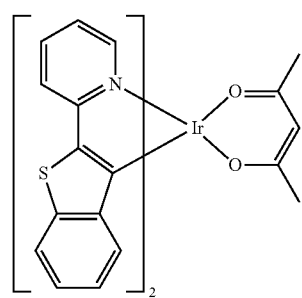

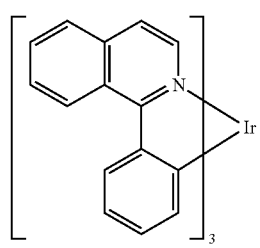

-continued

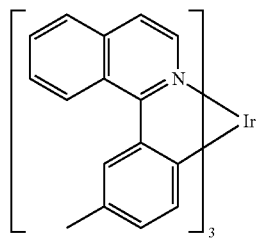

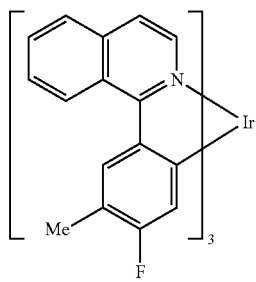

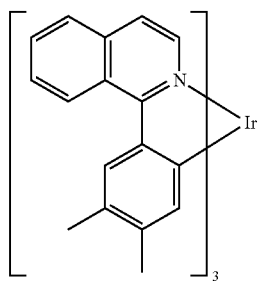

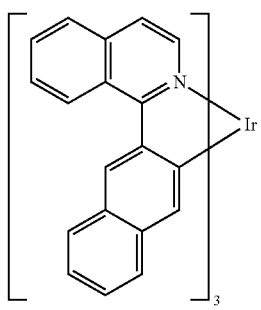

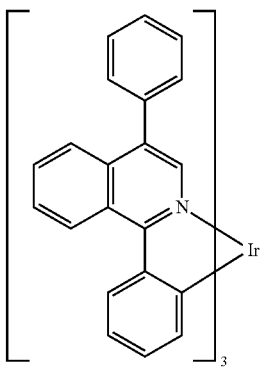

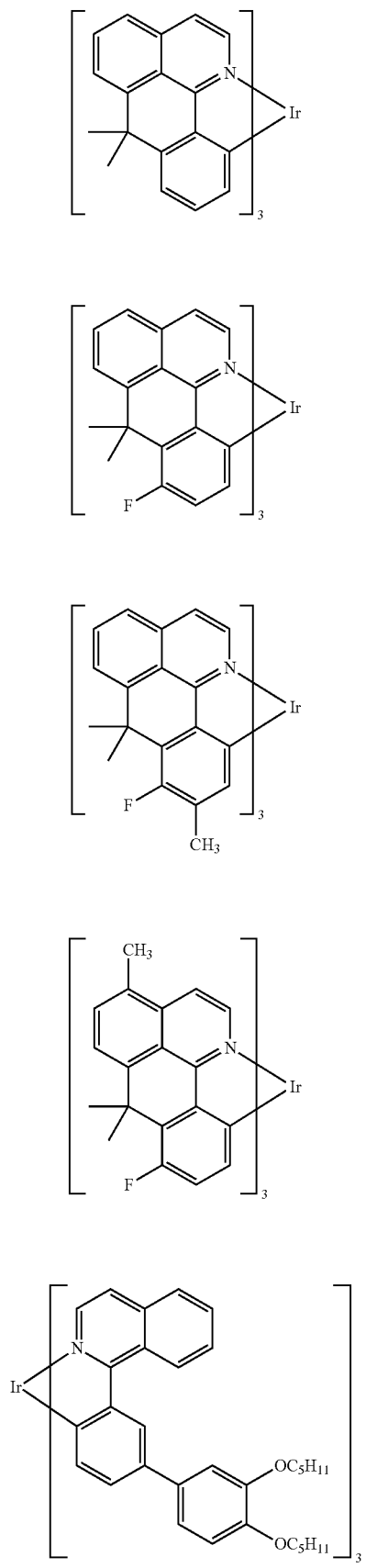
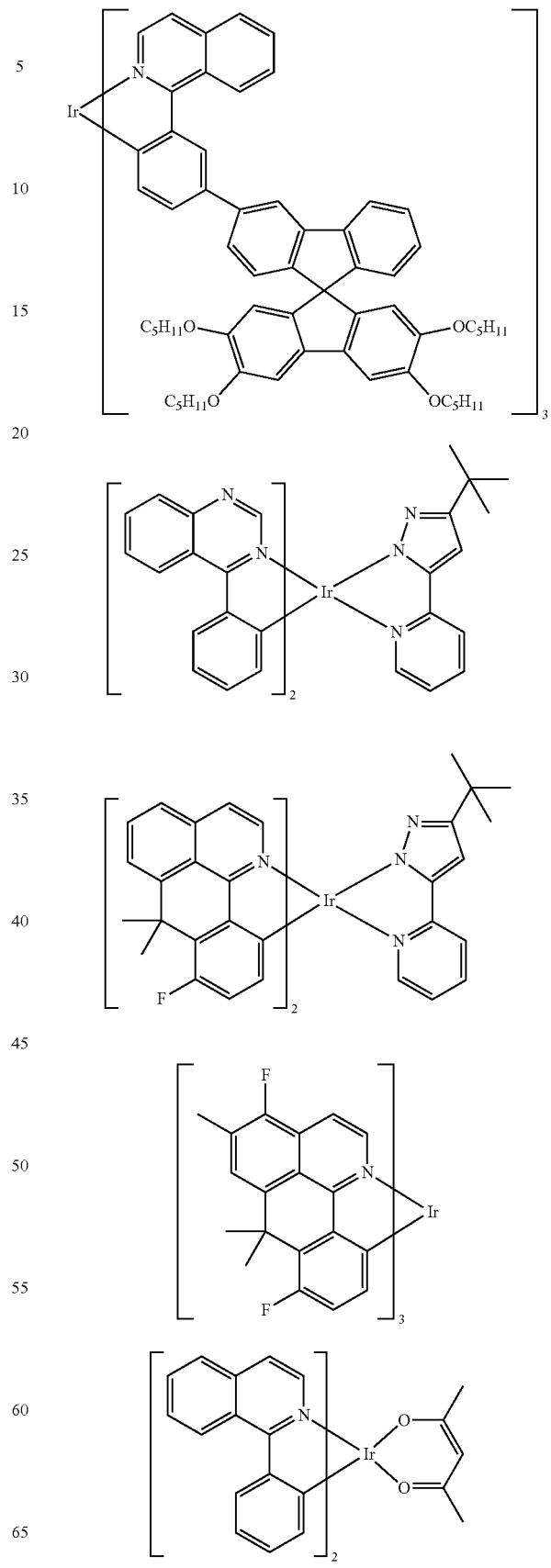

153
-continued
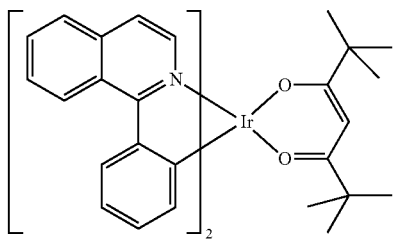
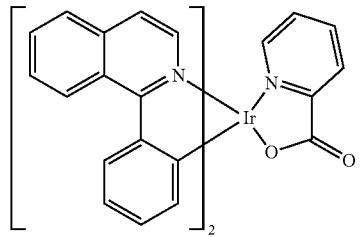
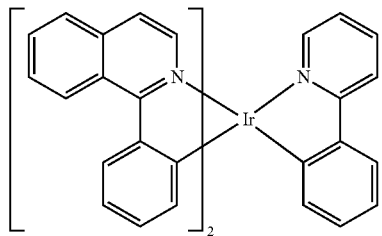
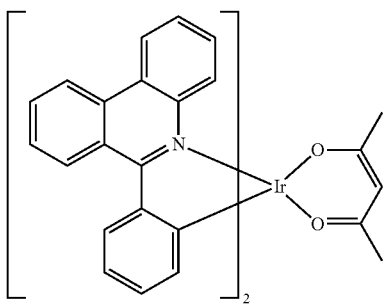
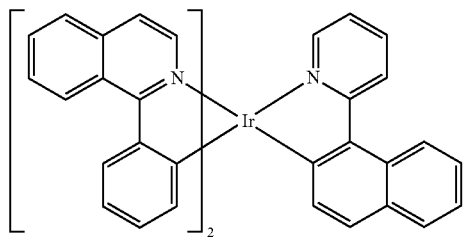
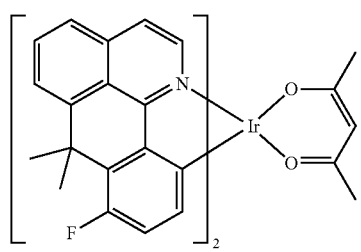
154
-continued
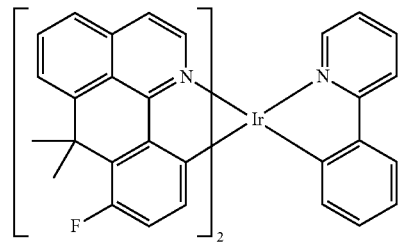
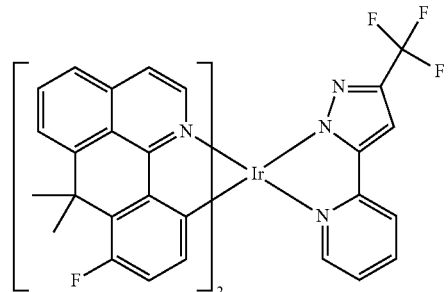
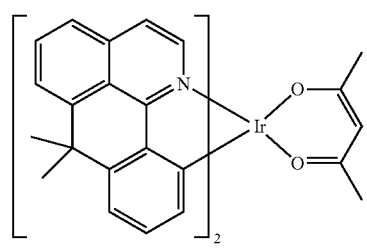
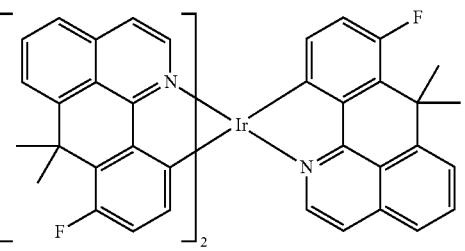
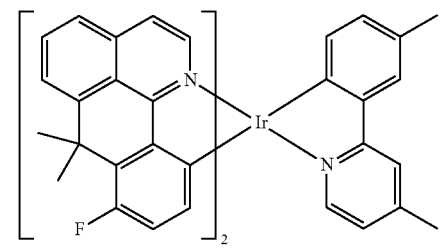
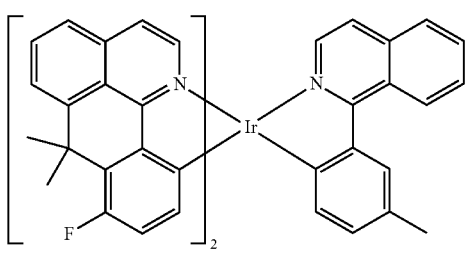

| 155 -continued | 156 -continued |
|---|---|
| 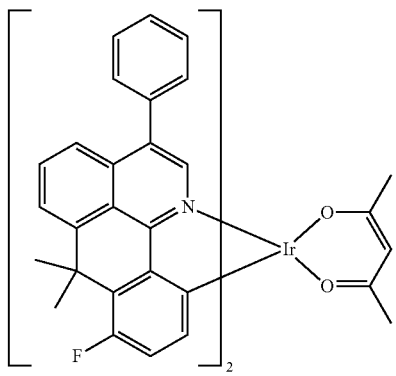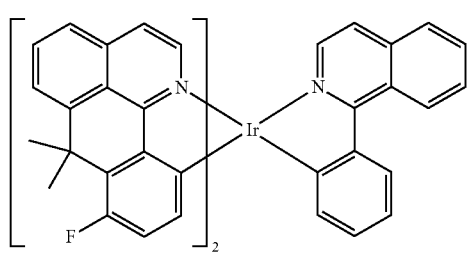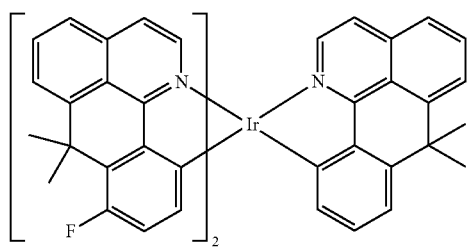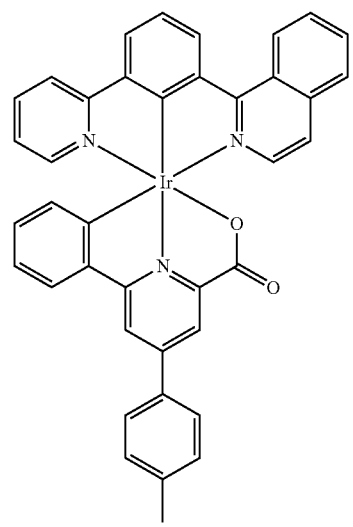 | 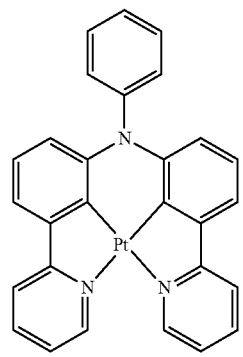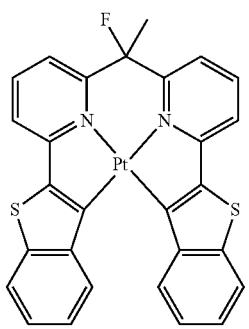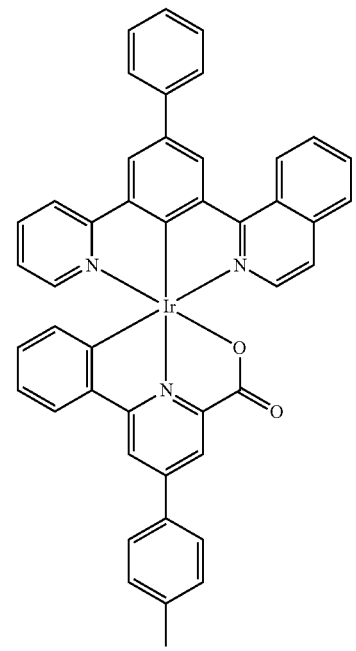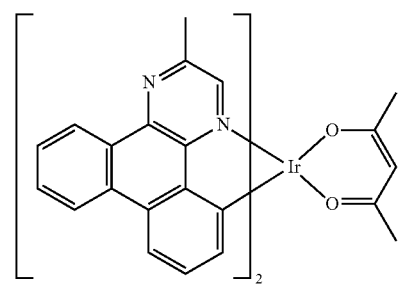 |

157
-continued
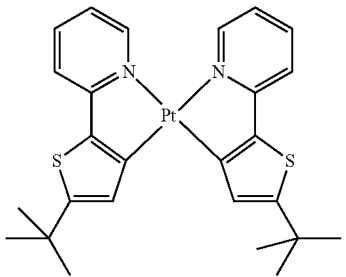
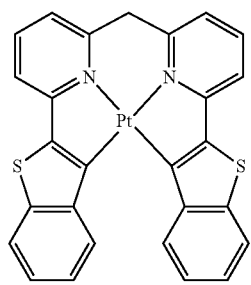
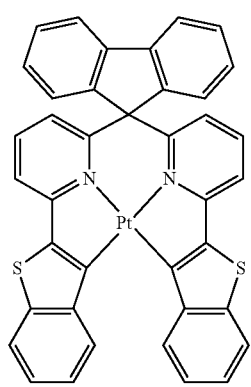
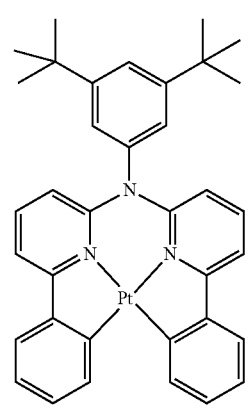
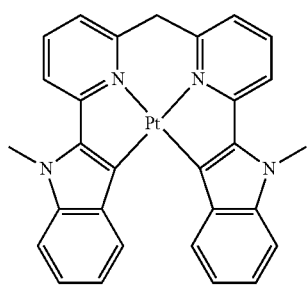
158
-continued
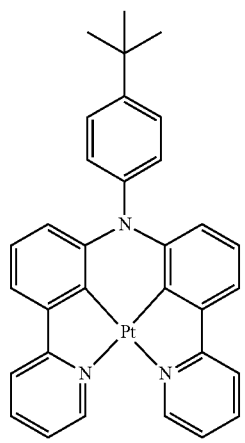
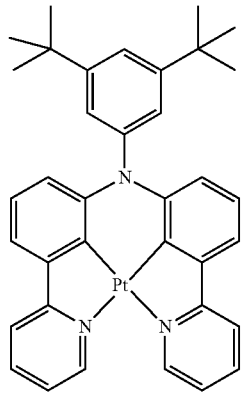
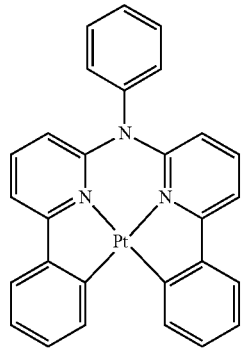
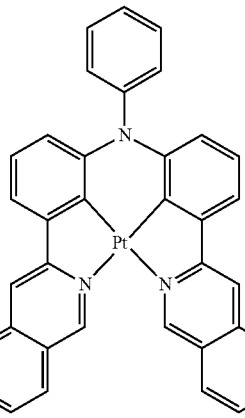

159
-continued
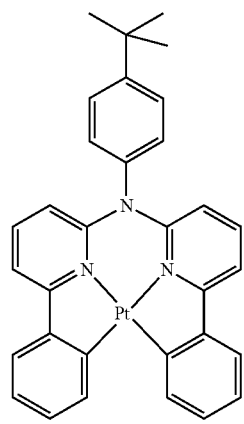
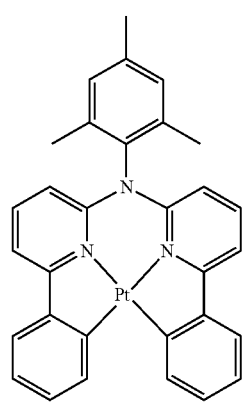
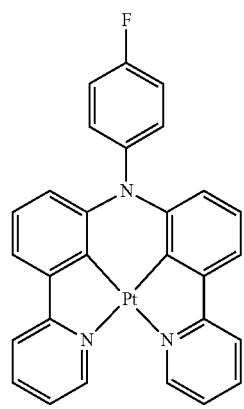
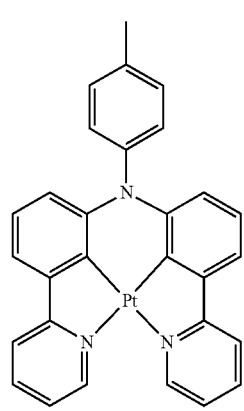
160
-continued
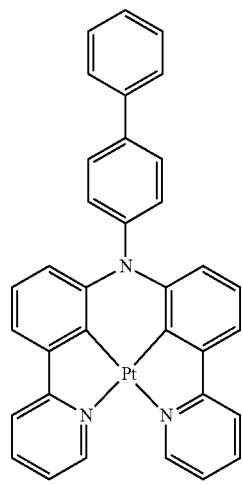
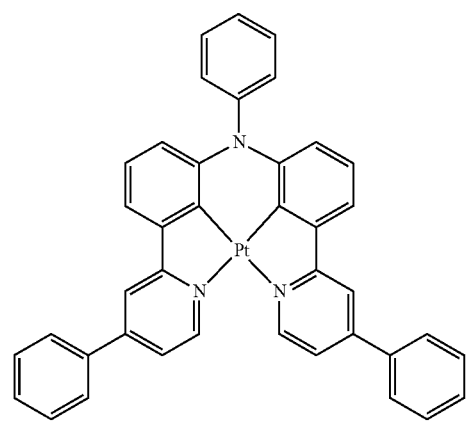
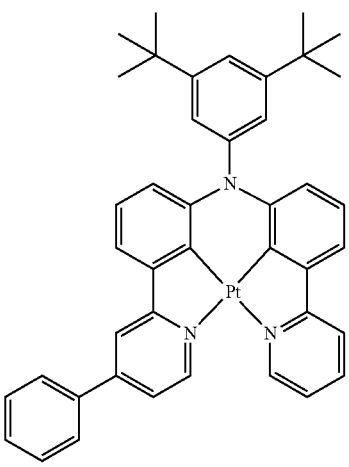

| 161 -continued | 162 -continued |
|---|---|
| 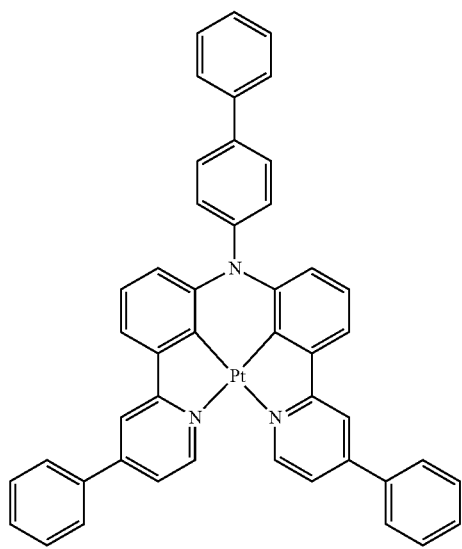 | 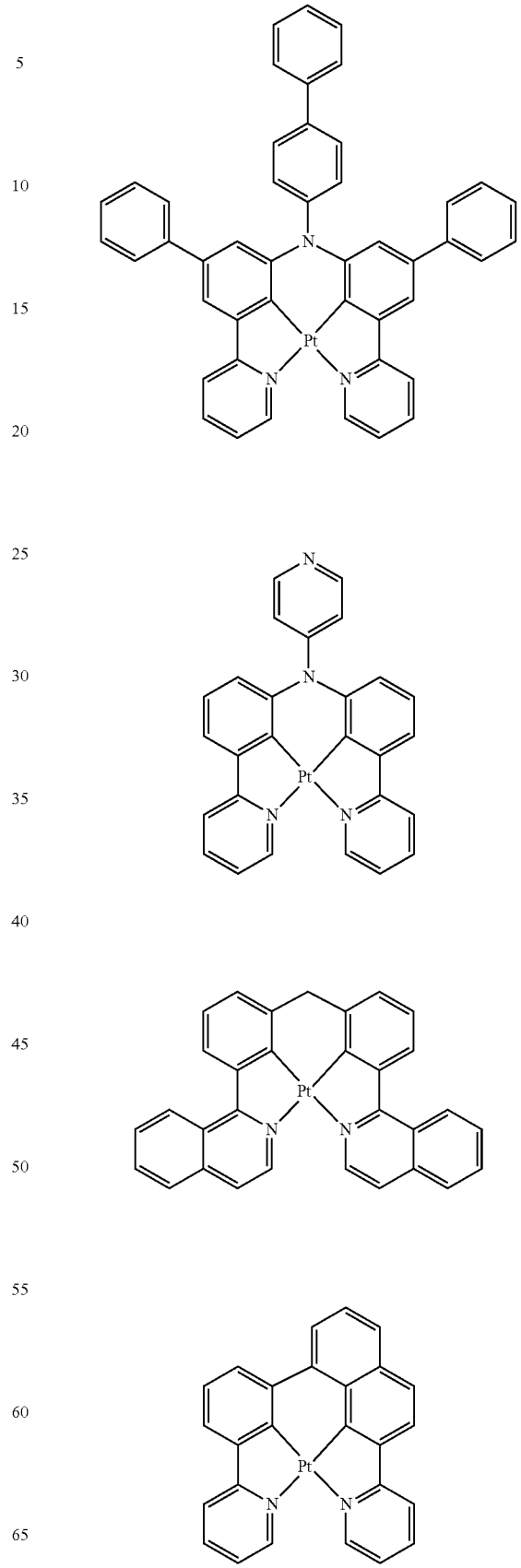 |

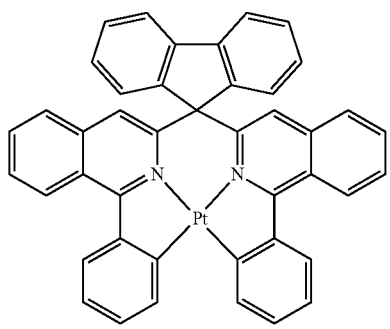
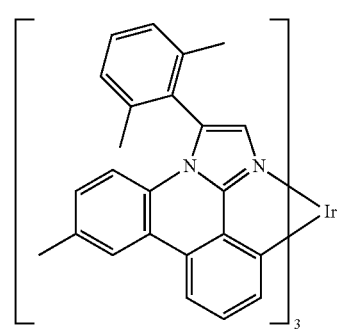
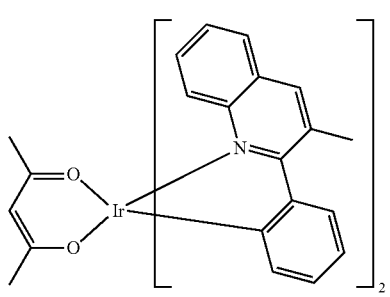
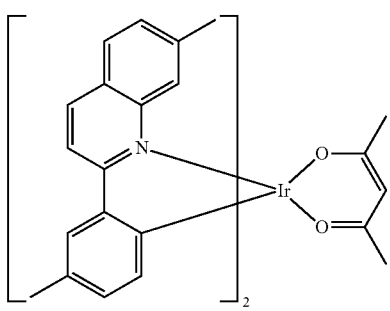
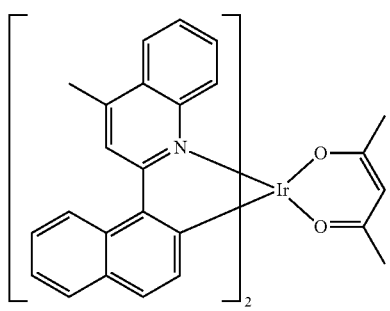
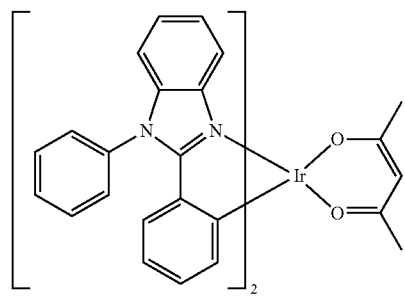
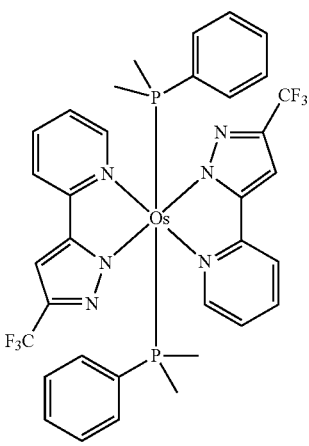
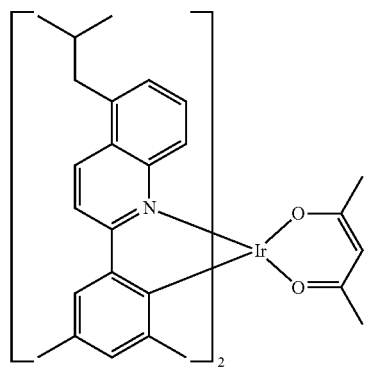
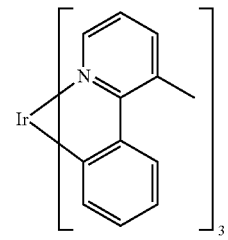
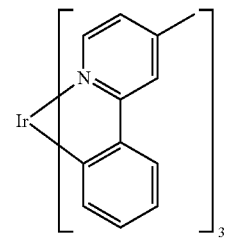

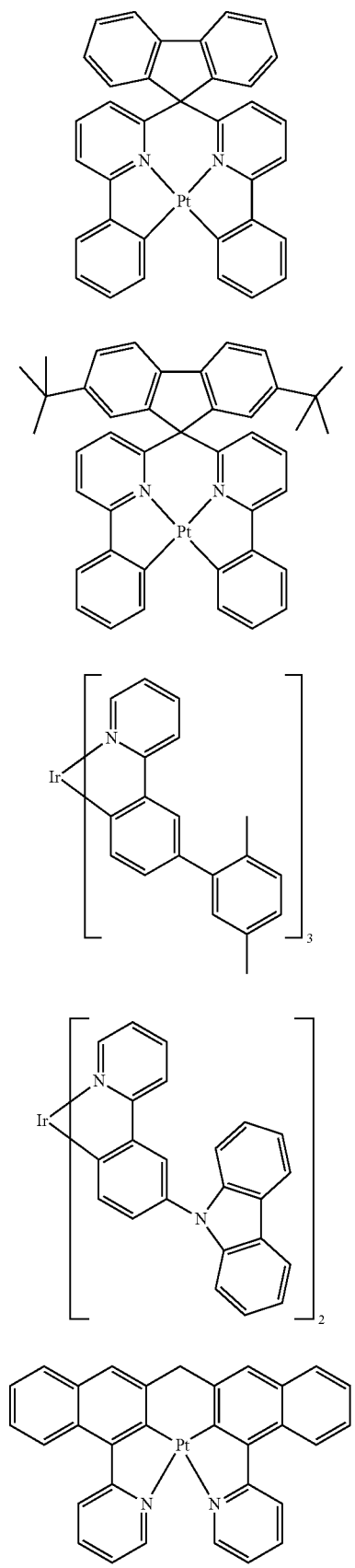

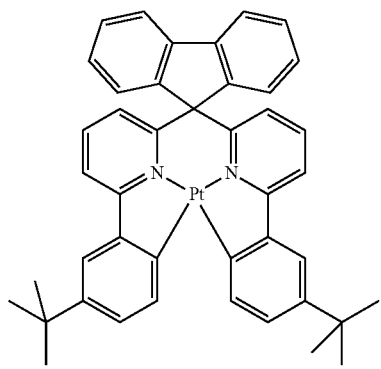
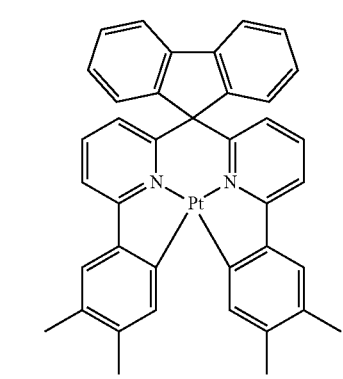
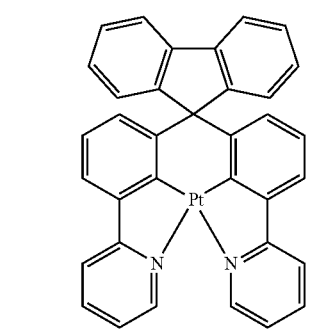
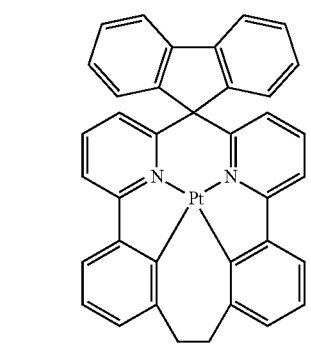
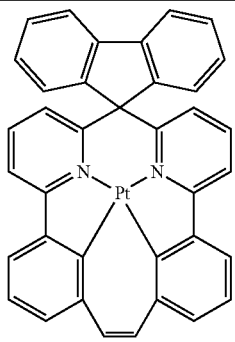
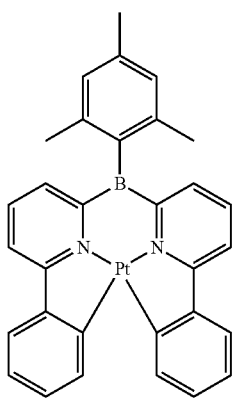
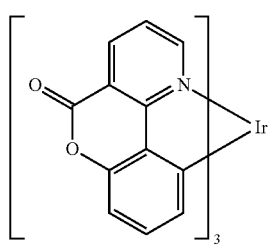
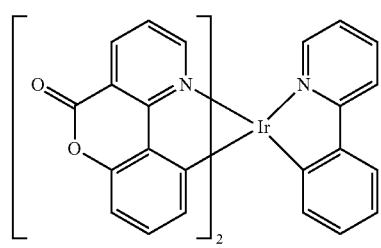
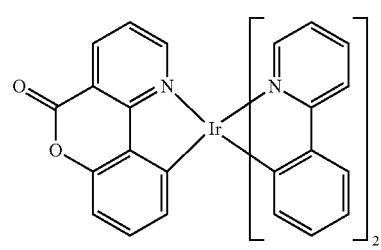

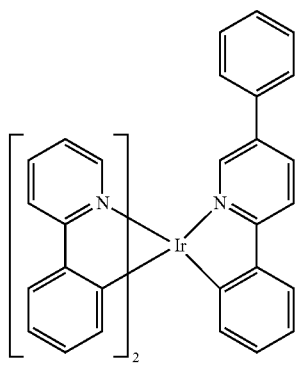
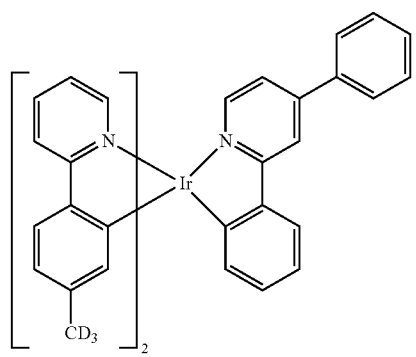
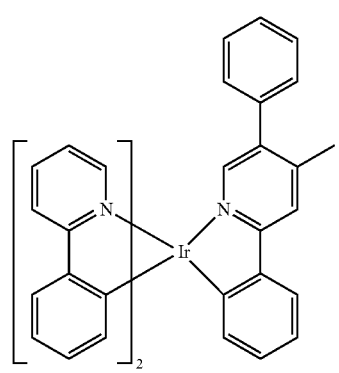
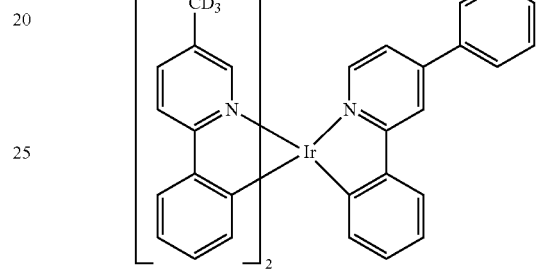
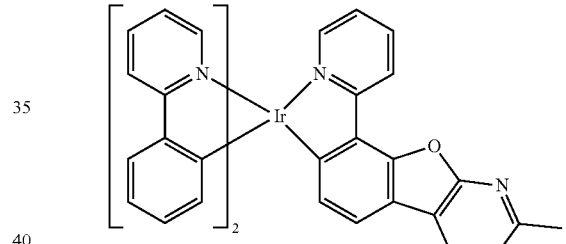
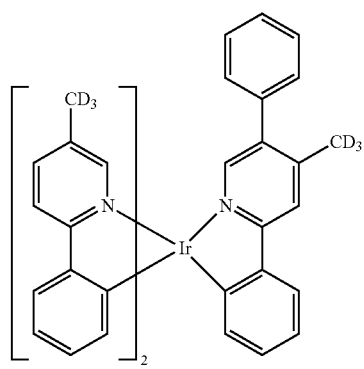
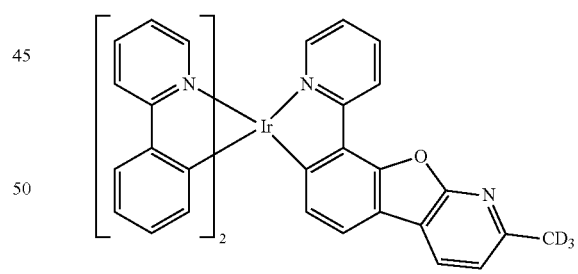
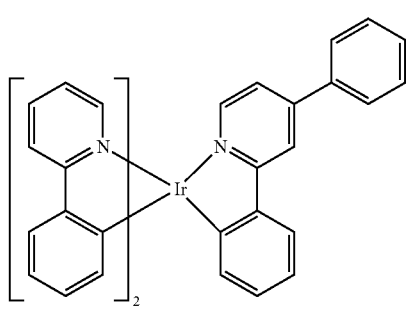
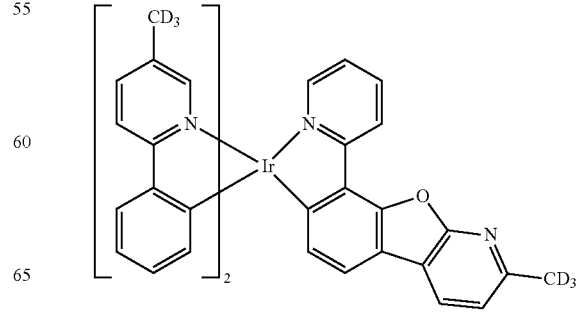

171
-continued
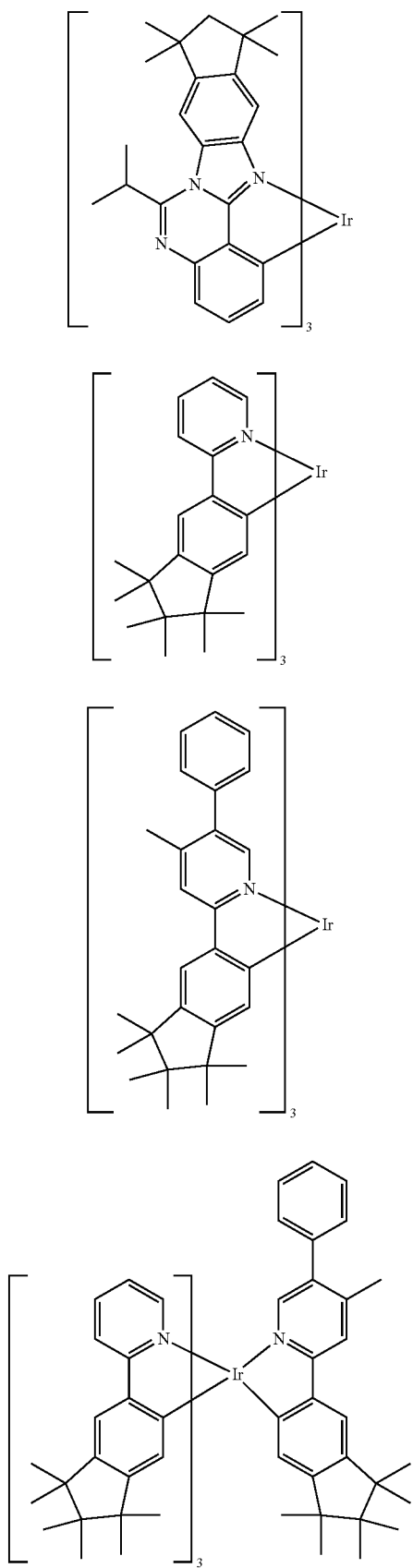
172
-continued
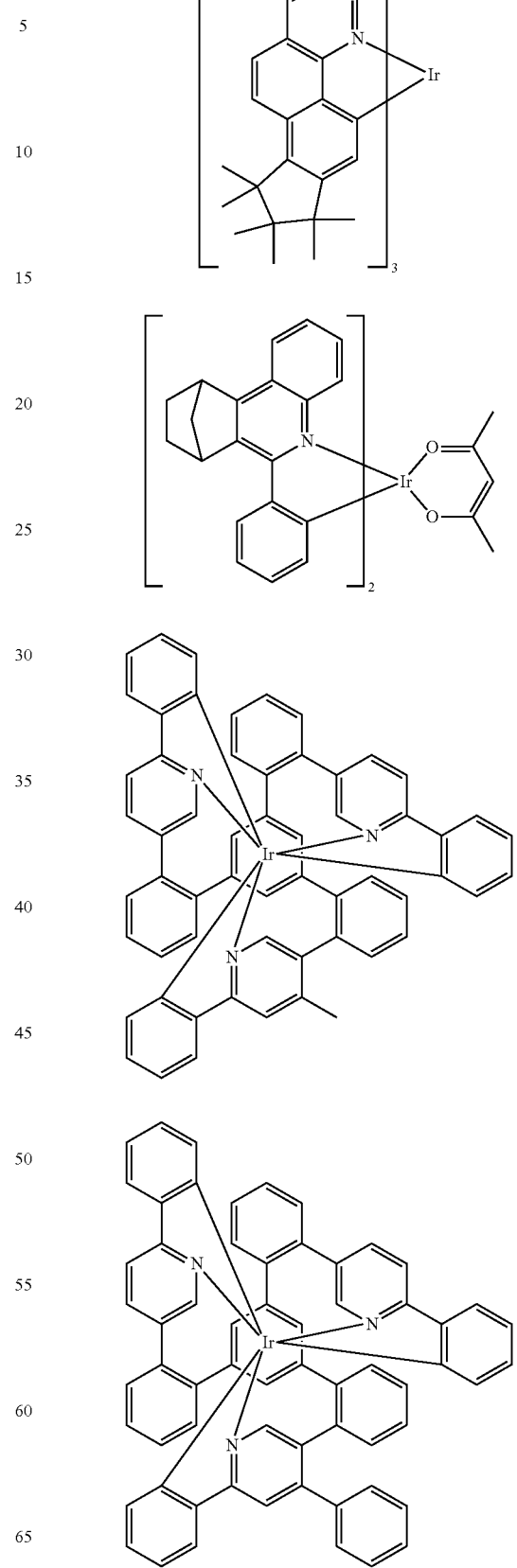

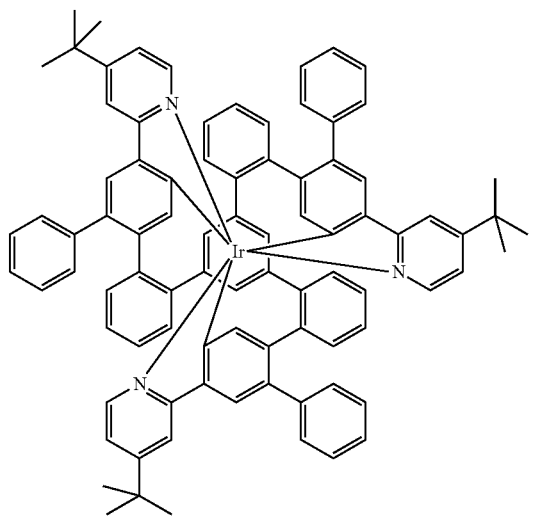

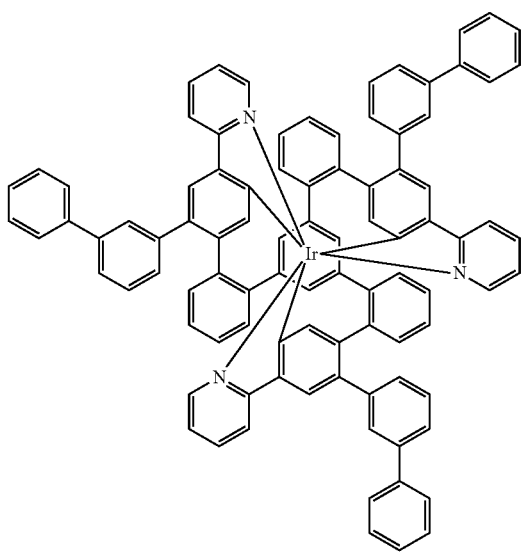

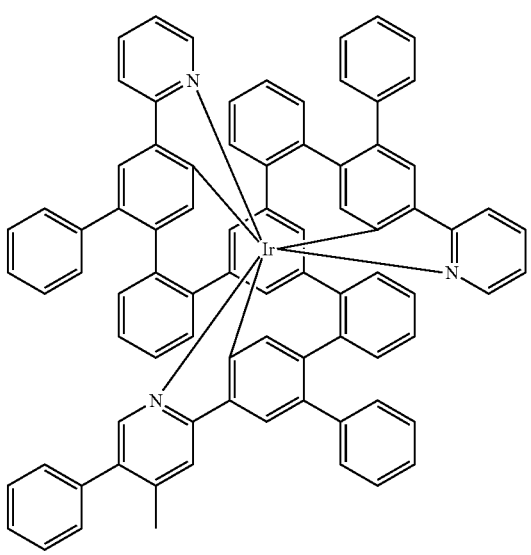

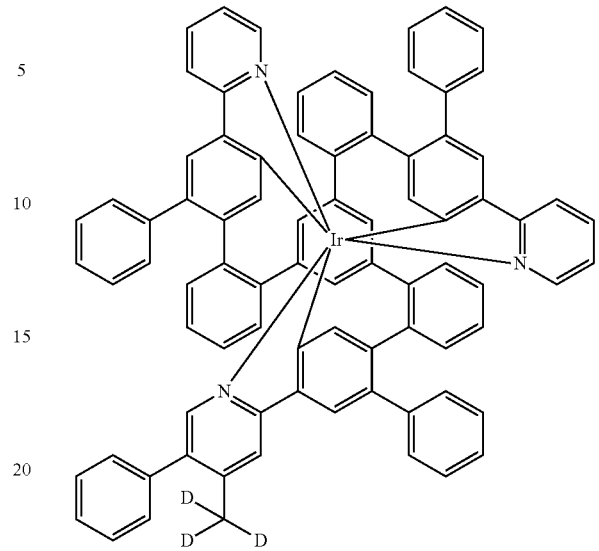

The compounds of the invention are especially also suitable as matrix materials for phosphorescent emitters in organic electroluminescent devices, as described, for example, in WO 98/24271, US 2011/0248247 and US 2012/0223633. In these multicolor display components, an additional blue emission layer is applied by vapor deposition over the full area to all pixels, including those having a color other than blue. It has been found that, surprisingly, the compounds of the invention, when they are used as matrix materials for the red and/or green pixel, especially for the red pixel, still lead to very good emission together with the blue emission layer applied by vapor deposition.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In the further layers of the organic electroluminescent device of the invention, it is possible to use any materials as typically used according to the prior art. The person skilled in the art will therefore be able, without exercising inventive skill, to use any materials known for organic electroluminescent devices in combination with the inventive compounds of formula (1) or the above-recited preferred embodiments.

Additionally preferred is an organic electroluminescent device characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. However, it is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured.

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution.

In addition, hybrid methods are possible, in which, for example, one or more layers are applied from solution and one or more further layers are applied by vapor deposition.

These methods are known in general terms to those skilled in the art and can be applied by those skilled in the art without exercising inventive skill to organic electroluminescent devices comprising the compounds of the invention.

The compounds of the invention and the organic electroluminescent devices of the invention are notable for one or more of the following surprising advantages over the prior art:
1. The compounds of the invention, used as matrix material for phosphorescent emitters, lead to long lifetimes.
2. The compounds of the invention lead to high efficiencies. This is especially true when the compounds are used as matrix material for a phosphorescent emitter.
3. The compounds of the invention lead to low operating voltages. This is especially true when the compounds are used as matrix material for a phosphorescent emitter.

These abovementioned advantages are not accompanied by a deterioration in the further electronic properties.

The invention is illustrated in more detail by the examples which follow, without any intention of restricting it thereby. The person skilled in the art will be able to use the information given to execute the invention over the entire scope disclosed and to prepare further compounds of the invention without exercising inventive skill and to use them in electronic devices or to employ the process of the invention.

EXAMPLES

The syntheses which follow, unless stated otherwise, are conducted under a protective gas atmosphere in dried solvents. The solvents and reagents can be purchased from ALDRICH or ABCR. The numbers given for the reactants that are not commercially available are the corresponding CAS numbers.

a) 1-Chloro-7-(9-phenyl-9H-carbazol-3-yl)-10H-phenothiazine

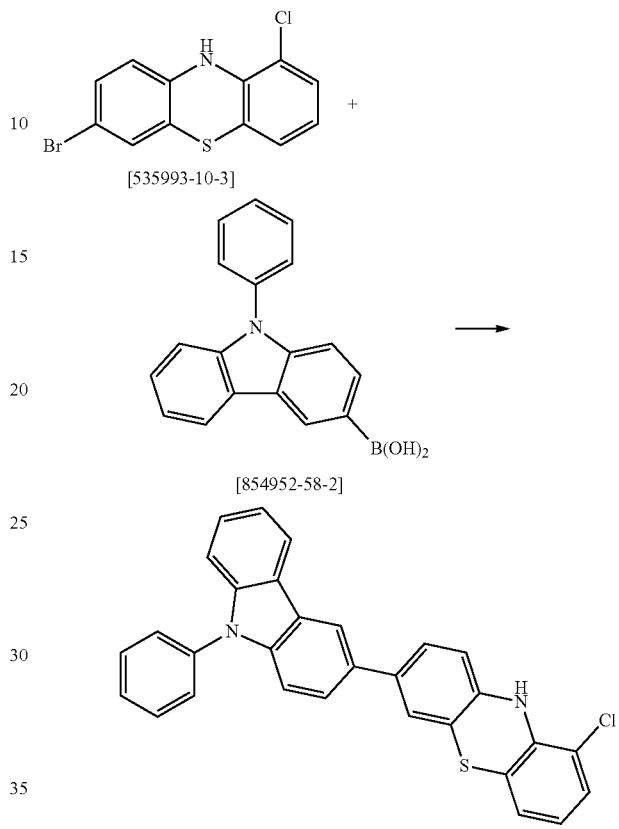

20.9 g (67 mmol) of 7-bromo-1-chloro-10H-phenothiazine, 17 g (664 mmol) of 2-N-phenylcarbazole-3-boronic acid and 13.7 g (100 mmol) of sodium tetraborate are dissolved in 100 ml of THF and 60 ml of water and degassed. 0.9 g (1.3 mmol) of bis(triphenylphosphine)palladium(II) chloride and 1 g (20 mmol) of hydrazinium hydroxide are added. The reaction mixture is then stirred under a protective gas atmosphere at 70° C. for 48 h. The cooled solution is supplemented with toluene, washed repeatedly with water, dried and concentrated. The product is purified via column chromatography on silica gel with toluene/heptane (1:2). Yield: 19.8 g (40 mmol), 62% of theory.

The following compounds are prepared in an analogous manner:

| | Reactant 1 | Reactant 2 | Product | Yield |
|---|---|---|---|---|
| 1a | [535993-10-3] | [162607-19-4] | | 34% |
| 2a | [535993-10-3] | [1379585-25-7] | | 36% |

-continued

| Reactant 1 | Reactant 2 | Product | Yield |
|---|---|---|---|
| 3a [535993-10-3] | [1379585-25-7] | | 48% |
| 4a [535993-10-3] | 1246562-39-9 | | 46% |
| 5a [535993-10-3] | [402936-15-6] | | 47% |

| | Reactant 1 | Reactant 2 | Product | Yield |
|---|---|---|---|---|
| 6a | [535993-10-3] | 854952-60-6 | | 44% |
| 7a | [535993-10-3] | 1357573-03-5 | | 38% |

| | Reactant 1 | Reactant 2 | Product | Yield |
|---|---|---|---|---|
| 8a | 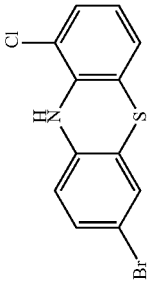 [535993-10-3] | 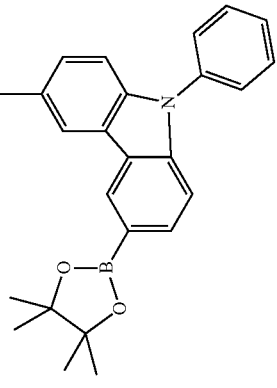 [1572537-61-1] | 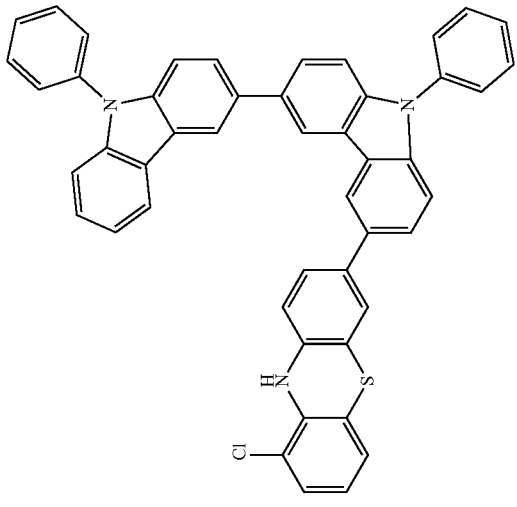 | |
| 9a | 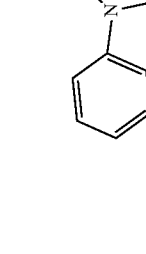 [1705595-53-4] | 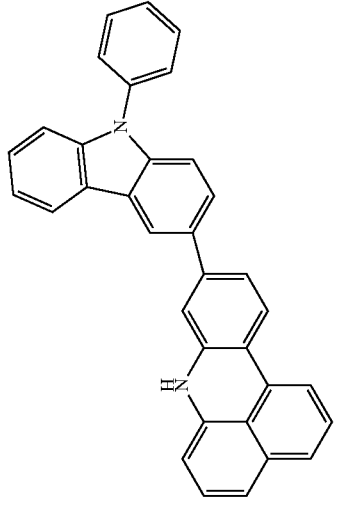 [854952-58-2] | 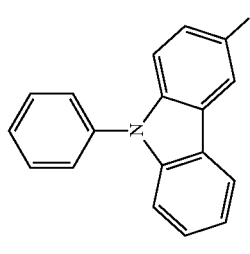 | 36% |

-continued

| | Reactant 1 | Reactant 2 | Product | Yield |
|---|---|---|---|---|
| 10a | [1799411-58-7] | [854952-58-2] | | 53% |
| 11a | [1799411-53-1] | [854952-58-2] | | 42% |
| 12a | [1803291-23-7] | [854952-58-2] | | 51% |

-continued
| | Reactant 1 | Reactant 2 | Product | Yield |
|---|---|---|---|---|
| 13a | 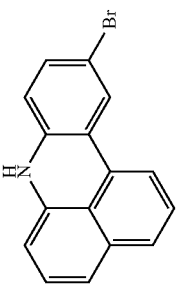 [1705595-50-1] | 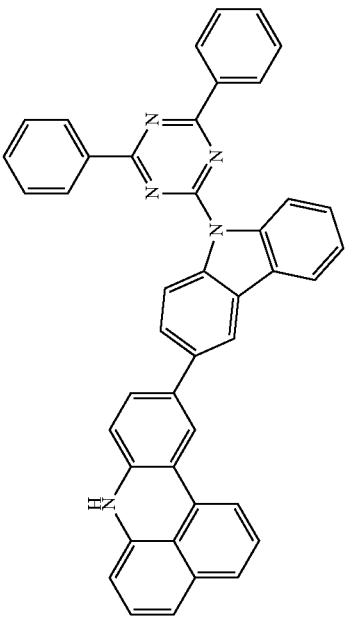 [1266389-18-7] | 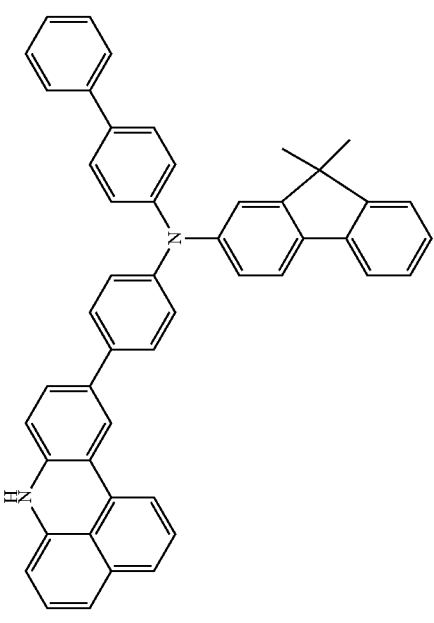 | 50% |
| 14a | 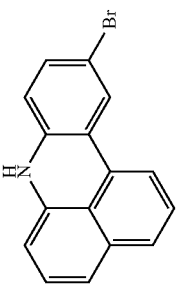 [1705595-50-1] | 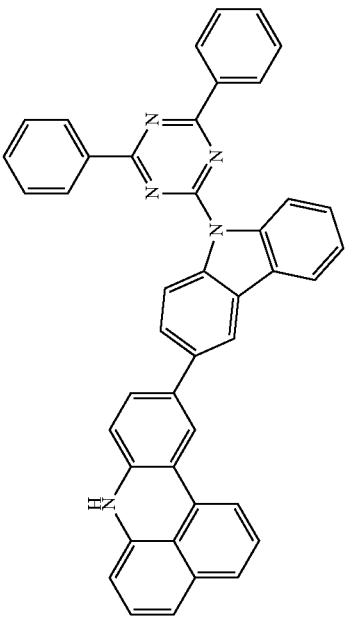 [1394815-87-2] | 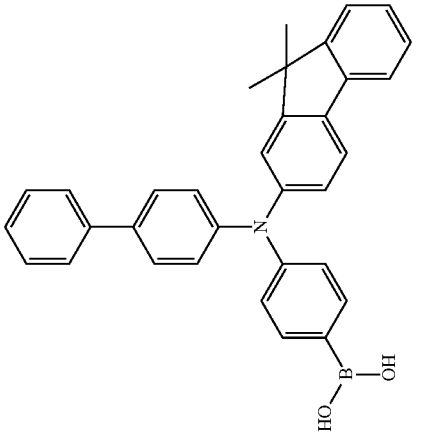 | 63% |

| | Reactant 1 | Reactant 2 | Product | Yield |
|---|---|---|---|---|
| 15a | [535993-10-3] | [1266389-18-7] | | 52% |
| 16a | [535993-10-3] | [1642121-58-1] | | 56% |

-continued

| | Reactant 1 | Reactant 2 | Product | Yield |
|---|---|---|---|---|
| 17a | [535993-10-3] | [1266389-16-5] | | 50% |
| 18a | [535993-10-3] | [1642121-53-6] | | 47% |

-continued

| | Reactant 1 | Reactant 2 | Product | Yield |
|---|---|---|---|---|
| 19a | [1584656-57-4] | [1266389-18-7] | | 42% |
| 20a | [1584656-43-8] | [1266389-18-7] | | 40% | b) 10-(8-Bromonaphth-1-yl)-10H-phenoxazine

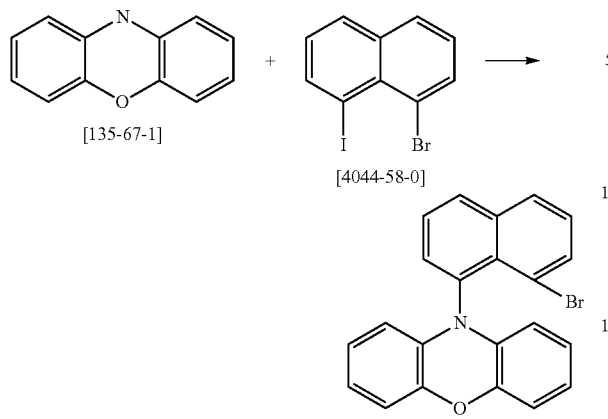

Under protective gas, 16.1 g (88 mmol) of 10H-phenoxazine, 29 g (88 mmol) of 1-bromo-8-iodobenzene and 0.8 g (0.88 mmol) of tris(dibenzylideneacetone)dipalladium were suspended in 500 ml of toluene. The reaction mixture is heated under reflux for 8 h. After cooling, the organic phase is removed, washed three times with 200 ml of water and then concentrated to dryness. The product is purified via column chromatography on silica gel with toluene/heptane (2:2). The purity is 98.0%. Yield: 26 g (67 mmol), 77% of theory.

The following compounds are prepared in an analogous manner:

| | Reactant 1 | Reactant 2 | Product | Yield |
|---|---|---|---|---|
| 2b | [92-84-2] | [4044-58-0] | | 66% |
| 3b | [6267-02-3] | [4044-58-0] | | 69% |
| 4b | [1883616-28-1] | [4044-58-0] | | 62% |

-continued

| | Reactant 1 | Reactant 2 | Product | Yield |
|---|---|---|---|---|
| 5b | [20474-15-1] | [4044-58-0] | | 64% |
| 6b | [92638-81-8] | [4044-58-0] | | 71% |
| 7b | [1885113-44-9] | [4044-58-0] | | 73% |
| 8b | [1480589-84-1] | [4044-58-0] | | 67% |
| 9b | [1303969-38-1] | [4044-58-0] | | 71% |

-continued
| | Reactant 1 | Reactant 2 | Product | Yield |
|---|---|---|---|---|
| 10b | 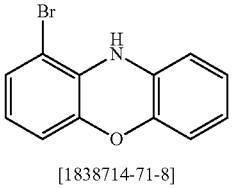 [SMILES: Brc1cccc2c1Nc1ccccc1O2] [1838714-71-8] | 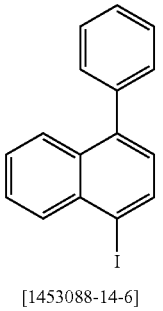 [SMILES: Ic1ccc(-c2ccccc2)c2ccccc12] [1453088-14-6] | 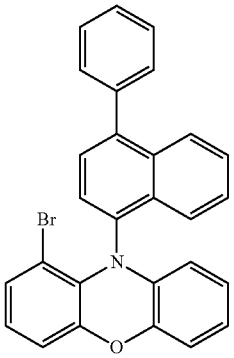 [SMILES: Brc1cccc2c1N(c1ccc(-c3ccccc3)c3ccccc13)c1ccccc1O2] | 70% |
| 11b | 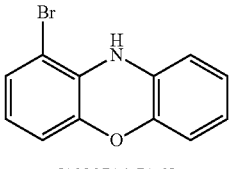 [1838714-71-8] | 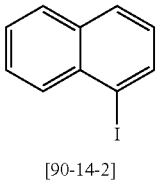 [SMILES: Ic1cccc2ccccc12] [90-14-2] | 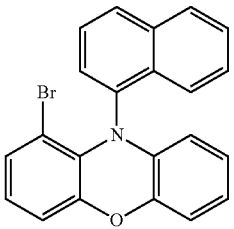 [SMILES: Brc1cccc2c1N(c1cccc3ccccc13)c1ccccc1O2] | 74% |
| 12b | 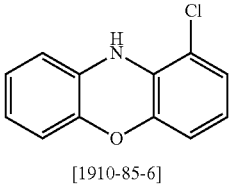 [SMILES: Clc1cccc2c1Nc1ccccc1O2] [1910-85-6] | 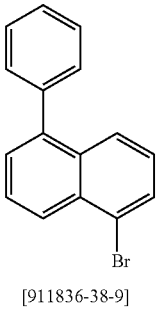 [SMILES: Brc1cccc2c(-c3ccccc3)cccc12] [911836-38-9] | 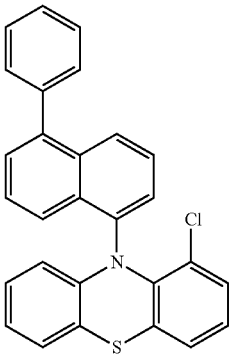 [SMILES: Clc1cccc2c1N(c1cccc3c(-c4ccccc4)cccc13)c1ccccc1S2] | 79% |
| 13b | 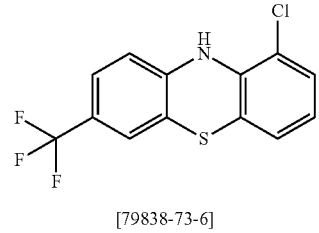 [SMILES: FC(F)(F)c1ccc2c(c1)Sc1cccc(Cl)c1N2] [79838-73-6] | 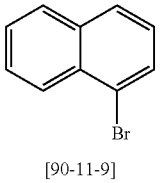 [SMILES: Brc1cccc2ccccc12] [90-11-9] | 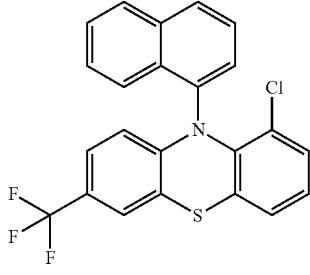 [SMILES: FC(F)(F)c1ccc2c(c1)Sc1cccc(Cl)c1N2c1cccc2ccccc12] | 70% |
| 15b | 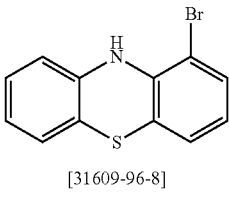 [SMILES: Brc1cccc2c1Nc1ccccc1S2] [31609-96-8] | 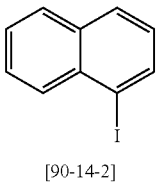 [SMILES: Ic1cccc2ccccc12] [90-14-2] | 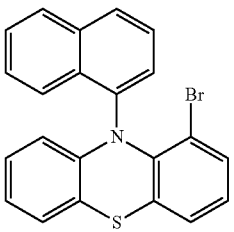 [SMILES: Brc1cccc2c1N(c1cccc3ccccc13)c1ccccc1S2] | 79% |

-continued
| | Reactant 1 | Reactant 2 | Product | Yield |
|---|---|---|---|---|
| 16b | 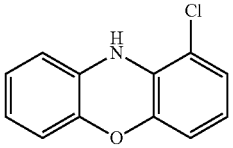 [116366-11-1] | 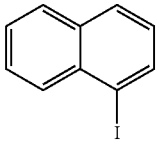 [90-14-2] | 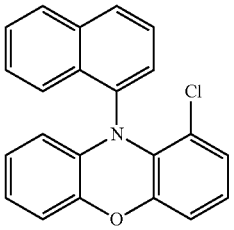 [SMILES: Clc1cccc2c1N(c1cccc3ccccc13)c1ccccc1O2] | 73% |
| 17b | 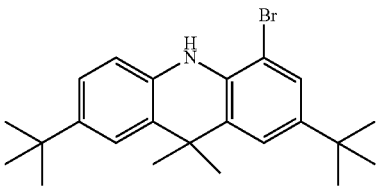 [1910-85-6] | 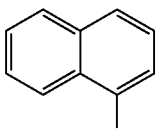 [90-14-2] | 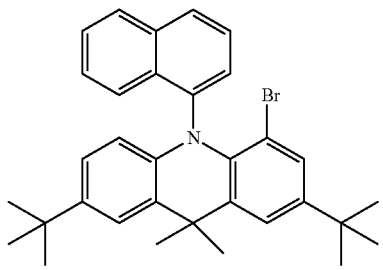 [SMILES: CC(C)(C)c1ccc2c(c1)C(C)(C)c1cc(C(C)(C)C)cc(Br)c1N2c1cccc2ccccc12] | 68% |
| 18b | 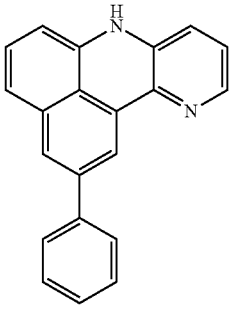 [1855013-91-0] | 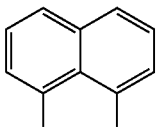 [4044-58-0] | 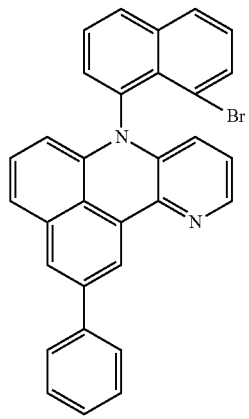 [SMILES: Brc1cccc2cccc(N3c4cccnc4-c4cc(-c5ccccc5)cc5cccc3c45)c12] | 71% |
| 19b | 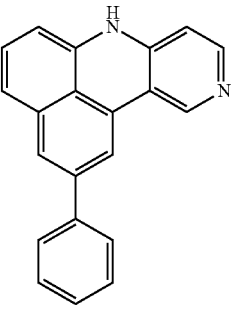 [1855013-90-9] | 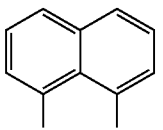 [4044-58-0] | 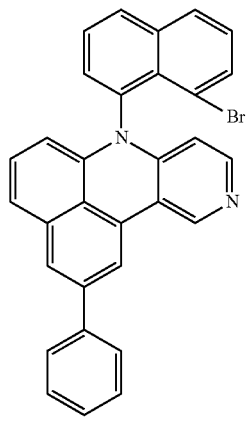 [SMILES: Brc1cccc2cccc(N3c4ccncc4-c4cc(-c5ccccc5)cc5cccc3c45)c12] | 70% |

-continued
| | Reactant 1 | Reactant 2 | Product | Yield |
|---|---|---|---|---|
| 20b | 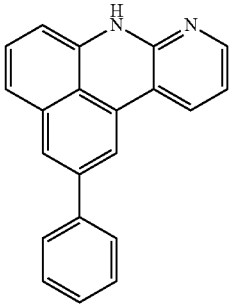<br>[1855013-88-5] | 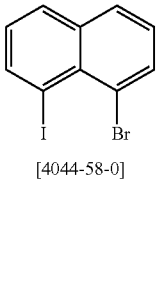 [SMILES: Brc1cccc2cccc(I)c12]<br>[4044-58-0] | 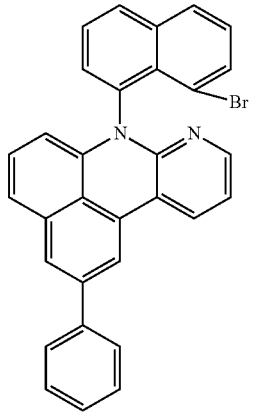 [SMILES: Brc1cccc2cccc(N3c4ncccc4-c4cc(-c5ccccc5)cc5cccc3c45)c12] | 72% |
| 21b | 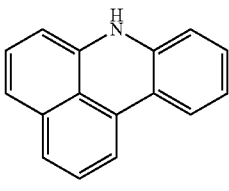<br>[200-22-6] | 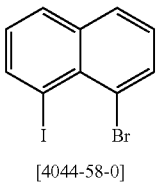 [SMILES: Brc1cccc2cccc(I)c12]<br>[4044-58-0] | 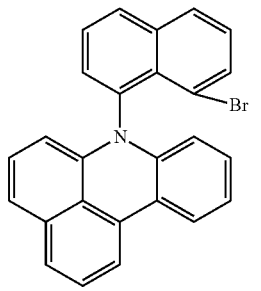 | 70% |
| 22b | 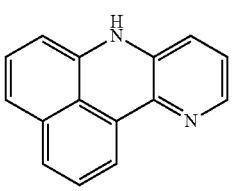<br>[1520093-71-3] | 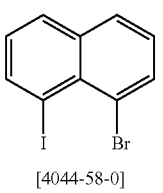 [SMILES: Brc1cccc2cccc(I)c12]<br>[4044-58-0] | 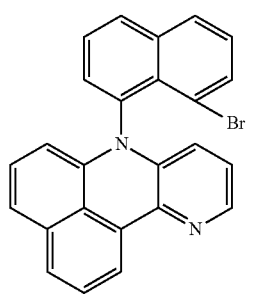 [SMILES: Brc1cccc2cccc(N3c4cccnc4-c4cccc5cccc3c45)c12] | 74% |
| 23b | 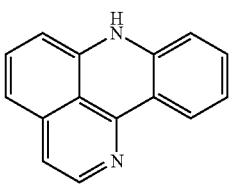<br>[198025-89-7] | 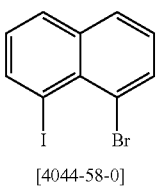 [SMILES: Brc1cccc2cccc(I)c12]<br>[4044-58-0] | 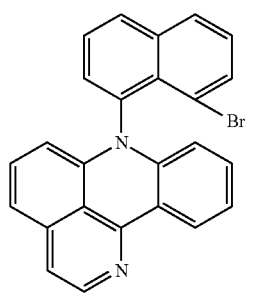 [SMILES: Brc1cccc2cccc(N3c4ccccc4-c4nccc5cccc3c45)c12] | 75% |

-continued
| | Reactant 1 | Reactant 2 | Product | Yield |
|---|---|---|---|---|
| 24b | 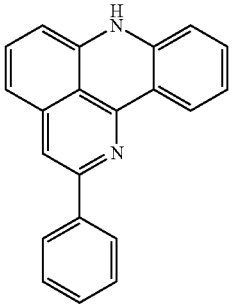 [203785-34-6] | 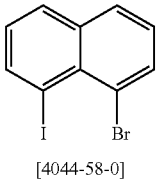 [SMILES: Brc1cccc2cccc(I)c12] [4044-58-0] | 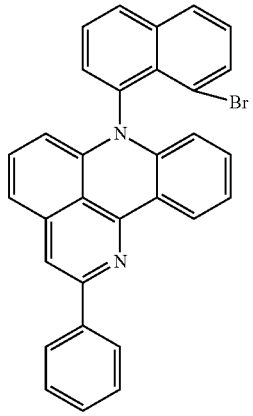 [SMILES: Brc1cccc2cccc(N3c4ccccc4-c4nc(-c5ccccc5)cc5cccc3c45)c12] | 77% |
| 25b | 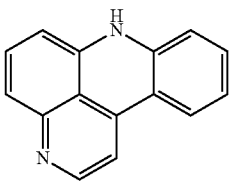 [144630-86-4] | 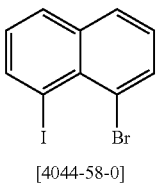 [SMILES: Brc1cccc2cccc(I)c12] [4044-58-0] | 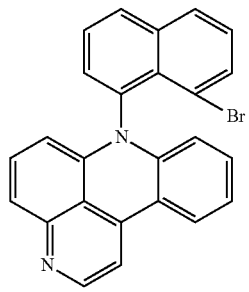 [SMILES: Brc1cccc2cccc(N3c4ccccc4-c4ccnc5cccc3c45)c12] | 79% |
| 26b | 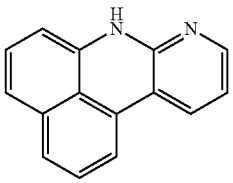 [140138-74-5] | 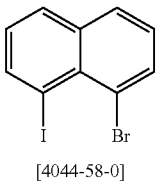 [SMILES: Brc1cccc2cccc(I)c12] [4044-58-0] | 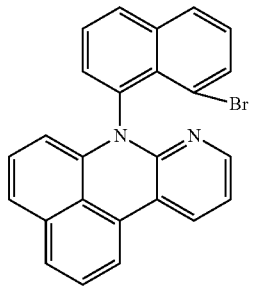 [SMILES: Brc1cccc2cccc(N3c4ncccc4-c4cccc5cccc3c45)c12] | 75% |
| 27b | 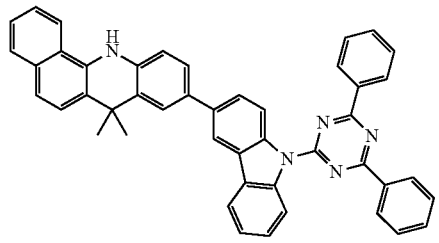 [SMILES: CC1(C)c2cc(-c3ccc4c(c3)c3ccccc3n4-c3nc(-c4ccccc4)nc(-c4ccccc4)n3)ccc2Nc2c1ccc1ccccc21] | 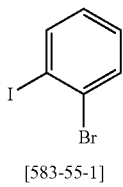 [583-55-1] | 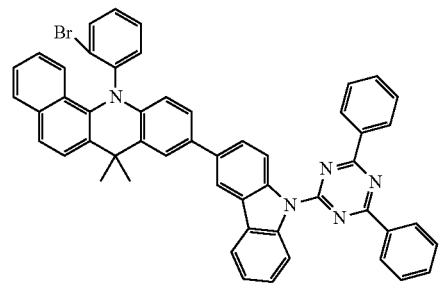 [SMILES: CC1(C)c2cc(-c3ccc4c(c3)c3ccccc3n4-c3nc(-c4ccccc4)nc(-c4ccccc4)n3)ccc2N(c2ccccc2Br)c2c1ccc1ccccc21] | 70% |

-continued
| | Reactant 1 | Reactant 2 | Product | Yield |
|---|---|---|---|---|
| 28b | 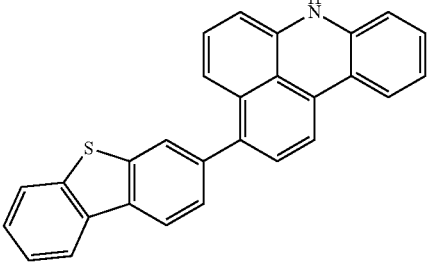 [1853267-41-0] | 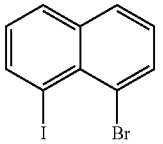 [4044-58-0] | 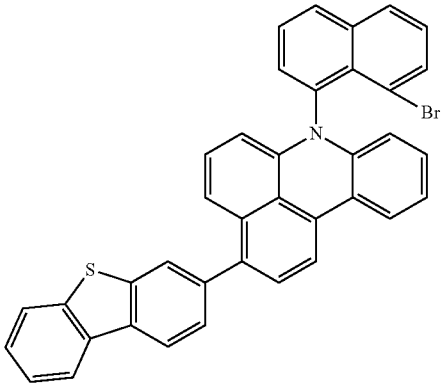 [SMILES: Brc1cccc2cccc(N3c4ccccc4-c4ccc(-c5ccc6c(c5)sc5ccccc56)c5cccc3c45)c12] | 74% |
| 29b | 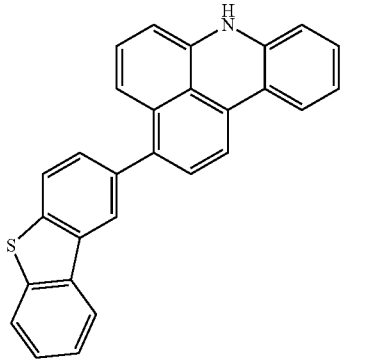 [1853265-49-2] | 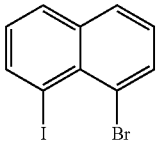 [4044-58-0] | 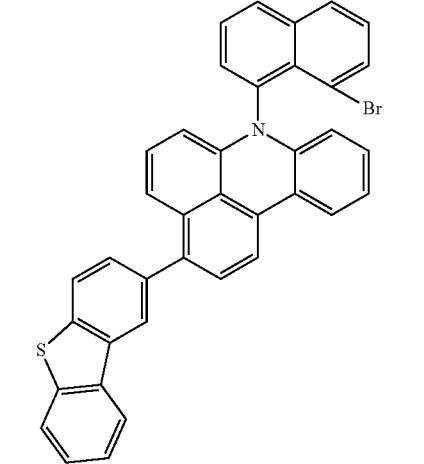 [SMILES: Brc1cccc2cccc(N3c4ccccc4-c4ccc(-c5ccc6sc7ccccc7c6c5)c5cccc3c45)c12] | 71% |
| 30b | 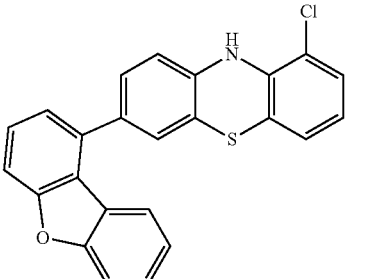 | 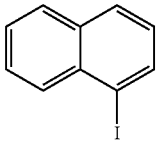 [90-14-2] | 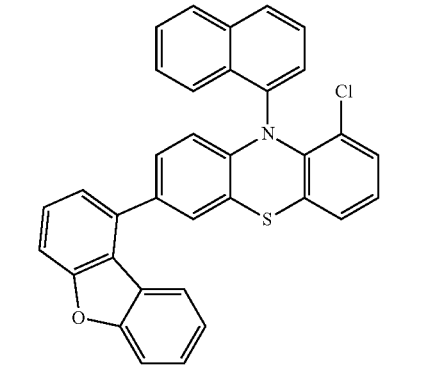 [SMILES: Clc1cccc2c1N(c1cccc3ccccc13)c1ccc(-c3cccc4oc5ccccc5c34)cc1S2] | 64% |
| 31b | 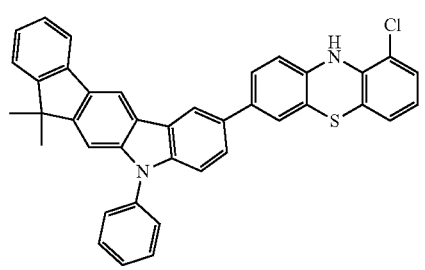 [SMILES: CC1(C)c2ccccc2-c2cc3c4cc(-c5ccc6c(c5)Sc5cccc(Cl)c5N6)ccc4n(-c4ccccc4)c3cc21] | 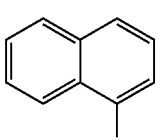 [90-14-2] | 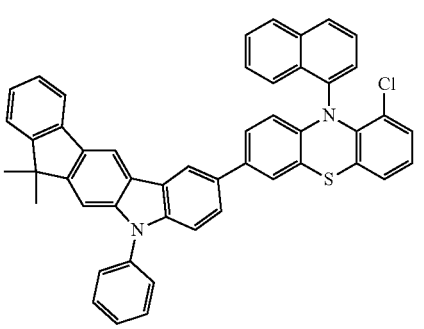 [SMILES: CC1(C)c2ccccc2-c2cc3c4cc(-c5ccc6c(c5)Sc5cccc(Cl)c5N6c5cccc6ccccc56)ccc4n(-c4ccccc4)c3cc21] | 70% |

-continued

| | Reactant 1 | Reactant 2 | Product | Yield |
|---|---|---|---|---|
| 32b | | [90-14-2] | | 73% |
| 33b | | [90-14-2] | | 64% |
| 34b | | [90-14-2] | | 58% |
| 35b | | [90-14-2] | | 767% |
| 36b | | [90-14-2] | | 72% |

-continued

| | Reactant 1 | Reactant 2 | Product | Yield |
|---|---|---|---|---|
| 37b | | [90-14-2] | | 61% |
| 38b | | [4044-58-0] | | 66% |
| 39b | | [4044-58-0] | | 70% |
| 40b | | [4044-58-0] | | 72% |

-continued

| | Reactant 1 | Reactant 2 | Product | Yield |
|---|---|---|---|---|
| 41b | | [4044-58-0] | | 71% |
| 42b | | [4044-58-0] | | 64% |
| 43b | | [4044-58-0] | | 58% |
| 44b | | [90-14-2] | | 59% |

-continued

| | Reactant 1 | Reactant 2 | Product | Yield |
|---|---|---|---|---|
| 45b | | [90-14-2] | | 63% |
| 46b | | [90-14-2] | | 64% |
| 47b | | [4044-58-0] | | 60% |
| 48b | [225-74-1] | [583-55-1] | | 76% |
| 49b | [1065116-73-5] | [583-55-1] | | 73% |

-continued
| | Reactant 1 | Reactant 2 | Product | Yield |
|---|---|---|---|---|
| 50b | 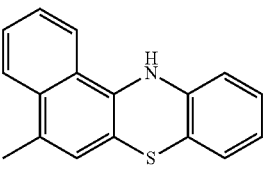 [911314-93-7] |  [583-55-1] | 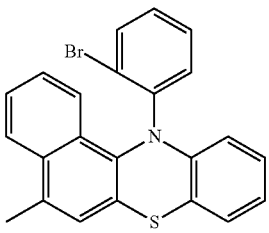 [SMILES: Cc1cc2c(c3ccccc13)N(c1ccccc1Br)c1ccccc1S2] | 70% |
| 51b | 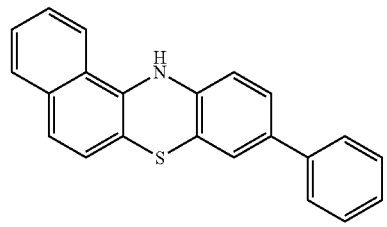 [855462-82-7] | 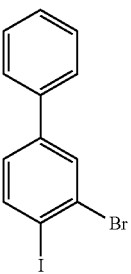 [900806-53-3] | 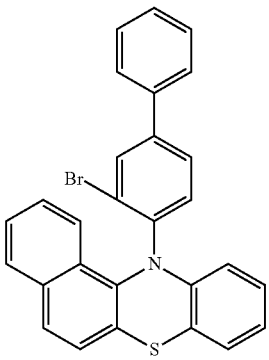 [SMILES: Brc1cc(-c2ccccc2)ccc1N1c2ccccc2Sc2ccc3ccccc3c21] | 71% |
| 52b | 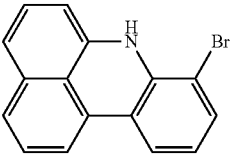 [1705595-51-2] | 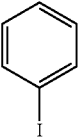 | 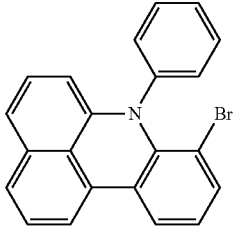 [SMILES: Brc1cccc2c1N(c1ccccc1)c1cccc3cccc-2c13] | 65% |
| 53b | 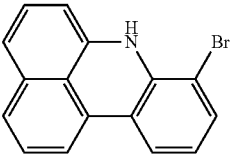 [1705595-51-2] | 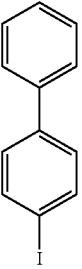 [SMILES: Ic1ccc(-c2ccccc2)cc1] | 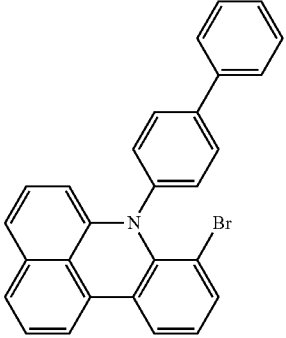 [SMILES: Brc1cccc2c1N(c1ccc(-c3ccccc3)cc1)c1cccc3cccc-2c13] | 64% |
| 54b | 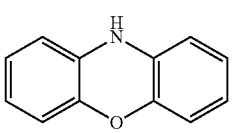 [135-67-1] | 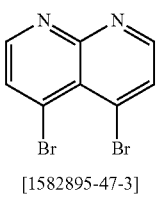 [1582895-47-3] | 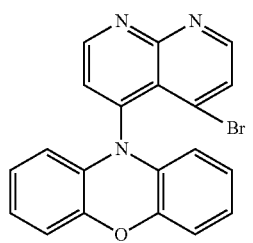 [SMILES: Brc1ccnc2nccc(N3c4ccccc4Oc4ccccc43)c12] | 53% |

| | Reactant 1 | Reactant 2 | Product | Yield |
|---|---|---|---|---|
| 55b | ![structure] [6267-02-3] | ![structure] [1629614-42-1] | ![structure] | 65% | c) 5-(8-Bromonaphth-1-yl)-5,10-dihydrophenazine

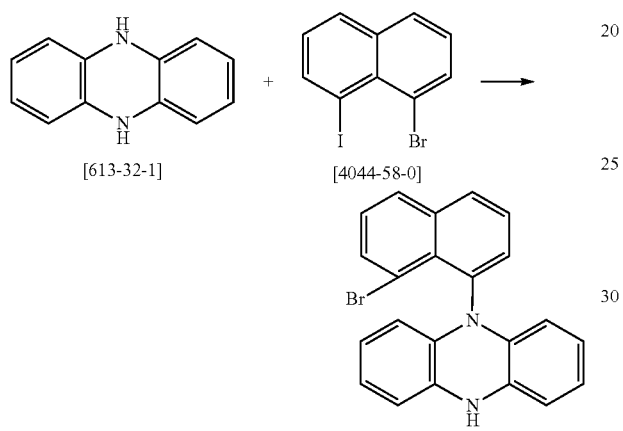

[613-32-1]  [4044-58-0]

Under protective gas, 15.8 g (87.8 mmol) of 9,10-dihydrophenazine, 20 g (87 mmol) of 1-bromo-8-iodonaphthalene and 0.8 g (0.88 mmol) of tris(dibenzylideneacetone)dipalladium were suspended in 500 ml of toluene. The reaction mixture is heated under reflux for 8 h. After cooling, the organic phase is removed, washed three times with 200 ml of water and then concentrated to dryness. The product is purified via column chromatography on silica gel with toluene/heptane (2:2). The purity is 94.0%. Yield: 21 g (56 mmol), 65% of theory.

The following compounds are prepared in an analogous manner:

| Ex. | Reactant 1 | Reactant 2 | Product | Yield |
|---|---|---|---|---|
| 1c | ![structure] | ![structure] [1823974-35-1] | ![structure] | 60% |
| 2c | ![structure] | ![structure] [1582895-47-3] | ![structure] | 62% |

| Ex. | Reactant 1 | Reactant 2 | Product | Yield |
|---|---|---|---|---|
| 3c | 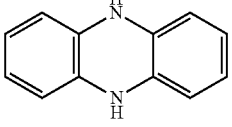 | 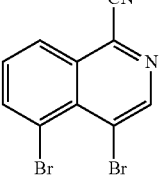
[1368343-19-4] | 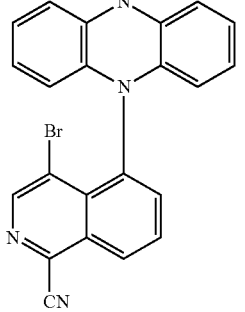 | 67% |
| 4c | 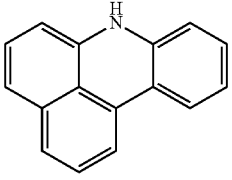
[200-22-6] | 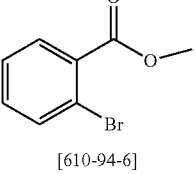
[610-94-6] | 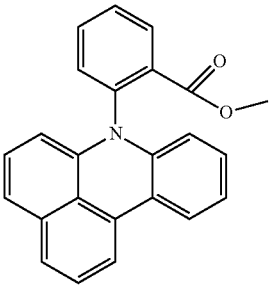 [SMILES: COC(=O)c1ccccc1N1c2ccccc2-c2cccc3cccc1c23] | 60% |
| 5c | 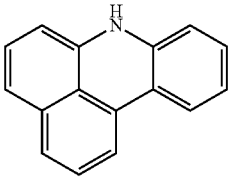
[200-22-6] | 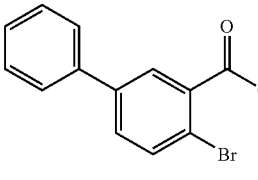
[727408-92-6] | 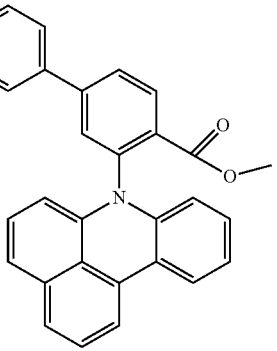 | 65% |
| 6c | 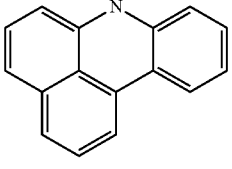
[200-22-6] | 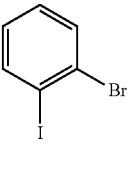 | 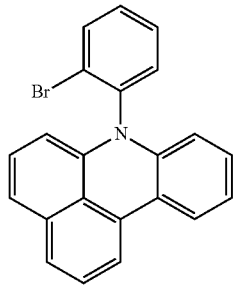 [SMILES: Brc1ccccc1N1c2ccccc2-c2cccc3cccc1c23] | 67% |

225 d) 5-(8-Bromonaphth-1-yl)-10-(4,6-diphenyl-[1,3,5]triazin-2-yl)-5,10-dihydrophenazine

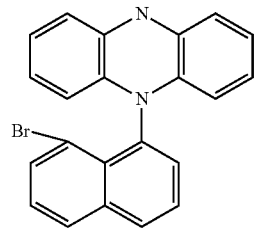

+

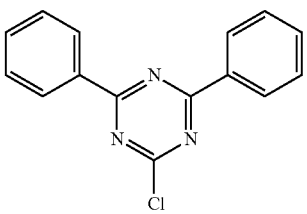

→

226

-continued

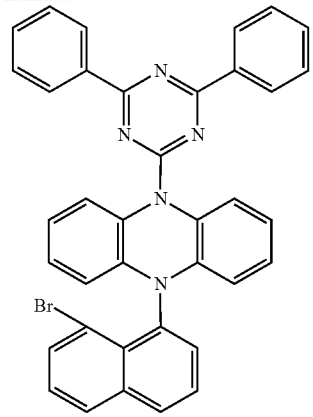

11.22 g (29 mmol) of 5-(8-bromonaphth-1-yl)-5,10-dihydrophenazine are dissolved in 225 ml of dimethylformamide under a protective gas atmosphere, and 1.5 g (37.5 mmol) of NaH, 60% in mineral oil, are added. After 1 h at room temperature, a solution of 2-chloro-4,6-diphenyl-[1,3,5]-triazine (8.5 g, 31.75 mmol) in 75 ml of dimethylformamide is added dropwise. The reaction mixture is stirred at room temperature for 12 h, then poured onto ice and extracted three times with dichloromethane. The combined organic phases are dried over $Na_2SO_4$ and concentrated. The residue is subjected to hot extraction with toluene. Yield: 14.3 g (23 mmol), 80% of theory.

The following compounds are prepared in an analogous manner:

| | Reactant 1 | Reactant 2 | Product | Yield |
|---|---|---|---|---|
| 1d | (phenazine with N-(8-bromonaphth-1-yl)) | 4-chloro-2-phenylquinazoline [6484-25-9] | (2-phenylquinazolin-4-yl with phenazine-N-(8-bromonaphth-1-yl)) | 82% |

-continued
| | Reactant 1 | Reactant 2 | Product | Yield |
|---|---|---|---|---|
| 2d | 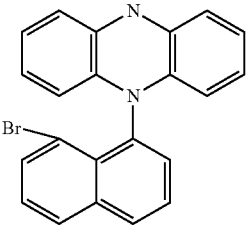 [SMILES: Brc1cccc2cccc(N3c4ccccc4Nc4ccccc43)c12] | 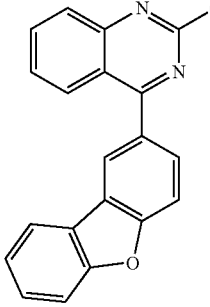  [1616499-38-7] | 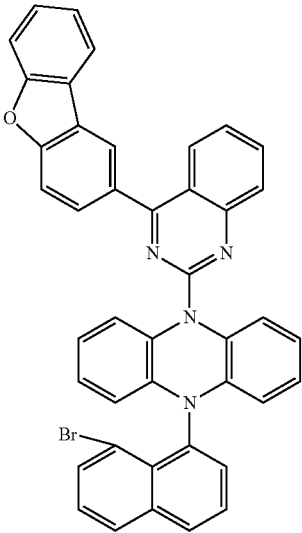 [SMILES: Brc1cccc2cccc(N3c4ccccc4N(c4nc(-c5ccc6oc7ccccc7c6c5)c5ccccc5n4)c4ccccc43)c12] | 83% |
| 3d | 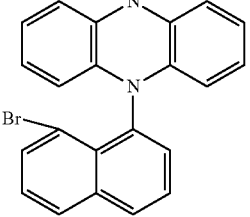 | 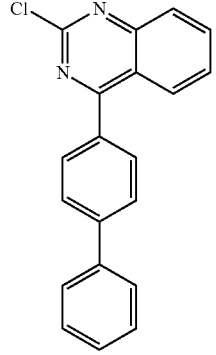  [1262866-93-2] | 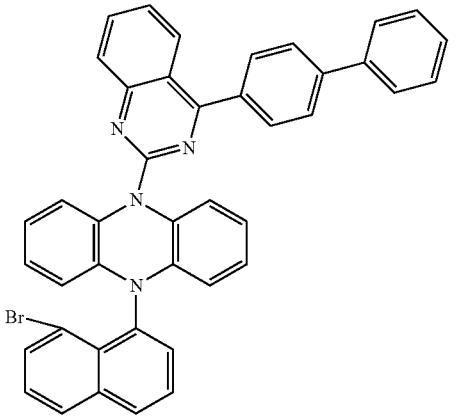 [SMILES: Brc1cccc2cccc(N3c4ccccc4N(c4nc(-c5ccc(-c6ccccc6)cc5)c5ccccc5n4)c4ccccc43)c12] | 81% |
| 4d | 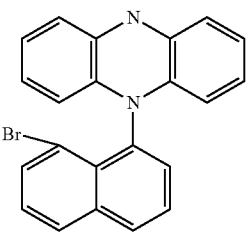 [SMILES: Brc1cccc2cccc(N3c4ccccc4Nc4ccccc43)c12] | 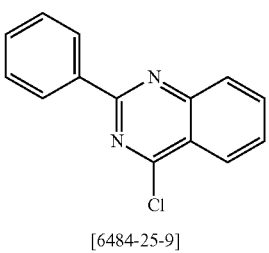 [SMILES: Clc1nc(-c2ccccc2)nc2ccccc12]  [6484-25-9] | 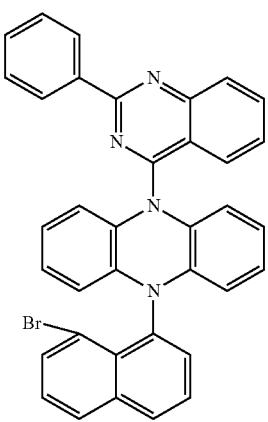 [SMILES: Brc1cccc2cccc(N3c4ccccc4N(c4nc(-c5ccccc5)nc5ccccc45)c4ccccc43)c12] | 86% |

| | Reactant 1 | Reactant 2 | Product | Yield |
|---|---|---|---|---|
| 5d | 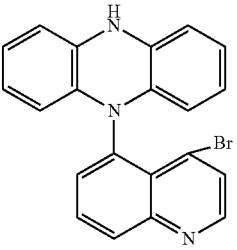 [SMILES: Brc1ccnc2cccc(N3c4ccccc4Nc4ccccc43)c12] | 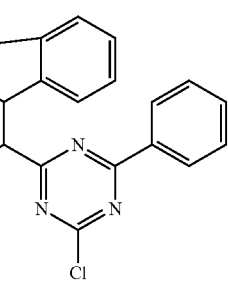
[1644054-73-8] | 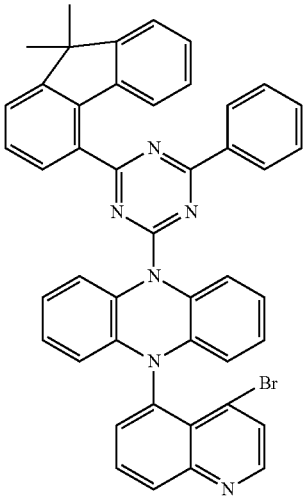 [SMILES: CC1(C)c2ccccc2-c2c(-c3nc(-c4ccccc4)nc(N4c5ccccc5N(c5cccc6nccc(Br)c56)c5ccccc54)n3)cccc21] | 80% |
| 6d | 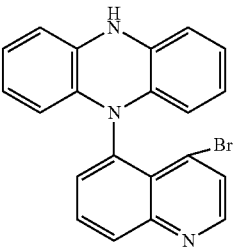 [SMILES: Brc1ccnc2cccc(N3c4ccccc4Nc4ccccc43)c12] | 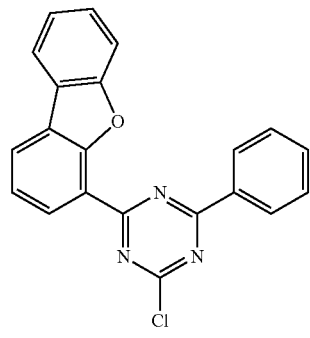
[1472729-25-1] | 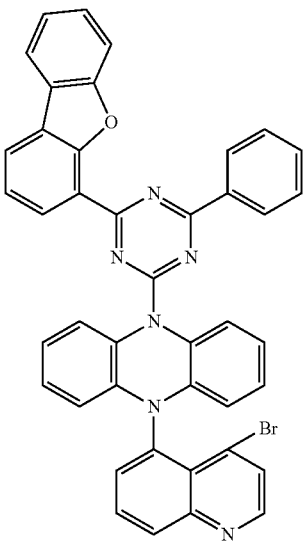 [SMILES: Brc1ccnc2cccc(N3c4ccccc4N(c4nc(-c5ccccc5)nc(-c5cccc6c5oc5ccccc56)n4)c4ccccc43)c12] | 84% |
| 7d | 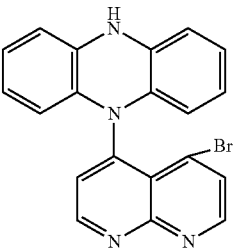 [SMILES: Brc1ccnc2nccc(N3c4ccccc4Nc4ccccc43)c12] | 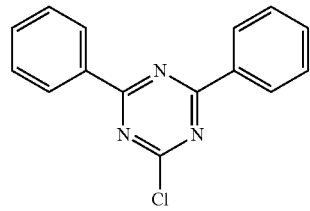 [SMILES: Clc1nc(-c2ccccc2)nc(-c2ccccc2)n1] | 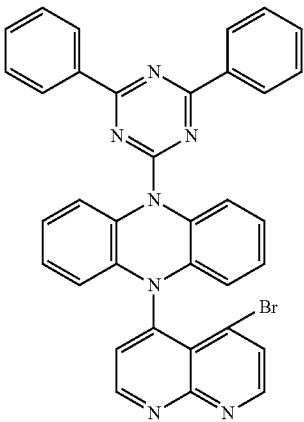 [SMILES: Brc1ccnc2nccc(N3c4ccccc4N(c4nc(-c5ccccc5)nc(-c5ccccc5)n4)c4ccccc43)c12] | 86% |

| Reactant 1 | Reactant 2 | Product | Yield |
|---|---|---|---|
| 8d | | | 80% | e) Cyclization

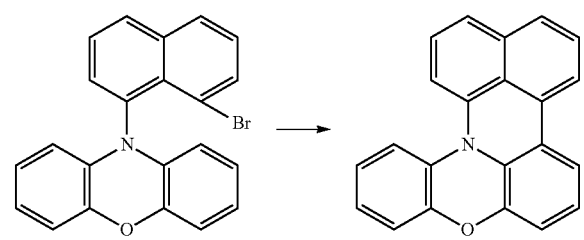 [SMILES: Brc1cccc2cccc(N3c4ccccc4Oc4ccccc43)c12 ; c1ccc2c(c1)oc1cccc3c1-n2c1cccc2cccc3c21]

Under protective gas, 58 g (150 mmol) of 10-(8-bromonaphth-1-yl)-10H-phenoxazine are dissolved in 500 ml of dimethylacetamide. To this solution are added 2.4 g (6.5 mmol) of tricyclohexyl tetrafluoroborate and 701 mg (3.1 mmol) of Pd(OAc)$_2$. Subsequently, the mixture is stirred at 120° C. for 9 h, then cooled to room temperature and extracted with dichloromethane. The combined organic phases are dried over Na$_2$SO$_4$ and concentrated. The residue is subjected to hot extraction with toluene, recrystallized from toluene and finally sublimed under high vacuum. The yield is 33 g (107 mmol), 72% of theory.

The following compounds are prepared in an analogous manner:

| | Reactant 1 | Product | Yield |
|---|---|---|---|
| 2e | | | 81% |
| 3e | | | 78% |

-continued

| | Reactant 1 | Product | Yield |
|---|---|---|---|
| 4e | | | 78% |
| 5e | | | 75% |
| 6e | | | 81% |
| 7e | | | 79% |
| 8e | | | 76% |

-continued

| | Reactant 1 | Product | Yield |
|---|---|---|---|
| 9e | | | 74% |
| 10e | | | 75% |
| 11e | | | 71% |
| 12e | | | 72% |
| 13e | | | 70% |

-continued

| | Reactant 1 | Product | Yield |
|---|---|---|---|
| 14e | | | 62% |
| 15e | | | 63% |
| 16e | | | 73% |
| 17e | | | 76% |
| 18e | | | 77% |

-continued

| Reactant 1 | Product | Yield |
|---|---|---|
| 19e | | 71% |
| 20e | | 73% |
| 21e | | 69% |
| 22e | | 72% |

-continued

| | Reactant 1 | Product | Yield |
|---|---|---|---|
| 23e | | | 56% |
| 24e | | | 63% |
| 25e | | | 80% |
| 26e | | | 84% |

-continued
| | Reactant 1 | Product | Yield |
|---|---|---|---|
| 27e | 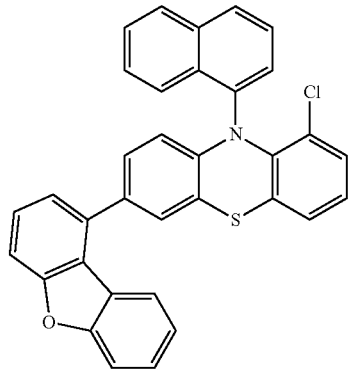 [SMILES: Clc1cccc2c1N(c1cccc3ccccc13)c1ccc(-c3cccc4oc5ccccc5c34)cc1S2] | 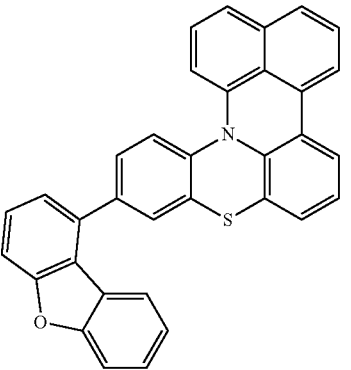 [SMILES: c1ccc2c(c1)oc1cccc(-c3ccc4c(c3)sc3cccc5c3-n4c3cccc4cccc5c43)c12] | 73% |
| 28e | 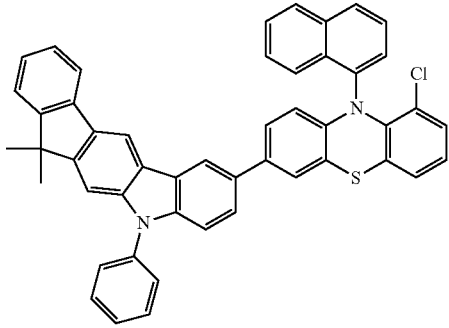 [SMILES: CC1(C)c2ccccc2-c2cc3c4cc(-c5ccc6c(c5)Sc5cccc(Cl)c5N6c5cccc6ccccc56)ccc4n(-c4ccccc4)c3cc21] | 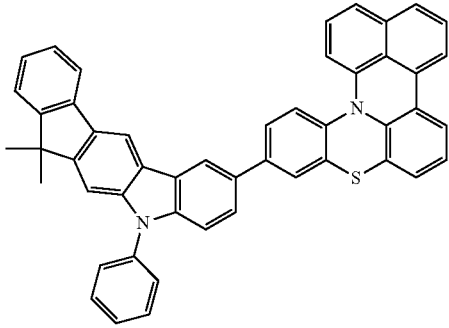 [SMILES: CC1(C)c2ccccc2-c2cc3c4cc(-c5ccc6c(c5)sc5cccc7c5-n6c5cccc6cccc7c65)ccc4n(-c4ccccc4)c3cc21] | 73% |
| 29e | 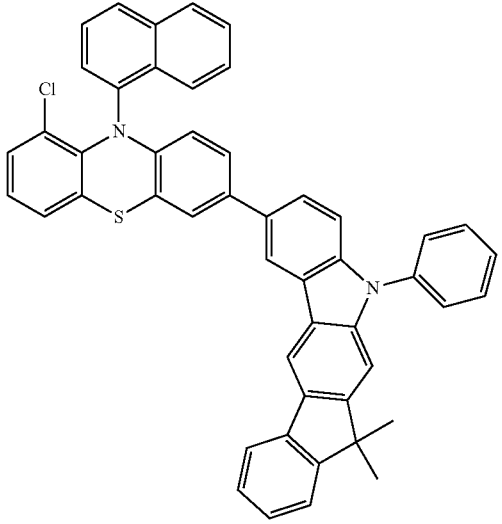 [SMILES: CC1(C)c2ccccc2-c2cc3c4cc(-c5ccc6c(c5)Sc5cccc(Cl)c5N6c5cccc6ccccc56)ccc4n(-c4ccccc4)c3cc21] | 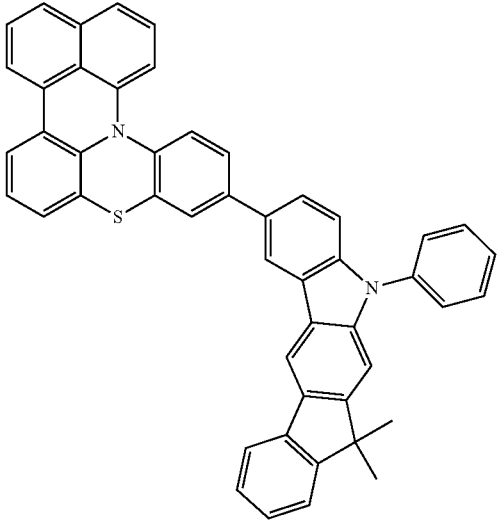 [SMILES: CC1(C)c2ccccc2-c2cc3c4cc(-c5ccc6c(c5)sc5cccc7c5-n6c5cccc6cccc7c65)ccc4n(-c4ccccc4)c3cc21] | 76% |

-continued

| | Reactant 1 | Product | Yield |
|---|---|---|---|
| 30e | | | 70% |
| 31e | | | 78% |
| 32e | | | 73% |
| 33e | | | 65% |

-continued
| Reactant 1 | Product | Yield |
|---|---|---|
| 34e 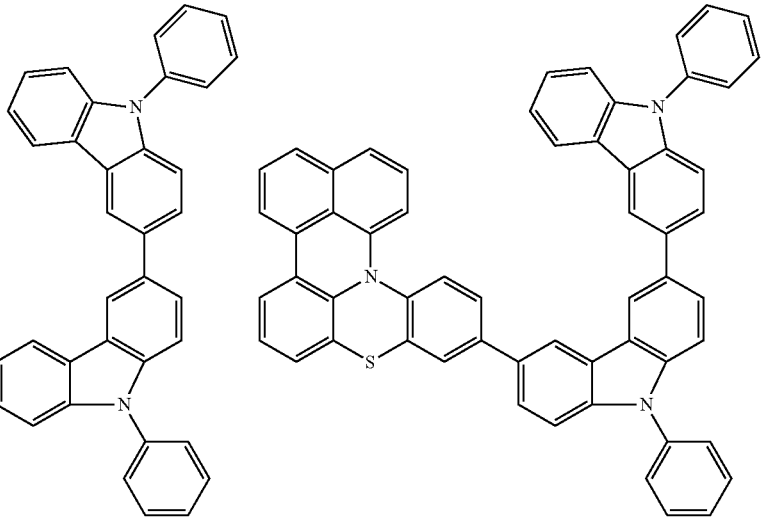 | | 64% |
| 35e 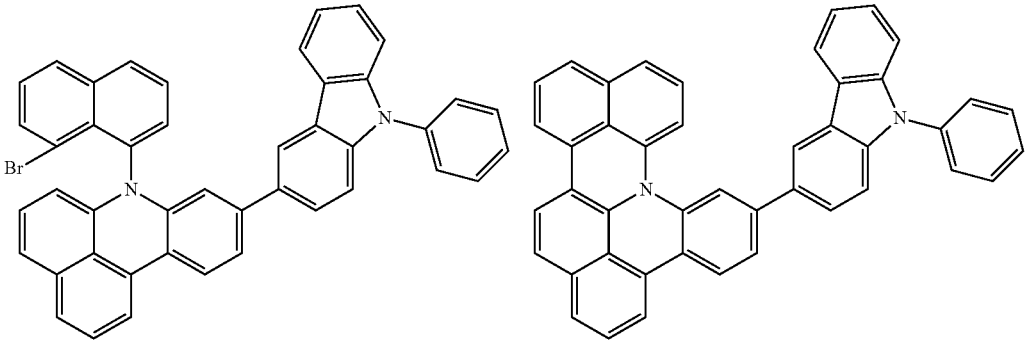 | | 73% |
| 36e 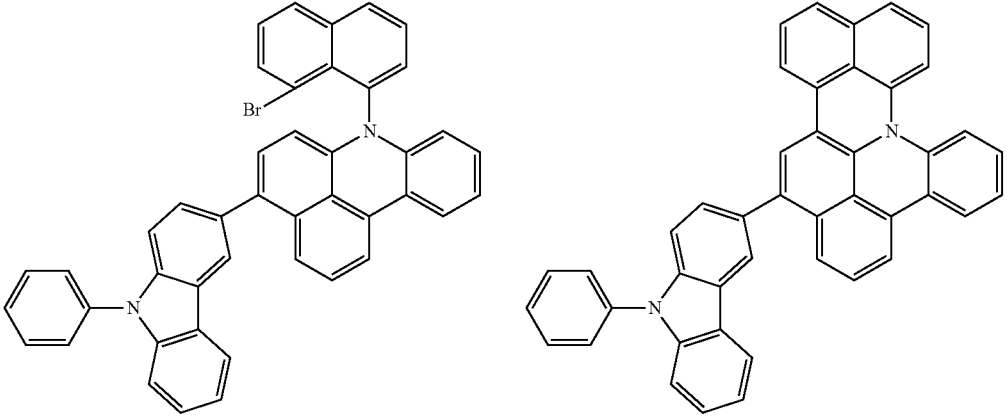 | | 76% |

-continued

| | Reactant 1 | Product | Yield |
|---|---|---|---|
| 37e | | | 79% |
| 38e | | | 70% |
| 39e | | | 76% |
| 40e | | | 67% |

|  | Reactant 1 | Product | Yield |
|---|---|---|---|
| 41e | | | 71% |
| 42e | | | 63% |
| 43e | | | 60% |
| 44e | | | 80% |

-continued

| | Reactant 1 | Product | Yield |
|---|---|---|---|
| 45e | | | 80% |
| 46e | | | 78% |
| 47e | | | 80% |
| 48e | | | 82% |
| 49e | | | 78% |

-continued
| Reactant 1 | Product | Yield |
|---|---|---|
| 50e 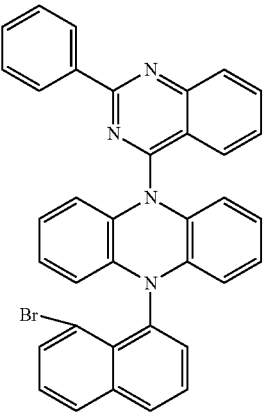 [SMILES: Brc1cccc2cccc(N3c4ccccc4N(c4nc(-c5ccccc5)nc5ccccc45)c4ccccc43)c12] | 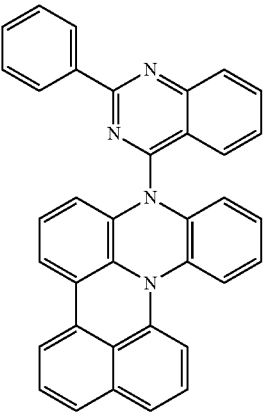 [SMILES: c1ccc(-c2nc(-n3c4cccc5c4-n(c4cccc6cccc5c64)c4ccccc43)c3ccccc3n2)cc1] | 79% |
| 51e 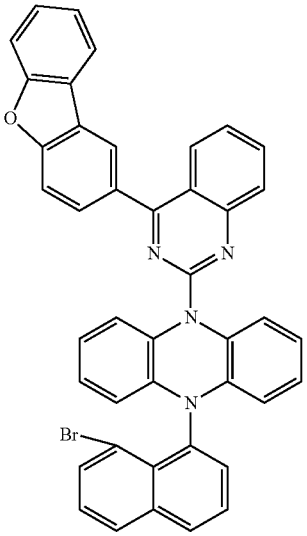 [SMILES: Brc1cccc2cccc(N3c4ccccc4N(c4nc(-c5ccc6oc7ccccc7c6c5)c5ccccc5n4)c4ccccc43)c12] | 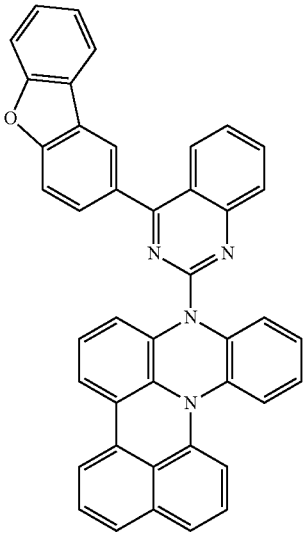 [SMILES: c1ccc2c(-c3ccc4oc5ccccc5c4c3)nc(-n3c4cccc5c4-n(c4cccc6cccc5c64)c4ccccc43)nc2c1] | 76% |
| 52e 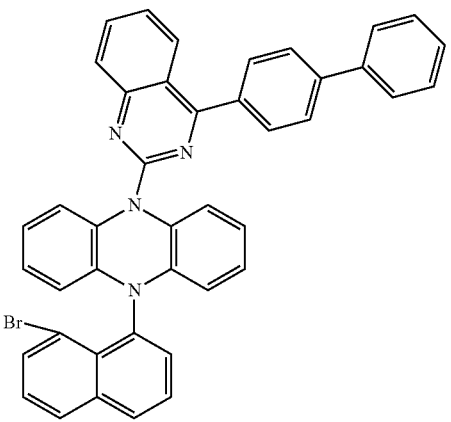 [SMILES: Brc1cccc2cccc(N3c4ccccc4N(c4nc(-c5ccc(-c6ccccc6)cc5)c5ccccc5n4)c4ccccc43)c12] | 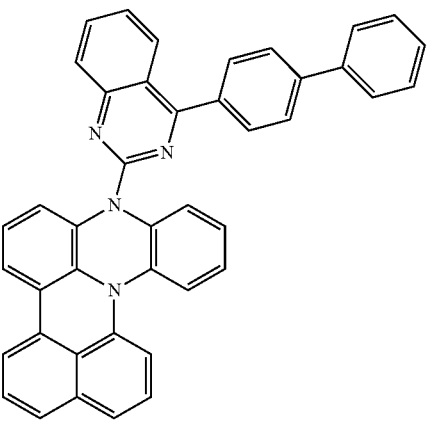 [SMILES: c1ccc(-c2ccc(-c3nc(-n4c5cccc6c5-n(c5cccc7cccc6c75)c5ccccc54)nc4ccccc34)cc2)cc1] | 81% |

-continued

| | Reactant 1 | Product | Yield |
|---|---|---|---|
| 53e | | | 79% |
| 54e | | | 75% |
| 55e | | | 72% |

| | Reactant 1 | Product | Yield |
|---|---|---|---|
| 56e | | | 74% |
| 57e | | | 70% |
| 58e | | | 42% |

-continued

| | Reactant 1 | Product | Yield |
|---|---|---|---|
| 59e | | | 67% |
| 60e | | | 65% |
| 61e | | | 67% | f) 2-[2-(7-Azabenzo[de]anthracen-7-yl)phenyl]propan-2-ol g) Cyclization

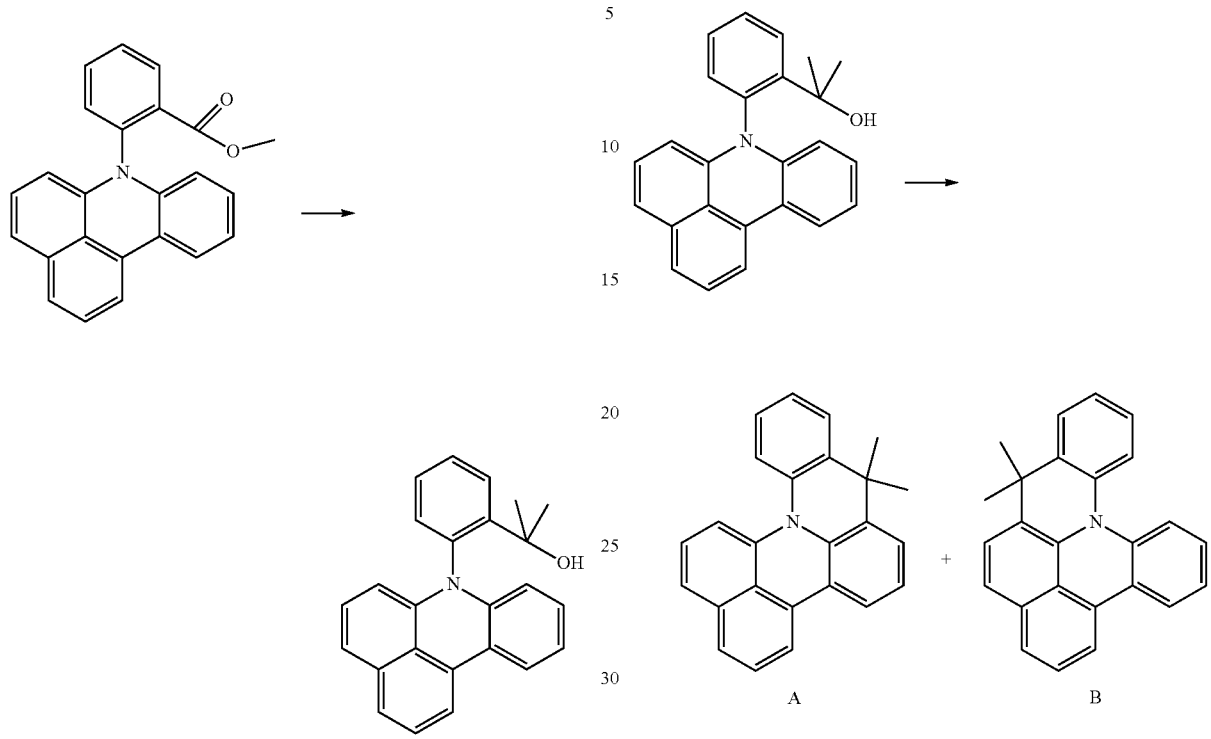

A            B 73 g (211 mmol) of methyl 2-(7-azabenzo[de]anthracen-7-yl)benzoate are dissolved in 1500 ml of dried THF and degassed. The mixture is cooled to −78° C., and 569 ml (853 mmol) of methyllithium are added within 40 min. The mixture is allowed to warm up to −40° C. within 1 h, and the conversion is monitored via TLC. On completion of conversion, the mixture is quenched cautiously with MeOH at −30° C. The reaction solution is concentrated to one third of its volume and 1 l of $CH_2Cl_2$ is added, the mixture is washed and the organic phase is dried over $MgSO_4$ and concentrated. The yield is 63 g (180 mmol), 87% of theory.

The following compound is prepared in an analogous manner:

15.5 g (43.6 mmol) of 2-[2-(7-azabenzo[de]anthracen-7-yl)phenyl]propan-2-ol are dissolved in 1200 ml of degassed toluene, a suspension of 40 g of polyphosphoric acid and 28 ml of methanesulfonic acid is added and the mixture is heated to 60° C. for 1 h. The mixture is cooled down and admixed with water. A solid precipitates out and is dissolved in $CH_2Cl_2$/THF (1:1). The solution is cautiously alkalized with 20% NaOH, and the phases are separated and dried over $MgSO_4$. The mixture of A and B is separated by chromatography. The yield is 11.6 g (34 mmol), 64% of theory, A 31%, B 33%.

The following compound is prepared in an analogous manner:

| | Reactant 1 | Product | Yield |
|---|---|---|---|
| 1f | | | 80% |

| Reactant 1 | Product 1 | Product 2 | Yield |
|---|---|---|---|
| 1g 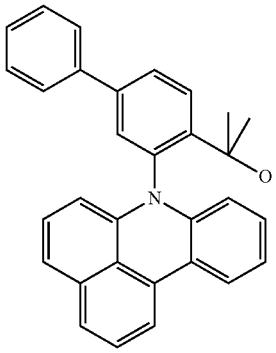 [SMILES: CC(C)(O)c1ccc(-c2ccccc2)cc1N1c2ccccc2-c2cccc3cccc1c23] | 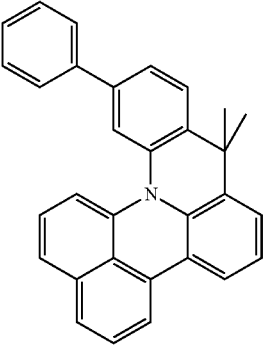 [SMILES: CC1(C)c2ccc(-c3ccccc3)cc2N2c3c(cccc31)-c1cccc3cccc2c13] | 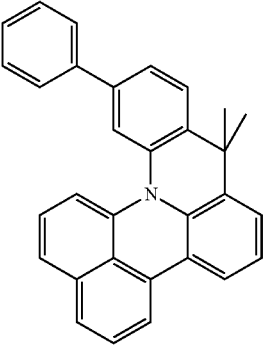 [SMILES: CC1(C)c2ccc(-c3ccccc3)cc2N2c3c(cccc31)-c1cccc3cccc2c13] | 28%: 29% | h) Bromination

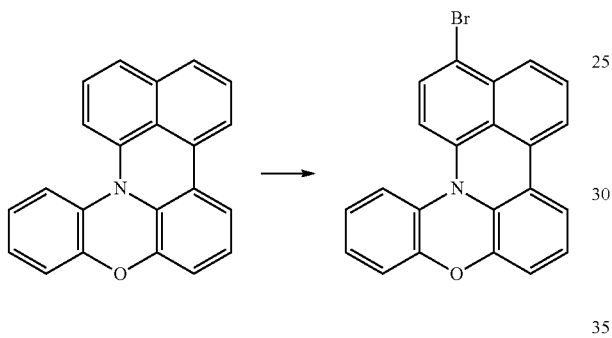

12.2 g (41 mmol) of product e are dissolved in 300 ml of chloroform. To this solution are added, in portions at 50° C. in the dark, 7 g (42 mmol) of NBS, and then the mixture is stirred for 1 h. After the solvent has been removed under reduced pressure, the residue is extracted by stirring in heptane/toluene 3:1 and filtered off while hot. Yield: 12.5 g (32 mmol), 81% of theory.

The following compounds are prepared in an analogous manner:

| Reactant 1 | Product | Yield |
|---|---|---|
| 2h 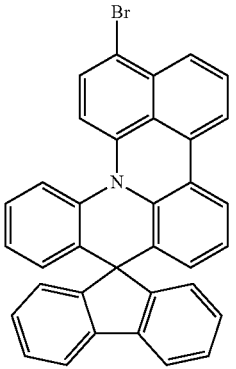 [SMILES: Brc1ccc2c3c(cccc13)-c1cccc3c1N2c1ccccc1C31c2ccccc2-c2ccccc21] | | 83% |

| | Reactant 1 | Product | Yield |
|---|---|---|---|
| 3h | | | 81% |
| 4h | | | 78% |
| 5h | | | 69% |
| 6h | | | 52% |

| | Reactant 1 | Product | Yield |
|---|---|---|---|
| 7h | 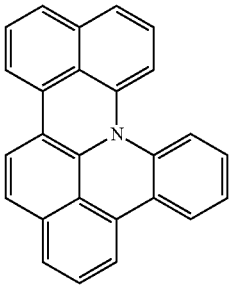 [SMILES: c1ccc2c(c1)-c1cccc3ccc4c(c13)N2c1cccc2cccc-4c12] | 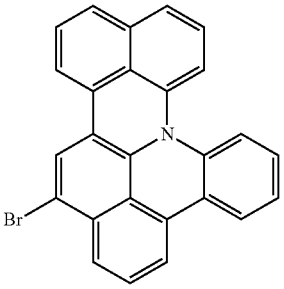 [SMILES: Brc1cc2c3c4c(cccc14)-c1ccccc1N3c1cccc3cccc-2c13] | 43% |
| 8h | 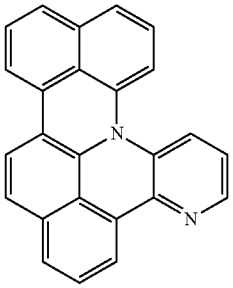 | 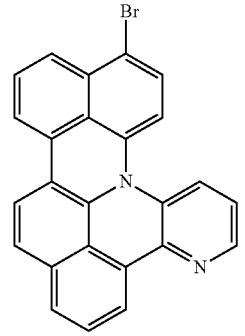 [SMILES: Brc1ccc2c3c(cccc13)-c1ccc3cccc4c3c1N2c1cccnc1-4] | 39% |
| 9h | 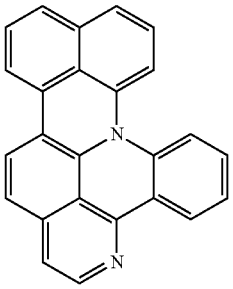 [SMILES: c1ccc2c(c1)-c1nccc3ccc4c(c13)N2c1cccc2cccc-4c12] | 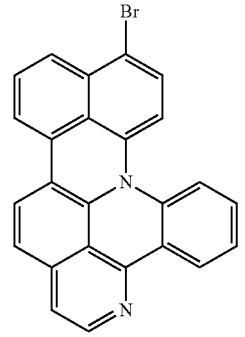 [SMILES: Brc1ccc2c3c(cccc13)-c1ccc3ccnc4c3c1N2c1ccccc1-4] | 67% |
| 10h | 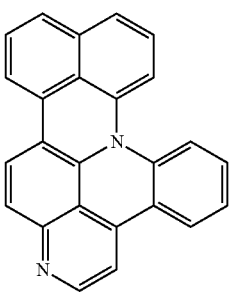 | 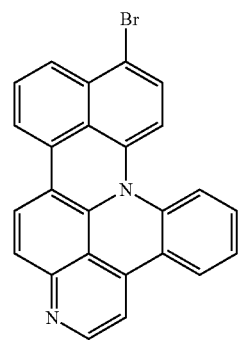 [SMILES: Brc1ccc2c3c(cccc13)-c1ccc3nccc4c3c1N2c1ccccc1-4] | 65% |
| 11h | 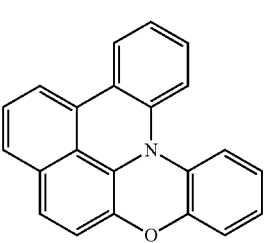 [SMILES: c1ccc2c(c1)oc1ccc3cccc4c5ccccc5n2-c1c34] | 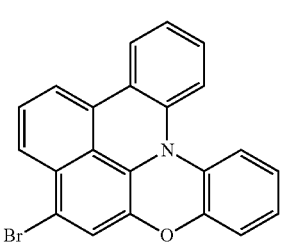 [SMILES: Brc1cc2oc3ccccc3n3c4ccccc4c4cccc1c4c2-3] | 72% |

| | Reactant 1 | Product | Yield |
|---|---|---|---|
| 12h | 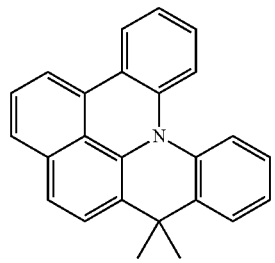 [SMILES: CC1(C)c2ccccc2N2c3ccccc3-c3cccc4ccc1c2c34] | 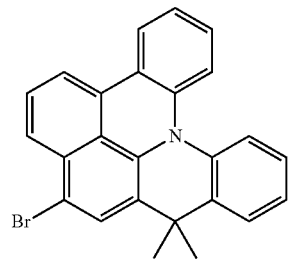 [SMILES: CC1(C)c2ccccc2N2c3ccccc3-c3cccc4c(Br)cc1c2c34] | 61% |
| 13h | 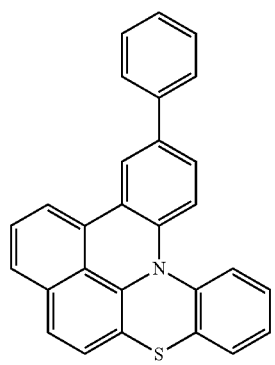 [SMILES: c1ccc(-c2ccc3c(c2)c2cccc4ccc5sc6ccccc6n3-c5c42)cc1] | 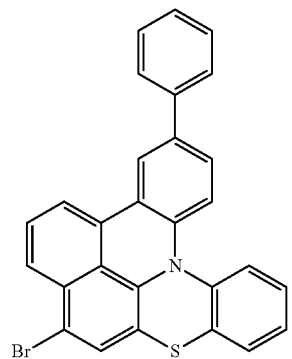 [SMILES: Brc1cc2sc3ccccc3n3c4ccc(-c5ccccc5)cc4c4cccc1c4c2-3] | 77% |
| 14h | 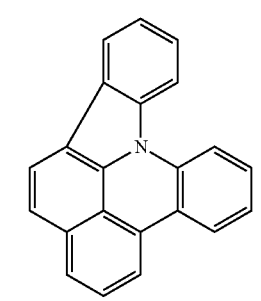 [SMILES: c1cc2ccc3c4ccccc4n4c5ccccc5c(c1)c2c34] | 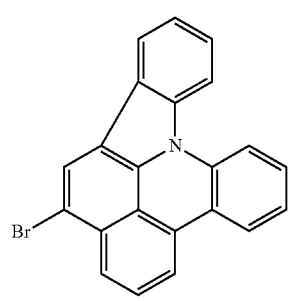 [SMILES: Brc1cc2c3ccccc3n3c4ccccc4c4cccc1c4c23] | 68% |
j) Suzuki Coupling
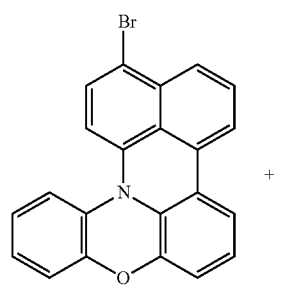 + 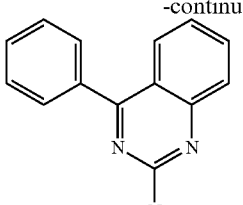 
[1842121-58-1]

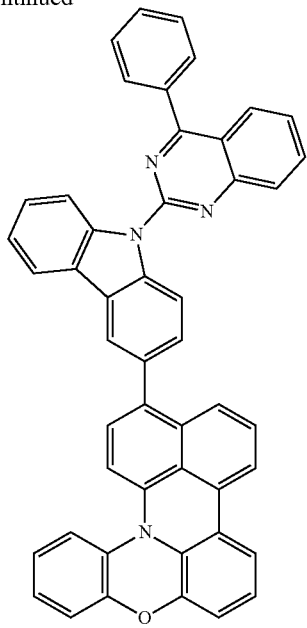

Under protective gas, 62 g (150 mmol) of B-[9-(4-phenyl-2-quinazolinyl)-9H-carbazol-3-yl]boronic acid, 55 g (145 mmol) of product h and 36 g (340 mmol) of sodium carbonate are suspended in 1000 ml of ethylene glycol dimethyl ether and 280 ml of water. 1.8 g (1.5 mmol) of tetrakis(triphenylphosphine)palladium(0) are added to this suspension, and the reaction mixture is heated under reflux for 16 h. After cooling, the organic phase is removed, filtered through silica gel, washed three times with 200 ml of water and then concentrated to dryness. The product is purified via column chromatography on silica gel with toluene/heptane (1:2) and finally sublimed under high vacuum (p=$5\times10^{-7}$ mbar) (99.9% purity). The yield is 75 g (111 mmol), 60% of theory.

The following compounds are prepared in an analogous manner:

| Reactant 1 | Reactant 2 |
|---|---|
| 1j | |

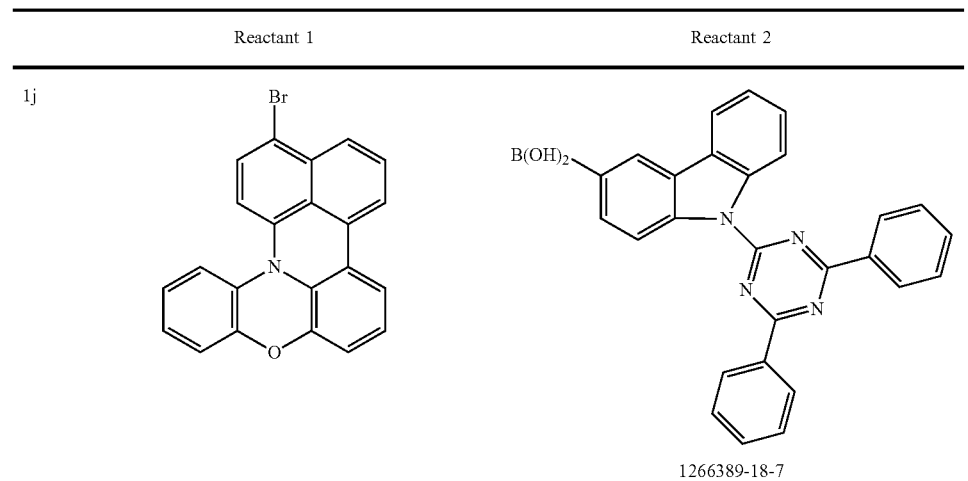

1266389-18-7

| 3j | |
|---|---|

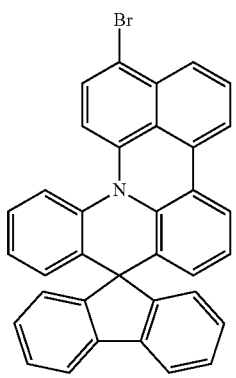
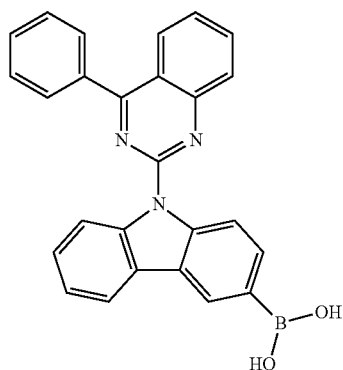

[1642121-58-1]

| | | |
|---|---|---|
| 4j | 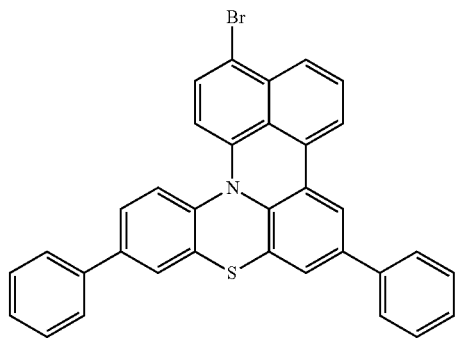 [SMILES: Brc1ccc2c3c1cccc3c1cc(-c3ccccc3)cc3sc4cc(-c5ccccc5)ccc4n2-c31] | 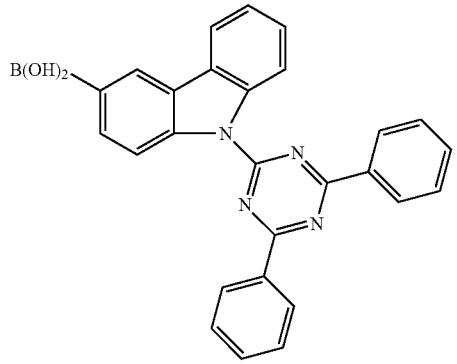
1266389-18-7 |
| 5j | 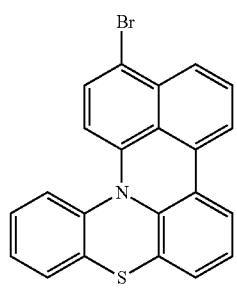 [SMILES: Brc1ccc2c3c1cccc3c1cccc3sc4ccccc4n2-c31] | 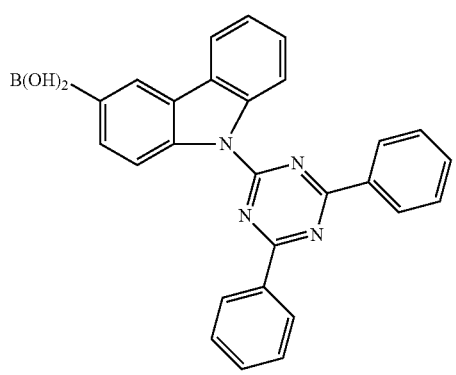
1266389-18-7 |
| 6j | 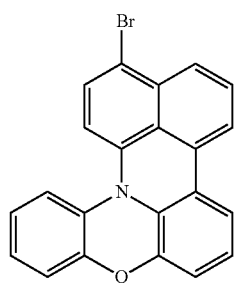 [SMILES: Brc1ccc2c3c1cccc3c1cccc3oc4ccccc4n2-c31] | 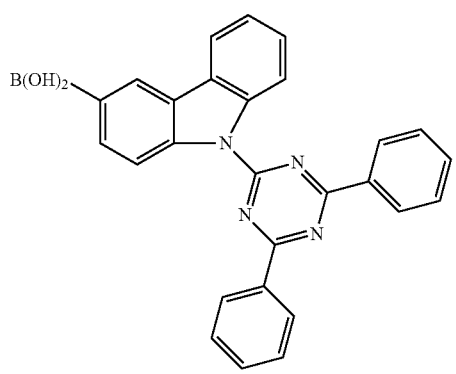
1266389-18-7 |
| 7j | 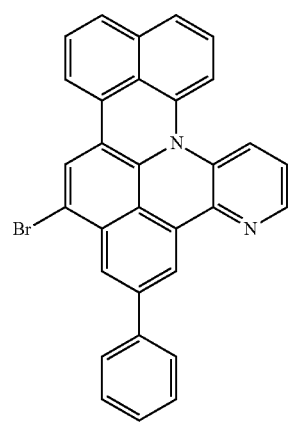 [SMILES: Brc1cc2c3c4c(cc(-c5ccccc5)cc14)-c1ncccc1N3c1cccc3cccc-2c13] | 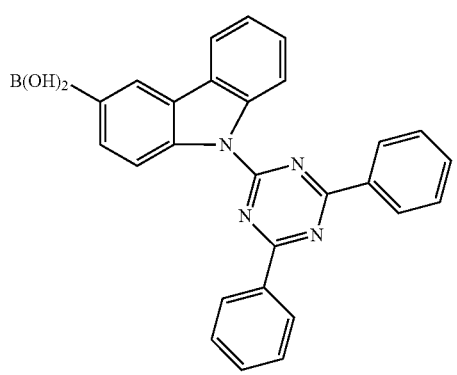
1266389-18-7 |

-continued
8j 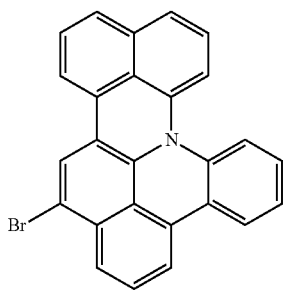 [SMILES: Brc1cc2c3c4c(cccc14)-c1ccccc1N3c1cccc3cccc-2c13]
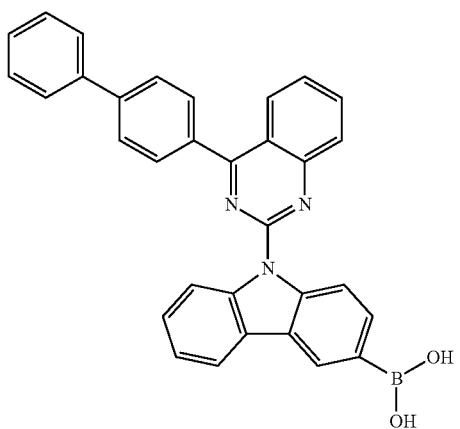
1377576-56-1]
9j 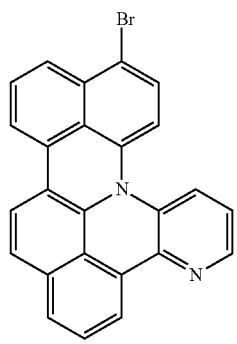 [SMILES: Brc1ccc2c3c(cccc13)-c1ccc3cccc4c3c1N2c1cccnc1-4]
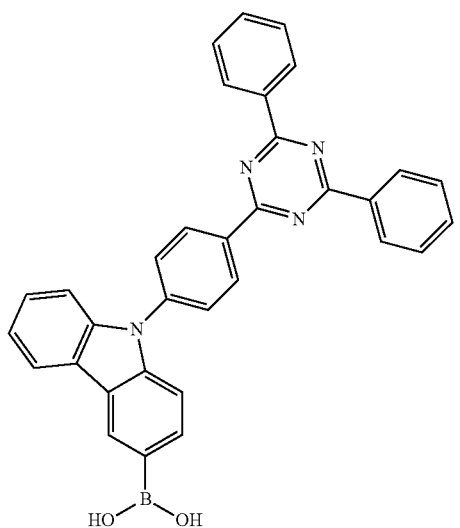 [SMILES: OB(O)c1ccc2c(c1)c1ccccc1n2-c1ccc(-c2nc(-c3ccccc3)nc(-c3ccccc3)n2)cc1]
10j 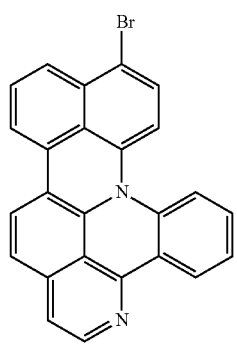 [SMILES: Brc1ccc2c3c(cccc13)-c1ccc3ccnc4c3c1N2c1ccccc1-4]
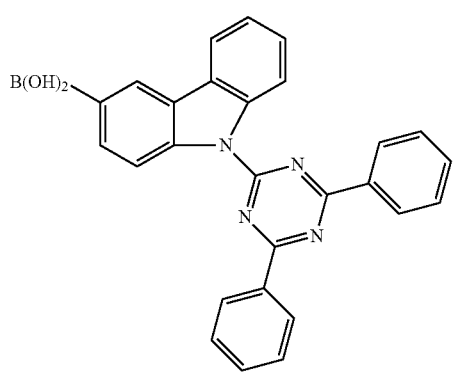
1266389-18-7

| | | |
|---|---|---|
| 11j | 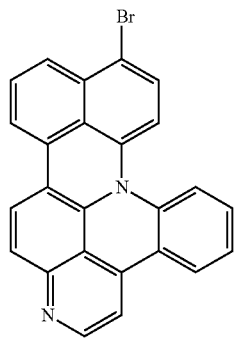 [SMILES: Brc1ccc2c3c(cccc13)-c1ccc3nccc4c3c1N2c1ccccc1-4] | 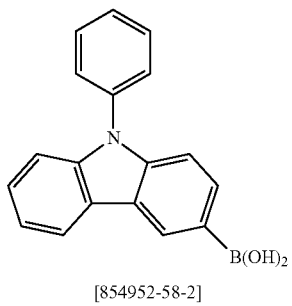 [SMILES: OB(O)c1ccc2c(c1)c1ccccc1n2-c1ccccc1]
[854952-58-2] |
| 12j | 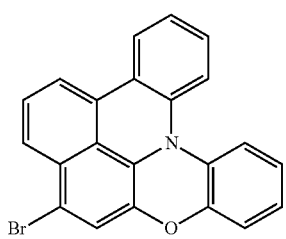 [SMILES: Brc1cc2oc3ccccc3n3c4ccccc4c4cccc1c4c2-3] | 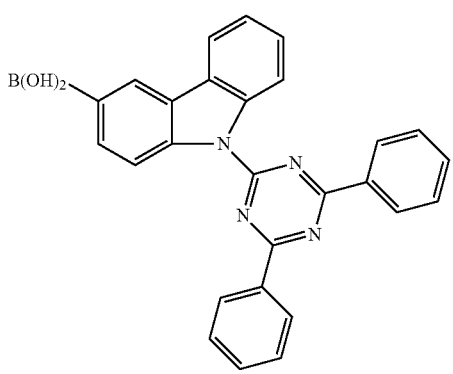
1266389-18-7 |
| 13j | 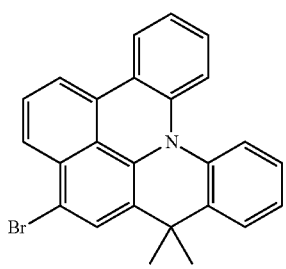 [SMILES: CC1(C)c2ccccc2N2c3ccccc3-c3cccc4c(Br)cc1c2c34] | 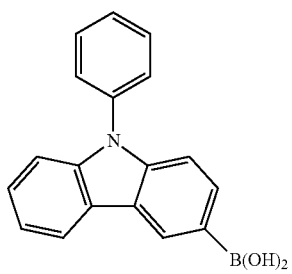
[854952-58-2] |
| 14j | 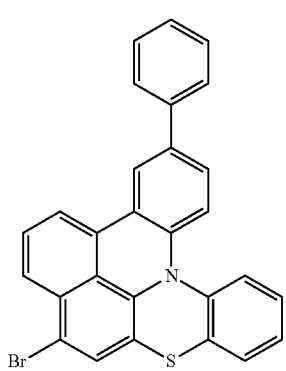 [SMILES: Brc1cc2sc3ccccc3n3c4ccc(-c5ccccc5)cc4c4cccc1c4c2-3] | 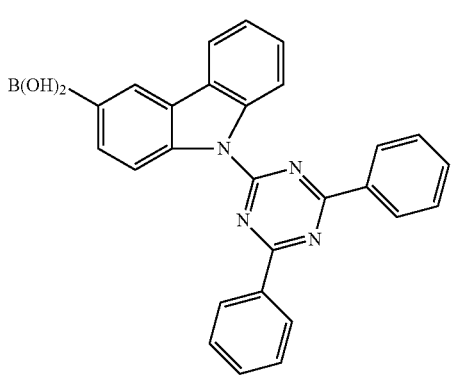
1266389-18-7 |

| | | |
|---|---|---|
| 15j | 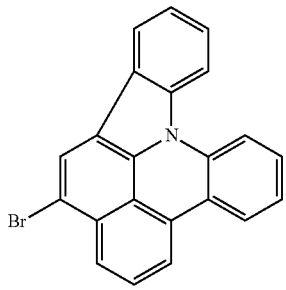 [SMILES: Brc1cc2c3ccccc3n3c4ccccc4c4cccc1c4c23] | 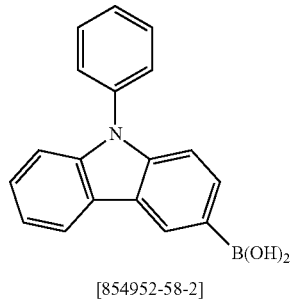 [SMILES: OB(O)c1ccc2c(c1)c1ccccc1n2-c1ccccc1]
[854952-58-2] |
| 16j | 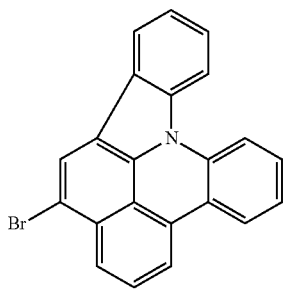 [SMILES: Brc1cc2c3ccccc3n3c4ccccc4c4cccc1c4c23] | 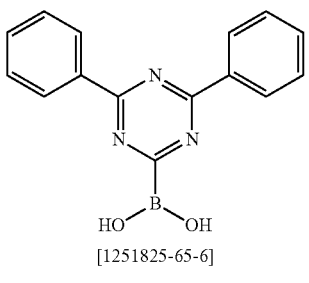 [SMILES: OB(O)c1nc(-c2ccccc2)nc(-c2ccccc2)n1]
[1251825-65-6] |
| 17j | 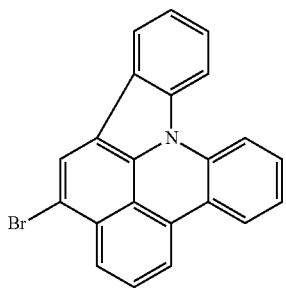 [SMILES: Brc1cc2c3ccccc3n3c4ccccc4c4cccc1c4c23] | 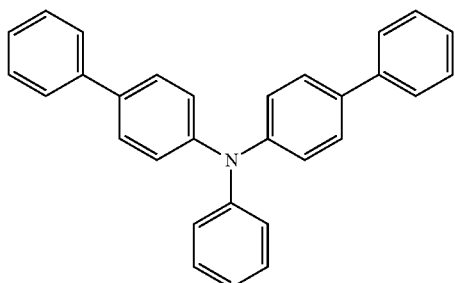
[943836-24-6] |
| 18j | 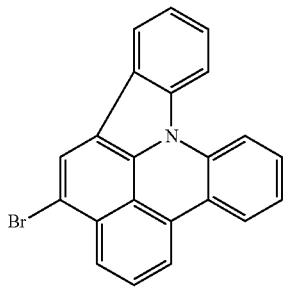 | 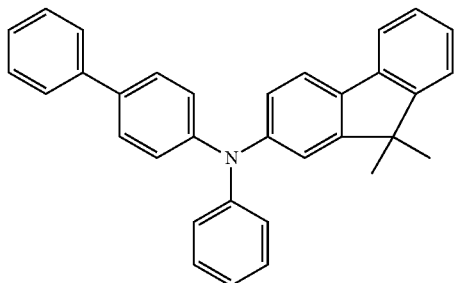
[1265177-27-2] |

-continued
19j 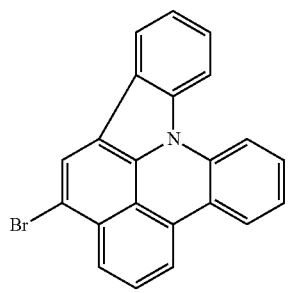 [SMILES: Brc1cc2c3ccccc3n3c4ccccc4c4cccc1c4c23] 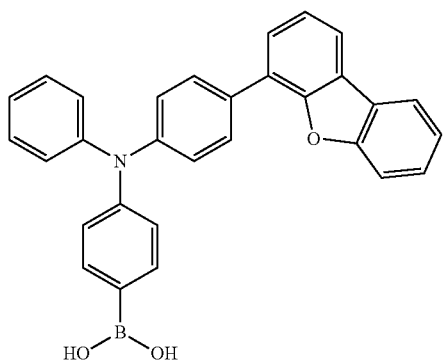
[1848986-77-5]
20j 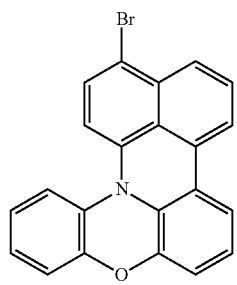 [SMILES: Brc1ccc2c3c1cccc3c1cccc3oc4ccccc4n2-c31] 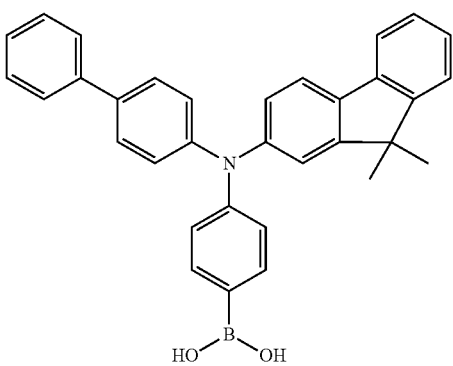
[1265177-27-2]
| Product | Yield |
|---|---|
| 1j 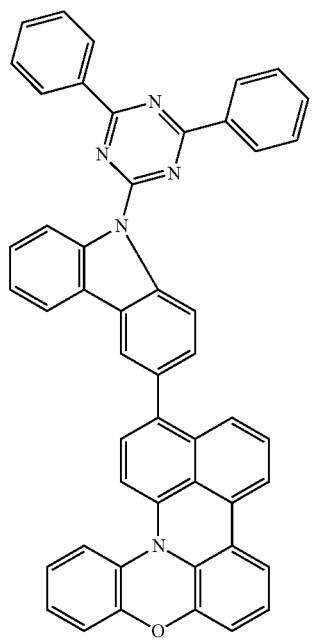 [SMILES: c1ccc(-c2nc(-c3ccccc3)nc(-n3c4ccccc4c4cc(-c5ccc6c7c5cccc7c5cccc7oc8ccccc8n6-c75)ccc43)n2)cc1] | 74% |

| | | |
|---|---|---|
| 3j | 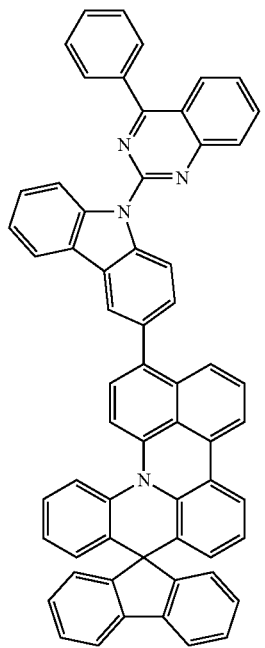 [SMILES: c1ccc(-c2nc(-n3c4ccccc4c4cc(-c5ccc6c7c(cccc57)-c5cccc7c5N6c5ccccc5C75c6ccccc6-c6ccccc65)ccc43)nc3ccccc23)cc1] | 81% |
| 4j | 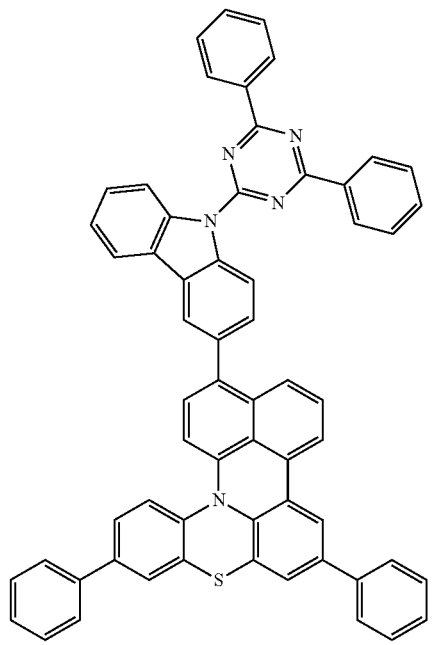 [SMILES: c1ccc(-c2ccc3c(c2)sc2cc(-c4ccccc4)cc4c2-n3c2ccc(-c3ccc5c(c3)c3ccccc3n5-c3nc(-c5ccccc5)nc(-c5ccccc5)n3)c3cccc4c32)cc1] | 78% |

| | | |
|---|---|---|
| 5j | 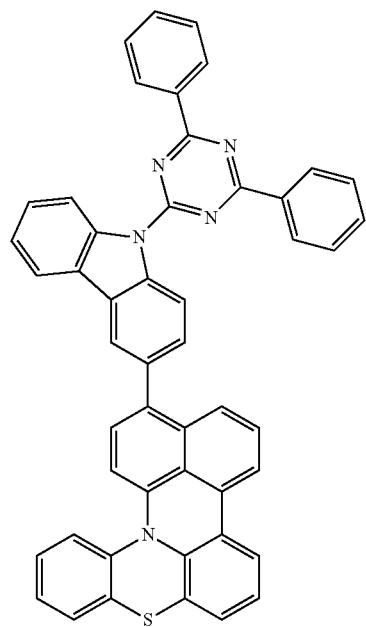 [SMILES: c1ccc(-c2nc(-c3ccccc3)nc(-n3c4ccccc4c4cc(-c5ccc6c7c5cccc7c5cccc7oc8ccccc8n6-c75)ccc43)n2)cc1] | 79% |
| 6j | 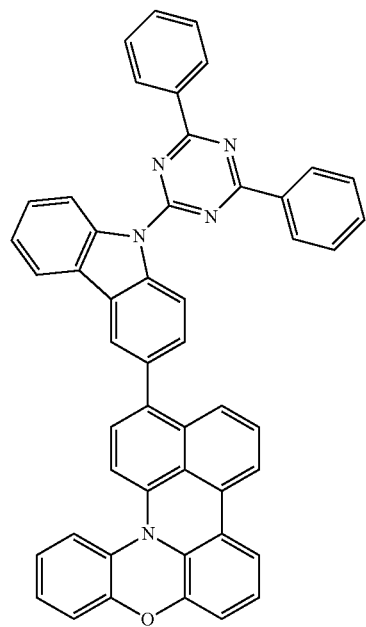 | 75% |

| | | |
|---|---|---|
| 7j | 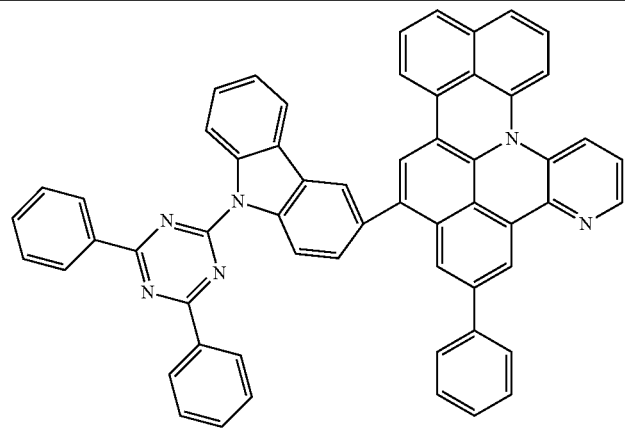 | 81% |
| 8j | 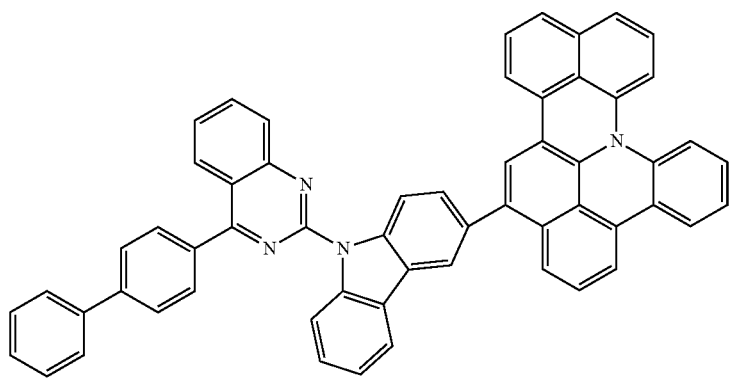 [SMILES: c1ccc(-c2ccc(-c3nc(-n4c5ccccc5c5cc(-c6cc7c8c9c(cccc69)-c6ccccc6N8c6cccc8cccc-7c68)ccc54)nc4ccccc34)cc2)cc1] | 78% |
| 9j | 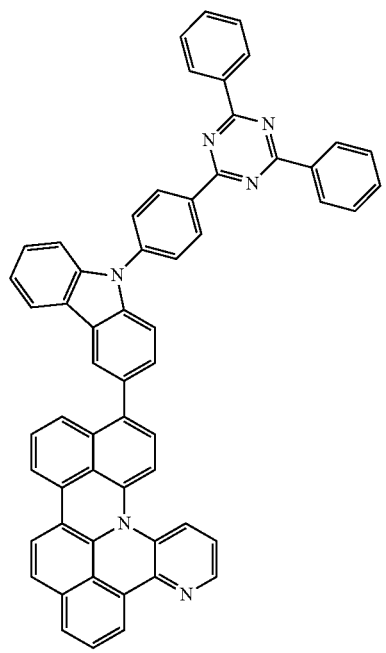 [SMILES: c1ccc(-c2nc(-c3ccccc3)nc(-c3ccc(-n4c5ccccc5c5cc(-c6ccc7c8c(cccc68)-c6ccc8cccc9c8c6N7c6cccnc6-9)ccc54)cc3)n2)cc1] | 75% |

| | | |
|---|---|---|
| 10j | 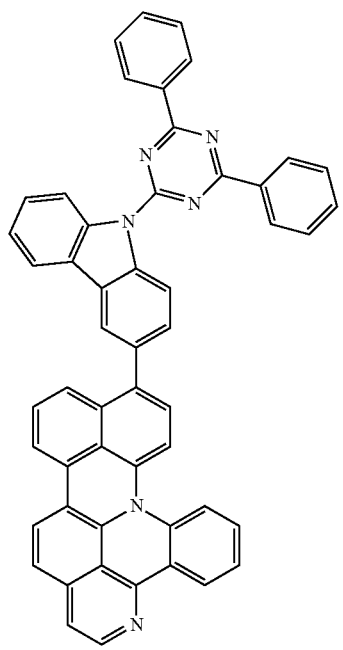 [SMILES: c1ccc(-c2nc(-c3ccccc3)nc(-n3c4ccccc4c4cc(-c5ccc6c7c(cccc57)-c5ccc7ccnc8c7c5N6c5ccccc5-8)ccc43)n2)cc1] | 70% |
| 11j | 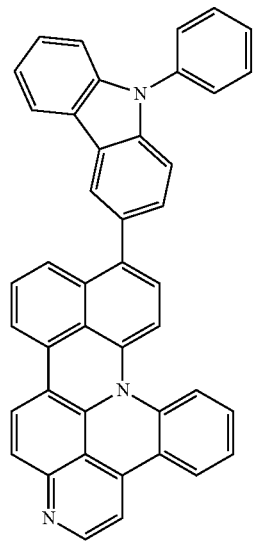 [SMILES: c1ccc(-n2c3ccccc3c3cc(-c4ccc5c6c(cccc46)-c4ccc6nccc7c6c4N5c4ccccc4-7)ccc32)cc1] | 73% |
| 12j | 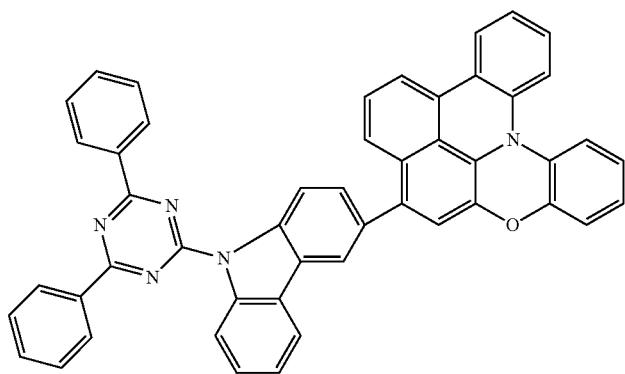 [SMILES: c1ccc(-c2nc(-c3ccccc3)nc(-n3c4ccccc4c4cc(-c5cc6oc7ccccc7n7c8ccccc8c8cccc5c8c6-7)ccc43)n2)cc1] | 72% |

| | | |
|---|---|---|
| 13j | 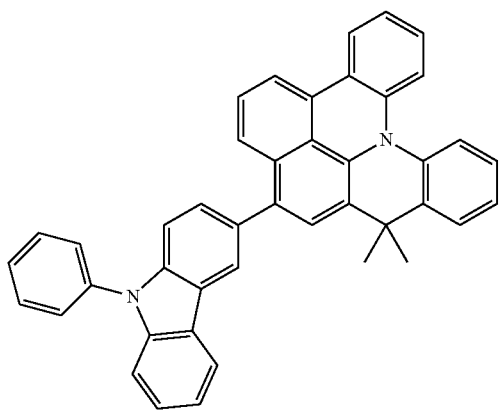 [SMILES: CC1(C)c2ccccc2N2c3ccccc3-c3cccc4c(-c5ccc6c(c5)c5ccccc5n6-c5ccccc5)cc1c2c34] | 76% |
| 14j | 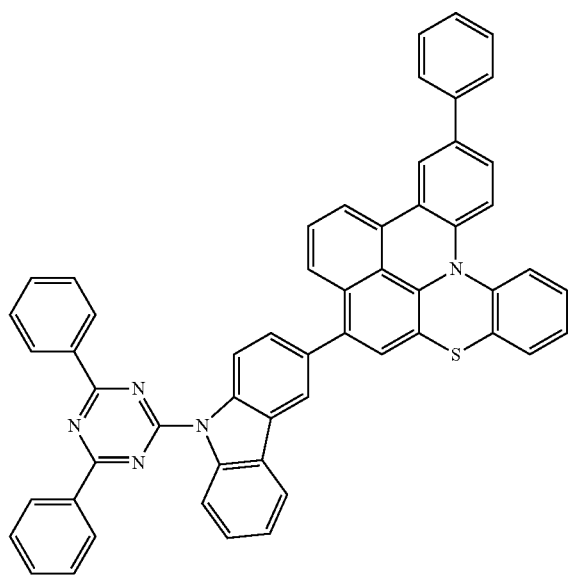 [SMILES: c1ccc(-c2ccc3c(c2)c2cccc4c(-c5ccc6c(c5)c5ccccc5n6-c5nc(-c6ccccc6)nc(-c6ccccc6)n5)cc5sc6ccccc6n3-c5c42)cc1] | 73% |
| 15j | 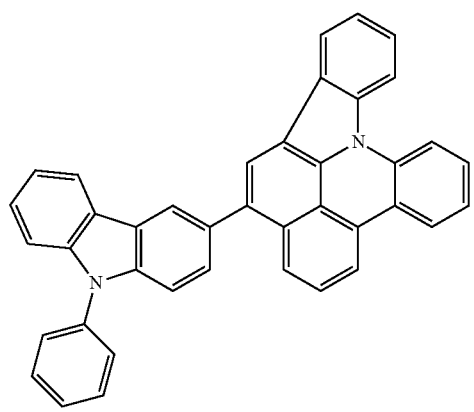 [SMILES: c1ccc(-n2c3ccccc3c3cc(-c4cc5c6ccccc6n6c7ccccc7c7cccc4c7c56)ccc32)cc1] | 78% |

| | | |
|---|---|---|
| 16j | 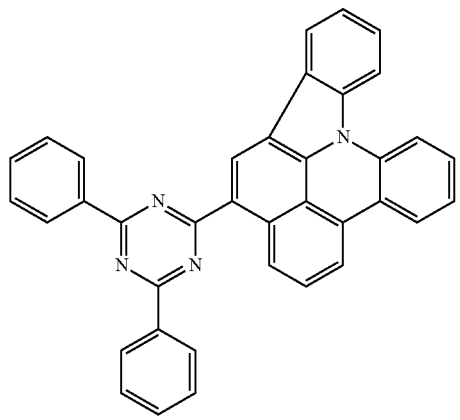 [SMILES: c1ccc(-c2nc(-c3ccccc3)nc(-c3cc4c5ccccc5n5c6ccccc6c6cccc3c6c45)n2)cc1] | 81% |
| 17j | 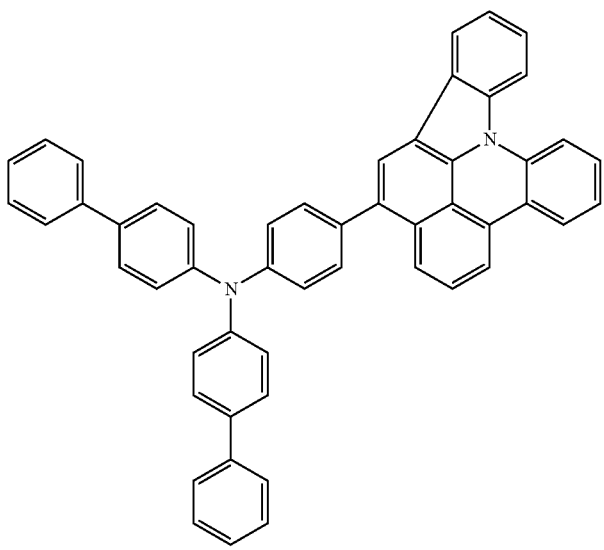 [SMILES: c1ccc(-c2ccc(N(c3ccc(-c4ccccc4)cc3)c3ccc(-c4cc5c6ccccc6n6c7ccccc7c7cccc4c7c56)cc3)cc2)cc1] | 76% |
| 18j | 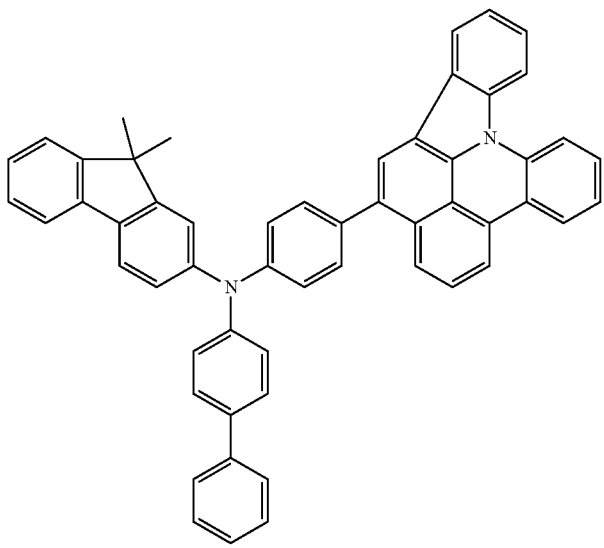 [SMILES: CC1(C)c2ccccc2-c2ccc(N(c3ccc(-c4ccccc4)cc3)c3ccc(-c4cc5c6ccccc6n6c7ccccc7c7cccc4c7c56)cc3)cc21] | 75% |

| | | |
|---|---|---|
| 19j | 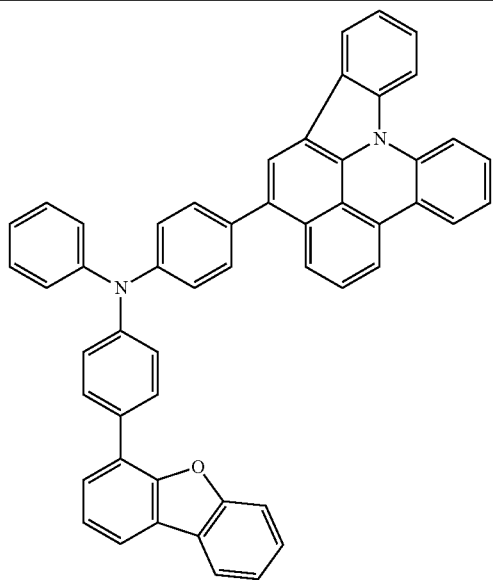 | 70% |
| 20j | 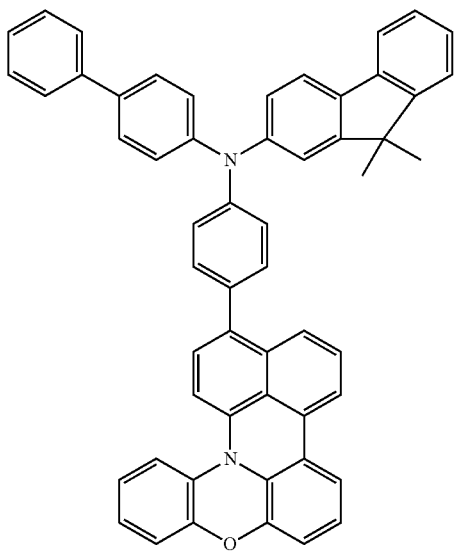 [SMILES: CC1(C)c2ccccc2-c2ccc(N(c3ccc(-c4ccccc4)cc3)c3ccc(-c4ccc5c6c4cccc6c4cccc6oc7ccccc7n5-c64)cc3)cc21] | 76% |

Production of the OLEDs

Examples I1 to I15 which follow (see Table 1) present the use of the materials of the invention in OLEDs.

Pretreatment for Examples I1-I15:

Glass plaques coated with structured ITO (indium tin oxide) of thickness 50 nm are treated prior to coating, first with an oxygen plasma, followed by an argon plasma. These plasma-treated glass plaques form the substrates to which the OLEDs are applied.

The OLEDs basically have the following layer structure: substrate/hole injection layer (HIL)/hole transport layer (HTL)/electron blocker layer (EBL)/emission layer (EML)/optional hole blocker layer (HBL)/electron transport layer (ETL)/optional electron injection layer (EIL) and finally a cathode. The cathode is formed by an aluminum layer of thickness 100 nm.

The exact structure of the OLEDs can be found in Table 1. The materials required for production of the OLEDs are shown in Table 2.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC1:IV1:TER1 (50%:45%:5%) mean here that the material IC1 is present in the layer in a proportion by volume of 50%, IV1 in a proportion of 45% and TER1 in a proportion of 5%. Analogously, the electron transport layer may also consist of a mixture of two materials.

The OLEDs are characterized in a standard manner. The electroluminescence spectra are determined at a luminance of 1000 cd/m², and the CIE 1931 x and y color coordinates are calculated therefrom.

Use of Mixtures of the Invention in OLEDs

The materials of the invention can be used in the emission layer in phosphorescent red OLEDs. The inventive compounds IV1 to IV7 are used in Examples I1 to I15 as matrix material in the emission layer. The color coordinates of the electroluminescence spectra of the OLEDs are CIEx=0.67 and CIEy=0.33. The materials are thus suitable for use in the emission layer of red OLEDs.

In addition, the materials of the invention can be used successfully in the hole blocker layer (HBL) or electron blocker layer (EBL). This is shown in examples I5 and I8 or I2, I10, I13 and I15. Here too, the color coordinates of the spectrum of each of the OLEDs are CIEx=0.67 and CIEy=0.33.

TABLE 1

Structure of the OLEDs

| Ex. | HIL thickness | HTL thickness | EBL thickness | EML thickness | HBL thickness | ETL thickness |
|---|---|---|---|---|---|---|
| I1 | HATCN 5 nm | SpMA1 125 nm | SpMA2 10 nm | IC1:IV1:TER1 (50%:45%:5%) 40 nm | — | ST1:LiQ (50%:50%) 35 nm |
| I2 | HATCN 5 nm | SpMA1 125 nm | IV1 10 nm | IC1:IV1:TER1 (50%:45%:5%) 40 nm | — | ST1:LiQ (50%:50%) 35 nm |
| I3 | HATCN 5 nm | SpMA1 125 nm | SpMA2 10 nm | IV2:TER1 (95%:5%) 40 nm | — | ST1:LiQ (50%:50%) 35 nm |
| I4 | HATCN 5 nm | SpMA1 125 nm | SpMA2 10 nm | IC2:IV2:TER1 (50%:45%:5%) 40 nm | — | ST1:LiQ (50%:50%) 35 nm |
| I5 | HATCN 5 nm | SpMA1 125 nm | SpMA2 10 nm | IV2:TER1 (95%:5%) 40 nm | IV2 5 nm | ST1:LiQ (50%:50%) 35 nm |
| I6 | HATCN 5 nm | SpMA1 125 nm | SpMA2 10 nm | IV3:TER1 (95%:5%) 40 nm | — | ST1:LiQ (50%:50%) 35 nm |
| I7 | HATCN 5 nm | SpMA1 125 nm | SpMA2 10 nm | IC2:IV3:TER1 (50%:45%:5%) 40 nm | — | ST1:LiQ (50%:50%) 35 nm |
| I8 | HATCN 5 nm | SpMA1 125 nm | SpMA2 10 nm | IV3:TER1 (95%:5%) 40 nm | IV3 5 nm | ST1:LiQ (50%:50%) 35 nm |
| I9 | HATCN 5 nm | SpMA1 125 nm | SpMA2 10 nm | IC1:IV4:TER1 (50%:45%:5%) 40 nm | — | ST1:LiQ (50%:50%) 35 nm |
| I10 | HATCN 5 nm | SpMA1 125 nm | IV4 10 nm | IC1:IV4:TER1 (50%:45%:5%) 40 nm | — | ST1:LiQ (50%:50%) 35 nm |
| I11 | HATCN 5 nm | SpMA1 125 nm | SpMA2 10 nm | IV5:TER1 (95%:5%) 40 nm | — | ST1:LiQ (50%:50%) 35 nm |
| I12 | HATCN 5 nm | SpMA1 125 nm | SpMA2 10 nm | IC1:IV5:TER1 (50%:45%:5%) 40 nm | — | ST1:LiQ (50%:50%) 35 nm |
| I13 | HATCN 5 nm | SpMA1 125 nm | IV1 10 nm | IC1:IV6:TER1 (50%:45%:5%) 40 nm | — | ST1:LiQ (50%:50%) 35 nm |
| I14 | HATCN 5 nm | SpMA1 125 nm | SpMA2 10 nm | IC1:IV7:TER1 (50%:45%:5%) 40 nm | — | ST1:LiQ (50%:50%) 35 nm |
| I15 | HATCN 5 nm | SpMA1 125 nm | IV1 10 nm | IC1:IV7:TER1 (50%:45%:5%) 40 nm | — | ST1:LiQ (50%:50%) 35 nm |

TABLE 2
Structural formulae of the materials for the OLEDs
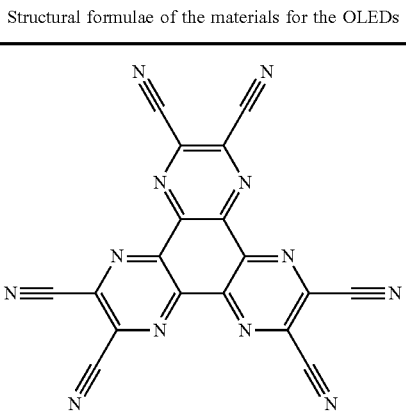
HATCN
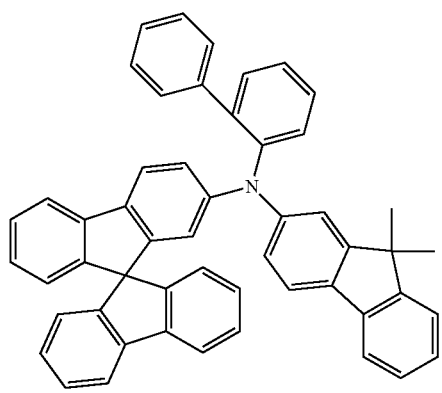 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
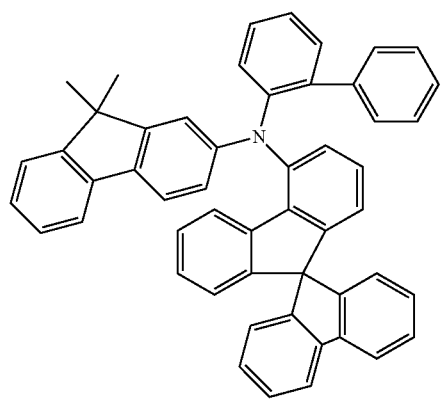 [SMILES: CC1(C)c2ccccc2-c2ccc(N(c3ccccc3-c3ccccc3)c3cccc4c3-c3ccccc3C43c4ccccc4-c4ccccc43)cc21]
SpMA2
TABLE 2-continued
Structural formulae of the materials for the OLEDs
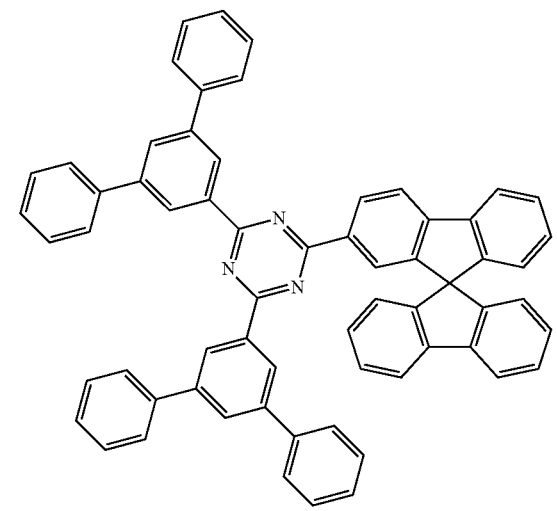 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST1
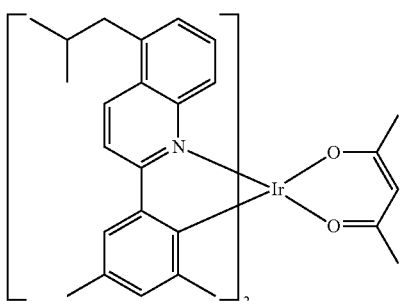
TER1
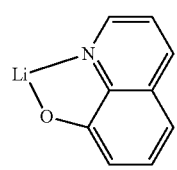
LiQ
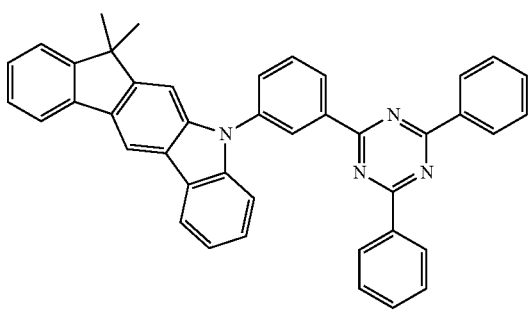 [SMILES: CC1(C)c2ccccc2-c2cc3c4ccccc4n(-c4cccc(-c5nc(-c6ccccc6)nc(-c6ccccc6)n5)c4)c3cc21]
IC1

TABLE 2-continued
Structural formulae of the materials for the OLEDs
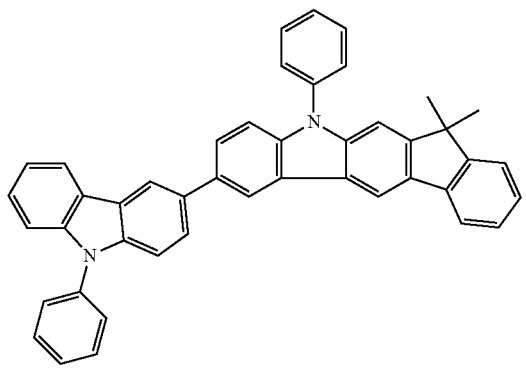 [SMILES: CC1(C)c2ccccc2-c2cc3c4cc(-c5ccc6c(c5)c5ccccc5n6-c5ccccc5)ccc4n(-c4ccccc4)c3cc21]
IC2
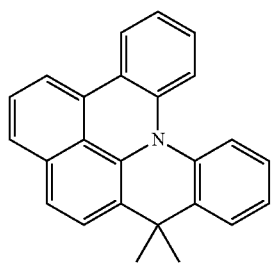 [SMILES: CC1(C)c2ccccc2N2c3ccccc3-c3cccc4ccc1c2c34]
IV1
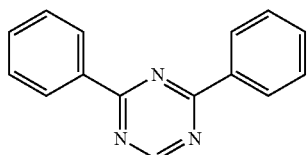
IV2
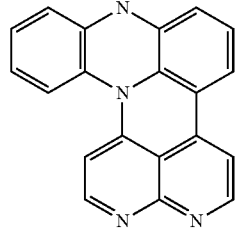
IV3
TABLE 2-continued
Structural formulae of the materials for the OLEDs
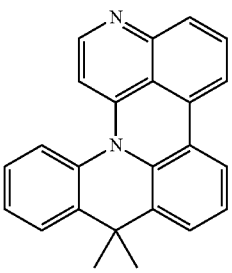 [SMILES: CC1(C)c2ccccc2N2c3c(cccc31)-c1cccc3nccc2c13]
IV4
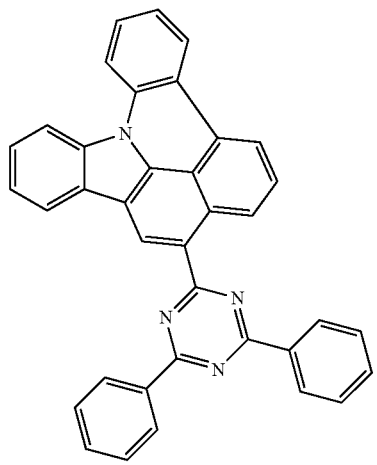 [SMILES: c1ccc(-c2nc(-c3ccccc3)nc(-c3cc4c5ccccc5n5c6ccccc6c6cccc3c6c45)n2)cc1]
IV5
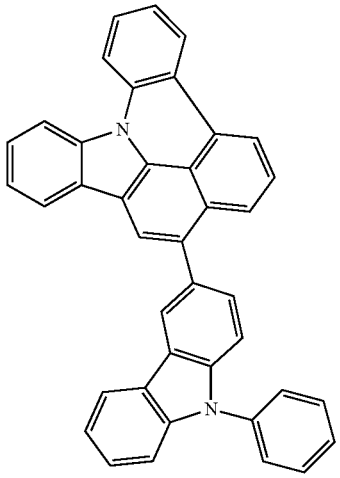 [SMILES: c1ccc(-n2c3ccccc3c3cc(-c4cc5c6ccccc6n6c7ccccc7c7cccc4c7c56)ccc32)cc1]
IV6

TABLE 2-continued

Structural formulae of the materials for the OLEDs

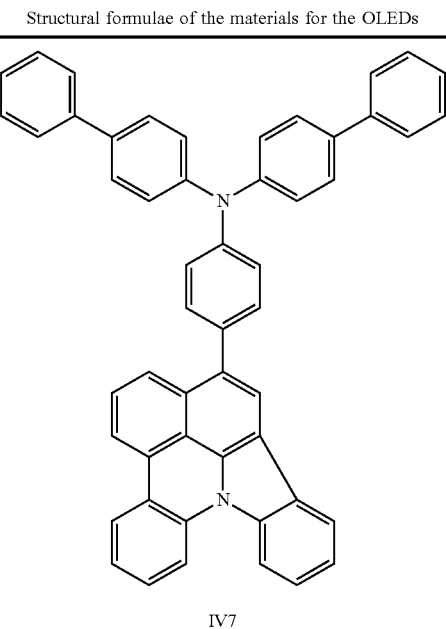

IV7

The invention claimed is:
1. A compound of formula (1)

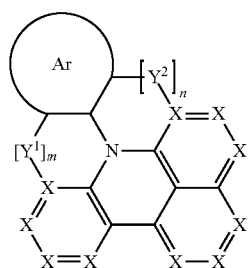

Formula (1)

where the symbols and indices used are as follows:
X is the same or different at each instance and is CR or N, where X=C when a $Y^1$ or $Y^2$ group is bonded to this X;
Ar together with the carbon atoms explicitly shown is an aryl or heteroaryl group which has 5 to 14 aromatic ring atoms and may be substituted by one or more R radicals;
$Y^1$ is C(R')2, NR', O, S, C=O, Si(R')2, BR', PR', P(=O) R', SO or $SO_2$;
$Y^2$ is a single bond, $C(R')_2$, $C(=C(R'')_2)$, NR', O, S, C'O, $Si(R')_2$, BR', PR', P(=O)R', SO or $SO_2$;
R is the same or different at each instance and is H, D, F, Cl, Br, I, $N(R^1)_2$, $N(Ar')_2$, CN, $NO_2$, $OR^1$, $SR^1$, $COOR^1$, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals and where one or more nonadjacent $CH_2$ groups is optionally replaced by $Si(R^1)_2$, C=O, $NR^1$, O, S or $CONR^1$, or an aromatic or heteroaromatic ring system which has 5 to 60 aromatic ring atoms, and or is optionally substituted in each case by one or more $R^1$ radicals; at the same time, two R radicals together optionally form an aliphatic or heteroaliphatic ring system;
R' is the same or different at each instance and is a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals and where one or more nonadjacent $CH_2$ groups may be replaced by $Si(R^1)_2$, C=O, $NR^1$, O, S or $CONR^1$, or an aromatic or heteroaromatic ring system which has 5 to 60 aromatic ring atoms, and may be substituted in each case by one or more $R^1$ radicals; at the same time, two R' radicals together may also form an aromatic, heteroaromatic, aliphatic or heteroaliphatic ring system;
R" is the same or different at each instance and is one of the following:
(a)R,
one R" is R and the other R" is $CR^1=CR^1$ or $CR^1=N$ or
(c) R" together with Ar, forms an aromatic or heteroaromatic ring system;
Ar' is the same or different at each instance and is an aromatic or heteroaromatic ring system which has 5 to 40 aromatic ring atoms and may be substituted by one or more $R^1$ radicals;
$R^1$ is the same or different at each instance and is H, D, F, Cl, Br, I, $N(R^2)_2$, CN, $NO_2$, $OR^2$, $SR^2$, $Si(R^2)_3$, $B(OR^2)_2$, $C(=O)R^2$, $P(=O)(R^2)_2$, $S(=O)R^2$, $S(=O)_2 R^2$, $OSO_2R^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^2$ radicals, where one or more nonadjacent $CH_2$ groups may be replaced by $Si(R^2)_2$, C=O, $NR^2$, O, S or $CONR^2$, or an aromatic or heteroaromatic ring system which has 5 to 40 aromatic ring atoms and may be substituted in each case by one or more $R^2$ radicals; at the same time, two or more $R^1$ radicals together may form a ring system;
$R^2$ is the same or different at each instance and is H, D, F or an aliphatic, aromatic or heteroaromatic organic radical having 1 to 20 carbon atoms, in which one or more hydrogen atoms may also be replaced by F;
M and n are independently 0 or 1, with the proviso that m+n=1 or 2; m=0 means that the $Y^1$ is absent and an R radical is bonded to the carbon atom in Ar to which $Y^1$ would be bonded; in addition, n=0 means that the $Y^2$ group is absent and an R radical is bonded to the carbon atom in Ar to which $Y^2$ would be bonded;
where the following compounds are excluded from the invention:

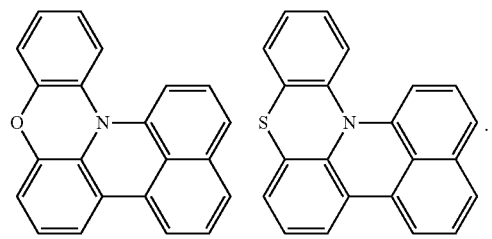

2. The compound as claimed in claim 1, wherein the compound of the formula (I) is of the formula (2a), (2b), (2c), (2d), (2e), (2f), (2g) or (2h)

Formula (2a)

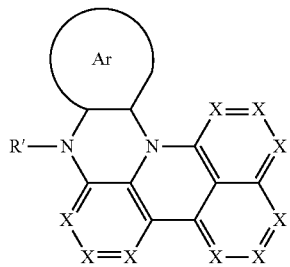

Formula (2b)

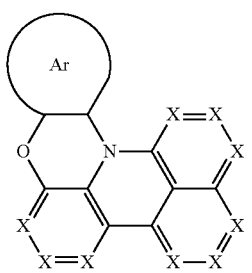

Formula (2c)

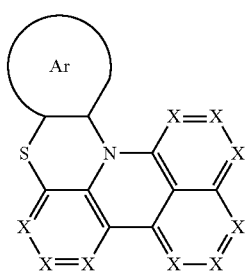

Formula (2d)

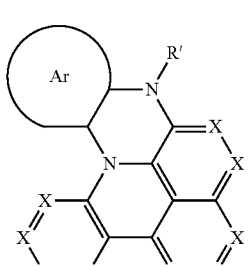

Formula (2e)

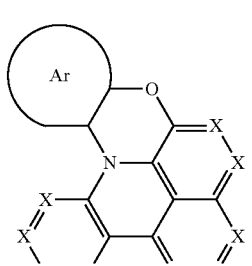

Formula (2f)

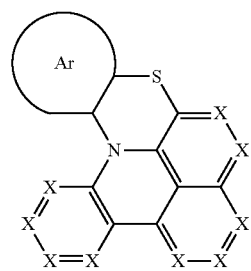

Formula (2g)

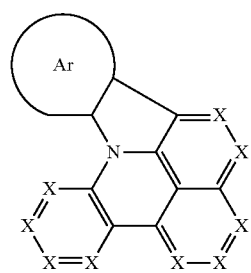

Formula (2h)

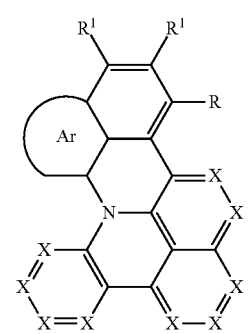

where the symbols used have the definitions given in claim 1.

3. The compound as claimed in claim 1, wherein Ar is selected from the groups of formulae (Ar-a), (Ar-b) and (Ar-c)

(Ar-a)

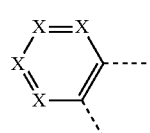

(Ar-b)

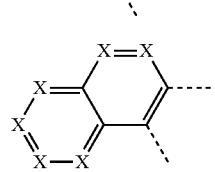

(Ar-c)

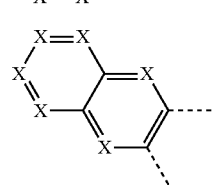

where one of the dotted bonds represents the bond to the nitrogen atom and the other dotted bond represents the bond to $Y^1$ or $Y^2$ and X has the definitions given in claim 1.

4. The compound as claimed in claim 1, wherein the compound of the formula (I) is a compound of formula (3)

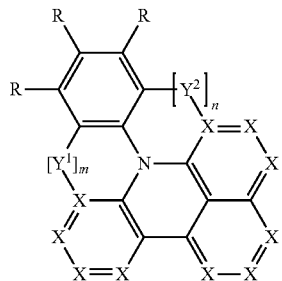

Formula (3)

where the symbols and indices used have the definitions given in claim 1 and where, when m=0 or n=0, and R radical is bonded at the position to which $Y^1$ or $Y^2$ would be bonded.

5. The compound as claimed in claim 1, wherein the compound is selected from the compounds of the formulae (4a) to (4h)

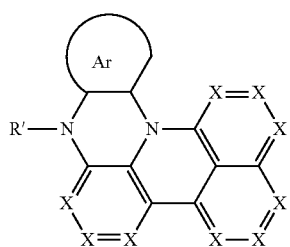

Formula (4a)

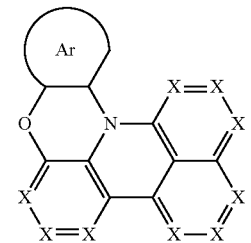

Formula (4b)

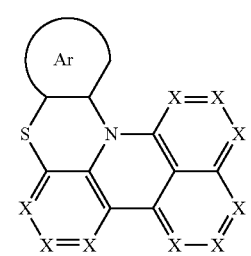

Formula (4c)

-continued

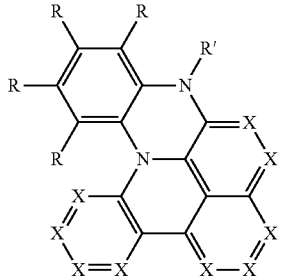

Formula (4d)

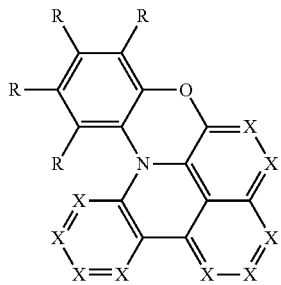

Formula (4e)

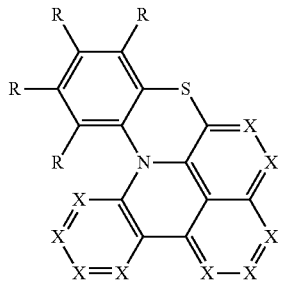

Formula (4f)

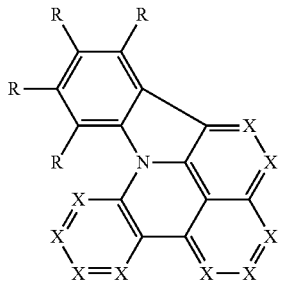

Formula (4g)

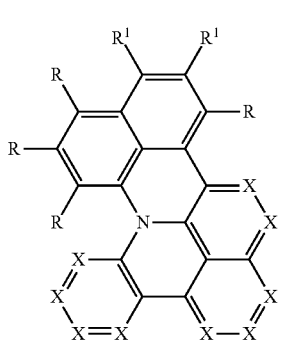

Formula (4h)

where the symbols used have the definitions given in claim 1.

6. The compound as claimed in claim 1, wherein the compound is selected from the compounds of the formulae (5a) to (5k)

Formula (5a)
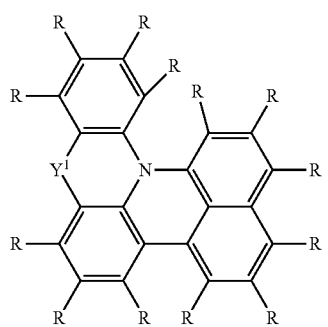
Formula (5b)
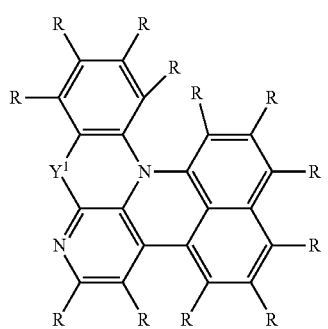
Formula (5c)
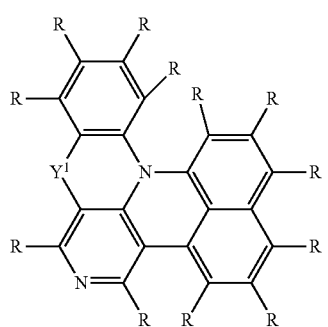
Formula (5d)
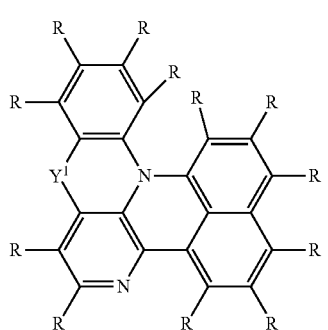
Formula (5e)
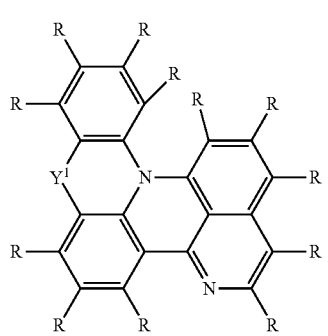
Formula (5f)
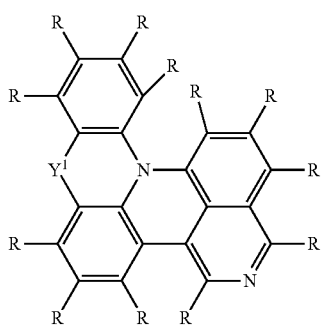
Formula (5g)
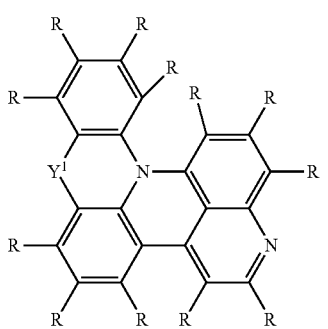
Formula (5h)
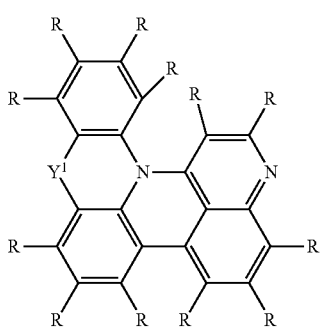
Formula (5i)
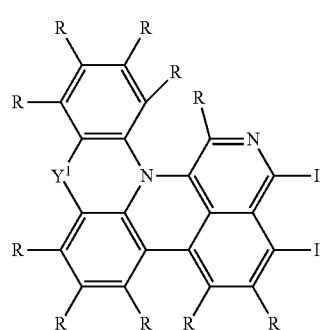
Formula (5j)
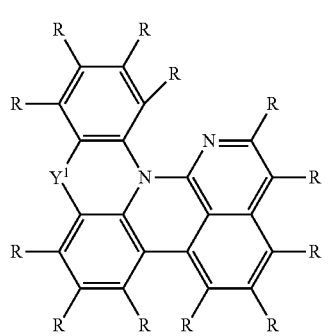

Formula (5k)
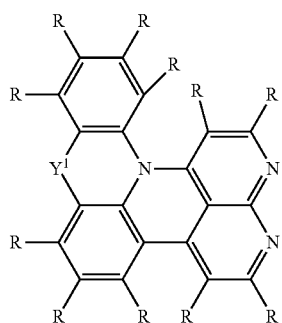
where the symbols used have the definitions given in claim 1.
7. The compound as claimed in claim 1, wherein the compound is selected from the compounds of the formulae (6a) to (6u)
Formula (6a)
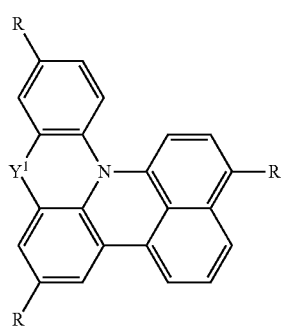
Formula (6b)
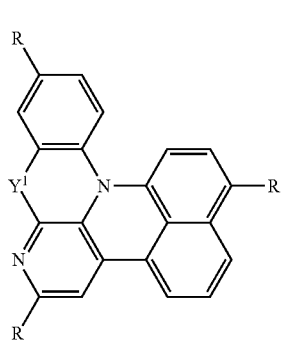
Formula (6c)
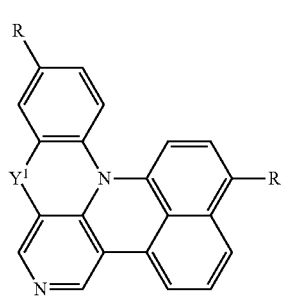
Formula (6d)
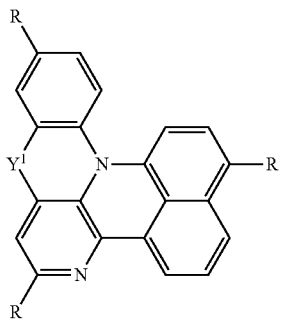
Formula (6e)
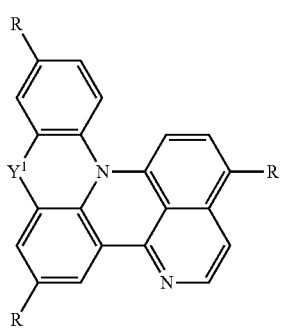
Formula (6f)
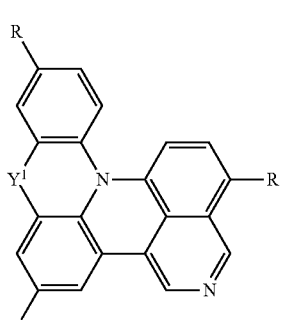
Formula (6g)
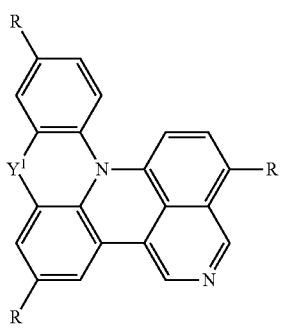
Formula (6h)
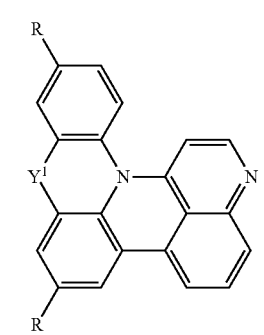

-continued
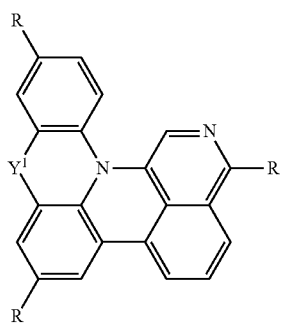
Formula (6i)
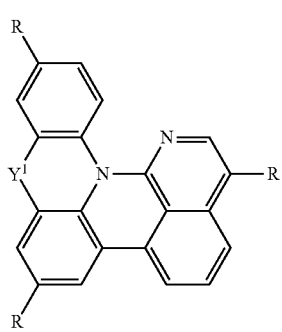
Formula (6j)
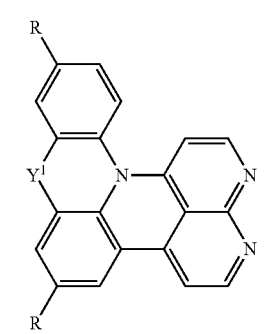
Formula (6k)
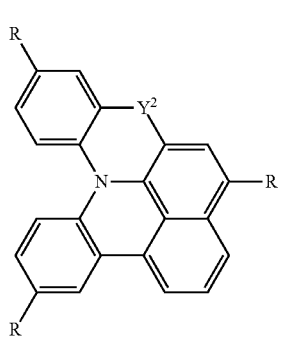
Formula (6l)
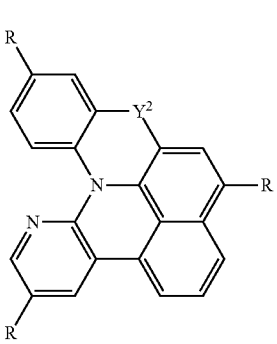
Formula (6m)
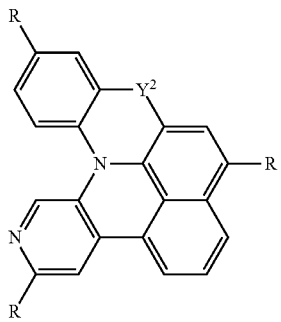
Formula (6n)
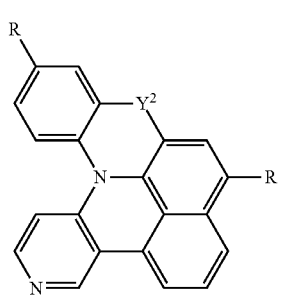
Formula (6o)
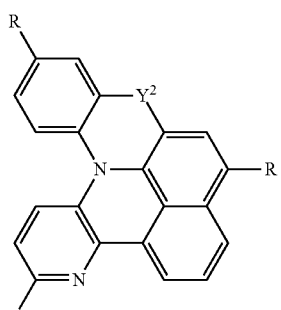
Formula (6p)
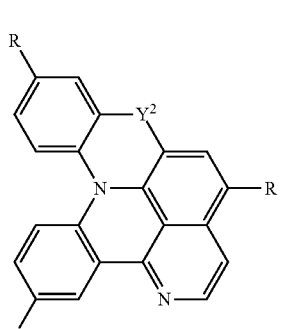
Formula (6q)
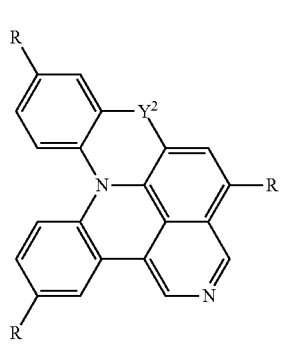
Formula (6r)

Formula (6s)
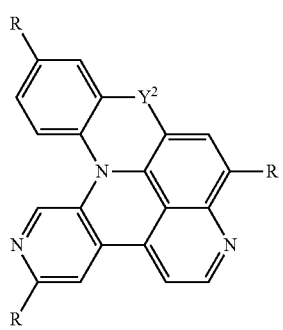
Formula (6t)
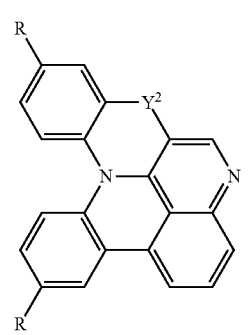
Formula (6u)
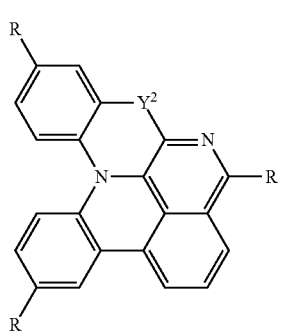
where the symbols used have the definitions given in claim 1.
8. The compound as claimed in claim 1, wherein the compound is selected from the compounds of the formulae (7a) to (7h)
Formula (7a)
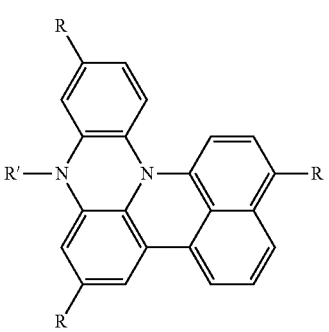
Formula (7b)
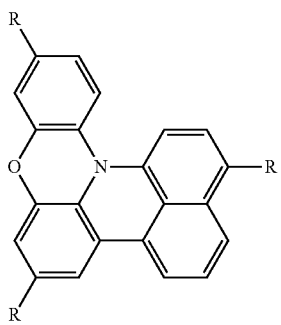
Formula (7c)
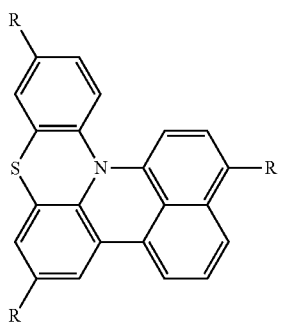
Formula (7d)
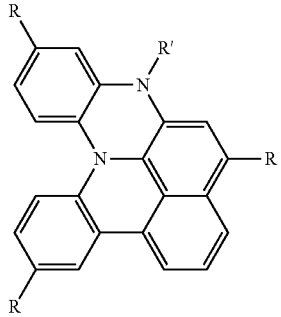
Formula (7e)
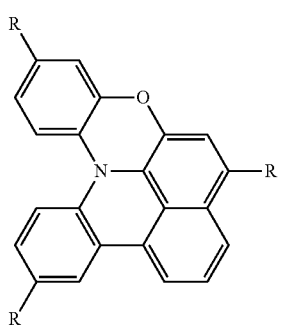
Formula (7f)
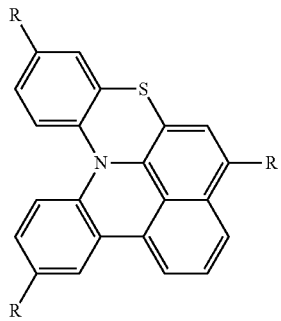

-continued

Formula (7g)

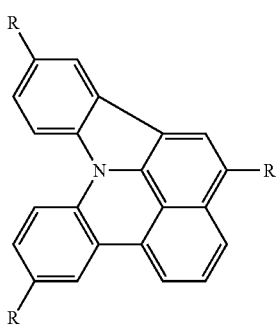

Formula (7h)

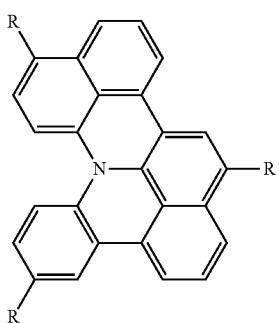

where the symbols used have the definitions given in claim 1.

9. The compound as claimed in claim 1, wherein R is the same or different at each instance and is selected from the group consisting of H, D, F, N(Ar')$_2$, CN, OR$^1$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may in each case be substituted by one or more R$^1$ radicals, and where one or more nonadjacent CH$_2$ groups may be replaced by O, or an aromatic or heteroaromatic ring system which has 6 to 30 aromatic ring atoms and may be substituted in each case by one or more R$^1$ radicals; at the same time, two R radicals together may also form an aliphatic ring system.

10. The compound as claimed in claim 1, wherein R' bonded to N, B or P is an aromatic or heteroaromatic ring system which has 6 to 30 aromatic ring atoms and may be substituted by one or more R$^1$ radicals, and in that R' bonded to C or Si is the same or different at each instance and is selected from the group consisting of a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may in each case be substituted by one or more R$^1$ radicals, and where one or more nonadjacent CH$_2$ groups may be replaced by O, or an aromatic or heteroaromatic ring system which has 6 to 30 aromatic ring atoms and may be substituted in each case by one or more R$^1$ radicals; at the same time, two R' radicals together may also form aromatic, heteroaromatic, aliphatic or heteroaliphatic ring system.

11. The compound as claimed in claim 1, wherein the compound contains
   (1) at least one substituent R which is
      (a) an aromatic or heteroaromatic ring system which has 5 to 60 aromatic ring atoms and is optionally substituted by one or more R$^1$ radicals, or
      (b) N(Ar')$_2$,
   (2) at least one Y$^1$ or Y$^2$ group which is NR' where R' from an aromatic or heteroaromatic ring system which has 5 to 40 aromatic ring atoms and is optionally substituted by one or more R$^1$ radicals.

12. A formulation comprising the compound as claimed in claim 1 and at least one solvent and/or at least one further organic or inorganic compound.

13. An electronic device comprising at least one compound as claimed in claim 1.

14. The electronic device as claimed in claim 13, wherein the device is an organic electroluminescent device.

15. An organic electroluminescent device which comprises the compound as claimed in claim 1 in an emitting layer as matrix material for phosphorescent or fluorescent emitters or for emitters that exhibit TADF, or in an electron transport layer and/or in a hole transport layer and/or in an exciton blocker layer and/or in a hole blocker layer.

16. The compound as claimed in claim 1, wherein
   R$^2$ is the same or different at each instance and is H, D, F or a hydrocarbyl radical having 1 to 20 carbon atoms, in which one or more hydrogen atoms may also be replaced by F.

* * * * *